US009874568B2

(12) United States Patent
Charretier et al.

(10) Patent No.: US 9,874,568 B2
(45) Date of Patent: Jan. 23, 2018

(54) METHOD OF DETECTING AT LEAST ONE MECHANISM OF RESISTANCE TO CARBAPENEMS BY MASS SPECTROMETRY

(71) Applicant: BIOMERIEUX, INC., Durham, NC (US)

(72) Inventors: Yannick Charretier, Courzieu (FR); Jean-Philippe Charrier, Tassin la Demi-Lune (FR); Christine Franceschi, Meximieux (FR); Gilles Zambardi, Chezeneuve (FR); Tiphaine Cecchini, Saint-Genis les Ollieres (FR); Elodie Degout-Charmette, Toussieux (FR)

(73) Assignee: BIOMERIEUX, INC., Durham, NC (US)

( * ) Notice: Subject to any disclaimer, the term of this patent is extended or adjusted under 35 U.S.C. 154(b) by 0 days.

(21) Appl. No.: 15/370,128

(22) Filed: Dec. 6, 2016

(65) Prior Publication Data
US 2017/0082636 A1 Mar. 23, 2017

Related U.S. Application Data

(62) Division of application No. 14/111,083, filed as application No. PCT/EP2012/057323 on Apr. 20, 2012, now Pat. No. 9,551,020.

(60) Provisional application No. 61/477,915, filed on Apr. 21, 2011.

(51) Int. Cl.
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| G01N 33/68 | (2006.01) |
| C12Q 1/04 | (2006.01) |
| C12Q 1/37 | (2006.01) |

(52) U.S. Cl.
CPC ............ *G01N 33/6848* (2013.01); *C12Q 1/04* (2013.01); *C12Q 1/37* (2013.01); *G01N 2333/948* (2013.01); *G01N 2333/976* (2013.01); *G01N 2333/986* (2013.01)

(58) Field of Classification Search
CPC ...... C12Q 1/04; C12Q 1/37; G01N 2333/948; G01N 2333/976; G01N 2333/986; G01N 33/6848
See application file for complete search history.

(56) References Cited

U.S. PATENT DOCUMENTS

| 9,074,236 B2 | 7/2015 | Stephenson, Jr. et al. |
| 2004/0229283 A1 | 11/2004 | Gygi et al. |
| 2007/0006950 A1 | 1/2007 | Okada et al. |
| 2007/0269895 A1 | 11/2007 | Aebersold et al. |
| 2011/0245105 A1 | 10/2011 | Citri |
| 2012/0196309 A1 | 8/2012 | Peaper et al. |
| 2012/0245128 A1 | 9/2012 | Haag et al. |
| 2012/0264156 A1 | 10/2012 | Beaulieu et al. |
| 2015/0255261 A1 | 9/2015 | Stephenson, Jr. et al. |

FOREIGN PATENT DOCUMENTS

| WO | 2005/098071 A1 | 10/2005 |
| WO | 2006/128492 A1 | 12/2006 |
| WO | 2008/066629 A2 | 6/2008 |
| WO | 2008/145763 A1 | 12/2008 |
| WO | 2011/045544 A2 | 4/2011 |

OTHER PUBLICATIONS

Peptide cutter results for the protein Q6XECO (Q6XECO) (OXA-48), trypsin digest, accessed online at http://web.expasy.org/cgi-bin/peptide_cutter/peptidecutter.pl on Mar. 22, 2017.*
Peptide cutter for a section of OXA-114a, trypsin digest, accessed online at http://web.expasy.org/cgi-bin/peptide_cutter/peptidecutter.pl on Mar. 21, 2017.*
Peptide cutter results for the protein VIM-1 (Q9XAY4), trypsin digest, accessed online at http://web.expasy.org/cgi-bin/peptide_cutter/peptidecutter.pl on Mar. 22, 2017.*
Wilcox et al. Single Ribosomal Protein Mutations in Antibiotic-Resistant Bacteria Analyzed by Mass Spectrometry. Antimicrobial Agents and Chemotherapy, Nov. 2001. vol. 45, No. 11, p. 3046-3055.*
Doi et al. Characterization of a Naturally Occurring Class D beta-Lactamase from Achromobacter xylosoxidans. Antimicrobial Agents and Chemotherapy, Jun. 2008. vol. 52, No. 6, pp. 1952-1956.*
Keshishian, H et al. "Quantitative, Multiplexed Assays for Low Abundance Proteins in Plasma by Targeted Mass Spectrometry and Stable Isotope Dilution." Molecular & Cellular Proteomics, 2007, pp. 2212-2229, vol. 6, No. 12, The American Society for Biochemistry and Molecular Biology, Inc.
Kondo, F., et al, "Identification of Shiga toxins in Shiga toxin-producing *Escherichia coli* using immunoprecipitation and high-performance liquid chromatography-electrospray ionization mass spectrometry." The Analyst, 2003, pp. 1360-1364,128(11).
Krishnamurthy, T. et al. "Rapid Identification of Bacteria by Direct Matrix-assisted Laser Desorption/Ionization Mass Spectrometric Analysis of Whole Cells." Rapid Communications in Mass Spectrometry, 1996, pp. 1992-1996, vol. 18, John Wiley & Sons, Ltd.
Li, M. et al, "Comparative proteomic analysis to identification of extracellular virulence factors of enterohemorrhagic *Escherichia coli* (EHEC) and enteropathogenic *Escherichia coli* (EPEC)." Faseb Journal, 2005, A1388, 19(5).

(Continued)

*Primary Examiner* — Marcela M Cordero Garcia
(74) *Attorney, Agent, or Firm* — Oliff PLC

(57) ABSTRACT

The present invention pertains to a method of detection, by mass spectrometry, of at least one marker of at least one mechanism of resistance to at least one antimicrobial, resistance of at least one microorganism contained in a sample, characterized in that the antimicrobial is a carbapenem, and said resistance markers are proteins or peptides. Preferably, said proteins or peptides are proteins from said microorganism.

14 Claims, No Drawings

(56) References Cited

OTHER PUBLICATIONS

Lin, Y.C. et al. "Differences in carbapenem resistance genes among Acinetobacter baumannii, Acinetobacter genospecies 3 and Acinetobacter genospecies 13TU in Taiwan." International Journal of Antimicrobial Agents, 2010, pp. 439-443, vol. 35.
Lin, Y.S. et al. "Affinity Capture Using Vancomycin-Bound Magnetic Nanoparticles for the MALDI-MS Analysis of Bacteria." Analytical Chemistry, Mar. 2005, pp. 1753-1760, vol. 77, No. 6, American Chemical Society.
López-Ferrer, D. et al. "Ultra Fast Trypsin Digestion of Proteins by High Intensity Focused Ultrasound." Journal of Proteome Research, 2005, pp. 1569-1574, vol. 4, American Chemical Society.
López-Ferrer, D. et al. "On-line Digestion System for Protein Characterization and Proteome Analysis." Analytical Chemistry, Dec. 2008, pp. 8930-8936, vol. 80, No. 23, American Chemical Society.
Mainardi, J. et al. "Resistance to cefotaxime and peptidoglycan composition in Enterococcus faecalis are influenced by exogenous sodium chloride." Microbiology, 1998, pp. 2679-2685, vol. 144, SGM.
Fortin, T. et al. "Clinical Quantitation of Prostate-specific Antigen Biomarker in the Low Nanogram/Milliliter Range by Conventional Bore Liquid Chromatography—Tandem Mass Spectrometry (Multiple Reaction Monitoring) Coupling and Correlation with ELISA Tests." Molecular & Cellular Proteomics, pp. 1006-1015, vol. 8, No. 5, The American Society for Biochemistry and Molecular Biology, Inc.
Fox, A. et al. ed., "Analytical Microbiology Methods: Chromatography and Mass Spectrometry." 1990, Plenum Press, New York, NY.
Fusaro, V. et al. "Prediction of high-responding peptides for targeted protein assays by mass spectrometry," Nature Biotechnology, Feb. 2009, pp. 190-198, vol. 27, No. 2, Nature America, Inc.
Gaskell, S. "Electrospray: Principles and Practice." Journal of Mass Spectrometry, 1997, pp. 677-688, vol. 32, John Wiley & Sons, Ltd.
Gröbner, S. et al. "Emergence of carbapenem-non-susceptible extended-spectrum beta-lactamase- producing Klebsiella pneumonia isolates at the university hospital of Tübingen, Germany." Journal of Medical Microbiology, 2009, pp. 912-922, vol. 58, SGM.
Han, B. et al. "Proteomics: from hypothesis to quantitative assay on a single platform. Guidelines for developing MRM assays using ion trap mass spectrometers." Briefings in Functional Genomics and Proteomics, Jun. 2008, pp. 340-354, vol. 7, No. 5, Oxford University Press, Oxford, UK.
Hernychova, L. et al. "Detection and Identification of Coxiella bumetii Based on the Mass Spectrometric Analyses of the Extracted Proteins." Analytical Chemistry, Sep. 2008, pp. 7097-7104, vol. 80, No. 18, American Chemical Society.
Ho, K., et al, "Using Biofunctionalized Nanoparticles to Probe Pathogenic Bacteria", Anal. Chem., 2004, pp. 7162-7168, 76.
Hofstadler, S. et al. "Tiger: the universal biosensor." International Journal of Mass Spectrometry, 2005, pp. 23-41, vol. 242.
Ding, D. et al. "Identification of protein components and quantitative immunoassay for SEC2 in Staphylococcin injection." Journal of Pharmaceutical and Biomedical Analysis, 2009, pp. 79-85, vol. 50.
Ecker, D. et al. "Ibis T5000: a universal biosensor approach for microbiology." Nature Reviews Microbiology, Jun. 2008, pp. 553-558, vol. 6, No. 7, Nature Publishing Group.
Everley, R. et al. "Characterization of Clostridium species utilizing liquid chromatography/mass spectrometry of intact proteins." Journal of Microbiological Methods, pp. 152-158, Feb. 2009, vol. 77.
Camara et al, "Discrimination between wild-type and ampicillin-resistant Escherichia coli by matrix-assisted laser desorption/ionization time-of-flight mass spectrometry." Analytical and Bioanal. Chemistry, 2007, pp. 1633-1638, 389(5).
Carbonnelle et al, "Rapid identification of Staphylococci isolated in clinical microbiology laboratories by matrix-assisted laser desorption ionization-time of flight mass spectrometry", Journal of Clinical Microbio., 2007, pp. 2156-2161, 45(7).

Chen, W. et al. "Functional Nanoparticle-Based Proteomic Strategies for Characterization of Pathogenic Bacteria." Analytical Chemistry, Dec. 2008, pp. 9612-9621, vol. 80, No. 24, American Chemical Society.
Claydon, M. et al. "The rapid identification of intact microorganisms using mass spectrometry." Nature Biotechnology, Nov. 1996, pp. 1584-1586, vol. 14.
Dare et al, "Staphylococci speciation and Panton-Valentine leukocidin detection by matrix assisted laser desorption ionisation time-of-flight mass spectrometry", Intern. Journal of Antimicrobial Agents, 2007, pp. 103-104, 29(2).
Desiere, F. et al. "The PeptideAtlas project." Nucleic Acids Research, 2006, pp. D655-D658, vol. 34, Database Issue, Oxford University Press, Oxford, UK.
Bundy, J. et al. "Lectin-Based Affinity Capture for MALDI-MS Analysis of Bacteria." Analytical Chemistry, Apr. 1999, pp. 1460-1463, vol. 71, No. 7, American Chemical Society.
Bush, K et al. "Updated Classification of beta-Lactamases." Antimicrobial Agents and Chemotherapy, Mar. 2010, pp. 969-976, vol. 54, No. 3, American Society for Microbiology.
Bernardo et al, "Identification of Staphylococcus aureus exotoxins by combined sodium dodecyl sulfate gel electrophoresis and matrix-assisted laser desorption/ionization-time of flight mass spectrometry." Proteomics, 2002, pp. 740-746, 2(6).
Anderson, L et al. "Quantitative Mass Spectrometric Multiple Reaction Monitoring Assays for Major Plasma Proteins." Molecular & Cellular Proteomics, 2006, pp. 573-588, vol. 5, No. 4. The American Society for Biochemistry and Molecular Biology, Inc.
Brun, V. et al. "Isotope-labeled Protein Standards Toward Absolute Quantitative Proteomics." Molecular & Cellular Proteomics, 2007, pp. 2139-2149, vol. 6, No. 12, The American Society for Biochemistry and Molecular Biology, Inc.
Bernardo et al, "Identification and discrimination of Staphylococcus aureus strains using matrix-assisted laser desorption/ionization-time of flight mass spectrometry" Proteomics, 2002, pp. 747-753, 2(6).
Fenselau, C. et al. "Identification of beta-Lactamase in Antibiotic-Resistant Bacillus cereus Spores." Applied and Environmental Microbiology. Feb. 2008, pp. 904-906, vol. 74, No. 3, American Society for Microbiology.
Sep. 6, 2016 Notice of Allowance in U.S. Appl. No. 14/111,083.
Sep. 4, 2014 Office Action issued in U.S. Appl. No. 14/111,118.
Jan. 3, 2014 Office Action issued in U.S. Appl. No. 13/502,020.
May 15, 2014 Office Action issued in U.S. Appl. No. 13/502,020.
Sauer, Sascha, et al., "Classification and Identification of Bacteria by Mass Spectrometry and Computational Analysis," vol. 3, Issue 7, Jul. 2008, pp. 1-10.
Dec. 5, 2014 Office Action issued in U.S. Appl. No. 14/111,083.
Apr. 24, 2015 Office Action issued in U.S. Appl. No. 14/111,118.
Ahmet et al., "Pyrolysis Mass Spectrometry of Cephalosporin-Resistant Enterobacter Cloacae," Journal of Hospital Infection, 1995, vol. 31, pp. 99-104.
Bush, "Extended-Spectrum Beta-Lactamases in North America, 1987-2006," Clin Microbiol and Infectious Diseases 2008, vol. 14 (Suppl 1), pp. 134-143.
Hope et al., "Efficacy of Practised Screening Methods for Detection of Cephalosporin-Resistant Enterobacteriaceae." J Antimicrob Chemotherapy 2007, vol. 59, pp. 110-113.
Moosdeen, "The Evolution of Resistance to Cephalosporins," Clinical Infectious Diseases, 1997, pp. 487-493.
ExPaSy Peptidecutter for KPC-1—http://web.expasy.org/cgi-bin/peptide_cutter/peptidecutter.pl, 2 pgs., accessed Jun. 8, 2015.
Savini et al., "Bacillus Cereus Heteroresistance to Carbapenems in a Cancer Patient," J. Hospital Infection, pp. 288-289, 2009.
Yigit et al., "Novel Carbapenem-Hydrolyzing Beta-Lactamase, KPC-1, from a Carbapenem-Resistant Strain of Klebsiella Pneumoniae," Antimicrobial Agents and Chemotherapy, vol. 45, No. 4, pp. 1151-1161, 2001.
Yigit et al., "Novel Carbapenem-Hydrolyzing Beta-Lactamase, KPC-1, from a Carbapenem-Resistant Strain of Klebisella Pneumoniae," Authors correction Antimicrobial Agents and Chemotherapy, vol. 52, No. 2, p. 809, 2008.

(56) References Cited

OTHER PUBLICATIONS

Kulkarni et al., "Use of Impipenem to Detect KPC, NDM, OXA, IMP, and VIM Carbapenemase Activity from Gram-Negative Rods in 75 Minutes Using Liquid Chromatography-Tandem Mass Spectrometry," JCM, vol. 52, No. 7, pp. 2500-2505, Jul. 2014.
Jun. 11, 2015 Office Action issued in U.S. Appl. No. 14/111,083.
Beccerril et al., "Combination of Analytical and Microbiological Techniques to Study the Antimicrobial Activity of a New Active Food Packaging Containing Cinnamon or Oregano Against *E. coli* and *S. aureus*," Anal Bioanal Chem, vol. 388, pp. 1003-1011, 2007.
Kuhn et al., "Quantification of C-Reactive Protein in the Serum of Patients with Rheumatoid Arthritis Using Multiple Reaction Monitoring Mass Spectrometry and 13C-Labeled Peptide Standards," Proteomics, vol. 4, pp. 1175-1186, 2004.
Keller et al., "A Uniform Proteomics MS/MS Analysis Platform Utilizing Open XML File Formats," Molecular Systems Biology, vol. 1, pp. 1-8, 2005.
Sep. 23, 2015 Office Action issued in U.S. Appl. No. 13/502,020.
Jan. 4, 2016 Office Action issued in U.S. Appl. No. 14/111,118.
Mar. 11, 2016 Office Action issued in U.S. Appl. No. 14/111,083.
U.S. Appl. No. 13/502,020, filed Jun. 29, 2012 in the name of Beaulieu et al.
Jul. 15, 2016 Notice of Allowance issued in U.S. Appl. No. 14/111,118.
Anhalt, J. et al. "Identification of Bacteria Using Mass Spectrometry." Analytical Chemistry, Feb. 1975, pp. 219-225, vol. 47, No. 2.
International Search Report issued in International Application No. PCT/EP2012/057323 (with English translation).
International Search Report issued in International Application No. PCT/FR2010/052181 (with English translation).
International Search Report issued in International Application No. PCT/EP2012/057322 (with English translation).
Written Opinion of the International Searching Authority for International Application No. PCT/EP2012/057323 (with English Translation).
Written Opinion of the International Searching Authority for International Application No. PCT/EP2012/057322 (with English Translation).
Written Opinion of the International Searching Authority for International Application No. PCT/FR2010/052181 (with English Translation).
U.S. Appl. No. 14/111,083 in the name of Charretier et al.
Savinova, T.A. et al, abstract of "A mass-spectrometric analysis of genetic markers of S. pneumonia resistance to beta-lactam antibiotics." XP002684331, Database accession No. NLM20882772, Database Medline, 2010, US National Library of Medicine, Bethesda, MD.
Seng, P. et al. "Ongoing Revolution in Bacteriology: Routine Identification of Bacteria by Matrix-Assisted Laser Desorption Ionization Time-of-Flight Mass Spectrometry." Clinical Infectious Diseases, Aug. 2009, pp. 543-51, vol. 49, Infectious Diseases Society of America.
Stahl-Zeng, J. et al. "High Sensitivity Detection of Plasma Proteins by Multiple Reaction Monitoring of N-Glycosites." Molecular & Cellular Proteomics, Jul. 2007, pp. 1809-1817, vol. 6, No. 10, The American Society for Biochemistry and Molecular Biology, Inc.
Takao, T., et al, "Identity of molecular structure of Shiga-like toxin I (VTI) from *Escherichia coli* 0157 : H7 with that of Shiga toxin." Microbial Pathogenesis, 1988, pp. 357-369, 5(5).

Teng, C.H. et al. "Gold Nanoparticles as Selective and Concentrating Probes for Samples in MALDI MS Analysis." Analytical Chemistry, Aug. 2004, pp. 4337-4342, vol. 76, No. 15, American Chemical Society.
Vaidyanathan, S. et al. "Discrimination of Aerobic Endospore-forming Bacteria via Electrospray-Ionization Mass Spectrometry of Whole Cell Suspensions." Analytical Chemistry, Sep. 2001, pp. 4134-4144, vol. 73, No. 17, American Chemical Society.
Wang, Ky. et al. "Multiplexed Immunoassay: Quantitation and Profiling of Serum Biomarkers Using Magnetic Nanoprobes and MALDI-TOF MS." Analytical Chemistry, Aug. 2008, pp. 6159-6167, vol. 80, No. 16, American Chemical Society.
Wybo, I. et al. "Differentiation of cfiA-Negative and cfiA-Positive Bacteroides fragilis Isolates by Matrix-Assisted Laser Desorption Ionization-Time of Flight Mass Spectrometry." Journal of Clinical Microbiology, May 2011, pp. 1961-1964, vol. 49, No. 5, American Society for Microbiology.
Zheng, K. "Elucidation of peptide metabolism by on-line immunoaffinity liquid chromatography mass spectrometry." Rapid Communications in Mass Spectrometry, 2000, pp. 261-269, vol. 14, John Wiley & Sons, Ltd.
Majcherczyk P., et al, "The discriminatory power of MALDI-TOF mass spectrometry to differentiate between isogenic teicoplanin-susceptible and teicoplanin-resistant strains of methicillin-resistant *Staphylococcus aureus*", Ferns Microbiol Letters, 2006, pp. 233-239, 255(2).
Manes, N. et al. "Targeted Protein Degradation by Salmonella under Phagosome-mimicking Culture conditions Investigated Using Comparative Peptidomics." Molecular & Cellular Proteomics, Jan. 2007, pp. 717-727, vol. 6, No. 4, MCP Papers in Press.
Marinach, C. et al, "MALDI-TOF MS-based drug susceptibility testing of pathogens: The example of Candida albicans and fluconazole" Proteomics, 2009, pp. 4627-4631, 9(20).
Mazzeo, M., et al, "Matrix-assisted laser desorption ionization-time of flight mass spectrometry for the discrimination of food-borne microorganisms", Applied and Env. Microbio., 2006, pp. 1180-1189,72(2).
Mead, J. et al. "MRMaid, the Web-based Tool for Designing Multiple Reaction Monitoring (MRM) Transitions." Molecular & Cellular Proteomics, 2009, pp. 696-705, vol. 8, No. 4, The American Society for Biochemistry and Molecular Biology, Inc.
Melanson, J., et al, "Targeted comparative proteomics by liquid chromatography/matrix-assisted laser desorption/ionization triple-quadruple mass spectrometry." Rapid Communications in Mass Spectrometry, 2006, pp. 904-910, 20(5).
Nandakumar, R. et al. "Proteomic analysis of endodontic infections by liquid chromatography-tandem mass spectrometry." Oral Microbiology and Immunology, 2009, pp. 347-352, vol. 24, John Wiley & Sons, Ltd.
Pratt, J. et al. "Multiplexed absolute quantification for proteomics using concatenated signature peptides encoded by QconCAT genes." Nature Protocols, 2006, pp. 1029-1043, vol. 1, No. 2, Nature Publishing Group.
Qian, J., et al, "MALDI-TOF mass signatures for differentiation of yeast species, strain grouping and monitoring of morphogenesis markers", Analytical and Bioanal. Chemistry, 2008, pp. 439-449, 392(3).

\* cited by examiner

METHOD OF DETECTING AT LEAST ONE MECHANISM OF RESISTANCE TO CARBAPENEMS BY MASS SPECTROMETRY

This is a Division of application Ser. No. 14/111,083 filed Oct. 10, 2013, which in turn is a national stage of PCT/EP2012/057323, filed Apr. 20, 2012, which claims the benefit of U.S. Provisional Application No. 61/477,915 filed Apr. 21, 2011. The disclosure of the prior applications is hereby incorporated by reference herein in its entirety.

The present invention relates to the field of microbiology. More precisely, the invention relates to the detection of at least one mechanism of resistance to carbapenems of at least one microorganism from a sample by using mass spectrometry.

Since Pasteur's discovery of microbes, microorganisms have been studied by microscopy and biochemical analyses. These conventional methods are often long and tedious, and analytical alternatives were sought very early on. This is why the analysis of bacteria by mass spectrometry was initiated from 1975 by J. Anhalt and C. Fenselau [1].

This preliminary work was followed by the study of fatty acids from the wall of the microorganisms using gas chromatography combined with mass spectrometry (GC-MS) [2]. This method was popularised under the English term FAME, standing for Fatty Acid Methyl Ester. It currently constitutes a reference method for taxonomic studies. However, its use remains limited to certain specialised laboratories dealing with the treatment of the sample by saponification, hydrolysis and derivation.

In 1996, the works by M. Claydon et al. [3] as well as by T. Krishnamurthy and P. Ross [4] demonstrated the possibility of identifying different bacterial species with a MALDI-TOF mass spectrometer (English acronym for Matrix Assisted Laser Desorption Ionization-Time Of Flight). The analysis combines the acquisition of a mass spectrum and the interpretation of expert software. It is extremely simple and can be carried out in a few minutes. However it has only been making it into medical analysis laboratories fairly recently [5]. Its clinical use is currently limited to the identification of bacteria and yeast species. It is not routinely used to identify resistances to antimicrobials.

Yet the identification of resistances to antimicrobials such as antibiotics is an essential element in ensuring optimal patient care.

Other mass spectrometry methods, particularly in tandem, have been proposed to meet these needs. By way of example, it is possible to cite the work of C. Fenselau et al. for identifying β-Lactamase with a quadripole-TOF (Q-TOF) [6].

However these research results are not applicable to routine clinical use. They were obtained with research instruments requiring highly qualified personnel. The analysis times, often greater than one hour per sample, are incompatible with the workload of a microbiological analysis laboratory.

More recently, S. Hofstadler et al. [7] proposed a method combining a microbial genome amplification by PCR to a detection of the PCR products by electrospray-TOF (ESI-TOF). This method is now fully automated [8]. However, it requires a PCR amplification with the flaws inherent in molecular biology, namely extraction yield, cost of the probes, etc.

In this context, the objective of the present invention is to propose a method of detecting mechanisms of resistance to carbapenems which makes it possible to overcome the disadvantages of the prior art methods, namely providing an inexpensive method, without reagents specific to each species, particularly compared to molecular biology methods, which gives a result in a short amount of time, less than one hour, and which can be used in routine clinical work, without requiring highly qualified personnel.

To this end, the invention proposes a new method of detecting, by mass spectrometry, at least one mechanism of resistance to at least one antimicrobial of at least one microorganism from a sample, characterised in that the antimicrobial is a carbapenem and in that proteins and/or peptides are detected as markers of said mechanism of resistance to at least one carbapenem-class antibiotic.

Preferably, the resistance markers are proteins from said at least one microorganism. Advantageously, markers of resistance to several different antimicrobials can be detected simultaneously.

As indicated in application PCT/FR2010/052181, markers of type and/or virulence of said microorganisms can be detected in the same way by mass spectrometry prior to or at the same time as the detection of the resistance mechanism markers.

Markers of resistance to at least one carbapenem-class antimicrobial is understood to mean molecules of protein origin which are characteristic of said properties.

Carbapenems are antibiotics belonging to the beta-lactam family and their main representatives are imipenem, meropenem, ertapenem and doripenem. These molecules are broken down by the beta-lactamases 2df, 2f and 3a of the classification by Bush and Jacoby ([9], Antimicrobial Agents and Chemotherapy, 2010; 54 (3): 969-976).

Determination of the resistance to at least one antimicrobial is understood to mean determining the susceptibility of a microorganism to being destroyed by an antimicrobial. The proteins involved in the resistance mechanisms will differ depending on the family and the species.

The nomenclature of the beta-lactamases, beta-lactam-resistant bacterial enzymes, is not standardised. They are either classified in four molecular classes (A to D) on the basis of their primary structure, or in functional groups on the basis of the target substrates and their resistance to inhibitors (for an overview, see [9] Bush and Jacoby, supra). For molecular classification, sequencing techniques have made more precise classification possible: for example, 183 variants of the TEM protein have been described (labelled TEM-i, with i being between 1 and 183). For the functional classification, Bush and Jacoby (supra) have proposed new functional subgroups:

the group 1 enzymes are cephalosporinases belonging to the molecular class C. CMY and FOX are plasmid-borne enzymes, belonging to this subgroup.

the group 2 enzymes belong to molecular classes A and D. This group is itself subdivided into subgroups, 2b, 2be, 2br, 2ber, 2d, 2de, 2df, 2f, etc. CTX-M (2be) and TEM (including 2be, 2br) are enzymes belonging to this subgroup. The subgroup 2b corresponds to broad-spectrum beta-lactamases which are inhibited by clavulanic acid, sulfobactam, or tazobactam. The subgroup 2be corresponds to extended-spectrum beta-lactamases (ESBL), which are also inhibited by clavulanic acid, sulfobactam or tazobactam. The subgroup 2br corresponds to beta-lactamases from the subgroup 2b which are insensitive to inhibition by clavulanic acid, sulfobactam or tazobactam. The subgroup 2df includes OXAs having a spectrum extended to carbapenems. Group 2f corresponds to carbapenemase beta-lactamases such as KPC.

group 3 encompasses the metallo-beta-lactamases which hydrolyse carbapenems, such as IMP, VIM, SPM, GIM, SIM, AIM, KHM, DIM or NDM.

NDM-1 beta-lactamase was described in 2010 (Kumarasamy et al., 2010, Lancet Infect. Dis., 10:597-602). It corresponds to a metallo-beta-lactamase which confers a resistance to all beta-lactams except aztreonam.

KPC beta-lactamases were described from 2001 in the United States (Yigit et al., 2001, Antimicrobio. Agents Chemother., 45:1151-1161) and then throughout the world. They correspond to class-A beta-lactamases which confer a resistance to cephalosporins and to carbapenems, in particular to imipenem and to meropenem. IMP beta-lactamases were described from 1994 in Japan (Osano et al., 1994, Antimicrobio. Agents Chemother., 38:71-78) and then throughout the world. They correspond to metallo-beta-lactamases which confer a resistance to cephalosporins and to carbapenems, but which do not confer resistance to Temocillin and to aztreonam.

VIM beta-lactamases were described from 1999 in Europe (Lauretti et al., 1999, Antimicrobio. Agents Chemother., 43:1584-1590) and then throughout the world. They correspond to metallo-beta-lactamases which confer a resistance to cephalosporins and to carbapenems, but which do not confer resistance to aztreonam.

The first GES beta-lactamase was isolated in 1998 in French Guiana (Poirel et al., 2000, Antimicrobio. Agents Chemother., 43:622-632). This enzyme (GES-1) conferred an ESBL resistance. The second isolate from a bacterium bearing a GES beta-lactamase was achieved in 2000 in South Africa (Poirel et al., 2001, Antimicrobio. Agents Chemother., 45:2598-2603). This enzyme (GES-2) conferred a resistance to cephalosporins and to carbapenems such as imipenem.

IND beta-lactamases were described for the first time in 1999 (Bellais et al., 1999, FEMS Microbio. Lett., 171:127-132). They correspond to metallo-beta-lactamases which confer a resistance to cephalosporins and to carbapenems.

SME beta-lactamases were described for the first time in 1994 (Naas et al., 1994, Antimicrobio. Agents Chemother., 38:1262-1270). They correspond to class-A beta-lactamases which confer a resistance to cephalosporins and to carbapenems.

OXA beta-lactamases (or oxacillinases) correspond to Class-D beta-lactamases. According to their primary sequence, they can confer resistances to cephalosporins or to cephalosporins and to carbapenems (Poirel et al., 2010, Antimicrobio. Agents Chemother., 54:24-38).

The method of the invention can be employed to detect mechanisms of resistance to carbapenems in bacteria. Thus, for example, as bacteria in which it is possible to seek a mechanism of resistance to carbapenems according to the method of the invention, non-exhaustive mention may be made of: *Escherichia coli, Klebsiella pneumoniae, Pseudomonas aeruginosa, Acinetobacter baumannii, Bacillus* spp, *Stenotrophomonas maltophilia, Aeromonas* spp, *Bacteroides fragilis, Pseudomonas otitidis* and *Enterobacter cloacae*, and more generally, the Enterobacteriaceae, which carry the $bla_{NDM-1}$ or $bla_{KPC}$ resistance gene. It should further be noted that the strains known to be resistant to carbapenems are also resistant to cephalosporins and to penicillins.

Thus, the method according to the invention also makes it possible to detect a mechanism of resistance to said antibiotics.

The sample on which the method of the invention can be employed is any sample susceptible of containing a target microorganism. The sample can be of biological origin, either animal, vegetable or human. In this case it may correspond to a specimen of biological fluid (whole blood, serum, plasma, urine, cerebrospinal fluid, organic secretion, for example), a tissue specimen or isolated cells. This specimen can be used such as it is, insofar as the markers of mechanisms of bacterial resistance to beta-lactams are available in the sample tested, or it can, prior to the analysis, undergo preparation by enrichment, extraction, concentration, purification, culturing, in accordance with methods known to the person skilled in the art.

The sample can be of industrial origin, or, according to a non-exhaustive list, can be an air specimen, a water specimen, a surface specimen, a part or a manufactured product, or a food product. Amongst the food samples, non-exhaustive mention can be made of a sample of a dairy product (yogurts, cheeses), of meat, of fish, of egg, of fruit, of vegetable, of water, of a beverage (milk, fruit juice, soda, etc.). These food samples can also come from sauces or ready meals. Finally, a food sample can come from an animal feed, such as animal meals.

Upstream of the detection by mass spectrometry, the sample to be analysed is preferably pretreated to produce peptides from the entirety of the proteins present in the sample to fragment these proteins into peptides, for example by digestion with a proteolytic enzyme (protease), or by the action of a chemical reagent. In fact, the cleaving of the protein can be performed by a physico-chemical treatment, by a biological treatment or by a combination of the two treatments. Amongst the useable treatments, mention can be made of treatment by hydroxyl radicals, in particular with $H_2O_2$. Treatment by hydroxyl radicals results in a cutting of the peptide bonds which takes place randomly on any of the protein's peptide bonds. The hydroxyl radical concentration determines the number of cleavages performed, and therefore the length of the peptide fragments obtained. Other chemical treatments can also be used such as, for example, cyanogen bromide (CNBr) treatment which specifically splits the peptide bonds at the carboxyl group of the methionyl residues. It is also possible to perform partial acid cleaving at the aspartyl residues by heating a solution of proteins in trifluoroacetic acid to 1000° C.

Treatment of the proteins by enzymatic digestion is nevertheless preferred over physico-chemical treatment because it preserves more of the structure of the protein, and is easier to control. "Enzymatic digestion" is understood to mean the single or combined action of one or more enzymes under appropriate reaction conditions. The enzymes carrying out the proteolysis, which are called proteases, cut the proteins at specific locations. Each protease generally recognises a sequence of amino acids within which it always makes the same cut. Certain proteases recognise a single amino acid or a sequence of two amino acids between which they perform a cleavage, whereas other proteases only recognise longer sequences. These proteases can be endoproteases or exoproteases. Amongst the known proteases, mention may be made of the following as described in WO2005/098071:

specific enzymes such as trypsin which splits the peptide bond at the carboxyl group of the Arg and Lys residues, endolysin which cleaves the peptide bond of the —CO group of the lysines, chymotrypsin which hydrolyses the peptide bond at the carboxylic group of the aromatic residues (Phe, Tyr and Trp), pepsin which makes a cut at the $NH_2$ group of the aromatic residues (Phe, Tyr and Trp), the protease V8 from the V8 strain of *Staphylococcus aureus* which cleaves the peptide bond at the carboxylic group of the Glu residue;

the non-specific enzymes such as thermolysin from the bacteria *Bacillus thermoproteolyticus* which hydrolyses the peptide bond of the $NH_2$ group of hydrophobic amino acids (Xaa-The, Xaa-Ile, Xaa-Phe), subtilisin and pronase which are bacterial proteases which hydrolyse practically all the bonds and can transform the proteins into oligopeptides under controlled reaction conditions (enzyme concentration and duration of reaction).

Several proteases may be used simultaneously, if their modes of action are compatible, or they may be used successively. Within the framework of the invention, the digestion of the sample is preferably performed by the action of a protease enzyme, for example trypsin.

The generation of peptides using a chemical reagent or a protease can be obtained by means of a simple reaction in solution. It can also be performed with a microwave oven [10], or under pressure [11], or even with an ultrasound device [12]. In these three latter cases, the protocol will be much faster.

Amongst the peptides thus obtained, the peptides specific to the protein are referred to as proteotypic peptides. It is these which will be assayed by mass spectrometry. According to the invention, the markers of the mechanisms of bacterial resistance to carbapenems are proteins from the bacterium in which the mechanisms of resistance to cephalosporins are to be sought. In particular, said proteins are digested into peptides, preferably by an enzyme, and more preferably by trypsin.

Similarly, the sample containing protein markers characterising mechanisms of bacterial resistance to carbapenems can also be pretreated for the purposes of purification. This purification pretreatment can be employed before or after the peptide production step as described above.

The sample purification pretreatment is widely known to the person skilled in the art and may in particular employ the techniques of centrifugation, filtration, electrophoresis or chromatography. These separating techniques can be used alone or in combination with one another to obtain a multidimensional separation. For example, multidimensional chromatography can be used by combining separation by ion exchange chromatography with reversed-phase chromatography, as described by T. Fortin et al. [13], or H. Keshishian et al. [14]. In these publications, the chromatography medium can be in a column or in a cartridge (solid-phase extraction).

The electrophoretic or chromatographic fraction (or the retention time in monodimensional or multidimensional chromatography) of the proteotypic peptides is characteristic of each peptide, and employing these techniques therefore makes it possible to select the proteotypic peptide or peptides to be assayed. Such a fractionation of the produced peptides makes it possible to increase the specificity of the subsequent assay by mass spectrometry.

An alternative to the electrophoresis or chromatography techniques for the fractionation of the peptides consists in specifically purifying the N-glycopeptides ([15] and patent application WO 2008/066629). However, such a purification only makes it possible to quantify the peptides which have undergone an N-glycosylation post-translational modification. Not all proteins are glycosylated though, which therefore limits its use.

The mass spectrometry to be employed in the method of the invention is widely known to the person skilled in the art as a powerful tool for analysing and detecting different types of molecules. Generally, any type of molecule able to be ionised can be detected according to its molecular mass with the aid of a mass spectrometer. According to the nature of the molecule to be detected, whether of protein or metabolic origin, certain mass spectrometry technologies can be more suitable. Nevertheless, whatever mass spectrometry method is used for the detection, this latter includes a step of ionising the target molecule into so-called molecular ions, in the present case a step of ionising the characterising markers, and a step of separating the molecular ions obtained according to their mass.

All mass spectrometers therefore comprise:
  an ionising source intended to ionise the markers present in the sample to be analysed, i.e. to confer a positive or negative charge upon these markers;
  a mass analyser intended to separate the ionised markers, or molecular ions, according to their mass-to-charge ratio (m/z);
  a detector intended to measure the signal produced either directly by the molecular ions, or by ions produced from molecular ions as detailed hereafter.

The ionisation step necessary for employing mass spectrometry can be performed via any method known to the person skilled in the art. The ionising source makes it possible to transform the molecules to be assayed into a gaseous and ionised state. An ionising source can be used either in positive mode to study the positive ions, or in negative mode to study the negative ions. Several types of sources exist and will be used depending on the result sought and the molecules analysed. In particular, mention may be made of:
  electron ionisation (EI), chemical ionisation (CI) and desorption chemical ionisation (DCI)
  fast atom bombardment (FAB), metastable atom bombardment (MAB) or ion bombardment (SIMS, LSIMS) http://fr.wikipedia.org/wiki/Spectrom%C3%A9trie_de_masse_%C3%A0_ionisation_secondaire
  inductively coupled plasma (ICP) http://fr.wikipedia.org/wiki/Torche_%C3%A0_plasma_(chimie)
  atmospheric-pressure chemical ionisation (APCI) and atmospheric-pressure photoionisation (APPI) http://fr.wikipedia.org/wiki/Ionisation_chimique_%C3%A0_pression_atmosph%C3%A9rique
  electronebulisation or electrospray (ESI) http://fr.wikipedia.org/wiki/Ionisation_par_%C3%A9lectron%C3%A9buliseur_(ESI)
  matrix-assisted laser desorption/ionisation (MALDI), surface-activated laser desorption/ionisation (SELDI) or desorption/ionisation on silicon (DIOS) http://fr.wikipedia.org/wiki/D%C3%A9sorption-ionisation_laser_assist%C3%A9e_par_matrice
  ionisation/desorption by interaction with metastable species (DART)

In particular, ionisation can be employed as follows: the sample containing the target molecules is introduced into an ionisation source, where the molecules are ionised in gaseous state and thus transformed into molecular ions which correspond to the initial molecules. An electrospray ionisation (ESI) source makes it possible to ionise a molecule by making it pass from a liquid state into a gaseous state. The molecular ions obtained therefore correspond to the molecules present in liquid state, with, in positive mode, one, two, or even three or more additional protons and therefore carry one, two, or even three or more charges. For example, when the target molecule is a protein, an ionisation of the proteotypic peptides obtained after fractionation of the target protein, by means of an electrospray source functioning in positive mode, leads to polypeptide ions in gaseous state, with one, two, or even three or more additional protons and which therefore carry one, two, or even three or more charges, and makes it possible to move from a liquid state to a gaseous state [16]. This type of source is particularly well suited when the target molecules or proteotypic peptides obtained are separated beforehand by reversed-phase liquid chromatography. Nevertheless, the ionisation yield of the molecules present in the sample may vary depending on the concentration and the nature of the different species present. This phenomenon leads to a matrix effect well known to the person skilled in the art.

A MALDI ionisation source will allow ionisation of the molecules from a solid-state sample.

The mass analyser in which the step of separating the ionised markers according to their mass-to-charge ratio (m/z) is performed is any mass analyser known to the person skilled in the art. Mention can be made of low-resolution analysers, quadripole or quadrupole (Q), 3D ion trap (IT) or linear ion trap (LIT), also called ion trap, and high-resolution analysers which make it possible to measure the exact mass of the analytes and which in particular use the magnetic sector linked to an electric sector, the time of flight (TOF), Fourier transform ion cyclotron resonance (FT-ICR), orbitrap.

The separation of the molecular ions depending upon their m/z ratio can be employed just once (single mass spectrometry or MS), or several successive MS separations can be conducted. When two successive MS separations are carried out, the analysis is called MS/MS or $MS^2$. When three successive MS separations are carried out, the analysis is called MS/MS/MS or $MS^3$, and more generally, when n successive MS separations are carried out, the analysis is called $MS^n$.

Amongst the techniques which employ several successive separations, SRM (Selected Reaction Monitoring) mode when detecting or assaying a single target molecule, or MRM (Multiple Reaction Monitoring) mode when detecting or assaying several target molecules are particular uses of $MS^2$ separation. Similarly the $MRM^3$ mode is a particular use of MS/MS/MS separation. This is referred to as targeted mass spectrometry.

In the case of a detection in single MS mode, it is the mass-to-charge ratio of the molecular ions obtained which is correlated to the target molecule to be detected.

In the case of detection in MS/MS mode, essentially two steps are added, compared to an MS assay, which are:
  a fragmentation of the molecular ions, then called precursor ions, to give ions called $1^{st}$ generation fragment ions, and
  a separation of the ions called $1^{st}$ generation fragment ions according to their mass $(m/z)_2$, the ratio $(m/z)_1$ corresponding to the ratio (m/z) of the precursor ions.

It is therefore the mass-to-charge ratio of the $1^{st}$ generation fragment ions thus obtained which is correlated to the target molecule to be detected. First-generation fragment ion is understood to be an ion derived from the precursor ion, following a fragmentation step and of which the mass-to-charge ratio m/z is different from the precursor ion.

The $(m/z)_1$ and $(m/z)_2$ pairs are called transitions and are representative of the characteristic ions to be detected.

The choice of the characteristic ions which are detected to be correlated to the target molecule is made by the person skilled in the art in accordance with the standard methods. Their selection will advantageously lead to the most sensitive, specific and robust assays possible, in terms of reproducibility and reliability. In the methods developed for the selection of proteotypic peptides $(m/z)_1$, and of the first-generation fragment $(m/z)_2$, the choice is essentially based on the intensity of the response. For more details, it is possible to refer to V. Fusaro et al. [17]. Commercially available software, such as the MIDAS and MRM Pilot software from Applied Biosystems or MRMaid [18] can be used by the person skilled in the art to allow him to predict all the possible transition pairs. He can also make use of a database called PeptideAtlas constructed by F Desiere et al. [19] to compile all of the MRM transitions of peptides described by the scientific community. This database PeptideAtlas is freely available on the internet. For non-protein molecules, it is also possible to use databases, such as, for example, the one accessible through the Cliquid software from the company Applied Biosystems (United States of America).

An alternative approach to selecting the proteotypic peptides $(m/z)_1$ and $(m/z)_2$ consists in using MS/MS fragmentation spectra obtained during other work. This work can be, for example, the phases of biomarker discovery and identification by proteomic analysis. This approach was proposed by Thermo Scientific during user conferences [18]. It makes it possible to generate a list of candidate transitions from the peptides identified through testing by the SIEVE (Thermo Scientific) software. Certain criteria were detailed by J. Mead et al. [18] for the choice of the ions $(m/z)_1$ and $(m/z)_2$ and are detailed hereafter:
  peptides with internal cleavage sites, i.e. with internal Lysine or Arginine, must be avoided, unless the Lysine or Arginine is followed by Proline,
  peptides with Aspargine or Glutamine must be avoided because they may deaminate,
  peptides with Glutamine or Glutamic Acid at the N-terminal must be avoided because they may cyclise spontaneously,
  peptides with Methionine must be avoided because they may be oxidised,
  peptides with Cysteine must be avoided because they may be non-reproducibly modified during a potential step of denaturation, reduction and blocking of the thiol functions,
  peptides with Proline may be considered to be favourable because they generally produce intense fragments in MS/MS with a very strong single peak. However, a very strong single fragment does not make it possible to validate the identity of the transition in a complex mixture. Indeed, only the simultaneous presence of several characteristic fragments makes it possible to verify that the precursor ion sought has actually been detected,
  the peptides having a Proline adjacent to the C-terminal (Position n-1) or in second position relative to the C-terminal (position n-2) should be avoided because, in this case, the size of the first-generation peptide fragment is generally considered to be too small to be sufficiently specific,
  the selection of fragments having a mass greater than the precursor should be given preference in order to promote specificity. To this end, it is necessary to select a dicharged precursor ion and select the most intense first-generation ion fragment having a mass greater than the precursor, i.e. a monocharged first-generation fragment ion.

The fragmentation of the selected precursor ions is performed in a fragmentation cell such as the triple quadripole model [20], ion trap model [21], or time-of-flight (TOE) model [22], which also make it possible to separate ions. The fragmentation or fragmentations will be conventionally performed by collision with an inert gas such as argon or nitrogen, within an electrical field, by photo-excitation or photo-dissociation using an intense light source, collision with electrons or radical species, by applying a potential difference, for example in a time-of-flight tube, or by any other activation mode. The characteristics of the electrical field determine the intensity and nature of the fragmentation. Thus, the electrical field applied in the presence of an inert gas, for example in a quadripole, determines the collision energy provided to the ions. This collision energy will be optimised, by the person skilled in the art, to increase the sensitivity of the transition to be assayed. By way of example, it is possible to vary the collision energy between 5 and 180 eV in q2 in an AB SCIEX QTRAP® 5500 mass spectrometer from the company Applied Biosystems (Foster City, United States of America). Similarly, the duration of the collision step and the excitation energy within, for example, an ion trap will be optimised by the person skilled in the art to lead to the most sensitive assay. By way of example, it is possible to vary this duration, called excitation time, between 0.010 et 50 ms and the excitation energy between 0 and 1 (arbitrary unit) in Q3 in an AB SCIEX QTRAP® 5500 mass spectrometer by the company Applied Biosystems.

Finally, the detection of the selected characteristic ions takes place in the conventional manner, particularly by means of a detector and a processing system. The detector collects the ions and produces an electrical signal whose intensity depends on the amount of ions collected. The signal obtained is then amplified such that it can be processed by computer. A computer data processing assembly makes it possible to transform the information received by the mass spectrum detector.

The principle of the SRM mode, or even of the MRM mode, is to specifically select a precursor ion, fragment it, and then specifically select one of its fragment ions. For such applications, triple quadripole or hybrid triple quadripole/ion trap devices are generally used.

In the case of a triple quadripole device (Q1q2Q3) used in $MS^2$ mode, with a view to assaying or detecting a target protein, the first quadripole (Q1) makes it possible to filter the molecular ions corresponding to the proteotypic peptides characteristic of the protein to be assayed and obtained during an earlier digestion step, depending on their mass-to-charge ratio (m/z). Only the peptides having the mass-to-charge ratio of the proteotypic peptide sought, which ratio is called $(m/z)_1$, are transmitted into the second quadripole (q2) and act as precursor ions for the subsequent fragmentation. The analyser q2 can fragment the peptides of mass-to-charge ratio $(m/z)_1$ into first-generation fragment ions. Fragmentation is generally obtained through collision of the precursor peptides with an inert gas, such as nitrogen or argon in q2. The first-generation fragment ions are transmitted into a third quadripole (Q3) which filters the first-generation fragment ions depending on a specific mass-to-charge ratio, called $(m/z)_2$. Only the first-generation fragment ions having the mass-to-charge ratio of a fragment characteristic of the sought proteotypic peptide $(m/z)_2$ are transmitted into the detector in order to be detected, or even quantified.

This mode of operation exhibits a double selectivity, with regard to the selection of the precursor ion on the one hand, and the selection of the first-generation fragment ion on the other hand. Mass spectrometry in SRM or MRM mode is therefore advantageous for quantification.

When the mass spectrometry employed in the method according to invention is tandem mass spectrometry ($MS^2$, $MS^3$, $MS^4$ or $MS^5$), several mass analysers can be linked to one another. For example, a first analyser separates the ions, a collision cell makes it possible to fragment the ions, and a second analyser separates the fragment ions. Certain analysers, such as the ion traps or the FT-ICR, constitute several analysers in one and make it possible to fragment the ions and analyse the fragments directly.

According to preferred embodiments of the invention, the method of the invention comprises one or more of the following characteristics:

the mass spectrometry employed for the properties of potential resistance to at least one antimicrobial is MS/MS spectrometry, which has the advantage of producing a fragment which is specific to the molecule to be detected or quantified, and thus of providing great specificity to the assaying method;

the MS/MS spectrometry is MRM which has the advantage of using an analysis cycle time in the mass spectrometer of several tens of milliseconds, which makes it possible to detect or quantify, with a high degree of sensitivity, a large number of different molecules in a multiplexed manner;

where applicable, the determination of the type properties and of the virulence factor is performed in the same mass spectrometry apparatus as the determination of the markers of resistance to at least one antimicrobial, preferably simultaneously, which has the advantage of reducing the analysis time and the cost of the instrument, which also facilitates the processing and the yielding of the results.

In addition to determining the resistance to an antibiotic, it is necessary to identify the microorganism or microorganisms present in the sample to be tested.

The methods of identifying microorganisms are widely known to the person skilled in the art, as described for example by Murray P. R. et al. in Manual of Clinical Microbiology, 2007, $9^{th}$ edition, and especially in Vol. I, Section III, chapters 15 and 16 for bacteria and yeasts, Vol. II, Section VI, chapter 82 for viruses, and Vol. II, Section X, chapter 135 for protozoa. As an example of conventional identification methods, mention can be made of the determination of the biological profile, by using the Vitek 2 (bioMérieux) identification cards, for example, or even by using molecular biology techniques with identification criteria based on the study of the presence of certain genes, and on the study of their sequence.

Identification can be performed directly from the sample in which the identification is made, or the microorganisms contained in the sample can be cultured using methods well known to the person skilled in the art with optimal culture media and culturing conditions tailored to the species of microorganisms to be sought, as described by Murray P. R. et al. in Manual of Clinical Microbiology, 2007, $9^{th}$ edition, Vol. I, Section III, chapter 14, and in particular in Vol. I, Section IV, chapter 21 for bacteria, and Vol. II, Section VI, chapter 81 for viruses, Vol. II, Section VIII, chapter 117 for yeasts, and Vol. II, Section X, chapter 134 for protozoa.

Thus, generally, in the case of an identification using a biochemical method of a bacterium in a specimen, it is first necessary to obtain it in a pure culture, for example after seeding on agar. Molecular biology (PCR) can in certain cases be applied directly to the sample to be analysed.

Instead of cultivating the microorganisms, they can be concentrated by capture directly in the sample by means of active surfaces. Such a method was described by W.-J. Chen et al. [10] who captured different bacterial species with the aid of magnetic beads with an $Fe_3O_4/TiO_2$-activated surface.

Capture by other means is also possible, such as a capture by lectins [23], or by antibodies [24], or by Vancomycin [25]. The capture makes it possible to concentrate the microorganisms and thus to reduce or even eliminate the culture step. This results in a considerable time saving.

The identification may also be performed by mass spectrometry, in accordance with the techniques described previously, preferably by MS, by MS/MS, or even by MS followed by MS/MS spectrometry, which constitutes one embodiment of the invention. In this case too, the sample can be subjected to a culture step beforehand, such as seeding on agar.

The use of an MS identification method is advantageous in that it may be carried out in a few minutes, and in that it requires a mass spectrometer with a single analyser, i.e. a less complex instrument than a tandem mass spectrometer used in MS/MS.

The use of a method of identification by MS followed by MS/MS spectrometry is also advantageous. It makes it possible to check the identity of the ions observed by MS, which increases the specificity of the analysis.

The use of an MRM-type MS/MS identification method has the advantage of being more sensitive and simpler than the conventional MS followed by MS/MS approaches. This method requires neither a high-performance software to process the information between the acquisition of the MS spectrum and of the MS/MS spectrum, nor a change in the setting of the machine parameters for linking up MS then MS/MS spectra.

The method of identification by MS may be employed with an electrospray source on a raw sample, as described by S. Vaidyanathan et al. [26] or by R. Everley et al. [27] after chromatographic separation. Different m/z ranges thus make it possible to identify the microorganisms. S. Vaidyanathan et al. used a window of between 200 and 2000 Th, and R. Everley et al. used a window of between 620 and 2450 Th. The mass spectra may also be deconvoluted to access the mass of the proteins independently of their charge state. R. Everley et al. therefore used masses of between about 5,000 and 50,000 Da. Alternatively, the method of identification by MS can also be employed with the aid of a MALDI-TOF, as described by Claydon et al. [3] and T. Krishnamurthy and P. Ross [4]. The analysis combines acquisition of a mass spectrum and interpretation of expert software. It is extremely simple and can be carried out in a few minutes. This method of identification is currently becoming more widespread in medical analysis laboratories [28].

The identification of bacteria by MS followed by MS/MS via their proteins present in the sample has been applied widely by a number of teams. By way of example, mention can be made of the recent work of Manes N. et al. [29], who studied the peptidome of *Salmonella enterica*, or the work of R. Nandakumar et al. [30] or of L. Hernychova et al. [31] who have studied the proteome of bacteria after digestion of the proteins with trypsin. The conventional approach consists in i) acquiring an MS spectrum, ii) successively selecting each precursor ion observed on the MS spectrum with an intense signal, iii) successively fragmenting each precursor ion and acquiring its MS/MS spectrum, iv) interrogating protein databases such as SWISS-PROT or NCBI, through software such as Mascot (Matrix Science, London, United Kingdom) or SEQUEST (Thermo Scientific, Waltham, United States of America), to identify the peptide which has a strong probability of matching the MS/MS spectrum observed. This method may lead to the identification of a microorganism if a protein or a peptide characteristic of the species is identified.

One of the advantages of the use of mass spectrometry lies in that it is particularly useful for quantifying molecules, in the present case the markers of the mechanisms of bacterial resistance to beta-lactams. To this end, the current intensity detected is used, which is proportional to the quantity of target molecule. The current intensity thus measured may serve as a quantitative measurement making it possible to determine the quantity of target molecule present, which is characterised by its expression in International System (SI) mol/m$^3$ or kg/m$^3$ units, or by multiples or sub-multiples of these units, or by the usual derivatives of the SI units, including multiples or sub-multiples thereof. As a non-limiting example, the units such as ng/ml or fmol/l are units characterising a quantitative measurement.

A calibration is nevertheless necessary in order to be able to correlate the measured area of the peak, which corresponds to the current intensity induced by the detected ions, to the quantity of target molecule to be assayed. For this purpose, the calibrations conventionally used in mass spectrometry may be employed, within the framework of the invention. MRM assays are conventionally calibrated with the aid of external standards or, preferably, with the aid of internal standards such as described by T. Fortin et al. [13]. If the target molecule is a proteotypic peptide which permits the assaying of a protein of interest, the correlation between the quantitative measurement and the quantity of target proteotypic peptide, and subsequently of protein of interest, is obtained by calibrating the measured signal relative to a standard signal for which the quantity to be assayed is known. The calibration may be performed using a calibration curve, for example obtained by successive injections of standard proteotypic peptide at different concentrations (external calibration), or preferably by internal calibration using a heavy peptide as an internal standard, for example in accordance with the AQUA, QconCAT or PSAQ methods detailed below. "Heavy peptide" is understood to mean a peptide corresponding to the proteotypic peptide, but in which one or more atoms of carbon 12 ($^{12}$C) is (are) replaced by carbon 13 ($^{13}$C), and/or one or more atoms of nitrogen 14 ($^{14}$N) is (are) replaced by nitrogen 15 ($^{15}$N).

The use of heavy peptides as internal standards (AQUA) was also proposed in US patent application 2004/0229283. The principle is to artificially synthesise proteotypic peptides with amino acids containing isotopes which are heavier than the usual natural isotopes. Such amino acids are obtained, for example, by replacing some of the atoms of carbon 12 ($^{12}$C) with carbon 13 ($^{13}$C), or by replacing some of the atoms of nitrogen 14 ($^{14}$N) with nitrogen 15 ($^{15}$N). The artificial peptide (AQUA) thus synthesised has strictly the same physicochemical properties as the natural peptide (with the exception of a higher mass). It is generally added, at a given concentration, to the sample, upstream of assaying by mass spectroscopy, for example between the treatment entailing the cleaving of the proteins in the sample of interest and the fractionation of the peptides obtained after the treatment step. Thus, the AQUA peptide is co-purified with the natural peptide to be assayed, during fractionation of the peptides. The two peptides are therefore injected simultaneously into the mass spectrometer, for assaying. They then undergo the same ionisation yield in the source. The comparison of the peak areas of the natural and AQUA peptides, whose concentration is known, makes it possible to calculate the concentration of the natural peptide and thus the concentration of the protein to be assayed. A variation of the AQUA technique was proposed by J.-M. Pratt et al. [32] under the name QconCat. This variant is also described in patent application WO 2006/128492. It consists in concatenating various AQUA peptides and producing the artificial polypeptide in the form of a heavy recombinant protein. The recombinant protein is synthesised with amino acids comprising heavy isotopes. In this way, it is possible to obtain a standard to calibrate the simultaneous assay of several proteins at lower cost. The QconCAT standard is added from the start, upstream of the treatment entailing the cleaving of the proteins and prior to the steps of protein fractionation, denaturation, reduction and blocking of the protein thiol functions, if these are present. The QconCAT standard therefore undergoes the same treatment cycle entailing the cleaving of the proteins as the natural protein, which makes it possible to take account of the yield from the treatment step which entails the cleaving of the proteins. In fact, the treatment, particularly by digestion, of the natural protein may not be complete. In this case, the use of an AQUA standard would lead to underestimating the quantity of natural protein. For full assaying, it may therefore be important to take into account the yields from treatment which entails the cleaving of the proteins. However, V. Brun et al. [33] have shown that the QconQAT standards sometimes do not exactly reproduce the treatment yield particularly by digestion of the natural protein, undoubtedly due to a three-dimensional conformation different from the Qcon-CAT protein.

V. Brun et al. [33] then proposed the use of a method dubbed PSAQ, and described in patent application WO 2008/145763. In this case, the internal standard is a recombinant protein having the same sequence as the natural protein but synthesised with heavy amino acids. The synthesis is performed ex-vivo with heavy amino acids. This standard has strictly the same physicochemical properties as the natural protein (with the exception of a higher mass). It is added from the start, before the protein fractionation step, when the latter is present. It is therefore co-purified with the native protein, during the protein fractionation step. It exhibits the same treatment yield, particularly by digestion, as the native protein. The heavy peptide obtained after cleaving is also co-purified with the natural peptide, if a peptide fractionation step is performed. The two peptides are therefore injected simultaneously into the mass spectrometer, to be quantitatively assayed. They then undergo the same ionisation yields in the source. Comparison of the peak areas of the natural and the reference peptides in the PSAQ method makes it possible to calculate the concentration of the protein to be assayed taking into account all of the steps of the assay method.

All of these techniques, namely AQUA, QconCAT or PSAQ or any other calibration technique, used in the mass spectrometry assays and in particular in MRM or MS assays, may be employed to carry out calibration, within the framework of the invention.

Preferably, the mass spectrometry used in the detection method according to the invention is MS/MS. More preferably, the mass spectrometry is MRM.

The method of the invention makes it possible to detect resistances to carbapenems, characterised by the detection of at least one peptide as a resistance marker. Said resistance marker peptide preferably belongs to the proteins NDM, KPC, GES, IMP, IND, SME, VIM or OXA.

In particular, the detection of a mechanism of resistance to carbapenems induced by the expression of an NDM protein is characterised by the detection of at least one peptide belonging to an NDM protein and its different sequence variants SEQ ID No. 1 and SEQ ID No. 1078 to SEQ ID No. 1080.

SEQ ID No. 1:
MELPNIMHPVAKLSTALAAALMLSGCMPGEIRPTIGQQMETGDQRFGDLV

FRQLAPNVWQHTSYLDMPGFGAVASNGLIVRDGGRVLVVDTAWTDDQTAQ

ILNWIKQEINLPVALAVVTHAHQDKMGGMDALHAAGIATYANALSNQLAP

QEGMVAAQHSLTFAANGWVEPATAPNFGPLKVFYPGPGHTSDNITVGIDG

TDIAFGGCLIKDSKAKSLGNLGDADTEHYAASARAFGAAFPKASMIVMSH

SAPDSRAAITHTARMADKLR

SEQ ID No. 1078
MELPNIMHPVAKLSTALAAALMLSGCMAGEIRPTIGQQMETGDQRFGDLV

FRQLAPNVWQHTSYLDMPGFGAVASNGLIVRDGGRVLVVDTAWTDDQTAQ

ILNWIKQEINLPVALAVVTHAHQDKMGGMDALHAAGIATYANALSNQLAP

QEGMVAAQHSLTFAANGWVEPATAPNFGPLKVFYPGPGHTSDNITVGIDG

TDIAFGGCLIKDSKAKSLGNLGDADTEHYAASARAFGAAFPKASMIVMSH

SAPDSRAAITHTARMADKLR

SEQ ID No. 1079
MELPNIMHPVAKLSTALAAALMLSGCMPGEIRPTIGQQMETGDQRFGDLV

FRQLAPNVWQHTSYLDMPGFGAVASNGLIVRDGGRVLLVDTAWTDDQTAQ

ILNWIKQEINLPVALAVVTHAHQDKMGGMDALHAAGIATYANALSNQLAP

QEGLVAAQHSLTFAANGWVEPATAPNFGPLKVFYPGPGHTSDNITVGIDG

TDIAFGGCLIKDSKAKSLGNLGDADTEHYAASARAFGAAFPKASMIVMSH

SAPDSRAAITHTARMADKLR

SEQ ID No. 1080
MELPNIMHPVAKLSTALAAALMLSGCMPGEIRPTIGQQMETGDQRFGDLV

FRQLAPNVWQHTSYLDMPGFGAVASNGLIVRDGGRVLVVDTAWTDDQTAQ

ILNWIKQEINLPVALAVVTHAHQDKMGGMDALHAAGIATYANALSNQLAP

QEGMVAAQHSLTFAANGWVEPATAPNFGPLKVFYPGPGHTSDNITVGIDG

TDIAFGGCLIKDSKAKSLGNLGDADTEHYAASARAFGAAFPKASMIVMSH

SAPDSRAAITHTARMADKLR said peptides being chosen, preferably, from the peptides of sequence SEQ ID No. 2 to SEQ ID No. 9 and SEQ ID No. 1083 as defined hereafter:

| Peptide SEQ ID No. | Amino acid sequence | Position of the peptide in the NDM protein(s) |
|---|---|---|
| SEQ ID No. 2 | AAITHTAR | 257-264 for the proteins of SEQ No. 1, 1078, 1079, 1080 |
| SEQ ID No. 3 | AFGAAFPK | 235-242 for the proteins of SEQ No. 1, 1078, 1079, 1080 |

| Peptide SEQ ID No. | Amino acid sequence | Position of the peptide in the NDM protein(s) |
|---|---|---|
| SEQ ID No. 4 | ASMIVMSHSAPDSR | 243-256 for the proteins of SEQ No. 1, 1078, 1079, 1080 |
| SEQ ID No. 5 | FGDLVFR | 46-52 for the proteins of SEQ No. 1, 1078, 1079, 1080 |
| SEQ ID No. 6 | MELPNIMHPVAK | 1-12 for the proteins of SEQ No. 1, 1078, 1079, 1080 |
| SEQ ID No. 7 | QEINLPVALAVVTHAHQDK | 107-125 for the proteins of SEQ No. 1, 1078, 1079, 1080 |
| SEQ ID No. 8 | SLGNLGDADTEHYAASAR | 217-234 for the proteins of SEQ No. 1, 1078, 1079, 1080 |
| SEQ ID No. 9 | VLVVDTAWTDDQTAQILNWIK | 86-106 for the proteins of SEQ No. 1, 1078, 1080 |
| SEQ ID No. 1081 | LSTALAAALMLSGCMAGEIR | 13-32 for the protein of SEQ No. 1078 |
| SEQ ID No. 1082 | LSTALAAALMLSGCMPGEIR | 13-32 for the protein of SEQ No. 1, 1079, 1080 |
| SEQ ID No. 1083 | VLLVDTAWTDDQTAQILNWIK | 86-106 for the protein of SEQ No. 1079 |

Preferably, the resistance markers are NDM markers, chosen from the peptides of sequence SEQ ID No. 2, SEQ ID No. 3, SEQ ID No. 5, or SEQ ID No. 7.

The detection of a mechanism of resistance to carbapenems induced by the expression of a KPC protein is characterised by the detection of at least one peptide belonging to a KPC protein and to its different sequence variants SEQ ID No. 10 to SEQ ID No. 19 and SEQ ID No. 1084 to SEQ ID No. 1093.

SEQ ID No. 10:
MSLYRRLVLLSCLSWPLAGFSATALTNLVAEPFAKLEQDFGGSIGVYAMD

TGSGATVSYRAEERFPLCSSFKGFLAAAVLARSQQQAGLLDTPIRYGKNA

LVPWSPISEKYLTTGMTVAELSAAAVQYSDNAAANLLLKELGGPAGLTAF

MRSIGDTTFRLDRWELELNSAIPGDARDTSSPRAVTESLQKLTLGSALAA

PQRQQFVDWLKGNTTGNHRIRAAVPADWAVGDKTGTCGVYGTANDYAVVW

PTGRAPIVLAVYTRAPNKDDKHSEAVIAAAARLALEGLGVNGQ

SEQ ID No. 11:
MSLYRRLVLLSCLSWPLAGFSATALTNLVAEPFAKLEQDFGGSIGVYAMD

TGSGATVSYRAEERFPLCSSFKGFLAAAVLARSQQQAGLLDTPIRYGKNA

LVPWSPISEKYLTTGMTVAELSAAAVQYSDNAAANLLLKELGGPAGLTAF

MRSIGDTTFRLDRWELELNSAIPGDARDTSSPRAVTESLQKLTLGSALAA

PQRQQFVDWLKGNTTGNHRIRAAVPADWAVGDKTGTCGVYGTANDYAVVW

PTGRAPIVLAVYTRAPNKDDKYSEAVIAAAARLALEGLGVNGQ

SEQ ID No. 12:
MSLYRRLVLLSCLSWPLAGFSATALTNLVAEPFAKLEQDFGGSIGVYAMD

TGSGATVSYRAEERFPLCSSFKGFLAAAVLARSQQQAGLLDTPIRYGKNA

LVRWSPISEKYLTTGMTVAELSAAAVQYSDNAAANLLLKELGGPAGLTAF

MRSIGDTTFRLDRWELELNSAIPGDARDTSSPRAVTESLQKLTLGSALAA

PQRQQFVDWLKGNTTGNHRIRAAVPADWAVGDKTGTCGGYGTANDYAVVW

PTGRAPIVLAVYTRAPNKDDKHSEAVIAAAARLALEGLGVNGQ

SEQ ID No. 13:
MSLYRRLVLLSCLSWPLAGFSATALTNLVAEPFAKLEQDFGGSIGVYAMD

TGSGATVSYRAEERFPLCSSFKGFLAAAVLARSQQQAGLLDTPIRYGKNA

LVRWSPISEKYLTTGMTVAELSAAAVQYSDNAAANLLLKELGGPAGLTAF

MRSIGDTTFRLDRWELELNSAIPGDARDTSSPRAVTESLQKLTLGSALAA

PQRQQFVDWLKGNTTGNHRIRAAVPADWAVGDKTGTCGVYGTANDYAVVW

PTGRAPIVLAVYTRAPNKDDKHSEAVIAAAARLALEGLGVNGQ

SEQ ID No. 14:
MSLYRRLVLLSCLSWPLAGFSATALTNLVAEPFAKLEQDFGGSIGVYAMD

TGSGATVSYRAEERFPLCSSFKGFLAAAVLARSQQQAGLLDTPIRYGKNA

LVPWSPISEKYLTTGMTVAELSAAAVQYSDNAAANLLLKELGGPAGLTAF

MRSIGDTTFRLDRWELELNSAIPGDARDTSSPRAVTESLQKLTLGSALAA

PQRQQFVDWLKGNTTGNHRIRAAVPADWAVGDKTGTCGGYGTANDYAVVW

PTGRAPIVLAVYTRAPNKDDKHSEAVIAAAARLALEGLGVNGQ

SEQ ID No. 15:
MSLYRRLVLLSCLSWPLAGFSATALTNLVAEPFAKLEQDFGGSIGVYAID

TGSGATVSYRAEERFPLCSSFKGFLAAAVLARSQQQAGLLDTPIRYGKNA

LVPWSPISEKYLTTGMTVAELSAAAVQYSDNAAANLLLKELGGPAGLTAF

MRSIGDTTFRLDRWELELNSAIPGDARDTSSPRAVTESLQKLTLGSALAA

PQRQQFVDWLKGNTTGNHRIRAAVPADWAVGDKTGTCGVYGTANDYAVVW

PTGRAPIVLAVYTRAPNKDDKYSEAVIAAAARLALEGLGVNGQ

SEQ ID No. 16:
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGGYGTANDYAVVW
PTGRAPIVLAVYTRAPNKDDKYSEAVIAAAARLALEGLGVNGQ

SEQ ID No. 17:
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGAYGTANDYAVVW
PTGRAPIVLAVYTRAPNKDDKYSEAVIAAAARLALEGLG

SEQ ID No. 18:
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVRWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKYSEAVIAAAARLALEGLGVNGQ

SEQ ID No. 19:
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVLWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKHSEAVIAAAARLALEGLGVNGQ

SEQ ID No. 1084
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGGYGTANDYAVVW
PTGRAPIVLAVYTRAPNKDDKHSEAVIAAAARLALEGLGVNGQ

SEQ ID No. 1085
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGGYGTANDYAVVW
PTGRAPIVLAVYTRAPNKDDKYSEAVIAAAARLALEGLGVNGQ

SEQ ID No. 1086
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKHSEAVIAAAARLALEGLGVNGQ

SEQ ID No. 1087
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKYSEAVIAAAARLALEGLGVNGQ

SEQ ID No. 1088
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELELNSAIPSDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKHSEAVIAAAARLALEGLGVNGQ

SEQ ID No. 1089
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVPWSPISEKYLTTGMTVAELSAAAVQYSDNAAANLLLKELGGPAGLTAF
MRSIGDTTFRLDRWELEMNSAIPGDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKHSEAVIAAAARLALEGLGVNGQ

SEQ ID No. 1090
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVRWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKHSEAVIAAAARLALEGLGVNGQ

SEQ ID No. 1091
MSLYRRLVLLSCLSWPLAGFSATALTNLVAEPFAKLEQDFGGSIGVYAMD
TGSGATVSYRAEERFPLCSSFKGFLAAAVLARSQQQAGLLDTPIRYGKNA
LVRWSPISEKYLTTGMTVAELSAAAVQYSDNAAANLLLKELGGPAGLTAF
MRSIGDTTFRLDRWELELNSAIPGDARDTSSPRAVTESLQKLTLGSALAA
PQRQQFVDWLKGNTTGNHRIRAAVPADWAVGDKTGTCGVYGTANDYAVVW
PTGRAPIVLAVYTRAPNKDDKYSEAVIAAAARLALEGLGVNGQ

SEQ ID No. 1092
RLVLLSCLSWPLAGFSATALTNLVAEPFAKLEQDFGGSIGVYAMDTGSGA

TVSYRAEERFPLCSSFKGFLAAAVLARSQQQAGLLDTPIRYGKNALVPWS

PISEKYLTTGMTVAELSAAAVQYSDNAAANLLLKELGGPAGLTAFMRSIG

DTTFRLDRWELELNSAIPGDARDTSSPRAVTESLQKLTLGSALAAPQRQQ

FVDWLKGNTTGNHRIRAAVPADWAVGDKTGTCGAYGTANDYAVVWPTGRA

PIVLAVYTRAPNKDDKYSEAVIAAAARLALEGLG

SEQ ID No. 1093
SLYRRLVLLSCLSWPLAGFSATALTNLVAEPFAKLEQDFGGSIGVYAMDT

GSGATVSYRAEERFPLCSSFKGFLAAAVLARSQQQAGLLDTPIRYGKNAL

VRWSPISEKYLTTGMTVAELSAAAVQYSDNAAANLLLKELGGPAGLTAFM

RSIGDTTFRLDRWELELNSAIPGDARDTSSPRAVTESLQKLTLGSALAAP

QRQQFVDWLKGNTTGNHRIRAAVPADWAVGDKTGTCGGYGTANDYAVVWP

TGRAPIVLAVYTRAPNKDDKHSEAVIAAAARLALEGLGVNGQ said peptides being chosen, preferably, from the peptides of sequence SEQ ID No. 20 to SEQ ID No. 33 and SEQ ID No. 1094 to SEQ ID No. 1097 as defined hereafter:

| Peptide SEQ ID No. | Amino acid sequence | Position of the peptide in the KPC protein(s) |
|---|---|---|
| SEQ ID No. 20 | AAVPADWAVGDK | 221-232 for the protein of SEQ No. 1093; 222-233 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 21 | APIVLAVYTR | 254-263 for the protein of SEQ No. 1093; 255-264 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 22 | AVTESLQK | 183-190 for the protein of SEQ No. 1093; 184-191 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 23 | ELGGPAGLTAFMR | 139-151 for the protein of SEQ No. 1093; 140-152 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 24 | FPLCSSFK | 64-71 for the protein of SEQ No. 1093; 65-72 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 25 | GFLAAAVLAR | 72-81 for the protein of SEQ No. 1093; 73-82 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 26 | GNTTGNHR | 211-218 for the protein of SEQ No. 1093; 212-219 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 27 | LALEGLGVNGQ | 282-292 for the protein of SEQ No. 1093; 283-293 for the proteins of sequence SEQ ID No. 10, 11, 12, 13, 14, 15, 16, 18, 19, 1084, 1085, 1086, 1087, 1088, 1089, 1090, 1091 |
| SEQ ID No. 28 | LTLGSALAAPQR | 191-202 for the protein of SEQ No. 1093; 192-203 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 29 | NALVPWSPISEK | 94-105 for the protein of SEQ No. 1092; 99-110 for the proteins of sequence SEQ ID No. 10, 11, 14, 15, 16, 17, 1084, 1085, 1086, 1087, 1088, 1089 |
| SEQ ID No. 30 | QQFVDWLK | 203-210 for the protein of SEQ No. 1093; 204-211 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 31 | SIGDTTFR | 152-159 for the protein of SEQ No. 1093; 153-160 for the proteins of sequence SEQ ID No. 10, 11, 12, 13, 14, 15, 16, 17, 18, 19, 1084, 1085, 1086, 1087, 1088, 1089, 1090, 1091, 1092 |

| Peptide SEQ ID No. | Amino acid sequence | Position of the peptide in the KPC protein(s) |
|---|---|---|
| SEQ ID No. 32 | SQQQAGLLDTPIR | 82-94 for the protein of SEQ No. 1093; 83-95 for the proteins of sequence SEQ ID No. 10, 11, 12, 13, 14, 15, 16, 17, 18, 19, 1084, 1085, 1086, 1087, 1088, 1089, 1090, 1091, 1092 |
| SEQ ID No. 33 | WELELNSAIPGDAR | 163-176 for the protein of SEQ No. 1093; 164-177 for the proteins of sequence SEQ ID No. 10, 11, 12, 13, 14, 15, 16, 17, 18, 19, 1084, 1085, 1086, 1087, 1090, 1091, 1092 |
| SEQ ID No. 1094 | NALVR | 98-102 for the proteins of SEQ No. 1093; 99-103 for the proteins of sequence SEQ ID No. 12, 13, 18, 1090, 1091 |
| SEQ ID No. 1095 | TGTCGAYGTANDYAVVWPTGR | 229-249 for the protein of SEQ No. 1092; 234-254 for the protein of sequence SEQ ID No. 17 |
| SEQ ID No. 1096 | WELELNSAIPSDAR | 164-177 for the protein of SEQ No. 1088 |
| SEQ ID No. 1097 | WELEMNSAIPGDAR | 164-177 for the protein of SEQ No. 1089 |

Preferably, the resistance markers are KPC markers, chosen from the peptides of sequence SEQ ID No. 20, SEQ ID No. 21, SEQ ID No. 23, SEQ ID No. 25, SEQ ID No. 28, SEQ ID No. 29, SEQ ID No. 31, or SEQ ID No. 32.

The detection of a mechanism of resistance to carbapenems and/or to cephalosporins induced by the expression of a GES protein is characterised by the detection of at least one peptide belonging to a GES protein and to its different sequence variants SEQ ID No. 34 to SEQ ID No. 50.

SEQ ID No. 34:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 35:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVKWS

PATERFLASGHMTVLEAAQAAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 36:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQLAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 37:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKEPEMNDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 38:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKEPEMSDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 39:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVKWS

PATERFLASGHMTVLEAAQAAVQLSDNGATNLLLREIGGPAAMTQYFRKI

GDSVSRLDRKEPEMSDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 40:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

-continued

PATERFLASGHMTVLEAAQAAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGSRNDIGFFKAQERD

YAVAVYTTAPKLSAVERDELVASVGQVITQLILSTDK

SEQ ID No. 41:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGARNDIGFFKAQERD

YAVAVYTTAPKLSAVERDELVASVGQVITQLILSTDK

SEQ ID No. 42:
MRFIHALLLAGTAHSAYASEKLTFKTDLEKLEREKAAQIGVAIVDPQGEI

VAGHRTAQRFAMCSTFKFPLAALVFERIDSGTERGDRKLSYGPDMIVEWS

PATERFLASGHMTVLEAAQAAVQLCDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 43:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVKWS

PATERFLASGHMTVLEAAQAAVQLSDNGATNLLLREIGGPAAMTQYFRKI

GDSVSRLDRKEPEMNDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 44:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKESEMSDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 45:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKEPEMSDNTPGDLRDTTTPIAMARTVAKVLYGGALTSTSTH

TIERWLIGNQTGDATLRAGFPKDWVVGEKTGTCANGARNDIGFFKAQERD

YAVAVYTTAPKLSAVERDELVASVGQVITQLILSTDK

SEQ ID No. 46:
MRFIHALLLAGIAHSAYASEKLTFKTDLEKLEREKAAEIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKEPEMSDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 47:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVKWS

PATERFLASGHMTVLEAAQAAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGARNDIGFFKAQERD

YAVAVYTTAPKLSAVERDELVASVGQVITQLILSTDK

SEQ ID No. 48:
MRFIHALLLAGIAHSAYASEKLTFKTDLEKLEREKAAQIGVAIVDPQGEI

VAGHRTAQRFAMCSTFKFPLAALVFERIDSGTERGDRKLSYGPDMIVKWS

PATERFLASGHMTVLEAAQAAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 49:
MRFIHALLLAGIAHSAYASEKLTFKTDLEKLEREKAAQIGVAIVDPQGEI

VAGHRTAQRFAMCSTFKFPLAALVFERIDSGTERGDRKLSYGPDMIVKWS

PATERFLASGHMTVLEAAQAAVQLSDNGATNLLLREIGGPAAMTQYFRKI

GDSVSRLDRKEPEMSDNTPGDLRDTTTPIAMARTVAKVLYGGALTSTSTH

TIERWLIGNQTGDATLRAGFPKDWVVGEKTGTCANGGRNDIGFFKAQERD

YAVAVYTTAPKLSAVERDELVASVGQVITQLILSTDK

SEQ ID No. 50:
MRFIHALLLAGIAHSAYASEKLTFKTDLEKLEREKAAQIGVAIVDPQGEI

VAGHRMAQRFAMCSTFKFPLAALVFERIDSGTERGDRKLSYGPDMIVEWS

PATERFLASGHMTVLEAAQAAVQLSDNGATNLLLREIGGPAAMTQYFRKI

GDSVSRLDRKEPEMGDNTPGDLRDTTTPIAMARTVAKVLYGGALTSTSTH

TIERWLIGNQTGDATLRAGFPKDWVVGEKTGACANGARNDIGFFKAQERD

YAVAVYTTAPKLSAVERDELVASVGQVITQLILSTDK said peptides being chosen, preferably, from the peptides of sequence SEQ ID No. 51 to SEQ ID No. 79 as defined hereafter:

| Peptide SEQ ID No. | Amino acid sequence | Position of the peptide in the GES protein(s) | Clinical interest |
|---|---|---|---|
| SEQ ID No. 51 | AAEIGVAIVDPQGEIVAGHR | 36-55 for the protein of SEQ No. 46 | carba |

-continued

| Peptide SEQ ID No. | Amino acid sequence | Position of the peptide in the GES protein(s) | Clinical interest |
|---|---|---|---|
| SEQ ID No. 52 | AAQIGVAIVDPQGEIVAGHR | 36-55 for the proteins of SEQ No. 34, 35, 36, 37, 38, 39, 40, 41, 42, 43, 44, 45, 47, 48, 49, 50 | ESBL |
| SEQ ID No. 53 | AGFPK | 218-222 for the proteins of SEQ No. 34, 35, 36, 37, 38, 39, 40, 41, 42, 43, 44, 45, 46, 47, 48, 49, 50 | ESBL |
| SEQ ID No. 54 | DTTTPIAMAR | 174-183 for the proteins of SEQ No. 34, 35, 36, 37, 38, 39, 40, 41, 42, 43, 44, 45, 46, 47, 48, 49, 50 | ESBL |
| SEQ ID No. 55 | DWVVGEK | 223-229 for the proteins of SEQ No. 34, 35, 36, 37, 38, 39, 40, 41, 42, 43, 44, 45, 46, 47, 48, 49, 50 | ESBL |
| SEQ ID No. 56 | DYAVAVYTTAPK | 250-261 for the proteins of SEQ No. 34, 35, 36, 37, 38, 39, 40, 41, 42, 43, 44, 45, 46, 47, 48, 49, 50 | ESBL |
| SEQ ID No. 57 | EIGGPAAMTQYFR | 136-148 for the proteins of SEQ No. 34, 35, 36, 37, 38, 39, 40, 41, 42, 43, 44, 45, 46, 47, 48, 49, 50 | ESBL |
| SEQ ID No. 58 | EPEMGDNTPGDLR | 161-173 for the proteins of SEQ No. 34, 35, 36, 40, 41, 42, 47, 48, 50 | ESBL |
| SEQ ID No. 59 | EPEMNDNTPGDLR | 161-173 for the proteins of SEQ No. 37, 43 | carba |
| SEQ ID No. 60 | EPEMSDNTPGDLR | 161-173 for the proteins of SEQ No. 38, 39, 45, 46, 49 | carba |
| SEQ ID No. 61 | ESEMSDNTPGDLR | 161-173 for the protein of SEQ No. 44 | carba |
| SEQ ID No. 62 | FAMCSTFK | 60-67 for the proteins of SEQ No. 34, 35, 36, 37, 38, 39, 40, 41, 42, 43, 44, 45, 46, 47, 48, 49, 50 | ESBL |
| SEQ ID No. 63 | FIHALLLAGTAHSAYASEK | 3-21 for the proteins of SEQ No. 34, 35, 36, 37, 38, 39, 40, 41, 43, 44, 45, 46, 47, 48, 49, 50 | ESBL |
| SEQ ID No. 64 | FIHALLLAGTAHSAYASEK | 3-21 for the protein of SEQ No. 42 | carba |
| SEQ ID No. 65 | FPLAALVFER | 68-77 for the proteins of SEQ No. 34, 35, 36, 37, 38, 39, 40, 41, 42, 43, 44, 45, 46, 47, 48, 49, 50 | ESBL |
| SEQ ID No. 66 | IDSGTER | 78-84 for the proteins of SEQ No. 34, 35, 36, 37, 38, 39, 40, 41, 42, 43, 44, 45, 46, 47, 48, 49, 50 | ESBL |
| SEQ ID No. 67 | IGDSVSR | 150-156 for the proteins of SEQ No. 34, 35, 36, 37, 38, 39, 40, 41, 42, 43, 44, 45, 46, 47, 48, 49, 50 | ESBL |
| SEQ ID No. 68 | LSAVER | 262-267 for the proteins of SEQ No. 34, 35, 36, 37, 38, 39, 40, 41, 42, 43, 44, 45, 46, 47, 48, 49, 50 | ESBL |
| SEQ ID No. 69 | LSYGPDMIVEWSPATER | 89-105 for the proteins of SEQ No. 34, 36, 37, 38, 40, 41, 42, 44, 45, 46, 50 | ESBL |
| SEQ ID No. 70 | LSYGPDMIVK | 89-98 for the proteins of SEQ No. 35, 39, 43, 47, 48, 49 | carba |
| SEQ ID No. 71 | NDIGFEK | 239-245 for the proteins of SEQ No. 34, 35, 36, 37, 38, 39, 40, 41, 42, 43, 44, 45, 46, 47, 48, 49, 50 | ESBL |
| SEQ ID No. 72 | TDLEK | 26-30 for the proteins of SEQ No. 34, 35, 36, 37, 38, 39, 40, 41, 42, 43, 44, 45, 46, 47, 48, 49, 50 | ESBL |
| SEQ ID No. 73 | TGACANGAR | 230-238 for the protein of SEQ No. 50 | carba |
| SEQ ID No. 74 | TGTCANGAR | 230-238 for the proteins of SEQ No. 41, 45, 47 | carba |
| SEQ ID No. 75 | TGTCANGGR | 230-238 for the proteins of SEQ No. 34, 35, 36, 37, 38, 39, 42, 43, 44, 46, 48, 49 | ESBL |
| SEQ ID No. 76 | TGTCANGSR | 230-238 for the protein of SEQ No. 40 | carba |

| Peptide SEQ ID No. | Amino acid sequence | Position of the peptide in the GES protein(s) | Clinical interest |
|---|---|---|---|
| SEQ ID No. 77 | VLYGGALTSTSTHTIER | 188-204 for the proteins of SEQ No. 34, 35, 36, 37, 38, 39, 40, 41, 42, 43, 44, 45, 46, 47, 48, 49, 50 | ESBL |
| SEQ ID No. 78 | WLIGNQTGDATLR | 205-217 for the proteins of SEQ No. 34, 35, 36, 37, 38, 39, 40, 41, 42, 43, 44, 45, 46, 47, 48, 49, 50 | ESBL |
| SEQ ID No. 79 | WSPATER | 99-105 for the proteins of SEQ No. 34, 35, 36, 37, 38, 39, 40, 41, 42, 43, 44, 45, 46, 47, 48, 49, 50 | carba |

In the clinical interest column, the ESBL and carba entries correspond to the GES beta-lactamase activities which the corresponding peptide makes it possible to detect. Therefore, the detection of a carba peptide will indicate the presence of a carbapenemase beta-lactamase capable of hydrolysing carbapenems.

If no peptide referred to as carba is detected, the detection of a peptide referred to as ESBL will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The detection of a mechanism of resistance to carbapenems induced by a GES protein is thus characterised by the detection of at least one resistance-marking carba peptide chosen from the sequences SEQ ID No. 51, 59, 60, 61, 64, 70, 73, 74, 76, 79.

The detection of a mechanism of resistance to carbapenems induced by the expression of an IMP protein is characterised by the detection of at least one peptide belonging to an IMP protein and to its different sequence variants SEQ ID No. 80 to SEQ ID No. 105.

SEQ ID No. 80:
MSKLSVFFIFLFCSIATAAESLPDLKIEKLDEGVYVHTSFEEVNGVVGVV

PKHGLVVLVNAEAYLIDTPFTAKDTEKLVTWFVERGYKIKGSISSHFHSD

STGGIEWLNSRSIPTYASELTNELLKKDGKVQATNSFSGVNYWLVKNKIE

VFYPGPGHTPDNVVVWLPERKILFGGCFIKPYGLGNLGDANIEAWPKSAK

LLKSKYGKAKLWPSHSEVGDASLLKLTLEQAVKGLNESKKPSKPSN

SEQ ID No. 81:
MKKLSVFFMFLFCSIAASGEALPDLKIEKLDEGVYVHTSFEEVNGWGWPK

HGLVVLVNTDAYLIDTPFTAKDTEKLVTVVFVERGYKIKGSISSHFHSDS

TGGIEWLNSOSIPTYASELTNELLKKDGKVQAKNSFSGASYVVLVKKKIE

IFYPGPGHTPDNVVVWLPEHRVLFGGCFVKPYGLGNLGDANLEAWPKSAK

LLVSKYGKAKLVVPSHSEVGDASLLKRTLEQAVKGLNESKKLSKPSN

SEQ ID No. 82:
MSKLSVFFIFLFCSIATAAEPLPDLKIEKLDEGVYVHTSFEEVNGWGVVP

KHGLVVLVDAEAYLIDTPFTAKDTEKLVTWFVERGYKIKGSISSHFHSDS

TGGIEWLNSQSIPTYASELTNELLKKDGKVQAKNSFGGVNYVVLVKNKIE

VFYPGPGHTPDNLVWLPERKILFGGCFIKPYGLGNLGDANLEAWPKSAK

LLISKYGKAKLVVPSHSEAGDASLLKLTLEQAVKGLNESKKPSKLSN

SEQ ID No. 83:
MKKLFVLCVCFLCSITAAGAALPDLKIEKLEEGVYVHTSFEEVNGWGVVS

KHGLVVLVNTDAYLIDTPFTATDTEKLVNWFVERGYKIKGTISSHFHSDS

TGGIEWLNSQSIPTYASELTNELLKKDGKVQAKNSFSGVSYWLVKNKIEV

FYPGPGHTQDNVVVVVLPEKKILFGGCFVKPDGLGNLGDANLEAWPKSAK

ILMSKYGKAKLVVSSHSEIGDASLLKRTWEQAVKGLNESKKPSQPSN

SEQ ID No. 84:
MSKLFVFFMFLFCSITAAAESLPDLKIEKLDEGVYVHTSFEEVNGWGWPK

HGLVVLVNTEAYLIDTPFTAKDTEKLVTWFVERGYKIKGSISSHFHSDST

GGIEWLNSQSIPTYASELTNELLKKDGKVQAKNSFSGASYVVLVKKKIEV

FYPGPGHTPDNVVVWLPENRVLFGGCFVKPYGLGNLGDANVEAWPKSAKL

LMSKYGKAKLVVPSHSEVGDASLLKRTLEQAVKGLNESKKPSKPSN

SEQ ID No. 85:
MSKLFVFFMFLFCSITAAGESLPDLKIEKLDEGVYVHTSFEEVNGWGVIP

KHGLVVLVNTDAYLIDTPFTAKDTENLVNWFVERGYRIKGSISSHFHSDS

TGGIEWLNSQSIPTYASELTNELLKKDGKVQAKYSFSGVSYVVLVKKKIE

VFYPGPGHAPDNVVVWLPENRVLFGGCFVKPYGLGNLGDANLEAWPKSAK

LLMSKYSKAKLWPSHSDIGDSSLLKLTVVEQTVKGFNESKKSTTAH

SEQ ID No. 86:
MKKLFVLCVFFFCNIAVAEEESLPDLKIEKLEEGVYVHTSFEEVKGWSVVT

KHGLVVLVKNDAYLIDTPITAKDTEKLVNWFVERGYKIKGSISTHFHGDS

TAGIEVVLNSQSIPTYASELTNELLKKDNKVQAKHSFNGVSYSLIKNKIE

VFYPGPGHTQDNVVVWLPEKKILFGGCFVKPDGLGYLGDANLEAINPKSA

KILMSKYGKAKLVVSSHSDIGDVSLLKRTVVEQAVKGLNESKKSSQPSD

SEQ ID No. 87:
MNKLSVFFMFMFCSITAAGESLPDLKIEKLDEGVYVHTSFEEVNGVVGVV

PKHGLVVLVNTEAYLIDTPFTAKDTEKLVTINFVERGYKIKGSISSHFHS

DSTGGIEWLNSQSIPTYASELTNELLKKDGKVQAKNSFSGGSYINLVNNK

IEVFYPGPGHTPDNVVVVVLPENRVLFGGCFVKPYGLGNLGDANLEAWPK

SAKILMSKYGKAKLVVSSHSETGNASLLKLTWEQAVKGLKESKKPSLPSN

SEQ ID No. 88:
MKKLFVLCVFFLCNIAAADDSLPDLKIEKLEKGVYVHTSFEEVKGWGVVT

KHGLVVLVKNDAYLIDTPITAKDTEKLVNINFIEHGYRIKGSISTHFHGD

STAGIEWLNSQSISTYASELTNELLKKDNKVQATNSFSGVSYSLIKNKIE

SEQ ID No. 88 (continued):
VFYPGPGHTQDNVVVVLPEKKILFGGCFVKPDGLGNLGDANLEAWPKSA
KILMSKYGKAKLVVSSHSEIGNASLLQRTVVEQAVKGLNESKKPLQPSS SEQ ID No. 89:
MKKLFVLCVFLFCSITAAGESLPDLKIEKLEEGVYVHTSFEEVNGWGVVS
KHGLVILVNTDAYLIDTPFTAKDTEKLVTVVFVERGYKIKGSISSHFHSD
STGGIEWLNSQSIPTYASELTNDLLKQNGKVQAKNSFSGVSYVVLVKNKI
EVFYPGPGHTQDNVVVINLPEKKILFGGCFVKPYGLGNLDDANVVAWPHS
AEILMSRYGNAKLVVPSHSDIGDASLLKLTWEQAVKGLKESKKPSEPSN SEQ ID No. 90:
MSKLSVFFIFLFCSIATAAESLPDLKIEKLDEGVYVHTSFKEVNGWGVVP
KHGLVVLVNAEAYLIDTPFTAKDTEKLVTVVFVERGYKIKGSISSHFHSD
STGGIEWLNSRSIPTYASELTNELLKKDGKVQATNSFSGVNYVVLVKNKI
EVFYPGPGHTPDNVWVVLPERKILFGGCFIKPYGLGNLGDANIEAWPKSA
KLLKSKYGKAKLVVPSHSEVGDASLLKLTLEQAVKGLNESKKPSKPSN SEQ ID No. 91:
MKKLFVLCVCFLCSITAAGAALPDLKIEKLEEGVYVHTSFEEVNGWGVVS
KHGLVVLVNTDAYLIDTPFTATDTEKLVNWFVERGYKIKGTISSHFHSDS
TGGIEWLNSQSIPTYASELTNELLKKDGKVQAKNSFSGVSYVVLVKNKIE
VFYPGPGHTQDNVVVWLPEKKILFGGCFVKPDGLGNLGDANLEAWPKSAK
ILMSKYVKAKLVVSSHSEIGDASLLKRTWEQAVKGLNESKKPSQPSN SEQ ID No. 92:
MKKLFVLCVCFLCSITAAGAALPDLKIEKLEEGVYVHTSFEEVNGWGWSK
HGLVVLVNTDAYLIDTPFTATDTEKLVNWFVERGYKIKGTISSHFHSDST
GGIEWLNSQSIPTYASELTNELLKKDGKVQAKNSFSGVSYWLVKNKIEVF
YPGPGHTQDNVVVWLPEKKILFGGCFVKPDGLGNLGDANLEAWPKSAKIL
MSKYGKAKLVVSSHSEIGDASLLKRTWEQAVKGLNESRKPSQPSN SEQ ID No. 93:
MSKLSVFFIFLFCSIATAAESLPDLKIEKLDEGVYVHTSFEEVNGWGVVP
KHGLVVLVNAEAYLIDTPFTAKDTEKLVTVVFVERGYKIKGSISSHFHSD
STGGIEWLNSRSIPTYASELTNELLKKDGKVQATNSFSGVNYVVLVKNKI
EVFYPGPGHTPDNVVVWLPERKILFGGCF1KPYGLGNLSDANIEAWPKSA
KLLKSKYGKAKLVVPGHSEVGDASLLKLTLEQAVKGLNESKKPSKPSN SEQ ID No. 94:
MSKLSVFFIFLFCSIATAAEPLPDLKIEKLDEGVYVHTSFEEVNGWGVFP
KHGLVVLVDAEAYLIDTPFTAKDTEKLVIVVFVERGYKIKGSISSHFHSD
STGGIEWLNSQSIPTYASELTNELLKKDGKVQAKNSFGGVNYWLVKNKIE
VFYPGPGHTPDNLVVVLPERKILFGGCFIKPYGLGNLGDANLEAWPKSA
KLLISKYGKAKLVVPSHSEAGDASLLKLTLEQAVKGLNESKKPSKLSN SEQ ID No. 95:
MKKLFVLCVFVFCSITVAGETLPNLRVEKLEEGVYVHTSYEEVNGKGWVVT
KHGLVVLIGADAYLIDTPFTAKDTEKLVNWFVERGYKIKGTVSSHFHSDS
TGGIEWLNSQSIPTYASELTNELLKKDGKVQAKNSFDGVSYVVLAKDKIE
VFYPGPGHTQDNVVVWLPEKEILFGGCFVKPHGLGNLGDANLEAWPESAK
ILMEKYGKAKLVVSGHSETGDATHLKRTWEQAVKGLKESKKTLQPSN SEQ ID No. 96:
MSKLSVFFIFLFCSIATAAESLPDLKIEKLDEGVYVHTSFEEVNGWGVVP
KHGLVVLVNAEAYLIDTPFTAKDTEKLVTWFVERGYKIKGSISSHFHSDS
TGGIGWLNSRSIPTYASELTNELLKKDGKVQATNSFSGVNYWLVKNKIEV
FYPGPGHTPDNVVVWLPERKILFGGCFIKPYGLGNLGDANIEAWPKSAKL
LKSKYGKAKLVVPGHSEVGDASLLKLTLEQAVKGLNESKKPSKPSN SEQ ID No. 97:
MSKLSVFFIFLFCSIATAAESLPDLKIEKLDEGVYVHTSFEEVNGWGVVP
KHGLVVLVNAEAYLIDTPFTAKDTEKLVIWFVERGYKIKGSISSHFHSDS
TGGIEWLNSRSIPTYASELTNELLKKDGKVQATNSFSGVNYWLVKNKIEV
FYPGPGHTPDNVVVVLPERKILFGGCFIKPYGLGNLGDANIEAWPKSAK
LLKSKYGKAKLVVPGHSEVGDASLLKLTLEQAVKGLNESKKPSKPSN SEQ ID No. 98:
MSKLSVFFIFLFCSIATAAESLPDLKIEKLDEGVYVHTSFEEVNGWGVFP
KHGLVVLVNAEAYLIDTPFTAKDTEKLVTVVFVERGYKIKGSISSHFHSD
STGGIEWLNSRSIPTYASELTNELLKKDGKVQATNSFSGVNYVVLVKNKI
EVFYPGPGHTPDNVVINVLPERKILFGGCFIKPYGLGNLGDANIEAWPKS
AKLLKSKYGKAKLVVPSHSEVGDASLLKLTLEQAVKGLNESKKPSKPSN SEQ ID No. 99:
MKKLFVLCIFLFCSITAAGASLPDLKIEKLEEGVYVHTSFEEVNGWGVVS
KHGLVVLVNTDAYLIDTPFTAKDTEKLVNWFVERGYKIKGSISSHFHSDS
TGGIEWLNSQSIPTYASVLTNELLKKDGKVQAKNSFSGVSYWLVKNKIEV
FYPGPGHTQDNVVVWLPKNKILFGGCFVKPYGLGNLDDANVEAWPHSAEK
LISKYGNAKLVVPSHSDIGDASLLKLIVVEQAVKGLNESKKSNTVH SEQ ID No. 100:
MKKLFVLCVCFLCSITAAGAALPDLKIEKLEEGVYVHTSFEEVNGWGVFS
KHGLVVLVNTDAYLIDTPFTATDTEKLVNWFVERGYKIKGTISSHFHSDS
TGGIEINLNSQSIPTYASELTNELLKKDGKVQAKNSFSGVSYVVLVKNKI
EVFYPGPGHTQDNVVVVLPEKKILFGGCFVKPDGLGNLGDANLEAVVPK
SAKILMSKYVKAKLVVSSHSEIGDASLLKRTVVEQAVKGLNESKKPSQPS
N SEQ ID No. 101:
MKKLFVLCIFLFCSITAAGASLPDLKIEKLEEGVYVHTSFEEVNGVVGVA
SKHGLVVLVNTDAYLIDTPFTAKDTEKLVNVVFVERGYKIKGSISSHFHS
DSTGGIEWLNSQSIPTYASVLTNELLKKDGKVQAKNSFSGVSYVVLVKNK
IEVFYPGPGHTQDNVVVVVLPKNILFGGCFVKPYGLGNLDDANVEAINP
HSAEKLISKYGNAKLVVPSHSDIGDASLLKLTVVEQAVKGLNESKKSNTV
H SEQ ID No. 102:
MKKLFVLCVCFLCSITAAGARLPDLKIEKLEEGVYVHTSFEEVNGVVGVV
SKHGLVVLVNTDAYLIDTPFTATDTEKLVNWFVERGYKIKGTISSHFHSD
STGGIEWLNSQSIPTYASELTNELLKKDGKVQAKNSFSGVSYVVLVKNKI
EVFYPGPGHTQDNVVVWLPEKKILFGGCFVKPDGLGNLGDANLEAVVPKS
AKILMSKYVKAKLVVSSHSEIGDASLLKRTVVEQAVKGLNESKKPSQPSN SEQ ID No. 103:
MKKLFVLCIFLFLSITASGEVLPDLKIEKLEEGVYLHTSFEEVSGINGVV

TKHGLVVLVNNDAYLIDTPFTNKDTEKLVAWFVGRGFTIKGSVSSHFHSD

STGGIEWLNSQSIPTYASELTNELLKKNGKVQATNSFSGVSYWLVKNKIE

IFYPGPGHTQDNVVVVVLPENKILFGGCFVKPDGLGNLDDANLKAWPKSA

KILMSKYGKAKLWSGHSEIGNASLLKLTWEQAVKGLKESKKPLLPSN

SEQ ID No. 104:
MKKLFVLCVCFFCSITAAGAALPDLKIEKLEEGVFVHTSFEEVNGWGVVT

KHGLWLVNTDAYLIDTPFTATDTEKLVNWFVERGYEIKGTISSHFHSDST

GGIEWLNSQSIPTYASELTNELLKKSGKVQAKYSFSEVSYVVLVKNKIEV

FYPGPGHTQDNLVVVVLPESKILFGGCFIKPHGLGNLGDANLEAWPKSAK

ILMSKYGKAKLVVSSHSEKGDASLMKRTWEQALKGLKESKKTSSPSN

SEQ ID No. 105:
MKKLFVLCIFLFCSITAAGESLPDLKIEKLEDGVYVHTSFEEVNGWGVVT

KHGLVFLVNTDAYLIDTPFAAKDTEKLVNWFVERGYKIKGSISSHFHSDS

SGGIEWLNSQSIPTYASELTNELLKKNGKVQAKNSFSGVSYWLLKNKIEI

FYPGPGHTQDNVVVWLPEKKILFGGCFVKPYGLGNLDDANVEAWPHSAEI

LMSRYGNAKLVVPSHSDVGDASLLKLTANEQAVKGLKESKKPSQPSN said peptides being chosen, preferably, from the peptides of sequence SEQ ID No. 106, SEQ ID No. 108 to SEQ ID No. 130, SEQ ID No. 133 to SEQ ID No. 173, SEQ ID No. 175 to SEQ ID No. 180, as defined hereafter:

| Peptide SEQ ID No. | Amino acid sequence | Position of the peptide in the IMP protein(s) |
|---|---|---|
| SEQ ID No. 106 | DTENLVNWFVER | 73-84 for the protein of SEQ No. 85 |
| SEQ ID No. 107 | EILFGGCFVK | 170-179 for the protein of SEQ No. 95 |
| SEQ ID No. 108 | EVNGWGVVPK | 42-51 for the proteins of SEQ No. 80, 81, 82, 84, 87, 90, 93, 96, 97 |
| SEQ ID No. 109 | GDASLMK | 219-225 for the protein of SEQ No. 104 |
| SEQ ID No. 110 | GFNESK | 234-239 for the protein of SEQ No. 85 |
| SEQ ID No. 111 | GFTIK | 85-89 for the protein of SEQ No. 103 |
| SEQ ID No. 112 | GLNESK | 234-239 for the proteins of SEQ No. 80, 81, 82, 83, 84, 86, 88, 90, 91, 93, 94, 96, 97, 98, 99, 100, 101, 102 |
| SEQ ID No. 113 | GLNESR | 234-239 for the protein of SEQ No. 92 |
| SEQ ID No. 114 | GSISSHFHSDSTGGIEWLNSR | 90-110 for the proteins of SEQ No. 80, 90, 93, 97, 98 |
| SEQ ID No. 115 | GSISSHFHSDSTGGIGWLNSR | 90-110 for the protein of SEQ No. 96 |
| SEQ ID No. 116 | GVYVHTSFEEVK | 33-44 for the proteins of SEQ No. 86, 88 |
| SEQ ID No. 117 | GWGVVTK | 45-51 for the proteins of SEQ No. 88, 95, 103, 104, 105 |
| SEQ ID No. 118 | GWSVVTK | 45-51 for the protein of SEQ No. 86 |
| SEQ ID No. 119 | GYEIK | 85-89 for the protein of SEQ No. 104 |
| SEQ ID No. 120 | HGLVFLVNTDAYLIDTPFAAK | 52-72 for the protein of SEQ No. 105 |
| SEQ ID No. 121 | HGLVILVNTDAYLIDTPFTAK | 52-72 for the protein of SEQ No. 89 |
| SEQ ID No. 122 | HGLVVLIGADAYLIDTPFTAK | 52-72 for the protein of SEQ No. 95 |
| SEQ ID No. 123 | HGLVVLVDAEAYLIDTPFTAK | 52-72 for the proteins of SEQ No. 82, 94 |

-continued

| Peptide SEQ ID No. | Amino acid sequence | Position of the peptide in the IMP protein(s) |
|---|---|---|
| SEQ ID No. 124 | HGLVVLVK | 52-59 for the proteins of SEQ No. 86, 88 |
| SEQ ID No. 125 | HGLVVLVNAEAYLIDTPFTAK | 52-72 for the proteins of SEQ No. 80, 90, 93, 96, 97, 98 |
| SEQ ID No. 126 | HGLVVLVNNDAYLIDTPFTNK | 52-72 for the protein of SEQ No. 103 |
| SEQ ID No. 127 | HGLVVLVNTDAYLIDTPFTAK | 52-72 for the proteins of SEQ No. 81, 85, 99, 101 |
| SEQ ID No. 128 | HGLVVLVNTEAYLIDTPFTAK | 52-72 for the proteins of SEQ No. 84, 87 |
| SEQ ID No. 129 | HSFNGVSYSLIK | 134-145 for the protein of SEQ No. 86 |
| SEQ ID No. 130 | IEVFYPGPGHTQDNVVVWLPK | 148-168 for the proteins of SEQ No. 99, 101 |
| SEQ ID No. 131 | ILFGGCFIK | 171-179 for the proteins of SEQ No. 80, 82, 90, 93, 94, 96, 97, 98, 104 |
| SEQ ID No. 132 | ILFGGCFVK | 171-179 for the proteins of SEQ No. 83, 86, 88, 89, 91, 92, 95, 99, 100, 101, 102, 103, 105 |
| SEQ ID No. 133 | ILMEK | 200-204 for the protein of SEQ No. 95 |
| SEQ ID No. 134 | ILMSK | 200-204 for the proteins of SEQ No. 83, 86, 87, 88, 91, 92, 100, 102, 103, 104 |
| SEQ ID No. 135 | LDEGVYVHTSFK | 30-41 for the protein of SEQ No. 90 |
| SEQ ID No. 136 | LEEGVYVHTSFEEVK | 30-44 for the protein of SEQ No. 86 |
| SEQ ID No. 137 | LEEGVYVHTSYEEVK | 30-44 for the protein of SEQ No. 95 |
| SEQ ID No. 138 | LFVLCVCFLCSITAAGAR | 4-21 for the protein of SEQ No. 102 |
| SEQ ID No. 139 | LLISK | 200-204 for the proteins of SEQ No. 82, 94 |
| SEQ ID No. 140 | LLMSK | 200-204 for the proteins of SEQ No. 84, 85 |
| SEQ ID No. 141 | LLVSK | 200-204 for the protein of SEQ No. 81 |
| SEQ ID No. 142 | LPDLK | 22-26 for the proteins of SEQ No. 80, 81, 82, 83, 84, 85, 86, 87, 88, 89, 90, 91, 92, 93, 94, 96, 97, 98, 99, 100, 101, 102, 103, 104, 105 |
| SEQ ID No. 143 | LTLEQAVK | 226-233 for the proteins of SEQ No. 80, 82, 90, 93, 94, 96, 97, 98 |
| SEQ ID No. 144 | LTWEQAVK | 226-233 for the proteins of SEQ No. 87, 89, 99, 101, 103, 105 |
| SEQ ID No. 145 | LTWEQTVK | 226-233 for the protein of SEQ No. 85 |
| SEQ ID No. 146 | LVAWFVGR | 77-84 for the protein of SEQ No. 103 |
| SEQ ID No. 147 | LVNWFIEHGYR | 77-87 for the protein of SEQ No. 88 |

-continued

| Peptide SEQ ID No. | Amino acid sequence | Position of the peptide in the IMP protein(s) |
|---|---|---|
| SEQ ID No. 148 | LVNWFVER | 77-84 for the proteins of SEQ No. 83, 85, 86, 91, 92, 95, 99, 100, 101, 102, 104, 105 |
| SEQ ID No. 149 | LVTWFVER | 77-84 for the proteins of SEQ No. 80, 81, 82, 84, 87, 89, 90, 93, 94, 96, 97, 98 |
| SEQ ID No. 150 | LVVPGHSEVGDASLLK | 210-225 for the proteins of SEQ No. 93, 96, 97 |
| SEQ ID No. 151 | LVVPSHSDIGDASLLK | 210-225 for the proteins of SEQ No. 89, 99, 101 |
| SEQ ID No. 152 | LVVPSHSDIGDSSLLK | 210-225 for the protein of SEQ No. 85 |
| SEQ ID No. 153 | LVVPSHSDVGDASLLK | 210-225 for the protein of SEQ No. 105 |
| SEQ ID No. 154 | LVVPSHSEAGDASLLK | 210-225 for the proteins of SEQ No. 82, 94 |
| SEQ ID No. 155 | LVVPSHSEVGDASLLK | 210-225 for the proteins of SEQ No. 80, 81, 84, 90, 98 |
| SEQ ID No. 156 | LVVSGHSEIGNASLLK | 210-225 for the protein of SEQ No. 103 |
| SEQ ID No. 157 | LVVSGHSETGDATHLK | 210-225 for the protein of SEQ No. 95 |
| SEQ ID No. 158 | LVVSSHSDIGDVSLLK | 210-225 for the protein of SEQ No. 86 |
| SEQ ID No. 159 | LVVSSHSEIGDASLLK | 210-225 for the proteins of SEQ No. 83, 91, 92, 100, 102 |
| SEQ ID No. 160 | LVVSSHSEIGNASLLQR | 210-226 for the protein of SEQ No. 88 |
| SEQ ID No. 161 | LVVSSHSEK | 210-218 for the protein of SEQ No. 104 |
| SEQ ID No. 162 | LVVSSHSETGNASLLK | 210-225 for the protein of SEQ No. 87 |
| SEQ ID No. 163 | NDAYLIDTPITAK | 60-72 for the proteins of SEQ No. 86, 88 |
| SEQ ID No. 164 | NSFDGVSYWLAK | 134-145 for the protein of SEQ No. 95 |
| SEQ ID No. 165 | NSFGGVNYWLVK | 134-145 for the proteins of SEQ No. 82, 94 |
| SEQ ID No. 166 | NSFSGASYWLVK | 134-145 for the proteins of SEQ No. 81, 84 |
| SEQ ID No. 167 | NSFSGGSYWLVNNK | 134-147 for the protein of SEQ No. 87 |
| SEQ ID No. 168 | NSFSGVSYWLLK | 134-145 for the protein of SEQ No. 105 |
| SEQ ID No. 169 | NSFSGVSYWLVK | 134-145 for the proteins of SEQ No. 83, 89, 91, 92, 99, 100, 101, 102, 103 |
| SEQ ID No. 170 | SIPTYASELTNELLK | 111-125 for the proteins of SEQ No. 80, 81, 82, 83, 84, 85, 86, 87, 90, 91, 92, 93, 94, 95, 96, 97, 98, 100, 102, 103, 104, 105 |
| SEQ ID No. 171 | TLEQAVK | 227-233 for the proteins of SEQ No. 80, 81, 82, 84, 90, 93, 94, 96, 97, 98 |
| SEQ ID No. 172 | TWEQALK | 227-233 for the protein of SEQ No. 104 |

| Peptide SEQ ID No. | Amino acid sequence | Position of the peptide in the IMP protein(s) |
|---|---|---|
| SEQ ID No. 173 | TWEQAVK | 227-233 for the proteins of SEQ No. 83, 86, 87, 88, 89, 91, 92, 95, 99, 100, 101, 102, 103, 105 |
| SEQ ID No. 174 | VLFGGCFVK | 171-179 for the proteins of SEQ No. 81, 84, 85, 87 |
| SEQ ID No. 175 | VQATNSFSGVNYWLVK | 130-145 for the proteins of SEQ No. 80, 90, 93, 96, 97, 98 |
| SEQ ID No. 176 | VQATNSFSGVSYSLIK | 130-145 for the protein of SEQ No. 88 |
| SEQ ID No. 177 | VQATNSFSGVSYWLVK | 130-145 for the protein of SEQ No. 103 |
| SEQ ID No. 178 | YGNAK | 205-209 for the proteins of SEQ No. 89, 99, 101, 105 |
| SEQ ID No. 179 | YSFSEVSYWLVK | 134-145 for the protein of SEQ No. 104 |
| SEQ ID No. 180 | YSFSGVSYWLVK | 134-145 for the protein of SEQ No. 85 |

The detection of a mechanism of resistance to carbapenems induced by the expression of the IND protein is characterised by the detection of at least one peptide belonging to the IND protein and to its different sequence variants SEQ ID No. 181 to SEQ ID No. 187.

SEQ ID No. 181:
MKKSIRFFIVSILLSPFASAQVKDFVIEPPIKNNLHIYKTFGVFGGKEYS

ANSMYLVTKKGVVLFDVPWEKIQYQSLMDTIKKRHNLPVVAVFATHSHDD

RAGDLSFFNNKGIKTYATAKTNEFLKKDGKATSTEIIKTGKPYRIGGEEF

VVDFLGEGHTADNVVVWFPKYNVLDGGCLVKSNSATDLGYIKEANVEQWP

KTINKLKAKYSKATLIIPGHDEWKGGGHVEHTLELLNKK

SEQ ID No. 182:
MKKSIQLLMMSMFLSPLINAQVKDFVIEPPVKPNLYLYKSFGVFGGKEYS

ANAVYLTTKKGVVLFDVPWQKEQYQTLMDTIQKRHHLPVIAVFATHSHDD

RAGDLSFYNQKGIKTYATAKTNELLKKDGKATSTEIIKTGKPYKIGGEEF

MVDFLGEGHTVDNVVVWFPKYKVLDGGCLVKSRTATDLGYTGEANVKQWP

ETMRKLKTKYAQATLVIPGHDEWKGGGHVQHTLDLLDKNKKPE

SEQ ID No. 183:
MKKSIQLLMMSMFLSPLINAQVKDFVIEPPVKPNLYLYKSFGVFGGKEYS

ANAVYLTTKKGWLFDVPWQKEQYQTLMDTIQKRHHLPVIAVFATHSHDDR

AGDLSFYNQKGIKTYATAKTNELLKKDGKATSTEIIKTGKPYKIGGEEFM

VDFLGEGHTVDNVVVWFPKYKVLDGGCLVKSRTATDLGYTGEANVKQWPE

TMRKLKTKYAQATLVIPGHEEWKGGGHVQHTLDLLDKNKKPE

SEQ ID No. 184:
MKKRIQFFMVSMMLSSLFSAQVKDFVIEPPIKKNLHIYKTFGVFGGKEYS

ANSVYLVTQKGVVLFDVPWEKVQYQSLMDTIQKRHNLPVIAVFATHSHDD

RAGDLSFFNNKGIKTYATSKTNEFLKKDGKATSTEIIKTGKPYRIGGEEF

VVDFLGEGHTADNVVVWFPKYNVLDGGCLVKSKAATDLGYIKEANVEQWP

KTINKLKSKYSKASLVIPGHDEWKGGGHVKHTLELLNKK

SEQ ID No. 185:
MRKNVRIFTVLSLFLINFFNAQARDFVIEQPFGKQLYLYKTFGVFDGKEY

STNALYLVTKKGVVLFDVPWQKTQYQSLMDTIKKRHNLPVIAVFATHSHS

DRAGDLSFYNKKGIPTYATAKTNELLKKEGKATSSKLTKIGKKYKIGGEE

FTVDFLGEGHTADNVVVWFPKYNVLDGGCLVKSSAAVDLGYTGEANVEQW

PATMKKLQAKYPSTAKVIPGHDEWKGNDHVKHTLELLDQQKQ

SEQ ID No. 186:
MKKRIQFFMVSMMLAPMFNAQVKDFVIEPPIKNNLHIYKTFGVFGGKEYS

ANSVYLVTKKGVVLFDVPWEKAQYQSLMDTIKKRHNLPVIAVFATHSHDD

RAGDLSFFNNKGIKTYATSKTNEFLKKDGKATSTEIIKTGKPYRIGGEEF

TVDFLGEGHTADNVVVVVFPKYNVLDGGCLVKSNSATDLGYIKEANVEQW

PITIDKLKAKYSKATLIIPGHDDWKGGGHVEHTLELLNKK

SEQ ID No. 187:
MKRRIQFFMVSMMLTPLFSAQVKDFVIEPPIKKNLYIYKTFGVFGGKEYS

ANSVYLVTKTGVVLFDVPWEKAQYQSLMDTIKKRHNLPVVAVFATHSHDD

RAGDLSFFNNKGIKTYATPKTNQFLKRDGKATSTELIKPGKPYRFGGEEF

VVDFLGEGHTADNVVVWFPKYKVLDGGCLVKSNSATDLGYIKEANLEQWP

KTMHKLKTKYSEAVLIIPGHDEWKGGGHVEHTLELLDKK said peptides being chosen, preferably, from the peptides of sequence SEQ ID No. 188 to SEQ ID No. 197, SEQ ID No. 200, SEQ ID No. 201, SEQ ID No. 203 to SEQ ID No. 262, as defined hereafter:

| Peptide SEQ ID No. | Amino acid sequence | Position of the peptide in the IND protein(s) |
|---|---|---|
| SEQ ID No. 188 | AATDLGYIK | 184-192 for the protein of SEQ No. 184 |
| SEQ ID No. 189 | AGDLSFFNNK | 102-111 for the proteins of SEQ No. 181, 184, 186, 187 |
| SEQ ID No. 190 | AGDLSFYNK | 103-111 for the protein of SEQ No. 185 |
| SEQ ID No. 191 | AGDLSFYNQK | 102-111 for the proteins of SEQ No. 182, 183 |
| SEQ ID No. 192 | AQYQSLMDTIK | 72-82 for the proteins of SEQ No. 186, 187 |
| SEQ ID No. 193 | ASLVIPGHDEWK | 213-224 for the protein of SEQ No. 184 |
| SEQ ID No. 194 | ATLIIPGHDDWK | 213-224 for the protein of SEQ No. 186 |
| SEQ ID No. 195 | ATLIIPGHDEWK | 213-224 for the protein of SEQ No. 181 |
| SEQ ID No. 196 | ATSSK | 132-136 for the protein of SEQ No. 185 |
| SEQ ID No. 197 | ATSTEIIK | 131-138 for the proteins of SEQ No. 181, 182, 183, 184, 186 |
| SEQ ID No. 198 | ATSTELIK | 131-138 for the protein of SEQ No. 187 |
| SEQ ID No. 199 | ATSTELIKPGK | 131-141 for the protein of SEQ No. 187 |
| SEQ ID No. 200 | ATSTELIKPGKPYR | 131-144 for the protein of SEQ No. 187 |
| SEQ ID No. 201 | DFVIEPPIK | 24-32 for the proteins of SEQ No. 181, 184, 186, 187 |
| SEQ ID No. 202 | DFVIEPPVK | 24-32 for the proteins of SEQ No. 182, 183 |
| SEQ ID No. 203 | DFVIEPPVKPNLYLYK | 24-39 for the proteins of SEQ No. 182, 183 |
| SEQ ID No. 204 | DFVIEQPFGK | 25-34 for the protein of SEQ No. 185 |
| SEQ ID No. 205 | EANLEQWPK | 193-201 for the protein of SEQ No. 187 |
| SEQ ID No. 206 | EANVEQWPITIDK | 193-205 for the protein of SEQ No. 186 |
| SEQ ID No. 207 | EANVEQWPK | 193-201 for the proteins of SEQ No. 181, 184 |
| SEQ ID No. 208 | EQYQTLMDTIQK | 72-83 for the proteins of SEQ No. 182, 183 |
| SEQ ID No. 209 | EYSANAVYLTTK | 48-59 for the proteins of SEQ No. 182, 183 |
| SEQ ID No. 210 | EYSANSMYLVTK | 48-59 for the protein of SEQ No. 181 |
| SEQ ID No. 211 | EYSANSVYLVTK | 48-59 for the proteins of SEQ No. 186, 187 |
| SEQ ID No. 212 | EYSANSVYLVTQK | 48-60 for the protein of SEQ No. 184 |
| SEQ ID No. 213 | EYSTNALYLVTK | 49-60 for the protein of SEQ No. 185 |

-continued

| Peptide SEQ ID No. | Amino acid sequence | Position of the peptide in the IND protein(s) |
|---|---|---|
| SEQ ID No. 214 | FFIVSILLSPFASAQVK | 7-23 for the protein of SEQ No. 181 |
| SEQ ID No. 215 | GGGHVEHTLELLDK | 225-238 for the protein of SEQ No. 187 |
| SEQ ID No. 216 | GGGHVEHTLELLNK | 225-238 for the proteins of SEQ No. 181, 186 |
| SEQ ID No. 217 | GGGHVK | 225-230 for the protein of SEQ No. 184 |
| SEQ ID No. 218 | GGGHVQHTLDLLDK | 225-238 for the proteins of SEQ No. 182, 183 |
| SEQ ID No. 219 | GIPTYATAK | 113-121 for the protein of SEQ No. 185 |
| SEQ ID No. 220 | GNDHVK | 226-231 for the protein of SEQ No. 185 |
| SEQ ID No. 221 | GVVLFDVPWEK | 61-71 for the proteins of SEQ No. 181, 184, 186, 187 |
| SEQ ID No. 222 | GVVLFDVPWQK | 62-72 for the protein of SEQ No. 185; 61-71 for the protein of sequence SEQ ID No. 182; 61-71 for the protein of sequence SEQ ID No. 183 |
| SEQ ID No. 223 | HHLPVIAVFATHSHDDR | 85-101 for the proteins of SEQ No. 182, 183 |
| SEQ ID No. 224 | HNLPVIAVFATHSHDDR | 85-101 for the proteins of SEQ No. 184, 186 |
| SEQ ID No. 225 | HNLPVIAVFATHSHSDR | 86-102 for the protein of SEQ No. 185 |
| SEQ ID No. 226 | HNLPVVAVFATHSHDDR | 85-101 for the proteins of SEQ No. 181, 187 |
| SEQ ID No. 227 | HTLELLDQQK | 232-241 for the protein of SEQ No. 185 |
| SEQ ID No. 228 | HTLELLNK | 231-238 for the proteins of SEQ No. 181, 184, 186 |
| SEQ ID No. 229 | IFTVLSLFLINFFNAQAR | 7-24 for the protein of SEQ No. 185 |
| SEQ ID No. 230 | IQFFMVSMMLAPMFNAQVK | 5-23 for the protein of SEQ No. 186 |
| SEQ ID No. 231 | IQFFMVSMMLSSLFSAQVK | 5-23 for the protein of SEQ No. 184 |
| SEQ ID No. 232 | IQFFMVSMMLTPLFSAQVK | 5-23 for the protein of SEQ No. 187 |
| SEQ ID No. 233 | IQYQSLMDTIK | 72-82 for the protein of SEQ No. 181 |
| SEQ ID No. 234 | NLHIYK | 34-39 for the proteins of SEQ No. 181, 184, 186 |
| SEQ ID No. 235 | NLYIYK | 34-39 for the protein of SEQ No. 187 |
| SEQ ID No. 236 | NNLHIYK | 33-39 for the proteins of SEQ No. 181, 186 |
| SEQ ID No. 237 | QLYLYK | 35-40 for the protein of SEQ No. 185 |
| SEQ ID No. 238 | QWPETMR | 198-204 for the proteins of SEQ No. 182, 183 |

| Peptide SEQ ID No. | Amino acid sequence | Position of the peptide in the IND protein(s) |
|---|---|---|
| SEQ ID No. 239 | SFGVFGGK | 40-47 for the proteins of SEQ No. 182, 183 |
| SEQ ID No. 240 | SIQLLMMSMFLSPLINAQVK | 4-23 for the proteins of SEQ No. 182, 183 |
| SEQ ID No. 241 | SNSATDLGYIK | 182-192 for the proteins of SEQ No. 181, 186, 187 |
| SEQ ID No. 242 | TATDLGYTGEANVK | 184-197 for the proteins of SEQ No. 182, 183 |
| SEQ ID No. 243 | TFGVFDGK | 41-48 for the protein of SEQ No. 185 |
| SEQ ID No. 244 | TFGVFGGK | 40-47 for the proteins of SEQ No. 181, 184, 186, 187 |
| SEQ ID No. 245 | TGKPYK | 139-144 for the proteins of SEQ No. 182, 183 |
| SEQ ID No. 246 | TGKPYR | 139-144 for the proteins of SEQ No. 181, 184, 186 |
| SEQ ID No. 247 | TGVVLFDVPWEK | 60-71 for the protein of SEQ No. 187 |
| SEQ ID No. 248 | TNEFLK | 121-126 for the proteins of SEQ No. 181, 184, 186 |
| SEQ ID No. 249 | TNELLK | 122-127 for the protein of SEQ No. 185; 121-126 for the proteins of sequence SEQ ID No. 182, 183 |
| SEQ ID No. 250 | TNQFLK | 121-126 for the protein of SEQ No. 187 |
| SEQ ID No. 251 | TQYQSLMDTIK | 73-83 for the protein of SEQ No. 185 |
| SEQ ID No. 252 | TYATAK | 116-121 for the protein of SEQ No. 185; 115-120 for the proteins of sequence SEQ ID No. 181, 182, 183 |
| SEQ ID No. 253 | TYATPK | 115-120 for the protein of SEQ No. 187 |
| SEQ ID No. 254 | TYATSK | 115-120 for the proteins of SEQ No. 184, 186 |
| SEQ ID No. 255 | VIPGHDEWK | 217-225 for the protein of SEQ No. 185; 216-224 for the protein of sequence SEQ ID No. 182; 216-224 for the protein of sequence SEQ ID No. 184 |
| SEQ ID No. 256 | VLDGGCLVK | 173-181 for the proteins of SEQ No. 181, 182, 183, 184, 186, 187; 174-182 for the protein of sequence SEQ ID No. 185 |
| SEQ ID No. 257 | VQYQSLMDTIQK | 72-83 for the protein of SEQ No. 184 |
| SEQ ID No. 258 | YAQATLVIPGHDEWK | 210-224 for the protein of SEQ No. 182 |
| SEQ ID No. 259 | YAQATLVIPGHEEWK | 210-224 for the protein of SEQ No. 183 |
| SEQ ID No. 260 | YNVLDGGCLVK | 171-181 for the proteins of SEQ No. 181, 184, 186; 172-182 for the protein of sequence SEQ ID No. 185 |
| SEQ ID No. 261 | YPSTAK | 211-216 for the protein of SEQ No. 185 |
| SEQ ID No. 262 | YSEAVLIIPGHDEWK | 210-224 for the protein of SEQ No. 187 |

The detection of a mechanism of resistance to carbapenems induced by the expression of the SME protein is characterised by the detection of at least one peptide belonging to the SME protein and to its different sequence variants SEQ ID No. 263 to SEQ ID No. 265.

SEQ ID No. 263:
MSNKVNFKTASFLFSVCLALSAFNAHANKSDAAAKQIKKLEEDFDGRIGV
FAIDIGSGNIFGYRSDERFPLCSSFKGFLAAAVLERVQQKKLDINQKVKY
ESRDLEYHSPITTKYKGSGMTLGDMASAALQYSDNGATNIIMERFLGGPE
GMTKFMRSIGDNEFRLDRWELELNTAIPGDKRDTSTPKAVANSLNKLALG
NVLNAKEKAIYQNWLKGNITGDARIRASVPADVVVVGDKTGSCGAYGTAN
DYAVIWPKNRAPLIVSIYTTRKSKDDKHSDKTIAEASRIAIQAID

SEQ ID No. 264:
MSNKVNFKTASFLFSVCLALSAFNAHANKSDAAAKQIKKLEEDFDGRIGV
FAIDTGSGNTFGYRSDERFPLCSSFKGFLAAAVLERVQQKKLDINQKVKY
ESRDLEYYSPITTKYKGSGMTLGDMASAALQYSDNGATNIIMERFLGGPE
GMTKFMRSIGDNEFRLDRWELELNTAIPGDKRDTSTPKAVANSLNKLALG
NVLNAKVKAIYQNWLKGNTTGDARIRASVPADWVVGDKTGSCGAYGTAND
YAVIWPKNRAPLIVSIYTTRKSKDDKHSDKTIAEASRIAIQAID

SEQ ID No. 265:
MSNKVNFKTASFLFSVCLALSAFNAHANKSDAAAKQIKKLEEDFDGRIGV
FAIDTGSGNTFGYRSDERFPLCSSFKGFLAAAVLERVQQKKLDINQKVKY
ESRDLEYHSPITTKYKGSGMTLGDMASAALQYSDNGATNIIMERFLGGPE
GMTKFMRSIGDNEFRLDRWELELNTAIPGDKRDTSTPKAVANSLNKLALG
NVLNAKVKAIYQNWLKGNTTGDARIRASVPADVINVGDKTGSCGAIGTAN
DYAVIWPKNRAPLIVSIYTTRKSKDDKHSDKTIAEASRIAIQAID said peptides being chosen, preferably, from the peptides of sequence SEQ ID No. 266 to SEQ ID No. 287 as defined hereafter:

| Peptide SEQ ID No. | Amino acid sequence | Position of the peptide in the SME protein(s) |
|---|---|---|
| SEQ ID No. 266 | AIYQNWLK | 209-216 for the proteins of SEQ No. 263, 264, 265 |
| SEQ ID No. 267 | APLIVSIYTTR | 260-270 for the proteins of SEQ No. 263, 264, 265 |
| SEQ ID No. 268 | ASVPADWVVGDK | 227-238 for the proteins of SEQ No. 263, 264, 265 |
| SEQ ID No. 269 | AVANSLNK | 189-196 for the proteins of SEQ No. 263, 264, 265 |
| SEQ ID No. 270 | DLEYHSPITTK | 104-114 for the proteins of SEQ No. 263, 265 |
| SEQ ID No. 271 | DLEYYSPITTK | 104-114 for the protein of SEQ No. 264 |
| SEQ ID No. 272 | DTSTPK | 183-188 for the proteins of SEQ No. 263, 264, 265 |
| SEQ ID No. 273 | FLGGPEGMTK | 145-154 for the proteins of SEQ No. 263, 264, 265 |
| SEQ ID No. 274 | GFLAAAVLER | 77-86 for the proteins of SEQ No. 263, 264, 265 |
| SEQ ID No. 275 | GNTTGDAR | 217-224 for the proteins of SEQ No. 263, 264, 265 |
| SEQ ID No. 276 | IGVFAIDTGSGNTFGYR | 48-64 for the proteins of SEQ No. 263, 264, 265 |
| SEQ ID No. 277 | LALGNVLNAK | 197-206 for the proteins of SEQ No. 263, 264, 265 |
| SEQ ID No. 278 | LDINQK | 92-97 for the proteins of SEQ No. 263, 264, 265 |
| SEQ ID No. 279 | LEEDFDGR | 40-47 for the proteins of SEQ No. 263, 264, 265 |
| SEQ ID No. 280 | SDAAAK | 30-35 for the proteins of SEQ No. 263, 264, 265 |
| SEQ ID No. 281 | SIGDNEFR | 158-165 for the proteins of SEQ No. 263, 264, 265 |

| Peptide SEQ ID No. | Amino acid sequence | Position of the peptide in the SME protein(s) |
|---|---|---|
| SEQ ID No. 282 | TASFLFSVCLALSAFNAHANK | 9-29 for the proteins of SEQ No. 263, 264, 265 |
| SEQ ID No. 283 | TGSCGAIGTANDYAVIWPK | 239-257 for the protein of SEQ No. 265 |
| SEQ ID No. 284 | TGSCGAYGTANDYAVIWPK | 239-257 for the proteins of SEQ No. 263, 264 |
| SEQ ID No. 285 | TIAEASR | 281-287 for the proteins of SEQ No. 263, 264, 265 |
| SEQ ID No. 286 | WELELNTAIPGDK | 169-181 for the proteins of SEQ No. 263, 264, 265 |
| SEQ ID No. 287 | FPLCSSFK | 69-76 for the proteins of SEQ No. 263, 264, 265 |

The detection of a mechanism of resistance to carbapenems induced by the expression of a VIM protein is characterised by the detection of at least one peptide belonging to a VIM protein and to its different sequence variants SEQ ID No. 288 to SEQ ID No. 313.

SEQ ID No. 288:
MFKLLSKLLVYLTASIMAIASPLAFSVDSSGEYPTVSEIPVGEVRLYQIA
DGVVVSHIATQSFDGAVYPSNGLIVRDGDELLLIDTAWGAKNTAALLAEI
EKQIGLPVTRAVSTHFHDDRVGGVDVLRAAGVATYASPSTRRLAEVEGNE
1PTHSLEGLSSSGDAVRFGPVELFYPGAAHSTDNLVVYVPSASVLYGGCA
IYELSRTSAGNVADADLAEWPTSIERIQQHYPEAQFVIPGHGLPGGLDLL
KHTTNVVKAHTNRSVVE

SEQ ID No. 289:
MFKLLSKLLVYLTASIMAIASPLAFSVDSSGEYPTVSEIPVGEVRLYQIA
DGVVVSHIATKSFDGAVYPSNGLIVRDGDELLLIDTAWGAKNTAALLAEI
EKQIGLPVTRAVSTHFHDDRVGGVDVLRAAGVATYASPSTRRLAEVEGSE
IPTHSLEGLSSSGDAVRFGPVELFYPGAAHSTDNLVVYVPSASVLYGGCA
IYELSRTSAGNVADADLAEWPTSIERIQQHYPEAQFVIPGHGLPGGLDLL
KHTTNVVKAHTNRSVVE

SEQ ID No. 290:
MLKVISSLLVYMTASVMAVASPLAHSGEPSGEYPTVNE1PVGEVRLYQIA
DGVVVSHIATQSFDGAVYPSNGLIVRDGDELLLIDTAWGAKNTAALLAEI
EKQIGLPVTRAVSTHFHDDRVGGVDVLRAAGVATYASPSTRRLAEAEGNE
IPTHSLEGLSSSGDAVRFGPVELFYPGAAHSTDNLVVYVPSANVLYGGCA
VHELSRTSAGNVADADLAEWPTSVERIQKHYPEAEWIPGHGLPGGLDLLQ
HTANVVKAHKNRSVAE

SEQ ID No. 291:
MLKVISSLLVYMTASVMAVASPLAHSGEPSGEYPTVNE1PVGEVRLYQIA
DGVWSHIATQSFDGAVYPSNGLIVRDGDELLLIDTAWGAKNTAALLAEIE
KQIGLPVTRAVSTHFHDDRVGGVDVLRKAGVATYASPSTRRLAEAEGNE1
PTHSLEGLSSSGDAVRFGPVELFYPGAAHSTDNLVVYVPSANVLYGGCAV
LALSRTSAGNVADADLAEWPTSVERIQKHYPEAEWIPGHGLPGGLDLLQH
TANVVTAHKNRSVAE

SEQ ID No. 292:
MFKLLSKLLVYLTASIMAIASPLAFSVDSSGEYPTVSEIPVGEVRLYQIA
DGVWSHIATRSFDGAVYPSNGLIVRDGDELLLIDTAWGAKNTAALLAEIE
KQIGLPVTRAVSTHFHDDRVGGVDVLRAAGVATYASPSTRRLAEVEGSEI
PTHSLEGLSSSGDAVRFGPVELFYPGAAHSTDNLVVYVPSASVLYGGCAI
YELSRTSAGNVADADLAEWPTSIERIQQHYPEAQFVIPGHGLPGGLDLLK
HTTNVVKAHTNRSVVE

SEQ ID No. 293:
MFKLLSKLLVYLTASIMAIASPLAFSVDSSGEYPTVSEIPVGEVRLYQIA
DGVWSHIATQSFDGAVYPSNGLIVRDGDELLLIDTAWGAKNTAALLAEIE
KQIGLPVTRAVSTHFHDDRVGGVDVLRAAGVATYASPSARRLAEVEGNEI
PTHSLEGLSSSGDAVRFGPVELFYPGAAHSTDNLVVYVPSASVLYGGCA1
YELSRTSAGNVADADLAEWPTSIERIQQHYPEAQFVIPGHGLPGGLDLLK
HTTNVVKAHTNRSVVE

SEQ ID No. 294:
MFKLLSKLLVYLTASIMAIASPLAFSVDSSGEYPTVSEIPVGEVRLYQ1A
DGVVVSHIATQSFDGAVYPSNGL1VRDGDELLLIDTAWGAKNTAALLAEI
EKQIGLPVTRAVSTHFHDDRVGGVDVLRAAGVATYASPSIRRLAEVEGNE
IPTHSLEGLSSSGDAVRFGPVELFYPGAAHSTDNLVVYVPSASVLYGGCA
IYELSRTSAGNVADADLAEWPTSIERIQQHYPEAQFVIPGHGLPGGLDLL
KHTTNVVKAHTNRSVVE

SEQ ID No. 296:
MFKLLSKLLVYLTASIMAIASPLAFSVDSSGEYPTVSEIPVGEVRLYQIA
DGVVVSHIATQSFDGAVYPSNGLIVRDGDELLLIDTAWGAKNTAALLAEI
EKQIGLPVTRAVSTHFHDDRVGGVDVLRAAGVATYASPSTRRLAEVEGNE
1PTHSLEGLSSSGDAVRFGPVELFYPGAAHSTDNLVVYVPSASVLYGGCA

SEQ ID No. 296:
MFKLLSKLLVYLTASIMAIASPLAFSVDSSGEYPTVSEIPVGEVRLYQIA
DGVWSH1ATQSFDGAVYPSNGLIVRDGDELLLIDTAWGAKNTAALLAEIE
KQIGLPVTRAVSTHFHDDRVGGVDVLRAAGVATYASPSTRRLAEVEGSEI
PTHSLEGLSSSGDAVRFGPVELFYPGAAHSTDNLVVYVPSASVLYGGCAI
YELSRTSAGNVADADLAEWPTSIERIQQHYPEAQFVIPGHGLPGGLDLLK
HTTNVVKAHTNRSVVE

SEQ ID No. 297:
MLKVISSLLVYMTASVMAVASPLAHSGEPSSEYPTVNE1PVGEVRLYQIA
DGVVVSHIATQSFDGAVYPSNGLIVRDGDELLLIDTAWGAKNTAALLAEI
EKQIGLPVTRAVSTHFHDDRVGGVDVLRAAGVATYASPSTRRLAEAEGNE
IPTHSLEGLSSSGDAVRFGPVELFYPGAAHSTDNLVVYVPSANVLYGGCA
VHELSRTSAGNVADADLAEWPTSVERIQKHYPEAEVVIPGHGLPGGLDLL
QHTANVVKAHKNRSVAE

SEQ ID No. 298:
MLKVISSLLVYMTASVMAVASPLAHSGEPSGEYPTVNE1PVGEVRLYQIA
DGV1NSHIATQSFDGAVYPSNGLIVRDGDELLLIDTAWGAKNTAALLAEI
EKQIGLPVTRAVSTHFHDDRVGGVDVLRAAGVATYASPSTRRLAEAEGNE
1PTHSLEGLSSSGDAVRFGPVELFYPGAAHSTDNLWYVPSANVLYGGCAV
HELSSTSAGNVADADLAEWPTSIERIQQHYPEAQFVIPGHGLPGGLDLLK
HTTNVVKAHTNRSVVE

SEQ ID No. 299:
MLKVISSLLFYMTASLMAVASPLAHSGESRGEYPTVSEIPVGEVRLYQID
DGVVVSHIATHTFDGVVYPSNGLIVRDGDELWDTAWGTKNTVALLAEIEK
QIGLPVTRSVSTHFHDDRVGGVDALRAAGVATYASPSTRRLAEAEGNEVP
THSLEGLSSSGDAVRFGPVELFYPGAAHSTDNLVVYVPSANVLYGGCAVL
ELSRTSAGNVADADLAEWPGSVERIQQHYPEAEVVIPGHGLPGGLDLLQH
TANVVKAHTNRSVAE

SEQ ID No. 300:
MFKLLSKLLVYLTASMMAIASPLAFSVDSSGEYPTVSEIPVGEVRLYQIA
DGVWSHIATQSFDGAVYPSNGLIVRDGDELLLIDTAWGAKNTAALLAEIE
KQ1GLPVTRAVSTHFHDDRVGGVDVLRAAGVATYASPSTRRLAEVEGNE1
PTHSLEGLSSSGDAVRFGPVELFYPGAAHSTDNLVVYVPSASVLYGGCA1
YELSRTSAGNVADADLAEWPTSIERIQQHYPEAQFVIPGHGLPGGLDLLK
HTTNVVKAHTNRSVVE

SEQ ID No. 301:
MFKLLSKLLVYLTASIMAIASPLAFSVDSSGEYPTVSEIPVGEVRLYQIA
DGVWSHIATQSFDGAVYPSNGLIVRDGDELLL1DTAWGAKNTAALLAEIE
KQIGLPVTRAVSTHFHDDRVGGVDVLRAAGVATYASPSTRRLAEVEGNEI
PTHSLEGLSSSGDAVRFGPVELFYPGAAHSTDNLVVYVPSASVLFGGCAI
YELSRTSAGNVADADLAEWPTSIERIQQHYPEAQFVIPGHGLPGGLDLLK
HTTNVVKAHTNRSVVE

SEQ ID No. 302:
MFKLLSKLLVYLTASIMAIASPLAFSVDSSGEYPTVSEIPVGEVRLYQIA
DGVWLHIATQSFDGAVYPSNGLIVRDGDELLLIDTAWGAKNTAALLAEIE
KQ1GLPVTRAVSTHFHDDRVGGVDVLRAAGVATYASPSTRRLAEVEGNE1
PTHSLEGLSSSGDAVRFGPVELFYPGAAHSTDNLVVYVPSASVLYGGCAI
YELSRTSAGNVADADLAEWPTSIERIQQHYPEAQFVIPGHGLPGGLDLLK
HTTNVVKAHTNRSVVE

SEQ ID No. 303:
MFKLLSKLLVYLTASIMAIASPLAFSVDSSGEYPTVSEIPVGEVRLYQIA
DGVWSHIATQSFDGAVYPSNGLIVRDGDELLLIDTAWGAKNTAALLAEIE
KQIGLPVTRAVSTHFHDDRVGGVDVLRAAGVATYASPSTRRLAEVEGNE1
PTHSLEGLSSSGDAVRFGPVELFYPGAAHSTDNLVVYVPSASVLYGGCAI
YELSSTSAGNVADADLAEWPTS1ERIQQHYPEAQFVIPGHGLPGGLDLLK
HTTNVVKAHTNRSVVE

SEQ ID No. 304:
MLKVISSLLVYMTASVMAVASPLAHSGEPSGEYPTVNEIPVGEVRLYQ1A
DGVWSHIATQSFDGAVYPSNGLIVRDGDELLLIDTAWGAKNTAALLAEIE
KQIGLPVTRAVSTHFHDDRVGGVDVLRAAGVATYASPSTRRLAEAEGNE1
PTHSLEGLSSSGDAVRFGPVELFYPGAAHSTDNLVVYVPSAKVLYGGCAV
HELSRTSAGNVADADLAEWPTSVERIQKHYPEAEVVIPGHGLPGGLDLLQ
HTANVVKAHKNRSVAE

SEQ ID No. 305:
MFKLLSKLLVYLTAS1MAIASPLAFSVDSSGEYPTVSEIPVGEVRLYQIA
DGVWSHIATQSFDGAVYPSNGLIVRDGDELLLIDTAWGAKNTAALLAEIE
KQIGLPVTRAVSTHFHDDRVGGVDVLRAAGVATYASPSTRRLAEVEGNEI
PTHSLEGLSSSGDAVRFGPVELFYPGAAHSTDNLVVYVPSASVLYGGCAI
YELSLTSAGNVADADLAEWPTSIERIQQHYPEAQFVIPGHGLPGGLDLLK
HTTNWKAHTNRSWE

SEQ ID No. 306:
MLKVISSLLVYMTASVMAVASPLAHSGEPSGEYPTVNEIPVGEVRLYQIA
DGVWSHIATQSFDGAVYPSNGLIVRDGDELLLIDTAWGAKNTAALLAEIE
KQIGLPVTRAVSTHFHDDRVGGVDVLRKAGVATYASPSTRRLAEAEGNEI
PTHSLEGLSSSGDAVRFGPVELFYPGAAHSTDNLVVYVPSANVLYGGCAV
LALSRTSAGNVADADLAEWPTSVERIQKHYPEAQFVIPGHGLPGGLDLLK
HTTNVVKAHTNRSVVE

SEQ ID No. 307:
MLKVISSLLVYMTASVMAVASPLAHSGEPSGEYPTVNE1PVGEVRLYQIA
DGVWSHISTQSFDGAVYPSNGLIVRDGDELLLIDTAWGAKNTAALLAEIE
KQIGLPVTRAVSTHFHDDRVGGVDVLRAAGVATYASPSTRRLAEAEGNE1
PTHSLEGLSSSGDAVRFGPVELFYPGAAHSTDNLVVYVPSANVLYGGCAV

HELSSTSAGNVADADLAEWPTSVERIQKHYPEAEVVIPGHGLPGGLDLLQ
HTANVVKAHKNRSVAE

SEQ ID No. 308:
MLKVISSLLVYMTASVMAVASPLAHSGEPSGEYPTVNE1PVGEVRLYQIA
DGVVVSHIATQSFDGAVYPSNGLIVRDGDELLLIDTAWGAKNTAALLAEI
EKQIGLPVTRAVSTHFHDDRVGGVDVLRAAGVATYASPSTRRLAEAEGNE
IPTHSLEGLSSSGDAVRFGPVELFYPGAAHSTDNLVVYVPSANVLYGGCA
VLELSRTSAGNVADADLAEWPTSVER1QKHYPEAEVVIPGHGLPGGLDLL
QHTANVVKAHKNRSVAE

SEQ ID No. 309:
MFKLLSKLLVYLTASIMAIASPLAFSVDSSGEYPTVNEIPVGEVRLYQIA
DGVWSHIATQSFDGAVYPSNGLIVRDGDELLLIDTAWGAKNTAALLAEIE
KQIGLPVTRAVSTHFHDDRVGGVDVLRAAGVATYASPSTRRLAEVEGNEI
PTHSLEGLSSSGDAVRFGPVELFYPGAAHSTDNLVVYVPSASVLYGGCAI
YELSRTSAGNVADADLAEWPTSIERIQQHYPEAQFVIPGHGLPGGLDLLK
HTTNVVKAHTNRSVVE

SEQ ID No. 310:
MLKVISSLLVYMTASVMAVASPLAHSGEPSGEYPTVNEIPVGEVRLYQ1A
DGVVVSHIATQSFDGAVYPSNGLIVRDGDELLLIDTAWGAKNTAALLAEI
EKQIGLPVTRAVSTHFHDDRVGGVDVLRAAGVATYASPSTRRLAEAEGNE
IPTHSLEGLSSSGDAVRFGPVELFYPGAAHSTDNLVVYVPSANVLYGGCA
VHELSSTSAGNVADADLAEWPTSVERIQKHYPEAEVVIPGHGLPGGLDLL
QHTANVVKAHKNRSVAE

SEQ ID No. 311:
MFQIRSFLVGISAFVMAVLGSAAYSAQPGGEYPTVDDIPVGEVRLYKIGD
GVVVSHIATQKLGDTVYSSNGLIVRDADELLLIDTAWGAKNTVALLAEIE
KQIGLPVTRSISTHFHDDRVGGVDVLRAAGVATYTSPLTRQLAEAAGNEV
PAHSLKALSSSGDVVRFGPVEVFYPGAAHSGDNLVVYVPAVRVLFGGCAV
HEASRESAGNVADANLAEWPATIKRIQQRYPEAEVVIPGHGLPGGLELLQ
HTTNWKTHKVRPVAE

SEQ ID No. 312:
MFKLLSKLLVYLTASIMAIASPLAFSVDSSGEYPTVSEIPVGEVRLYQIA
DGVWSHIATRSFDGAVYPSNGLIVRDGDELLLIDTAWGAKNTAALLAEIE
KQIGLPVTRAVSTHFHDDRVGGVDVLRAAGVATYASPSTRRLANEIPTHS
LEGLSSSGDAVRFGPVELFYPGAAHSTDNLVVYVPSASVLYGGCAIYELS
RTSAGNVADADLAEWPTSIERIQQHYPEAQFVIPGHGLPGGLDLLKHTTN
VVKAHTNRSVVE

SEQ ID No. 313:
MLKVISSLLVYMTASVMAVASPLAHSGEPSGEYPTVNEIPVGEVRLYQIA
DGVVVSHIATQSFDGAVYPSNGLIVRDGDELLLIDTAWGAKNTAALLAEI
EKQIGLPVTRAVSTHFHDDRVGGVDVLRAAGVATYASPSTRRLAEAEGNE
IPTHSLEGLSSSGDAVRFGPVELFYPGAAHSTDNLVVYVPSANVLYGGCA
VLELSSTSAGNVADADLAEWPTSVERIQKHYPEAEVVIPGHGLPGGLDLL
QHTANVVKAHKNRSVAE said peptides being chosen, preferably, from the peptides of sequence SEQ ID No. 314 to SEQ ID No. 346 as defined hereafter:

| Peptide SEQ ID No. | Amino acid sequence | Position of the peptide in the VIM protein(s) |
|---|---|---|
| SEQ ID No. 314 | AAGVATYASPSAR | 128-140 for the protein of SEQ No. 293 |
| SEQ ID No. 315 | AAGVATYASPSIR | 128-140 for the protein of SEQ No. 294 |
| SEQ ID No. 316 | AAGVATYASPSTR | 128-140 for the proteins of SEQ No. 288, 289, 290, 292, 295, 296, 297, 298, 299, 300, 301, 302, 303, 304, 305, 307, 308, 309, 310, 312, 313 |
| SEQ ID No. 317 | AAGVATYTSPLTR | 127-139 for the protein of SEQ No. 311 |
| SEQ ID No. 318 | AGVATYASPSTR | 129-140 for the proteins of SEQ No. 288, 289, 290, 291, 292, 295, 296, 297, 298, 299, 300, 301, 302, 303, 304, 305, 306, 307, 308, 309, 310, 312, 313 |
| SEQ ID No. 319 | AHTNR | 254-258 for the protein of SEQ No. 312; 258-262 for the proteins of sequence SEQ ID No. 288, 289, 292, 293, 294, 295, 296, 298, 299, 300, 301, 302, 303, 305, 306, 309 |
| SEQ ID No. 320 | ALSSSGDVVR | 156-165 for the protein of SEQ No. 311 |
| SEQ ID No. 321 | AVSTHFHDDR | 110-119 for the proteins of SEQ No. 288, 289, 290, 291, 292, 293, 294, 295, 296, 297, 298, |

-continued

| Peptide SEQ ID No. | Amino acid sequence | Position of the peptide in the VIM protein(s) |
|---|---|---|
| | | 300, 301, 302, 303, 304, 305, 306, 307, 308, 309, 310, 312, 313 |
| SEQ ID No. 322 | DADELLLIDTAWGAK | 75-89 for the protein of SEQ No. 311 |
| SEQ ID No. 323 | DGDELLLIDTAWGAK | 76-90 for the proteins of SEQ No. 288, 289, 290, 291, 292, 293, 294, 295, 296, 297, 298, 300, 301, 302, 303, 304, 305, 306, 307, 308, 309, 310, 312, 313 |
| SEQ ID No. 324 | DGDELLLIDTAWGTK | 76-90 for the protein of SEQ No. 299 |
| SEQ ID No. 325 | ESAGNVADANLAEWPATIK | 205-223 for the protein of SEQ No. 311 |
| SEQ ID No. 326 | GEYPTVSEIPVGEVR | 31-45 for the proteins of SEQ No. 288, 289, 292, 293, 294, 295, 296, 299, 300, 301, 302, 303, 305, 312 |
| SEQ ID No. 327 | HTTNVVK | 247-253 for the protein of SEQ No. 312; 251-257 for the proteins of sequence SEQ ID No. 288, 289, 292, 293, 294, 295, 296, 298, 300, 301, 302, 303, 305, 306, 309; 250-256 for the protein of sequence SEQ ID No. 311 |
| SEQ ID No. 328 | IGDGVWSHIATQK | 48-60 for the protein of SEQ No. 311 |
| SEQ ID No. 329 | LANEIPTHSLEGLSSSGDAVR | 142-162 for the protein of SEQ No. 312 |
| SEQ ID No. 330 | LGDTVYSSNGLIVR | 61-74 for the protein of SEQ No. 311 |
| SEQ ID No. 331 | LYQIADGVWSHIATK | 46-60 for the protein of SEQ No. 289 |
| SEQ ID No. 332 | LYQIADGVWSHIATR | 46-60 for the proteins of SEQ No. 292, 312 |
| SEQ ID No. 333 | NTAALLAEIEK | 91-101 for the proteins of SEQ No. 288, 289, 290, 291, 292, 293, 294, 295, 296, 297, 298, 300, 301, 302, 303, 304, 305, 306, 307, 308, 309, 310, 312, 313 |
| SEQ ID No. 334 | NTVALLAEIEK | 90-100 for the protein of SEQ No. 311; 91-101 for the protein of sequence SEQ ID No. 299 |
| SEQ ID No. 335 | QIGLPVTR | 102-109 for the proteins of SEQ No. 288, 289, 290, 291, 292, 293, 294, 295, 296, 297, 298, 299, 300, 301, 302, 303, 304, 305, 306, 307, 308, 309, 310, 312, 313; 101-108 for the protein of sequence SEQ ID No. 311 |
| SEQ ID No. 336 | QLAEAAGNEVPAHSLK | 140-155 for the protein of SEQ No. 311 |
| SEQ ID No. 337 | SFDGAVYPSNGLIVR | 61-75 for the proteins of SEQ No. 288, 289, 290, 291, 292, 293, 294, 295, 296, 297, 298, 300, 301, 302, 303, 304, 305, 306, 307, 308, 309, 310, 312, 313 |
| SEQ ID No. 338 | SISTHFHDDR | 109-118 for the protein of SEQ No. 311 |
| SEQ ID No. 339 | SVSTHFHDDR | 110-119 for the protein of SEQ No. 299 |
| SEQ ID No. 340 | TSAGNVADADLAEWPGSVER | 206-225 for the protein of SEQ No. 299 |
| SEQ ID No. 341 | TSAGNVADADLAEWPTSIER | 202-221 for the protein of SEQ No. 312; 206-225 for the protein of sequence SEQ ID No. 288, |

-continued

| Peptide SEQ ID No. | Amino acid sequence | Position of the peptide in the VIM protein(s) |
|---|---|---|
| | | 289, 292, 293, 294, 295, 296, 298, 300, 301, 302, 303, 305, 309 |
| SEQ ID No. 342 | TSAGNVADADLAEWPTSVER | 206-225 for the proteins of SEQ No. 290, 291, 297, 304, 306, 307, 308, 310, 313 |
| SEQ ID No. 343 | VGGVDALR | 120-127 for the protein of SEQ No. 299 |
| SEQ ID No. 344 | VGGVDVLR | 120-127 for the proteins of SEQ No. 288, 289, 290, 291, 292, 293, 294, 295, 296, 297, 298, 300, 301, 302, 303, 304, 305, 306, 307, 308, 309, 310, 312, 313; 119-126 for the protein of sequence SEQ ID No. 311 |
| SEQ ID No. 345 | VLFGGCAVHEASR | 192-204 for the protein of SEQ No. 311 |
| SEQ ID No. 346 | VLYGGCAVHELSR | 193-205 for the proteins of SEQ No. 290, 297, 304 |

The detection of a mechanism of resistance to carbapenems and/or to cephalosporins induced by the expression of an OXA protein is characterised by the detection of at least one peptide belonging to an OXA protein and to its different sequence variants SEQ ID No. 347 to SEQ ID No. 508.

SEQ ID No. 347:
MSRLLLSGLLATGLLCAVPASAASGCFLYADGNGQTLSSEGDCSSQLPPASTFKIPL

ALMGYDSGFLVNEEHPALPYKPSYDGWLPAWRETTTPRRWETYSVVWFSQQITE

WLGMERFQQYVDRFDYGNRDLSGNPGKHDGLTQAWLSSSLAISPEEQARFLGKM

VSGKLPVSAQTLQYTANILKVSEVEGWQIHGKTGMGYPKKLDGSLNRDQQIGWFV

GWASKPGKQLIFVHTVVQKPGKQFASIKAKEEVLAALPAQLKKL

SEQ ID No. 348:
IACLSSTALAGSITENTSWNKEFSAEAVNGVFVLCKSSSKSCATNDLARASKEYLPA

STFKIPNAIIGLETGVIKNEHQVFKWDGKPRAMKQWERDLTLRGAIQVSAVPVFQQI

AREVGEVRMQKYLKKFSYGNQNISGGIDKFWLEDQLRISAVNQVEFLESLYLNKLSA

SKENQLIVKEALVTEAAPEYLVHSKTGFSGVGTESNPGVAWWVGWVEKETEVYFF

AFNMDIDNESKLPLRKSIPTKIMESEGIIGG

SEQ ID No. 349:
MKKILLLHMLVFVSATLPISSVASDEVETLKCTIIADAITGNTLYETGECARRVSPCSS

FKLPLAIMGFDSGILQSPKSPTWELKPEYNPSPRDRTYKQVYPALWQSDSVVWFSQ

QLTSRLGVDRFTEYVKKFEYGNQDVSGDSGKHNGLTQSWLMSSLTISPKEQIQFLL

RFVAHKLPVSEAAYDMAYATIPQYQAAEGWAVHGKSGSGWLRDNNGKINESRPQ

GWFVGWAEKNGRQVVFARLEIGKEKSDIPGGSKAREDILVELPVLMGNK

SEQ ID No. 350:
MAIRIFAILFSIFSLATFAHAQEGTLERSDWRKFFSEFQAKGTIWADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNAGPSTSNGDYWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 351:
MQRSLSMSGKRHFIFAVSFVISTVCLTFSPANAAQKLSCTLVIDEASGDLLHREGSC

DKAFAPMSTFKLPLAIMGYDADILLDATTPRWDYKPEFNGYKSQQKPTDPTIWLKDS

IVWYSQELTRRLGESRFSDYVQRFDYGNKDVSGDPGKHNGLTHAWLASSLKISPEE

QVRFLRRFLRGELPVSEDALEMTKAVVPHFEAGDWDVQGKTGTGSLSDAKGGKAP

IGWFIGWATRDDRRVVFARLTVGARKGEQPAGPAARDEFLNTLPALSENF

SEQ ID No. 352:
MKTFAAYVIIACLSSTALAGSITENTSWNKEFSAEAVNGVFVLCKSSSKSCATNDLAR

ASKEYLPASTFKIPNAIIGLETGVIKNEHQVFKWDGKPRAMKQWERDLTLRGAIQVS

AVPVFQQIAREVGEVRMQKYLKKFSYGNQNISGGIDKFWLEGQLRISAVNQVEFLE

SLYLNKLSASKENQLIVKEALVTEAAPEYLVHSKTGFSGVGTESNPGVAWWVGWVE

KETEVYFFAFNMDIDNESKLPLRKSIPTKIMESEGIIGG

SEQ ID No. 353:
IACLSSTALAGSITENTSWNKEFSAEAVNGVFVLCKSSSKSCATNDLARASKEYLPA

STFKIPNAIIGLETGVIKNEHQVFKWDGKPRAMKQWERDLTLRGAIQVSAVPVFQQIT

REVGEVRMQKYLKKFSYGNQNISGGIDKFWLEDQLRISAVNQVEFLESLYLNKLSAS

KENQLIVKEALVTEAAPEYLVHSKTGFSGVGTESNPGVAWWVGWVEKETEVYFFA

FNMDIDNESKLPLRKSIPTKIMESEGIIGG

SEQ ID No. 354:
IACLSSTALAGSITENTSWNKEFSAEAVNGVFVLCKSSSKSCATNDLARASKEYLPA

STFKIPSAIIGLETGVIKNEHQVFKWDGKPRAMKQWERDLTLRGAIQVSAVPVFQQIA

REVGEVRMQKYLKKFSYGNQNISGGIDKFWLEGQLRISAVNQVEFLESLYLNKLSAS

KENQLIVKEALVTEAAPEYLVHSKTGFSGVGTESNPGVAWWVGWVEKETEVYFFA

FNMDIDNESKLPLRKSIPTKIMESEGIIGG

SEQ ID No. 355:
MIIRFLALLFSAVVLVSLGHAQEKTHESSNWGKYFSDFNAKGTIVVVDERTNGNSTS

VYNESRAQQRYSPASTFKIPHTLFALDAGAVRDEFHVFRWDGAKRSFAGHNQDQN

LRSAMRNSTVWVYQLFAKEIGENKARSYLEKLNYGNADPSTKSGDYWIDGNLAISA

NEQISILKKLYRNELPFRVEHQRLVKDLMIVEAKRDWILRAKTGWDGQMGWWVGW

VEWPTGPVFFALNIDTPNRMEDLHKREAIARAILQSVNALPPN

SEQ ID No. 356:
MAIRIFAILFSTFVFGTFAHAQEGMRERSDWRKFFSEFQAKGTIVVADERQTDRVILV

FDQVRSEKRYSPASTFKIPHTLFALDAGAARDEFQVFRWDGIKRSFAAHNQDQDLR

SAMRNSTVWIYELFAKEIGEDKARRYLKQIDYGNADPSTSNGDYWIDGNLAIAAQEQ

IAFLRKLYHNELPFRVEHQRLVKDLMIVEAGRNWILRAKTGWEGRIGWWVGWVEW

PTGPVFFALNIDTPNRMDDLFKREAIVRAILRSIEALPPNPAVNSDAAR

SEQ ID No. 357:
MKTFAAYVITACLSSTALASSITENTSWNKEFSAEAVNGVFVLCKSSSKSCATNNLA

RASKEYLPASTFKIPSAIIGLETGVIKNEHQVFKWDGKPRAMKQWERDLSLRGAIQV

SAVPVFQQIAREVGEVRMQKYLKKFSYGNQNISGGIDKFWLEGQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

SEQ ID No. 358:
MKTFAAYVITACLSSTALASSITENTSWNKEFSAEAVNGVFVLCKSSSKSCATNNLA

RASKEYLPASTFKIPNAIIGLETGVSKNEHQVFKWDGKPRAMKQWERDLSLRGAIQV

SAVPVFQQIAREVGEVRMQKYLKKFSYGNQNISGGIDKFWLEDQLRISAVNQVEFLE

SLFLNKLSASKENQLIVKEALVTEAAPEYLVHSKTGFSGVGTESNPGVAWWVGWVE

KGTEVYFFAFNMDIDNENKLPLRKSIPTKIMASEGIIGG

SEQ ID No. 359:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFGLEGQLRISAVNQVEFLE

SLFLNKLSASKENQLIVKEALVTEAAPEYLVHSKTGFSGVGTESNPGVAWWVGWVE

KGTEVYFFAFNMDIDNENKLPLRKSIPTKIMASEGIIGG

SEQ ID No. 360:
MKNTIHINFAIFLIIANIIYSSASASTDISTVASPLFEGTEGCFLLYDASTNAEIAQFNKA

KCATQMAPDSTFKIALSLMAFDAEIIDQKTIFKWDKTPKGMEIWNSNHTPKTWMQFS

VVWVSQEITQKIGLNKIKNYLKDFDYGNQDFSGDKERNNGLTEAWLESSLKISPEEQ

IQFLRKIINHNLPVKNSAIENTIENMYLQDLDNSTKLYGKTGAGFTANRTLQNGWFEG

FIISKSGHKYVFVSALTGNLGSNLTSSIKAKKNAITILNTLNL

SEQ ID No. 361:
ANIIYSSASASTDISTVASPLFEGTEGCFLLYDVSTNAEIAQFNKAKCATQMAPDSTF

KIALSLMAFDAEIIDQKTIFKWDKTPKGMEIWNSNHTPKTWMQFSVVWVSQEITQKI

GLNKIKNYLKDFDYGNQDFSGDKERNNGLTEAWLESSLKISPEEQIQFLRKIINHNLP

VKNSAIENTIENMYLQDLENSTKLYGKTGAGFTANRTLQNGWFEGFIISKSGHKYVF

VSALTGNLGSNLTSSIKAKKNAITIL

SEQ ID No. 362:
IFSLATFAHAQEGTLERSDWRKFFSEFQAKGTIVVADERQADRAMLVFDPVRSKKR

YSPASTFKIPHTLFALDAGAVRDEFQIFRWDGVNRGFAGHNQDQDLRSAMRNSTV

WVYELFAKEIGDDKARRYLKKIDYGNAYPSTSNGDYWIEGSLAISAQEQIAFLRKLYR

NELPFRVEHQRLVKDLMIVEAGRNWILRAKTGWEGRMGWWVGWVEWPTGSVFFA

LNIDTPNRMDDLFKREAIVRAIL

SEQ ID No. 363:
MIIRFLALLFSAVVLVSLGHAQDKTHESSNWGKYFSDFNAKGTIVVVDERTNGNSTS

VYNESRAQQRYSPASTFKIPHTLFALDAGAVRDEFHVFRWDGAKRSFAGHNQDQN

LRSAMRNSTVWVYQLFAKEIGENKARSYLEKLNYGNADPSTKSGDYWIDGNLAISA

NEQISILKKLYRNELPFRVEHQRLVKDLMIVEAKRDWILRAKTGWDGQMGWWVGW

VEWPTGPVFFALNIDTPNRMEDLHKREAIARAILQSVNALPPN

SEQ ID No. 364:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVEKMLLIKEVNGSKIYAKSGWGMGVTPQV

GWLTGWVEQANGKKIPFSLNLEMKEGMSGSIRNEITYKLLENLGII

-continued

SEQ ID No. 365:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMGVTPQV

GWLTGWVEQANGKKIPFSLNLEMKEGMTGSIRNEITYKSLENLGII

SEQ ID No. 366:
MNKYFTCYVVASLFLSGCTVQHNLINETPSQIVQGHNQVIHQYFDEKNTSGVLVIQT

DKKINLYGNALSRANTEYVPASTFKMLNALIGLENQKADINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALKMEMRSEMPASIRNELLMKSLKQLNII

SEQ ID No. 367:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYCIEGSLAISAQEQ

IAFLRKLYRNELPFRVEHQRLVKDLMIVEAGRNWILRAKTGWEGRMGWWVGWVE

WPTGSVFFALNIDTPNRMDDLFKREAIVRAIL

SEQ ID No. 368:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFWLEGQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

SEQ ID No. 369:
MAIRFLTILLSTFFLTSFVHAQEHVLERSDWKKFFSDLRAEGAIVISDERQAEHALLVF

GQERAAKRYSPASTFKLPHTLFALDADAVRDEFQVFRWDGVKRSFAGHNQDQDLR

SAMRNSAVWVYELFAKEIGKDKARHYLKQIDYGNADPSTIKGDYWIDGNLEISAHEQ

ISFLRKLYRNQLPFQVEHQRLVKDLMITEAGRNWILRAKTGWEGRFGWWVGWVE

WPTGPVFFALNIDTPNRTDDLFKREAIARAILRSIDALPPN

SEQ ID No. 370:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYWIEGSIAISAQEQ

IAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 371:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMGVTPQV

GWLTGWVEQANGKKIPFSLNLEMKEGMSGSIRNEITYKSLENLGII

SEQ ID No. 372:
MAIRFLTILLSTFFLTSFVHAQEHVLERSDWKKFFSDLRAEGAIVISDERQAEHALLVF

GQERAAKRYSPASTFKLPHTLFALDADAVRDEFQVFRWDGVKRSFAGHNQDQDLR

SAMRNSAVVWYELFAKEIGEDKARRYLKQIDYGNADPSTIKGDYWIDGNLEISAHEQ

ISFLRKLYRNQLPFQVEHQRLVKDLMITEAGRNWILRAKTGWEGRFGWWVGWVE

WPTGPVFFALNIDTPNRTDDLFKREAIARAILRSIDALPPN

SEQ ID No. 373:
MAIRFFTILLSTFFLTSFVYAQEHVVIRSDWKKFFSDLQAEGAIVIADERQAKHTLSVF

DQERAAKRYSPASTFKIPHTLFALDADAVRDEFQVFRWDGVNRSFAGHNQDQDLR

SAMRNSTVWVYELFAKDIGEDKARRYLKQIDYGNVDPSTIKGDYWIDGNLKISAHEQ

ILFLRKLYRNQLPFKVEHQRLVKDLMITEAGRSWILRAKTGWEGRFGWWVGWIEW

PTGPVFFALNIDTPNRTDDLFKREAIARAILRSIDALPPN

SEQ ID No. 374:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVERIGFGNAEIGQQVDNFWLVGPL

KVTPIQEVEFVSQLAHTQLPFSEKVQANVKNMLLLEESNGYKIFGKTGWAAMDIKPQ

VGWLTGWVEQPDGKIVAFALNMEMRSEMPASIRNELLMKSLKQLNII

SEQ ID No. 375:
MAIQIFAILFSTFVLATFAHAQDGTLERSDWGKFFSDFQAKGTIVVADERQADHAILV

FDQARSMKRYSPASTFKIPHTLFALDAGAVRDEFQIFRWDGVKRSFAGHNKDQDLR

SAMRNSTVWVYELFAKEIGDGKARRYLKQIGYGNADPSTSHGDYWIEGSLAISAQE

QIAFLRKLYQNDLPFRVEHQRLVKDLMIVEAGRNWILRAKTGWEGSMGWWVGWV

EWPTGPVFFALNIDTPNRMDDLFKREAIARAILLSIEALPPNPAVHSDAAR

SEQ ID No. 376:
MKNTIHINFAIFLIIANIIYSSASASTDISTVASQLFEGTEGCFLLYDASTNAEIAQFNKA

KCAAQMAPDSTFKIALSLMAFDAEIIDQKTIFKWDKIPKGMEIWNSNHTPKTWMQFS

VVWVSQEITQKIGLNKIKNYLKDFDYGNQDFSGDKERNNGLTEAWLESSLKISPEEQ

IQFLRKIINHNLPVRNSAIENTIDNMYLQDLENSTKLYGKTGAGFTANRTLQNGWFEG

FIISKSGHKYVFVSALTGSLGSNLTSSIKAKKNAITILNTLNL

SEQ ID No. 377:
MLLFMFSIISFGNENQFMKEIFERKGLNGTFVVYDLKNDKIDYYNLDRANERFYPASS

FKIFNTLIGLENGIVKNVDEMFYYYDGSKVFLDSWAKDSNLRYAIKVSQVPAYKKLAR

ELGKERMQEGLNKLNYGNKEIGSEIDKFWLEGPLKISAMEQVKLLNLLSQSKLPFKL

ENQEQVKDITILEKKDDFILHGKTGWATDNIWPIGWFVGWIETSDNIYSFAINLDISD

SKFLPKREEIVREYFKNINVIK

SEQ ID No. 378:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIATWNRDHNLI

TAMKYSVVPVYQEFARQIGEARMSKMLHAFDYGNEDISGNVDSFWLDGGIRISATE

QISFLRKLYHNKLHVSERSQRIVKQAMLTEANGDYIIRAKTGYSTRIEPKIGWWVGW

VELDDNVWFFAMNMDMPTSDGLGLRQAITKEVLKQEKIIP

SEQ ID No. 379:
MLSRYSKTLAFAVVACTLAISTATAHAELWRNDLKRVFDDAGVSGTFVLMDITADR

TYVVDPARAARSIHPASTFKIPNSLIAFDTGAVRDDQEVLPYGGKPQPYEQWEHDM

ALPEAIRLSAVPIYQEVARRVGFERMQAYVDAFDYGNRQLGSAIDQFWLRGPLEISA

FEEARFTSRMALKQLPVKPRTWDMVQRMLLIEQQGDAALYAKTGVATEYQPEIGW

WAGWVERAGHVYAFALNIDMPREGDMAKRIPLGKQLMRALEVWPAP

SEQ ID No. 380:
MRPLLFSALLLLSGHTQASEWNDSQAVDKLFGAAGVKGTFVLYDVQRQRYVGHDR

ERAETRFVPASTYKVANSLIGLSTGAVRSADEVLPYGGKPQRFKAWEHDMSLRDAI

KASNVPVYQELARRIGLERMRANVSRLGYGNAEIGQVVDNFWLVGPLKISAMEQTR

FLLRLAQGELPFPAPVQSTVRAMTLLESGPGWELHGKTGWCFDCTPELGWWVGW

VKRNERLYGFALNIDMPGGEADIGKRVELGKASLKALGILP

SEQ ID No. 381:
MNKGLHRKRLSKRLLLPMLLCLLAQQTQAVAAEQTKVSDVCSEVTAEGWQEVRRW

DKLFESAGVKGSLLLWDQKRSLGLSNNLSRAAEGFIPASTFKLPSSLIALETGAVRD

ETSRFSWDGKVREIAVWNRDQSFRTAMKYSVVPVYQQLAREIGPKVMAAMVRQLE

YGNQDIGGQADSFWLDGQLRITAFQQVDFLRQLHDNKLPVSERSQRIVKQMMLTE

ASTDYIIRAKTGYGVRRTPAIGWWVGWLELDDNTVYFAVNLDLASASQLPLRQQLV

KQVLKQEQLLP

SEQ ID No. 382:
MNTIISRRWRAGLWRRLVGAVVLPATLAATPAAYAADVPKAALGRITERADWGKLF

AAEGVKGTIVVLDARTQTYQAYDAARAEKRMSPASTYKIFNSLLALDSGALDNERAII

PWDGKPRRIKNWNAAMDLRTAFRVSCLPCYQVVSHKIGRRYAQAKLNEVGYGNRT

IGGAPDAYWVDDSLQISAREQVDFVQRLARGTLPFSARSQDIVRQMSIVEATPDYVL

HGKTGWFVDKKPDIGWWVGWIERDGNITSVAINIDMLSEADAPKRARIVKAVLKDLK

LI

SEQ ID No. 383:
MKTFAAYVITACLSSTALASSITENTFWNKEFSAEAVNGVFVLCKSSSKSCATNNLA

RASKEYLPASTFKIPNAIIGLETGVIKNEHQIFKWDGKPRAMKQWERDLSLRGAIQVS

AVPVFQQIAREVGEVRMQKYLKKFSYGNQNISGGIDKFWLEGQLRISAVNQVEFLE

SLFLNKLSASKENQLIVKEALVTEAAPEYLVHSKTGFSGVGTESNPGVAWWVGWVE

KGAEVYFFAFNMDIDNENKLPLRKSIPTKIMASEGIIGG

SEQ ID No. 384:
MRVLALSAVLVVASIVGMPAMANEWQEKPSWNTHFSEHKAQGVIVLWNENKQQGF

TNNLKRANQAFLPASTFKIPNSLIALDLGVVKDEHQVFKWDGQTRDIAAWNRDHDLI

TAMKYSVVPVYQEFARQIGQARMSKMLHAFDYGNEDISGNLDSFWLDGGIRISATE

QVAFLRKLYHNKLHVSERSQRIVKQAMLTEANSDYIIRAKTGYSTRIEPQIGWWVGW

VELDDNVWFFAMNMDMPTADGLGLRQAITKEVLKQEKIIP

SEQ ID No. 385:
MKKITLFLLFLNLVFGQDKILNNWFKEYNTSGTFVFYDGKTWASNDFSRAMETFSPA

STFKIFNALIALDSGVIKTKKEIFYHYRGEKVFLSSWAQDMNLSSAIKYSNVLAFKEVA

RRIGIKTMQEYLNKLHYGNAKISKIDTFWLDNSLKISAKEQAILLFRLSQNSLPFSQEA

MNSVKEMIYLKNMENLELFGKTGFNDGQKIAWIVGFVYLKDENKYKAFALNLDIDKF

EDLYKREKILEKYLDELVKKVKNDG

SEQ ID No. 386:
MSKKNFILIFIFVILISCKNTEKISNETTLIDNIFTNSNAEGTLVIYNLNDDKYIIHNKERAE

QRFYPASTFKIYNSLIGLNEKAVKDVDEVFYKLMAKSFLESWAKDSNLRYAIKNSQV

PAYKELARRIGIKKMKENIEKLDFGNKSIGDSVDTFWLEGPLEISAMEQVKLLTKLAQ

NELQYPIEIQKAISDITITRANLHITLHGKTGLADSKNMTTEPIGWFVGWLEENDNIYV

FALNIDNINSDDLAKRINIVKESLKALNLLK

SEQ ID No. 387:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALKMEMRSEMPASIRNELLMKSLKQLNII

SEQ ID No. 388:
MNIQALLLITSAIFISACSPYIVTANPNYSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRIGYGNADIGTQVDNFWLVGPLKI

TPQQEAQFAYKLANKTLPFSQKVQDEVQSMLFIEEKNGNKIYAKSGWGWDVNPQV

GWLTGWVVQPQGNIVAFSLNLEMKKGISSSVRKEITYRGLEQLGIL

SEQ ID No. 389:
MNIKALLLITSAIFISACSPYIVTANPNHSASKSDEKGEKIKNLFNEAHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 390:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 391:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 392:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQEVQDEVQSMLFIEEKNGNKIYAKSGWGWDVNPQV

GWLTGWVVQPQGNIVAFSLNLEMKKGIPSSVRKEITYKSLEQLGIL

SEQ ID No. 393:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 394:
MNIKALLLITSAIFISACSPYIVTANPNHSASKSDKKAEKIKNLFNEAHTTGVLVIQQGQ

TQQSYGNDLARASTEYVPASTFKMLNALIGLEHHKATTTEVFKWNGQKRLFPEWEK

DMTLGDAMKASAIPVYQDLARRIGLELMSNEVKRVGYGNADIGTQVDNFWLVGPLK

ITPQQEAQFAYKLANKTLPFSQKVQHEVQSMLFIEEKNGNKIYAKSGWGWDVDPQV

GWLTGWVVQPQGNIVAFSLNLEMKKGIPSSVRKEITYKSLEQLGIL

SEQ ID No. 395:
MNIKALLLITSAIFISACSPYIVTANPNHSASKSDEKAEKIKNLFNEAHTTGVLVIQQGQ

TQQSYGNDLARASTEYVPASTFKMLNALIGLEHHKTTTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 396:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTAVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGTPSSVRKEITYKSLEQLGIL

SEQ ID No. 397:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLPRRIGLELMSNEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 398:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEKLGIL

SEQ ID No. 399:
MNIKTLLLITSTIFISACSPYIVTANPNHSTSKSDEKAEKIKNLFNEAHTTGVLVIQQGQ

TQQSYGNDLARASIEYVPASTFKMLNALIGLEHHKATTTEIFKWDGQKRLFPEWEKD

MTLGDAMKASAIPVYQDLARRIGLELMSKEVKRVGYGNADIGTQVDNFWLVGPLKIT

PQQEAQFAYKLANKTLPFSLKVQDEVQSMLFIEEKNGNKIYAKSGWGWDVDPQVG

WLTGWVVQPQGNIVAFSLNLEMKKGIPSSVRKEITYKSLEQLGIL

SEQ ID No. 400:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAISVYQDLARRIGLELMSKEVKRVGYGNADIGTQVDNFWLAGPL

KITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 401:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASALPVYQDLARRIGLELMSKEVKRVGYGNADIGTQVDNFWLVGPL

KITPGQEAQFAYKLANKTLPFSQKVQDEVQSMLFIEEKNGNKIYAKSGWGWDVNPQ

VGWLTGWVVQPQGNIVAFSLNLEMKKGIPSSVRKEITYKSLEQLGIL

SEQ ID No. 402:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGSVVQPQGNIVAFSLNLEMKKGIPSSVRKEITYKSLEQLGIL

SEQ ID No. 403:
MNIKTLLLITSTIFISACSPYIVTANPNHSTSKSDEKAEKIKNLFNEAHTTGVLVIQQGQ

TQQSYGNDLARASIEYVPASTFKMLNALIGLEHHKATTTEIFKWDGQKRLFPEWEKD

MTLGDAMKASAIPVYQDLARRIGLELMSKEVKRVGYGNADIGTQVDNFWLVGPLKIT

PQQEAQFAYKLANKTLPFSLKAQDEVQSMLFIEEKNGNKIYAKSGWGWDVDPQVG

WLTGWVVQPQGNIVAFSLNLEMKKGIPSSVRKEITYKSLEQLGIL

SEQ ID No. 404:
MNIKALLLITSAIFISACSPYIVTANPNHSASKSDKKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 405:
MNIKTLLLITSAIFISACSHYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFTYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 406:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 407:
MNIKALLLITSTIFISACSPYIVTANPNHSASKSDEKAEKIKNLFNEAHTTGVLVIQQGQ

TQQSYGNDLARASTEYVPASTFKMLNALISLEHHKATTTEVFKWDGQKRLFPEWEK

DMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 408:
MNIQALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPHGNIVAFSLNLEMKKGIPSSVRKEITYKSLEQLGIL

SEQ ID No. 409:
MNIKALFLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 410:
MKLLKILSLVCLSISIGACAEHSMSRAKTSTIPQVNNSIIDQNVQALFNEISADAVFVTY

DGQNIKKYGTHLDRAKTAYIPASTFKIANALIGLENHKATSTEIFKWDGKPRFFKAWD

KDFTLGEAMQASTVPVYQELARRIGPSLMQSELQRIGYGNMQMGTEVDQFWLKGP

LTITPIQEVKFVYDLAQGQLPFKPEVQQQVKEMLYVERRGENRLYAKSGWGMAVD

PQVGWYVGFVEKADGQVVAFALNMQMKAGDDIALRKQLSLDVLDKLGVFHYL

SEQ ID No. 411:
MNIKALLLITSTIFISACSPYIVTANPNHSTSKSDEKAEKIKNLFNEAHTTGVLVIQQGQ

TQQSYGNDLARASTEYVPASTFKMLNALIGLEHHKATTTEIFKWDGQKRLFPEWEK

DMTLGDAMKASAIPVYQDLARRIGLELMSKEVKRVGYGNADIGTQVDNFWLVGPLK

ITPQQEAQFAYKLANKTLPFSLKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 412:
MNIKTLLLITSAIFISACSPYIVTANPNHSASKSDEKAEKIKNLFNEVHTTGVLVIRQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEMNGNKIYAKSGWGWDVDPQV

GWLTGWVVQPQGNIVAFSLNLEMKKGIPSSVRKEITYKSLEQLGIL

SEQ ID No. 413:
MKLLKILSLVCLSISIGACAEHSMSRAKTSTIPQVNNSIIDQNVQALFNEISGDAVFVTY

DGQNIKKYGTHLDRAKTAYIPASTFKIANALIGLENHKATSTEIFKWDGKPRFFKAWD

KDFTLGEAMQASTVPVYQELARRIGPSLMQSELQRIGYGNMQIGTEVDQFWLKGPL

TITPIQEVKFVYDLAQGQLPFKPEVQQQVKEMLYVERRGENRLYAKSGWGMAVDP

QVGWYVGFVEKADGQVVAFALNMQMKAGDDIALRKQLSLDVLDKLGVFHYL

SEQ ID No. 414:
MKKFILPIFSISILVSLSACSSIKTKSEDNFHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMDVTPQV

GWLTGWVEQANGKKIPFSLNLEMKEGMSGSIRNEITYKSLENLGII

SEQ ID No. 415:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYWIESSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 416:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 417:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAILVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 418:
MNIKALLLITSAIFISACSPYIVTANPNHSASKSDKKAEKIKNLFNEAHTTGVLVIQQGQ

TQQSYGNDLARASTEYVPASTFKMLNALIGLEHHKATTTEVFKWNGQKRLFPEWEK

DMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 419:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 420:
MNIKALLLITSAIFISACSPYIVTTNPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNTDIGTQVDNFWVVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 421:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIQVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 422:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASALPVYQDLARRIGLELMSKEVKRVGYGNADIGTQVDNFWLVGPL

KITPQQEAQFAYKLANKTLPFSQKVQDEVQSMLFIEEKNGNKIYAKSGWGWDVNPQ

VGWLTGWVVQPQGNIVAFSLNLEMKKGIPSSVRKEITYKSLEQLGIL

SEQ ID No. 423:
MNIKTLLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEMNGNKIYAKSGWGWDVDPQV

GWLTGWVVQPQGNIVAFSLNLEMKKGIPSSVRKEITYKSLEQLGIL

SEQ ID No. 424:
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWDGEKRLFPEWEK

NMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFPLNLEMKKGIPSSVRKEITYKSLEQLGIL

SEQ ID No. 425:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGGDVNPQV

GWLTGWVVQPQGNIVAFSLNLEMKKGIPSSVRKEITYKSLEQLGIL

SEQ ID No. 426:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAILVYQDLARRIGLELMSKEVKRVGYGNADIGTQVDNFWLVGPLKI

TPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 427:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 428:
MNIKALLLITSAIFISACSPYIVTANPNHSASKSDEKAEKIKNLFNEAHTTGVLVIQQGQ

TQQSYGNDLARASTEYVPASTFKMLNALIGLEHHKTTTTEVFKWDGQKRLFPEWEK

DMTLGDAMKASAIPVYQDLARRIGLELMSKEVKRVGYGNADIGTQVDNFWWGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 429:
MSKKNFILIFIFVILISCKNTEKISNETTLIDNIFTNSNAEGTLVIYNLNDDKYIIHNKERAE

QRFYPASTFKIYNSLIGLNEKAVKDVDEVFYKYNGEKVFLESWAKDSNLRYAIKNSQ

VPAYKELARRIGLKKMKENIEKLDFGNKSIGDSVDTFWLEGPLEISAMEQVKLLTKLA

QNELPYPIEIQKAVSDITILEQTYNYTLHGKTGLADSKNMTTEPIGWFVGWLEENDNI

YVFALNIDNINSDDLAKRINIVKESLKALNLLK

SEQ ID No. 430:
MSKKNFILIFIFVILTSCKNTEKISNETTLIDNIFTNSNAEGTLVIYNLNDDKYIIHNKERA

EQRFYPASTFKIYNSLIGLNEKAVKDVDEVFYKYNGEKVFLESWAKDSNLRYAIKNS

QVPAYKELARRIGLKKMKENIEKLDFGNKSIGDSVDTFWLEGPLEISAMEQIKLLTKL

AQNELPYPIEIQKAVSDITILEQTYNYTLHGKTGLADSKNMTTEPIGWFVGWLEENDN

IYVFALNIDNINSDDLAKRINIVKESLKALNLLK

SEQ ID No. 431:
LLITSAIFISACSPYIVSANPNHSASKSDDKAEKIKNLFNEAHTTGVLVIQQGQTQQSY

GNDLARASTEYVPASTFKMLNALIGLEHHKATTTEVFKWDGQKRLFPEWEKNMTLG

DAMKASAIPVYQDLARRIGLELMSNEVKRVGYGNADIGTQVDNFWLVGPLKITPQQ

EAQFAYKLANKTLPFSQKVQDEVQSMLFIEEKNGNKIYAKSGWGWDVDPQVGWLT

GWVVQPQGNIVAFSLNLEMKKGIPSSVRKEITYKSL

SEQ ID No. 432:
LLITSAIFISACSPYIVSANPNHSASKSDEKAEKIKNLFNEAHTTGVLVIQQGQTQQSY

GNDLARASTEYVPASTFKMLNALIGLEHHKATTTEVFKWDGQKRLFPEWEKNMTLG

DAMKASAIPVYQDLARRIGLELMSNEVKRVGYGNADIGTQVDNFWLVGPLKITPQQ

EAQFAYKLANKTLPFSQKVQDEVQSMLFIEEKNGNKIYAKSGWGWDVNPQVGWLT

EWVVQPQGNIVAFSLNLEMKKGIPSSVRKEITYKSL

SEQ ID No. 433:
MTVRRLSCALGAALSLSALGGGPVQAAVLCTVVADAADGRILFQQGTQQACAERYT

PASTFKLAIALMGADAGILQGPHEPVWNYQPAYPDWGGDAWRQPTDPARWIKYSV

VWYSQLTAKALGQDRFQRYTSAFGYGNADVSGEPGKHNGTDGAWIISSLRISPLEQ

LAFLRKLVNRQLPVKAAAYELAENLFEAGQADGWRLYGKTGTGSPGSNGVYTAAN

AYGWFVGWARKDGRQLVYARLLQDERATRPNAGLRARDELVRDWPAMAGAWRP

SEQ ID No. 434:
MNIKALLLITSAIFISACSPYIVSANPNHSASKSDEKAEKIKNLFNEAHTTGVLVIQQGQ

TQQSYGNVLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQEVQDEVQSMLFIEEKNGNKIYAKSGWGWDVNPQV

GWLTGWVVQPQGNIVAFSLNLEMKKGIPSSVRKEITYKSLEQLGIL

SEQ ID No. 435:
MKTFAAYVIIACLSSTALAGSITENTSWNKEFSAEAVNGVFVLCKSSSKSCATNDLAR

ASKEYLPASTFKIPSAIIGLETGVIKNEHQVFKWDGKPRAMKQWERDLTLRGAIQVS

AVPVFQQIAREVGEVRMQKYLKKFSYGNQNISGGIDKFWLEDQLRISAVNQVEFLES

LYLNKLSASKENQLIVKEALVTEAAPEYLVHSKTGFSGVGTESNPGVAWWVGWVEK

ETEVYFFAFNMDIDNESKLPLRKSIPTKIMESEGIIGG

SEQ ID No. 436:
MNIKTLLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 437:
MNIKALLLITSAIFISACSPYIVTTNPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNTDIGTQVDNFWLVGPLKI

TPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 438:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAVPVYQDLARRIGLELMSKEVKRVGYGNADIGTQVDNFWLVGPL

KITPQQEAQFAYKLANKTLPFSQKVQDEVQSMLFIEEKNGNKIYAKSGWGWDVNQ

QVGWLTGWVVQPQGNIVAFSLNLEMKKGIPSSVRKEITYKSLEQLGIL

SEQ ID No. 439:
MNIKTLLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEMTYKSLEQLGIL

SEQ ID No. 440:
MNKYFTCYVVASLFFSGCTVQHNLINETQSQIVQGHNQVIHQYFDEKNTSGVLVIQT

DKKINLYGNALSRANTEYVPASTFKMLNALIGLENQKTDINEIFKWKGEKRSFTTWE

KDMTLGEAMKLSAVPVYQELARRIGLDLMQKEVERIDFGNAEIGQQVDNFWLIGPLK

VTPIQEVEFVSQLAHTQLPFSEKVQANVKNMLLLEENNGYKIFGKTGWAMDIKPQV

GWLTGWVEQPDGKIVAFALNMEMRSEMPASIRNELLMKSLKQLNII

SEQ ID No. 441:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAAMDIKPQ

VGWLTGWVEQPDGKIVAFALNMEMRSEMPASIRNELLMKSLKQLNII

SEQ ID No. 442:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFLLEGQLRISAVNQVEFLE

SLFLNKLSASKENQLIVKEALVTEAAPEYLVHSKTGFSGVGTESNPGVAWWVGWVE

KGTEVYFFAFNMDIDNENKLPLRKSIPTKIMASEGIIGG

SEQ ID No. 443:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGDADPSTSNGDYWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 444:
MNIKALLLITSAIFISACSPYIVTANPNHSASKSDKKAEKIKNLFNEAHTTGVLVIQQGQ

TQQSYGNDLARASTEYVPASTFKMLNALIGLEHHKASTTEVFKWNGQKRLFPEWEK

DMTLGDAMKASAIPVYQDLARRIGLELMSNEVKRVGYGNADIGTQVDNFWLVGPLK

ITPQQEAQFAYKLANKTLPFSQKVQDEVKSMLFIEEKNGNKIYAKSGWGWDVDPQV

GWLTGWVVQPQGNIVAFSLNLEMKKGIPSSVRKEITYKSLEQLGIL

SEQ ID No. 445:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKHVGYGNADIGTQVDNFWLVGPLK

ITPQQEAQFAYKLANKTLPFSPKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 446:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKHVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 447:
MKKFILPILSISTLLSVSACSSIQTKFEDTFHTSNQQHEKAIKSYFDEAQTQGVIIIKKG

KNISTYGNNLTRAHTEYVPASTFKMLNALIGLENHKATTTEIFKWDGKKRSYPMWEK

DMTLGDAMALSAVPVYQELARRTGLDLMQKEVKRVGFGNMNIGTQVDNFWLVGPL

KITPIQEVNFADDFANNRLPFKLETQEEVKKMLLIKEFNGSKIYAKSGWGMDVTPQV

GWVEKSNGEKVAFSLNIEMKQGMPGSIRNEITYKSLENLGII

SEQ ID No. 448:
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQEVQDEVQSILFIEEKNGNKIYAKSGWGWDVNPQV

GWLTGWVVQPQGNIVAFSLNLEMKKGIPSSVRKEITYKSLEQLGIL

SEQ ID No. 449:
MKKFILPIFSISILVSLSACSSIKTKSEDNPHISSQQHEKAIKSYFDEAQTQGVIIIKEGK

NLSTYGNALARANKEYVPASTFKMLNALIGLENHKATTNEIFKWDGKKRTYPMWEK

DMTLGEAMALSAVPVYQELARRTGLELMQKEVKRVNFGNTNIGTQVDNFWLVGPL

KITPVQEVNFADDLAHNRLPFKLETQEEVKKMLLIKEVNGSKIYAKSGWGMGVTSQV

GWLTGWVEQANGKKIPFSLNLEMKEGMSGSIRNEITYKSLENLGII

SEQ ID No. 450:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIATWNRDHNLI

TAMKYSVVPVYQEFARQIGEARMSKMLHAFDYGNEDISGNVDSFWLDGGIRISATE

QISFLRKLYHNKLHVSERSQRIVKQAMLTEANGDYIIRAKTGYSARIEPKIGWWVGW

VELDDNVWFFAMNMDMPTSDGLGLRQAITKEVLKQEKIIP

SEQ ID No. 451:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAVPVYQDLARRIGLELMSKEVKRVGYGNADIGTQVDNFWLVGPL

KITPQQEAQFAYKLANKTLPFSQKVQDEVQSMLFIEEKNGNKIYAKSGWGLDVNPQ

VGWLTGWVVQPQGNIVAFSLNLEMKKGIPSSVRKEITYKSLEQLGIL

SEQ ID No. 452:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAVPVYQDLARRIGLELMSKEVKRVGYGNADIGTQVDNFWLVGPL

KITPQQEAQFAYKLANKTLPFSQKVQDEVQSMLFIEEKNGNKIYAKSGWGLDVNLQ

VGWLTGWVVQPQGNIVAFSLNLEMKKGIPSSVRKEITYKSLEQLGIL

SEQ ID No. 453:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEKLGIL

SEQ ID No. 454:
MNIKALLLITSAIFISACSPYIVTANPNHSASKSDVKAEKIRNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 455:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDSKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 456:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDGVQSMLFIEEKNGNKIYAKSGWGWDVNPQ

VGWLTGWVVQPQGNIVAFSLNLEMKKGIPSSVRKEITYKSLEQLGIL

SEQ ID No. 457:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDSKKRLFPEWEK

DMTLGDAMKASAILVYQDLARRIGLELMSKEVKRVGYGNADIGTQVDNFWLVGPLKI

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 458:
MKLLKILSLVCLSISIGACAEHSMSRAKTSTIPQVNNSIIDQNVQALFNEISADAVFVTY

DGQNIKKYGTHLDRAKTAYIPASTFKIANALIGLENHKATSTEIFKWDGKPRFLKAWD

KDFTLGEAMQASTVPVYQELARRIGPSLMQSELQRIGYGNMQIGTEVDQFWLKGPL

TITPIQEVKFVYDLAQGQLPFKPEVQQQVKEMLYVERRGENRLYAKSGWGMAVDP

QVGWYVGFVEKADGQVVAFALNMQMKAGDDIALRKQLSLDVLDKLGVFHYL

SEQ ID No. 459:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDVKPQ

VGWLTGWVEQPDGKIVAFALNMEMRSEMPASIRNELLMKSLKQLNII

SEQ ID No. 460:
MNKYFTCYVVASLFLSGCTVQHNLINETPSQIVQGHNQVIHQYFDEKNTSGALVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPV

GWLTGWVEQPDGKIVAFALNMEMRSEMPASIRNELLMKSLKQLNII

SEQ ID No. 461:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASIRNELMMKSLKQLNII

SEQ ID No. 462:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLAGWVEQPDGKIVAFALNMEMRSEMPASIRNELLMKSLKQLNII

SEQ ID No. 463:
MNKYFTCYVVASLFLSGCTVQHNLINETPSQIVQGHNQVIHQYFDERNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASIRNELLMKSLKQLNII

SEQ ID No. 464:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEKSNGYKIFGKTGWAMDIKPQV

GWLTGWVEQPDGKIVAFALNMEMRSEMPASIRNELLMKSLKQLNII

SEQ ID No. 465:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASTRNELLMKSLKQLNII

SEQ ID No. 466:
MKKFILPIFSISILLSLSACSSIQTKFEDTFHISNQKHEKAIKSYFDEAQTQGVIIIKEGKN

ISSYGNNLVRAHTEYVPASTFKMLNALIGLENHKATTNEIFKWDGKKRSYPMWEKD

MTLGEAMALSAVPVYQDLARRIGLNLMQKEVKRVGFGNMNIGTQVDNFWLIGPLKI

TPIQEVNFADDLANNRLPFKLETQEEVKKMLLIKEVNGSKIYAKSGWGMDVSPQVG

WLTGWVEKSNGEKVSFSLNIEMKQGMSGSIRNEITYKSLENLGII

SEQ ID No. 467:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAMKASAIAVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 468:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAIKASAIPVYQDLARRIGLELMSKEVKRVGYGNADIGTQVDNFWLVGPLKI

TPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 469:
MKILIFLPLLSCLGLTACSLPVSSLPSQSISTQAIASLFDQAQSSGVLVIQRDQQVQVY

GNDLNRANTEYVPASTFKMLNALIGLQHGKATTNEIFKWDGKKRSFTAWEKDMTLG

QAMQASAVPVYQELARRIGLELMQQEVQRIQFGNQQIGQQVDNFWLVGPLKVTPK

QEVQFVSALAREQLAFDPQVQQQVKAMLFLQERKAYRLYVKSGWGMDVEPQVGW

LTGWVETPQAEIVAFSLNMQMQNGIDPAIRLEILQQALAELGLYPKAEG

SEQ ID No. 470:
MHKHMSKLFIAFLAFLLSVPAAAEDQTLAELFAQQGIDGTIVISSLHNGKTFIHNDPRA

KQRFSTASTFKILNTLISLEEKAISGKDDVLKWDGHIYDFPDWNRDQTLESAFKVSCV

WCYQALARQVGAEKYRNYLRKSVYGELREPFEETTFWLDGSLQISAIEQVNFLKKV

HLRTLPFSASSYETLRQIMLIEQTPAFTLRAKTGWATRVKPQVGWYVGHVETPTDV

WFFATNIEVRDEKDLPLRQKLTRKALQAKGIIE

SEQ ID No. 471:
MKTFAAYVITACLSSTALASSITENTSWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGTDKFWLEDQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

SEQ ID No. 472:
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAILVYQDLARRIGLELMSKEVKRVGYGNADIGTQVDNFWLVGPLKI

TPQQEAQFAYKLANKTLPFSQKVQDEVQSMLFIEEKNGNKIYAKSGWGLDVDPQV

GWLTGWVVQPQGNIVAFSLNLEMKKGIPSSVRKEITYKSLEQLGIL

SEQ ID No. 473:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIQVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 474:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAMPVYQDLARRIGLELMSKEVKRVGYGNADIGTQVDNFWLVGPL

KITPQQEAQFAYKLANKTLPFSQKVQDEVQSMLFIEEKNGNKIYAKSGWGWDVNPQ

VGWLTGWVVQPQGNIVAFSLNLEMKKGIPSSVRKEITYKSLEQLGIL

SEQ ID No. 475:
MNIKALLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGKKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 476:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIATWNRDHNLI

TAMKYSVVPVYQEFARQIGEARMSKMLHAFDYGNEDISGNVDSFWLDGGIRISATE

QISFLRKLYHNKLHVSERSQRIVKQAMLTEANGDYIIRAKTGYDTKIGWWVGWVELD

DNVWFFAMNMDMPTSDGLGLRQAITKEVLKQEKIIP

SEQ ID No. 477:
MSKKNFILIFIFVILISCKNTEKTSNETTLIDNIFTNSNAEGTLVIYNLNDDKYIIHNKERA

EQRFYPASTFKIYNSLIGLNEKAVKDVDEVFYKYNGEKVFLESWAKDSNLRYAIKNS

QVPAYKELARRIGLEKMKENIEKLDFGNKNIGDSVDTFWLEGPLEISAMEQVKLLTKL

AQNELPYPIEIQKAVSDITILEQTDNYTLHGKTGLADSENMTTEPIGWLVGWLEENNN

IYVFALNIDNINSDDLAKRINIVKESLKALNLLK

SEQ ID No. 478:
MNIKALFLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 479:
MNIKALFLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPSSQKVQDEVQSMLFIEEKNGNKMYAKSGWGWDVNPQ

VGWLTGWVVQPQGNIVAFSLNLEMKKGIPSSVRKEITYKSLEQLGIL

SEQ ID No. 480:
MNIKALFLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWVVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEIAYKSLEQLGIL

SEQ ID No. 481:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDCWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 482:
MNIKTLLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWVVGPLK

ITPQQEAQFAYKLANKTLPFSPKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 483:
MNIKTLLLITSAIFISACSPYIVTANPNHSASKSDEKAEKIKNLFNEVHTTGVLVIQQGQ

TQQSYGNDLARASTEYVPASTFKMLNALIGLEYHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 484:
MAIRFLTILLSTFFLTSFVHAQEHVVVRSDWKKFFSDLQAEGAIVIADERQAEHALLV

FGQERAAKRYSPASTFKLPHTLFALDAGAVRDEFQVFRWDGVKRSFAGHNQDQDL

RSAMRNSAVWVYELFAKEIGEDNARRYLKQIDYGNADPSTIKGNYWIDGNLEISAHE

QISFLRKLYRNQLPFQVEHQRLVKYLMITEAGRNWILRAKTGWEGRFGWWIGWVE

WPTGPVFFALNIDTPNRTDDLFKREAIARAILRSIDALPPN

SEQ ID No. 485:
MRVLALSAVFLVASIIGMPAVAKEWQENKSWNAHFTEHKSQGVVVLWNENKQQGF

TNNLKRANQAFLPASTFKIPNSLIALDLGVVKDEHQVFKWDGQTRDIAAWNRDHDLI

TAMKYSVVPVYQEFARQIGEARMSKMLHAFDYGNEDISGNVDSFWLDGGIRISATQ

QIAFLRKLYHNKLHVSERSQRIVKQAMLTEANGDYIIRAKTGYSTRIEPKIGWWVGW

VELDDNVWFFAMNMDMPTSDGLGLRQAITKEVLKQEKIIP

SEQ ID No. 486:
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKSQV

GWLTGWVEQPDGKIVAFALNMEMRSEMPASIRNELLMKSLKQLNII

SEQ ID No. 487:
MNIKALLLITSAIFISACSPYIVTANPNHSASKSDVKAEKIKNLFNEAHTTGVLVIQQGQ

TQQSYGNDLARASTEYVPASTFKMLNALIGLEHHKATTTEVFKWDGKKRLFPEWEK

DMTLGDAMKASAISVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 488:
MAIRIFAILFSIFSLATFAHAQEGTLERSDWRKFFSEFQAKGTIVVADERQADRAMLV

FDPVRSKKRYSPASTFKIPHTLFALDAGAVRDEFQIFRWDGVNRGFAGHNQDQDLR

SAMRNSTVWVYELFAKEIGDDKARRYLKKIDYGNADPSTSNGDYWIEGSLAISAQE

QIAFLRKLYRNELPFRVEHQRLVKDLMIVEAGRNWILRAKTGWEGRMGWWVGWVE

WPTGSVFFALNIDTPNRMDDLFKREAIVRAILRSIEALPPNPAVNSDAAR

SEQ ID No. 489:
MKTIAAYLVLVFYASTALSESISENLAWNKEFSSESVHGVFVLCKSSSNSCTTNNAA

RASTAYIPASTFKIPNALIGLETGAIKDERQVFKWDGKPRAMKQWEKDLKLRGAIQV

SAVPVFQQIAREVGEIRMQKYLNLFSYGNANIGGGIDKFWLEGQLRISAFNQVKFLE

SLYLNNLPASKANQLIVKEAIVTEATPEYIVHSKTGYSGVGTESSPGVAWWVGWVE

KGTEVYFFAFNMDIDNESKLPSRKSISTKIMASEGIIGG

SEQ ID No. 490:
MKTFAAYVITACLSSTALASSITENTFWNKEFSAEAVNGVFVLCKSSSKLACATNNLA

RASKEYLPASTFKIPNAIIGLETGVIKNEHQIFKWDGKPRAMKQWERDLSLRGAIQVS

AVPVFQQIAREVGEVRMQKYLKKFSYGNQNISGGIDKFWLEGQLRISAVNQVEFLE

SLFLNKLSASKENQLIVKEALVTEAPEYLVHSKTGFSGVGTESNPGVAWWVGWVEK

GAEVYFFAFNMDIDNENKLPLRKSIPTKIMASEGIIGG

SEQ ID No. 491:
MAIRIFAILFSTFVFGTFAHAQEGMRERSDWRKFFSEFQAKGTIVVADERQTDRVILV

FDQVRSEKRYSPASTFKIPHTLFALDAGAARDEFQVFRWDGIKRSFAAHNQDQDLR

SAMRNSTVWIYELFAKEIGEDKARRYLKQIDYGNADPSTSNGDYWIDGNLAIAAQEQ

IAFLRKLYHNELPFRVEHQRLVKDLMIVEAGRNWILRAKTGWEGRMGWWVGWVE

WPTGPVFFALNIDTPNRMDDLFKREAIVRAILRSIEALPPNPAVNSDAAR

SEQ ID No. 492:
MKTFAAYVIIACLSSTALAGSITENTSWNKEFSAEAVNGVFVLCKSSSKSCATNDLAR

ASKEYLPASTFKIPNAIIGLETGVIKNEHQVFKWDGKPRAMKQWERDLTLRGAIQVS

AVPVFQQIAREVGEVRMQKYLKKFSYGSQNISGGIDKFWLEDQLRISAVNQVEFLES

LYLNKLSASKENQLIVKEALVTEAAPEYLVHSKTGFSGVGTESNPGVAWWVGWVEK

ETEVYFFAFNMDIDNESKLPLRKSIPTKIMESEGIIGG

SEQ ID No. 493
MNKYFTCYVVASLFLSGCTVQHNLINETPSQIVQGHNQVIHQYFDEKNTSGVLVIQT

DKKINLYGNALSRANTEYVPASTFKMLNALIGLENQKTDINEIFKWKGEKRSFTAWE

KDMTLGEAMKLSAVPVYQELARRIGLDLMQKEVKRIGFGNAEIGQQVDNFWLVGPL

KVTPIQEVEFVSQLAHTQLPFSEKVQANVKNMLLLEESNGYKIFGKTGWAMDIKPQV

GWLTGWVEQPDGKIVAFALNMEMRSEMPASIRNELLMKSLKQLNII

SEQ ID No. 494
MKKLSVLLWLTLFYCGTIWAQSTCFLVQENQTVLKHEGKDCNKRFAPESTFKIALSL

MGFDSGILKDTLNPEWPYKKEYELYLNVWKYPHNPRTWIRDSCVWYSQVLTQQLG

MTRFKNYVDAFHYGNQDISGDKGQNNGLTHSWLSSSLAISPSEQIQFLQKIVNKKLS

VNPKAFTMTKDILYIQELAGGWKLYGKTGNGRQLTKDKSQKLSLQHGWFIGWIEKD

GRVITFTKHIADSKKHVTFASFRAKNETLNQLFYLINELEK

SEQ ID No. 495
MNIKTLLLITSAIFISACSPYIVTANPNHSASKSDEKAEKIKNLFNEVHTTGVLVIQQGQ

TQQSYGNDLARASTEYVPASTFKMLNALIGLEHHKATTTEVFKWDGQKRLFPEWEK

DMTLGDAMKASAIPVYQDLARRIGLELMSKEVKRVGYGNADIGTQVDNFWLVGPLK

ITPQQEAQFAYKLANKTLPFSPKVQDEVQSMLFIEEKNGNKIYAKSGWGWDVDPQV

GWVVQPQGNIVAFSLNLEMKKGIPSSVRKEITYKSLEQLGIL

SEQ ID No. 496
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYSVVWYSQQV

AHHLGAQRFAQYAKAFGYGNADVSGDPGQNNGLDRAWIGSSLQISPLEQLEFLGK

MLNRKLPVSPTAVDMTERIVESTTLADGTWHGKTGVSYPLLADGTRDWARGSGW

FVGWIVRGNQTLVFARLTQDERKQPVSAGIRTREAFLRDLPRLLAAR

SEQ ID No. 497
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYPVVWYSQQV

AHHLGAQRFAQYAKAFGYGNADVSGDPGQNNGLDRAWIGSSLQISPLEQLEFLGK

MLNRKLPVSPTAVDMTERIVESTTLADGTVVHGKTGVSYPLLADGTRDWARGSGW

FVGWIVRGKQTLVFARLTQDERKQPVSAGIRTREAFLRDLPRLLAAR

SEQ ID No. 498
MRGKHTVILGAALSALFAGAAGAQMLECTLVADAASGQELYRKGACDKAFAPMSTF

KVPLAVMGYDAGILVDAHNPRWDYKPEFNGYKFQQKTTDPTIWEKDSIVWYSQQLT

RKMGQKRFAAYVAGFGYGNGDISGEPGKSNGLTHSWLGSSLKISPEGQVRFVRDL

LSAKLPASKDAQQMTVSILPHFAAGDWAVQGKTGTGSFIDARGAKAPLGWFIGWAT

HEERRVVFARMTAGGKKGEQPAGPAARDAFLKALPDLAKRF

SEQ ID No. 499
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYSVVWYSQQV

AHHLGAQRFAQYAKAFGYGNADVSGDPGQNNGLDRAWIGSSLQISPLEQLEFLGK

MLDRKLPVSPTAVDMTERIVESTTLADGTVVHGKTGVSYPLLADGTRDWARGSGW

FVGWIVRGKQTLVFARLTQDERKQPVSAGIRTREAFLRDLPRLLAAR

SEQ ID No. 500
MKFRHALSSAFVLLGCIAASAHAKTICTAIADAGTGKLLVQDGDCGRRASPASTFKIA

ISLMGYDAGFLRNEHDPVLPYRDSYIAWGGEAWKQPTDPTRWLKYSVVWYSQQV

AHHLGAQRFAQYAKAFGYGNADVSGDPGQNNGLDRAWIGSSLQISPLEQLEFLGK

MLNRKLPVSPTAVDMTERIVESTTILADGTVVHGKTGVSYPLLADGTRDWARGSGW

FVGWIVRGKQTLVFARLTQDERKQPVSAGIRTREAFLRDLPRLLAAR

SEQ ID No. 501
MKTFAAYVIIACLSSTALAGSITENTSWNKEFSAEAVNGVFVLCKSSSKSCATNDLAR

ASKEYLPVSTFKIPSAIIGLETGVIKNEHQVFKWDGKPRAMKQWERDLTLRGAIQVS

AVPVFQQIAREVGEVRMQKYLKKFSYGNQNISGGIDKFWLEGQLRISAVNQVEFLE

SLYLNKLSASKENQLIVKEALVTEAAPEYLVHSKTGFSGVGTESNPGVAWWVGWVE

KETEVYFFAFNMDIDNESKLPLRKSIPTKIMESEGIIGG

SEQ ID No. 502
MNIKALLLITSAIFISACSPYIVTANPNHSASKSDEKAEKIKNLFNEAHTTGVLVIQQGQ

TQQSYGNDLARASTEYVPASTFKMLNALIGLEHHKATTTEVFKWDGKKRLFPEWEK

DMTLGDAMKASAIPVYQDLARRIGLELMSKEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 503
MNIKALLLITSAIFISACSPYIVSANPNHSASKSDEKAEKIKNLFNEAHTTGVLVIQQGQ

TQQSYGNDLARASTEYVPASTFKMLNALIGLEHHKATTTEVFKWDGQKRLFPEWEK

NMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVNPQV

GWLTGWVVQPQGNIVAFSLNLEMKKGIPSSVRKEITYKSLEQLGIL

SEQ ID No. 504
MKTFAAYVITACLSSTALASSITENTFWNKEFSAEAVNGVFVLCKSSSKSCATNNLA

RASKEYLPASTFKIPNAIIGLETGVIKNEHQVFKWDGKPRAMKQWERDLSLRGAIQV

SAVPVFQQIAREVGEVRMQKYLKKFSYGNQNISGGIDKFWLEGQLRISAVNQVEFL

ESLFLNKLSASKENQLIVKEALVTEAAPEYLVHSKTGFSGVGTESNPGVAWWVGWV

EKGTEVYFFAFNMDIDNENKLPLRKSIPTKIMASEGIIGG

-continued

SEQ ID No. 505
MKTIAAYLVLVFFAGTALSESISENLAWNKEFSSESVHGVFVLCKSSSNSCTTNNAT

RASTAYIPASTFKIPNALIGLETGAIKDARQVFKWDGKPRAMKQWEKDLTLRGAIQV

SAVPVFQQIARDIGKKRMQKYLNLFSYGNANIGGGIDKFWLEGQLRISAVNQVKFLE

SLYLNNLPASKANQLIVKEAIVTEATPEYIVHSKTGYSGVGTESNPGVAWWVGWVE

KGTEVYFFAFNMDIDNESKLPSRKSIPTKIMASEGIIIGG

SEQ ID No. 506
MKKFILPIFSISILVSLSACSSIKTKSEDNFHISSQQHEKAIKSYFDEAQTQGVIIIKEGK

NLSTYGNALARANKEYVPASTFKMLIALIGLENHKATTNEIFKWDGKKRTYPMWEKD

MTLGEAMALSAVPVYQELARRTGLELMQKEVKRVNFGNTNIGTQVDNFWLVGPLKI

TPVQEVNFADDLAHNRLPFKLETQEEVKKMLLIKEVNGSKIYAKSGWGMGVTPQVG

WLTGWVEQANGKKIPFSLNLEMKEGMSGSIRNEITYKSLENLGII

SEQ ID No. 507
MNIKALLLITSAIFISACSPYIVTANPNHSASKSDDKAEKIKNLFNEAHTTGVLVIHQGQ

TQQSYGNDLARASTEYVPASTFKMLNALIGLEHHKATTTEVFKWNGQKRLFPEWEK

DMTLGDAMKASAIPVYQDLARRIGLELMSNEVKRVGYGNADIGTQVDNFWLVGPLK

ITPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL

SEQ ID No. 508
MNIKALLLITSAISISACSPYIVTANPNHSASKSDEKAEKIKNLFNEAHTTGVLVIQQGQ

TQQSYGNDLARASTEYVPASTFKMLNALIGLEHHKATTTEVFKWDGQKRLFPEWEK

DMTLGDAIKASAIPVYQDLARRIGLELMSKEVKRVGYGNADIGTQVDNFWLVGPLKI

TPQQEAQFAYKLANKTLPFSQKVQDEVQSMLFIEEKNGNKIYAKSGWGWDVDPQV

GWLTGWVVQPQGNIVAFSLNLEMKKGIPSSVRKEITYKSLEQLGIL said peptides being chosen, preferably, from the peptides of sequence SEQ ID No. 509 to SEQ ID No. 523, SEQ ID No. 525 to SEQ ID No. 572, SEQ ID No. 574 to SEQ ID No. 604, SEQ ID No. 606 to SEQ ID No. 618, SEQ ID No. 620 to SEQ ID No. 696, SEQ ID No. 698 to SEQ ID No. 1077 and SEQ ID No. 1098 to SEQ ID No. 1109, as defined hereafter:

| Peptide SEQ ID No. | Amino acid sequence | Position of the peptide in the OXA protein(s) | Clinical interest |
|---|---|---|---|
| SEQ ID No. 509 | AAAYELAENLFEAGQADGWR | 183-202 for the protein of SEQ No. 433 | 2d |
| SEQ ID No. 510 | AAEGFIPASTFK | 86-97 for the protein of SEQ No. 381 | 2df |
| SEQ ID No. 511 | AALGR | 41-45 for the protein of SEQ No. 382 | 2df |
| SEQ ID No. 512 | ADGQVVAFALNMQMK | 241-255 for the proteins of SEQ No. 410, 413, 458 | 2df |
| SEQ ID No. 513 | ADINEIFK | 95-102 for the protein of SEQ No. 366 | 2df |
| SEQ ID No. 514 | ADWGK | 50-54 for the protein of SEQ No. 382 | 2df |
| SEQ ID No. 515 | AEGAIVISDER | 40-50 for the proteins of SEQ No. 369, 372 | OXA |
| SEQ ID No. 516 | AFALNLDIDK | 222-231 for the protein of SEQ No. 385 | 2d |

-continued

| Peptide SEQ ID No. | Amino acid sequence | Position of the peptide in the OXA protein(s) | Clinical interest |
|---|---|---|---|
| SEQ ID No. 517 | AFAPMSTFK | 49-57 for the protein of SEQ No. 498; 60-68 for the protein of sequence SEQ ID No. 351 | OXA |
| SEQ ID No. 518 | AFGYGNADVSGDPGQNNGLDR | 127-147 for the proteins of SEQ No. 496, 497, 499, 500 | 2d |
| SEQ ID No. 519 | AFTMTK | 174-179 for the protein of SEQ No. 494 | 2d |
| SEQ ID No. 520 | AGDDIALR | 256-263 for the proteins of SEQ No. 410, 413, 458 | 2df |
| SEQ ID No. 521 | AGHVYAFALNIDMPR | 233-247 for the protein of SEQ No. 379 | 2df |
| SEQ ID No. 522 | AGLWR | 11-15 for the protein of SEQ No. 382 | 2df |
| SEQ ID No. 523 | AHTEYVPASTFK | 73-84 for the proteins of SEQ No. 447, 466 | 2df |
| SEQ ID No. 524 | AIIPWDGK | 112-119 for the protein of SEQ No. 382 | 2df |
| SEQ ID No. 525 | AIIPWDGKPR | 112-121 for the protein of SEQ No. 382 | 2df |
| SEQ ID No. 526 | AISDITITR | 190-198 for the protein of SEQ No. 386 | 2d |
| SEQ ID No. 527 | AISGK | 82-86 for the protein of SEQ No. 470 | 2df |
| SEQ ID No. 528 | ALGQDR | 121-126 for the protein of SEQ No. 433 | 2d |
| SEQ ID No. 529 | ALPDLAK | 256-262 for the protein of SEQ No. 498 | 2d |
| SEQ ID No. 530 | ALQAK | 254-258 for the protein of SEQ No. 470 | 2df |
| SEQ ID No. 531 | AMETFSPASTFK | 50-61 for the protein of SEQ No. 385 | 2d |
| SEQ ID No. 532 | AMLFLQER | 196-203 for the protein of SEQ No. 469 | 2df |
| SEQ ID No. 533 | AMLVFDPVR | 55-63 for the proteins of SEQ No. 350, 367, 370, 415, 443, 481, 488; 44-52 for the protein of sequence SEQ ID No. 362 | OXA |
| SEQ ID No. 534 | AMTLLESGPGWELHGK | 189-204 for the protein of SEQ No. 380 | 2d |
| SEQ ID No. 535 | ANLHITLHGK | 199-208 for the protein of SEQ No. 386 | 2d |
| SEQ ID No. 536 | ANQLIVK | 183-189 for the proteins of SEQ No. 489, 505 | OXA |
| SEQ ID No. 537 | ANTEYVPASTFK | 71-82 for the proteins of SEQ No. 366, 374, 387, 440, 441, 459, 460, 461, 462, 463, 464, 465, 486, 493; 66-77 for the protein of sequence SEQ ID No. 469 | 2df |
| SEQ ID No. 538 | ANVSR | 133-137 for the protein of SEQ No. 380 | 2d |
| SEQ ID No. 539 | APIGWFIGWATR | 224-235 for the protein of SEQ No. 351 | 2de |
| SEQ ID No. 540 | APLGWFIGWATHEER | 213-227 for the protein of SEQ No. 498 | 2d |

-continued

| Peptide SEQ ID No. | Amino acid sequence | Position of the peptide in the OXA protein(s) | Clinical interest |
|---|---|---|---|
| SEQ ID No. 541 | AQDEVQSMLFIEEK | 196-209 for the protein of SEQ No. 403 | 2df |
| SEQ ID No. 542 | AQGVIVLWNENK | 40-51 for the protein of SEQ No. 384 | 2df |
| SEQ ID No. 543 | ASAIAVYQDLAR | 126-137 for the protein of SEQ No. 467 | 2df |
| SEQ ID No. 544 | ASAILVYQDLAR | 126-137 for the proteins of SEQ No. 417, 426, 457, 472 | 2df |
| SEQ ID No. 545 | ASAIPVYQDLAR | 126-137 for the proteins of SEQ No. 388, 389, 390, 391, 392, 393, 394, 395, 396, 398, 399, 402, 403, 404, 405, 406, 407, 408, 409, 411, 412, 416, 418, 419, 420, 423, 424, 425, 427, 428, 434, 436, 437, 439, 444, 445, 446, 448, 453, 454, 455, 456, 468, 475, 478, 479, 480, 482, 483, 495, 502, 503, 507, 508; 120-131 for the proteins of sequence SEQ ID No. 431, 432 | 2df |
| SEQ ID No. 546 | ASAIPVYQDLPR | 126-137 for the protein of SEQ No. 397 | 2df |
| SEQ ID No. 547 | ASAIQVYQDLAR | 126-137 for the proteins of SEQ No. 421, 473 | 2df |
| SEQ ID No. 548 | ASAISVYQDLAR | 126-137 for the proteins of SEQ No. 400, 487 | 2df |
| SEQ ID No. 549 | ASALPVYQDLAR | 126-137 for the proteins of SEQ No. 401, 422 | 2df |
| SEQ ID No. 550 | ASAMPVYQDLAR | 126-137 for the protein of SEQ No. 474 | 2df |
| SEQ ID No. 551 | ASAVPVYQDLAR | 126-137 for the proteins of SEQ No. 438, 451, 452 | 2df |
| SEQ ID No. 552 | ASIEYVPASTFK | 72-83 for the proteins of SEQ No. 399, 403 | 2df |
| SEQ ID No. 553 | ASNVPVYQELAR | 113-124 for the protein of SEQ No. 380 | 2d |
| SEQ ID No. 554 | ASPASTFK | 49-56 for the proteins of SEQ No. 496, 497, 499, 500 | 2d |
| SEQ ID No. 555 | ASTAYIPASTFK | 59-70 for the proteins of SEQ No. 489, 505 | OXA |
| SEQ ID No. 556 | ASTEYVPASTFK | 72-83 for the proteins of SEQ No. 388, 389, 390, 391, 392, 393, 394, 395, 396, 397, 398, 400, 401, 402, 404, 405, 406, 407, 408, 409, 411, 412, 416, 417, 418, 419, 420, 421, 422, 423, 424, 425, 426, 427, 428, 434, 436, 437, 438, 439, 444, 445, 446, 448, 451, 452, 453, 454, 455, 456, 457, 467, 468, 472, 473, 474, 475, 478, 479, 480, 482, 483, 487, 495, 502, 503, 507, 508; 66-77 for the proteins of sequence SEQ ID No. 431, 432 | 2df |
| SEQ ID No. 557 | ASTTEVFK | 96-103 for the protein of SEQ No. 444 | 2df |
| SEQ ID No. 558 | ATSTEIFK | 99-106 for the proteins of SEQ No. 410, 413, 458 | 2df |
| SEQ ID No. 559 | ATTNEIFK | 97-104 for the proteins of SEQ No. 364, 365, 371, 414, 449, 466, 506; 90-97 for the protein of sequence SEQ ID No. 469 | 2df |
| SEQ ID No. 560 | ATTTAVFK | 96-103 for the protein of SEQ No. 396 | 2df |

-continued

| Peptide SEQ ID No. | Amino acid sequence | Position of the peptide in the OXA protein(s) | Clinical interest |
|---|---|---|---|
| SEQ ID No. 561 | ATTTEIFK | 97-104 for the protein of SEQ No. 447; 96-103 for the proteins of sequence SEQ ID No. 399, 403, 411 | 2df |
| SEQ ID No. 562 | ATTTEVFK | 96-103 for the proteins of SEQ No. 388, 389, 390, 391, 392, 393, 394, 397, 398, 400, 401, 402, 404, 405, 406, 407, 408, 409, 412, 416, 417, 418, 419, 420, 421, 422, 423, 424, 425, 426, 427, 434, 436, 437, 438, 439, 445, 446, 448, 451, 452, 453, 454, 455, 456, 457, 467, 468, 472, 473, 474, 475, 478, 479, 480, 482, 483, 487, 495, 502, 503, 507, 508; 90-97 for the proteins of sequence SEQ ID No. 431, 432 | 2df |
| SEQ ID No. 563 | AVSDITILEQTDNYTLHGK | 191-209 for the protein of SEQ No. 477 | OXA |
| SEQ ID No. 564 | AVSDITILEQTYNYTLHGK | 191-209 for the proteins of SEQ No. 429, 430 | 2d |
| SEQ ID No. 565 | AVVPHFEAGDWDVQGK | 195-210 for the protein of SEQ No. 351 | 2de |
| SEQ ID No. 566 | AWEHDMSLR | 100-108 for the protein of SEQ No. 380 | 2d |
| SEQ ID No. 567 | AWIGSSLQISPLEQLEFLGK | 148-167 for the proteins of SEQ No. 496, 497, 499, 500 | 2d |
| SEQ ID No. 568 | CAAQMAPDSTFK | 63-74 for the protein of SEQ No. 376 | 2d |
| SEQ ID No. 569 | CATQMAPDSTFK | 48-59 for the protein of SEQ No. 361; 63-74 for the protein of sequence SEQ ID No. 360 | 2d |
| SEQ ID No. 570 | CTIIADAITGNTLYETGECAR | 32-52 for the protein of SEQ No. 349 | 2d |
| SEQ ID No. 571 | DAFLK | 251-255 for the protein of SEQ No. 498 | 2d |
| SEQ ID No. 572 | DDFILHGK | 189-196 for the protein of SEQ No. 377 | 2d |
| SEQ ID No. 573 | DDQEVLPYGGK | 92-102 for the protein of SEQ No. 379 | 2df |
| SEQ ID No. 574 | DDVLK | 87-91 for the protein of SEQ No. 470 | 2df |
| SEQ ID No. 575 | DEFHVFR | 90-96 for the proteins of SEQ No. 355, 363 | 2d |
| SEQ ID No. 576 | DEFQIFR | 90-96 for the proteins of SEQ No. 350, 367, 370, 375, 415, 443, 481, 488; 79-85 for the protein of sequence SEQ ID No. 362 | OXA |
| SEQ ID No. 577 | DEFQVFR | 90-96 for the proteins of SEQ No. 356, 369, 372, 373, 484, 491 | 2d |
| SEQ ID No. 578 | DELVR | 260-264 for the protein of SEQ No. 433 | 2d |
| SEQ ID No. 579 | DETSR | 112-116 for the protein of SEQ No. 381 | 2df |
| SEQ ID No. 580 | DFDYGNQDFSGDK | 141-153 for the proteins of SEQ No. 360, 376; 126-138 for the protein of sequence SEQ ID No. 361 | 2d |
| SEQ ID No. 581 | DFTLGEAMQASTVPVYQELAR | 120-140 for the proteins of SEQ No. 410, 413, 458 | 2df |
| SEQ ID No. 582 | DGNITSVAINIDMLSEADAPK | 250-270 for the protein of SEQ No. 382 | 2df |

-continued

| Peptide SEQ ID No. | Amino acid sequence | Position of the peptide in the OXA protein(s) | Clinical interest |
|---|---|---|---|
| SEQ ID No. 583 | DHDLITAMK | 108-116 for the proteins of SEQ No. 384, 485 | 2df |
| SEQ ID No. 584 | DIAAWNR | 101-107 for the proteins of SEQ No. 384, 485 | 2df |
| SEQ ID No. 585 | DIGEDK | 131-136 for the protein of SEQ No. 373 | 2d |
| SEQ ID No. 586 | DILYIQELAGGWK | 180-192 for the protein of SEQ No. 494 | 2de |
| SEQ ID No. 587 | DITILEK | 181-187 for the protein of SEQ No. 377 | 2d |
| SEQ ID No. 588 | DLLSAK | 166-171 for the protein of SEQ No. 498 | 2d |
| SEQ ID No. 589 | DLMITEAGR | 195-203 for the proteins of SEQ No. 369, 372, 373 | 2d |
| SEQ ID No. 590 | DLMIVEAGR | 195-203 for the proteins of SEQ No. 350, 356, 367, 370, 375, 415, 443, 481, 488, 491; 184-192 for the protein of sequence SEQ ID No. 362 | OXA |
| SEQ ID No. 591 | DLMIVEAK | 195-202 for the proteins of SEQ No. 355, 363 | 2d |
| SEQ ID No. 592 | DLPLR | 243-247 for the protein of SEQ No. 470 | 2df |
| SEQ ID No. 593 | DLSGNPGK | 131-138 for the protein of SEQ No. 347 | 2d |
| SEQ ID No. 594 | DLSLR | 105-109 for the proteins of SEQ No. 357, 358, 359, 368, 383, 442, 471, 504; 106-110 for the protein of sequence SEQ ID No. 490 | OXA |
| SEQ ID No. 595 | DLTLR | 105-109 for the proteins of SEQ No. 352, 435, 492, 501, 505; 96-100 for the proteins of sequence SEQ ID No. 348, 353, 354 | OXA |
| SEQ ID No. 596 | DMTLGDAIK | 117-125 for the proteins of SEQ No. 468, 508 | 2df |
| SEQ ID No. 597 | DMTLGDAMALSAVPVYQELAR | 118-138 for the protein of SEQ No. 447 | 2df |
| SEQ ID No. 598 | DMTLGDAMK | 117-125 for the proteins of SEQ No. 389, 390, 391, 394, 395, 398, 399, 400, 401, 403, 404, 407, 408, 409, 411, 412, 417, 418, 420, 421, 423, 425, 426, 427, 428, 436, 437, 438, 439, 444, 451, 452, 453, 454, 455, 456, 457, 467, 472, 473, 474, 478, 479, 480, 482, 483, 487, 495, 502, 507 | 2df |
| SEQ ID No. 599 | DMTLGEAMALSAVPVYQDLAR | 118-138 for the protein of SEQ No. 466 | 2df |
| SEQ ID No. 600 | DMTLGEAMALSAVPVYQELAR | 118-138 for the proteins of SEQ No. 364, 365, 371, 414, 449, 506 | 2df |
| SEQ ID No. 601 | DMTLGEAMK | 116-124 for the proteins of SEQ No. 366, 374, 387, 440, 441, 459, 460, 461, 462, 463, 464, 465, 486, 493 | 2df |
| SEQ ID No. 602 | DMTLGQAMQASAVPVYQELAR | 111-131 for the protein of SEQ No. 469 | 2df |
| SEQ ID No. 603 | DNNGK | 214-218 for the protein of SEQ No. 349 | 2d |
| SEQ ID No. 604 | DQDLR | 110-114 for the proteins of SEQ No. 350, 356, 367, 369, 370, 372, 373, 375, 415, 443, | 2d |

| Peptide SEQ ID No. | Amino acid sequence | Position of the peptide in the OXA protein(s) | Clinical interest |
|---|---|---|---|
| | | 481, 484, 488, 491; 99-103 for the protein of sequence SEQ ID No. 362 | |
| SEQ ID No. 605 | DQQIGWFVGWASK | 213-225 for the protein of SEQ No. 347 | 2d |
| SEQ ID No. 606 | DQQIGWFVGWASKPGK | 213-228 for the protein of SEQ No. 347 | 2d |
| SEQ ID No. 607 | DQQVQVYGNDLNR | 53-65 for the protein of SEQ No. 469 | 2df |
| SEQ ID No. 608 | DQSFR | 132-136 for the protein of SEQ No. 381 | 2df |
| SEQ ID No. 609 | DQTLESAFK | 105-113 for the protein of SEQ No. 470 | 2df |
| SEQ ID No. 610 | DSCVWYSQVLTQQLGMTR | 98-115 for the protein of SEQ No. 494 | 2de |
| SEQ ID No. 611 | DSIVWYSQELTR | 113-124 for the protein of SEQ No. 351 | 2de |
| SEQ ID No. 612 | DSIVWYSQQLTR | 102-113 for the protein of SEQ No. 498 | 2d |
| SEQ ID No. 613 | DSNLR | 109-113 for the proteins of SEQ No. 429, 430, 477; 96-100 for the proteins of sequence SEQ ID No. 377, 386 | 2d |
| SEQ ID No. 614 | DSYIAWGGEAWK | 81-92 for the proteins of SEQ No. 496, 497, 499, 500 | 2d |
| SEQ ID No. 615 | DTLNPEWPYK | 67-76 for the protein of SEQ No. 494 | 2de |
| SEQ ID No. 616 | DVDEVFYK | 88-95 for the proteins of SEQ No. 386, 429, 430, 477 | 2d |
| SEQ ID No. 617 | DVSGDPGK | 144-151 for the protein of SEQ No. 351 | 2de |
| SEQ ID No. 618 | DWILR | 204-208 for the proteins of SEQ No. 355, 363 | 2d |
| SEQ ID No. 619 | DWPAMAGAWR | 265-274 for the protein of SEQ No. 433 | 2d |
| SEQ ID No. 620 | EAFLR | 256-260 for the proteins of SEQ No. 496, 497, 499, 500 | 2d |
| SEQ ID No. 621 | EAIAR | 250-254 for the proteins of SEQ No. 355, 363, 369, 372, 373, 375, 484 | 2d |
| SEQ ID No. 622 | EAIVR | 250-254 for the proteins of SEQ No. 350, 356, 367, 370, 415, 443, 481, 488, 491; 239-243 for the protein of sequence SEQ ID No. 362 | OXA |
| SEQ ID No. 623 | EAIVTEATPEYIVHSK | 190-205 for the proteins of SEQ No. 489, 505 | OXA |
| SEQ ID No. 624 | EALVTEAAPEYLVHSK | 190-205 for the proteins of SEQ No. 352, 357, 358, 359, 368, 383, 435, 442, 471, 492, 501, 504; 181-196 for the proteins of sequence SEQ ID No. 348, 353, 354 | OXA |
| SEQ ID No. 625 | EALVTEAPEYLVHSK | 191-205 for the protein of SEQ No. 490 | 2d |
| SEQ ID No. 626 | EEIVR | 240-244 for the protein of SEQ No. 377 | 2d |
| SEQ ID No. 627 | EEVLAALPAQLK | 251-262 for the protein of SEQ No. 347 | 2d |

-continued

| Peptide SEQ ID No. | Amino acid sequence | Position of the peptide in the OXA protein(s) | Clinical interest |
|---|---|---|---|
| SEQ ID No. 628 | EFNGSK | 209-214 for the protein of SEQ No. 447 | 2df |
| SEQ ID No. 629 | EFSAEAVNGVFVLCK | 31-45 for the proteins of SEQ No. 352, 357, 358, 359, 368, 383, 435, 442, 471, 490, 492, 501, 504; 22-36 for the proteins of sequence SEQ ID No. 348, 353, 354 | OXA |
| SEQ ID No. 630 | EFSSESVHGVFVLCK | 31-45 for the proteins of SEQ No. 489, 505 | OXA |
| SEQ ID No. 631 | EGDMAK | 248-253 for the protein of SEQ No. 379 | 2df |
| SEQ ID No. 632 | EGMSGSIR | 254-261 for the proteins of SEQ No. 364, 371, 414, 449, 506 | 2df |
| SEQ ID No. 633 | EGMTGSIR | 254-261 for the protein of SEQ No. 365 | 2df |
| SEQ ID No. 634 | EGSCDK | 54-59 for the protein of SEQ No. 351 | 2de |
| SEQ ID No. 635 | EIAVWNR | 125-131 for the protein of SEQ No. 381 | 2df |
| SEQ ID No. 636 | EIAYK | 262-266 for the protein of SEQ No. 480 | 2df |
| SEQ ID No. 637 | EIFER | 20-24 for the protein of SEQ No. 377 | 2d |
| SEQ ID No. 638 | EIFYHYR | 79-85 for the protein of SEQ No. 385 | 2d |
| SEQ ID No. 639 | EIGDDK | 131-136 for the proteins of SEQ No. 350, 367, 370, 415, 443, 481, 488; 120-125 for the protein of sequence SEQ ID No. 362 | OXA |
| SEQ ID No. 640 | EIGDGK | 131-136 for the protein of SEQ No. 375 | 2d |
| SEQ ID No. 641 | EIGEDK | 131-136 for the proteins of SEQ No. 356, 372, 491 | 2d |
| SEQ ID No. 642 | EIGEDNAR | 131-138 for the protein of SEQ No. 484 | OXA |
| SEQ ID No. 643 | EIGENK | 131-136 for the proteins of SEQ No. 355, 363 | 2d |
| SEQ ID No. 644 | EIGPK | 153-157 for the protein of SEQ No. 381 | 2df |
| SEQ ID No. 645 | EIGSEIDK | 136-143 for the protein of SEQ No. 377 | 2d |
| SEQ ID No. 646 | EITYK | 262-266 for the proteins of SEQ No. 389, 390, 391, 392, 393, 394, 395, 396, 397, 398, 399, 400, 401, 402, 403, 404, 405, 406, 407, 408, 409, 411, 412, 416, 417, 418, 419, 420, 421, 422, 423, 424, 425, 426, 427, 428, 434, 436, 437, 438, 444, 445, 446, 448, 451, 452, 453, 454, 455, 456, 457, 467, 468, 472, 473, 474, 475, 478, 479, 482, 483, 487, 495, 502, 503, 507, 508; 263-267 for the proteins of sequence SEQ ID No. 364, 365, 371, 414, 447, 449, 466, 506; 256-260 for the proteins of sequence SEQ ID No. 431, 432 | 2df |
| SEQ ID No. 647 | EITYR | 262-266 for the protein of SEQ No. 388 | 2df |
| SEQ ID No. 648 | EMIYLK | 181-186 for the protein of SEQ No. 385 | 2d |

-continued

| Peptide SEQ ID No. | Amino acid sequence | Position of the peptide in the OXA protein(s) | Clinical interest |
|---|---|---|---|
| SEQ ID No. 649 | EMLYVER | 205-211 for the proteins of SEQ No. 410, 413, 458 | 2df |
| SEQ ID No. 650 | EMTYK | 262-266 for the protein of SEQ No. 439 | 2df |
| SEQ ID No. 651 | ENIEK | 138-142 for the proteins of SEQ No. 429, 430, 477; 137-141 for the protein of sequence SEQ ID No. 386 | 2d |
| SEQ ID No. 652 | ENQLIVK | 183-189 for the proteins of SEQ No. 352, 357, 358, 359, 368, 383, 435, 442, 471, 492, 501, 504; 174-180 for the proteins of sequence SEQ ID No. 348, 353, 354; 184-190 for the protein of sequence SEQ ID No. 490 | OXA |
| SEQ ID No. 653 | EQAILLFR | 156-163 for the protein of SEQ No. 385 | 2d |
| SEQ ID No. 654 | EQIQFLLR | 165-172 for the protein of SEQ No. 349 | 2d |
| SEQ ID No. 655 | EQLAFDPQVQQQVK | 182-195 for the protein of SEQ No. 469 | 2df |
| SEQ ID No. 656 | EQVDFVQR | 189-196 for the protein of SEQ No. 382 | 2df |
| SEQ ID No. 657 | ETEVYFFAFNMDIDNESK | 229-246 for the proteins of SEQ No. 352, 435, 492, 501; 220-237 for the proteins of sequence SEQ ID No. 348, 353, 354 | OXA |
| SEQ ID No. 658 | ETTTPR | 90-95 for the protein of SEQ No. 347 | 2d |
| SEQ ID No. 659 | EVGEIR | 126-131 for the protein of SEQ No. 489 | 2d |
| SEQ ID No. 660 | EVGEVR | 126-131 for the proteins of SEQ No. 352, 357, 358, 359, 368, 383, 435, 442, 471, 492, 501, 504; 117-122 for the proteins of sequence SEQ ID No. 348, 353, 354; 127-132 for the protein of sequence SEQ ID No. 490 | OXA |
| SEQ ID No. 661 | EVNGSK | 209-214 for the proteins of SEQ No. 364, 365, 371, 414, 449, 466, 506 | 2df |
| SEQ ID No. 662 | EWQENK | 24-29 for the proteins of SEQ No. 378, 450, 476, 485 | 2df |
| SEQ ID No. 663 | EYELYLNVWK | 78-87 for the protein of SEQ No. 494 | 2de |
| SEQ ID No. 664 | EYLPASTFK | 62-70 for the proteins of SEQ No. 352, 357, 358, 359, 368, 383, 435, 442, 471, 492, 504; 53-61 for the proteins of sequence SEQ ID No. 348, 353, 354; 63-71 for the protein of sequence SEQ ID No. 490 | OXA |
| SEQ ID No. 665 | EYLPVSTFK | 62-70 for the protein of SEQ No. 501 | 2de |
| SEQ ID No. 666 | EYNTSGTFVFYDGK | 27-40 for the protein of SEQ No. 385 | 2d |
| SEQ ID No. 667 | EYVPASTFX | 75-83 for the proteins of SEQ No. 388, 389, 390, 391, 392, 393, 394, 395, 396, 397, 398, 399, 400, 401, 402, 403, 404, 405, 406, 407, 408, 409, 411, 412, 416, 417, 418, 419, 420, 421, 422, 423, 424, 425, 426, 427, 428, 434, 436, 437, 438, 439, 444, 445, 446, 448, 451, 452, 453, 454, 455, 456, 457, 467, 468, 472, 473, 474, 475, 478, 479, 480, 482, 483, 487, | 2df |

-continued

| Peptide SEQ ID No | Amino acid sequence | Position of the peptide in the OXA protein(s) | Clinical interest |
|---|---|---|---|
| | | 495, 502, 503, 507, 508; 69-77 for the proteins of sequence SEQ ID No. 431, 432, 469; 74-82 for the proteins of sequence SEQ ID No. 366, 374, 387, 440, 441, 459, 460, 461, 462, 463, 464, 465, 486, 493; 76-84 for the proteins of sequence SEQ ID No. 364, 365, 371, 414, 447, 449, 466, 506 | |
| SEQ ID No. 668 | FAAYVAGFGYGNGDISGEPGK | 120-140 for the protein of SEQ No. 498 | 2d |
| SEQ ID No. 669 | FAPESTFK | 45-52 for the protein of SEQ No. 494 | 2de |
| SEQ ID No. 670 | FAQYAK | 121-126 for the proteins of SEQ No. 496, 497, 499, 500 | 2d |
| SEQ ID No. 671 | FDYGNK | 138-143 for the protein of SEQ No. 351 | 2de |
| SEQ ID No. 672 | FDYGNR | 146-151 for the protein of SEQ No. 379; 125-130 for the protein of sequence SEQ ID No. 347 | 2d |
| SEQ ID No. 673 | FEDLYK | 232-237 for the protein of SEQ No. 385 | 2d |
| SEQ ID No. 674 | FEDTFHISNQK | 27-37 for the protein of SEQ No. 466 | 2df |
| SEQ ID No. 675 | FEDTFHTSNQQHEK | 27-40 for the protein of SEQ No. 447 | 2df |
| SEQ ID No. 676 | FEYGNQDVSGDSGK | 133-146 for the protein of SEQ No. 349 | 2d |
| SEQ ID No. 677 | FFSDFQAK | 34-41 for the protein of SEQ No. 375 | 2d |
| SEQ ID No. 678 | FFSDLQAEGAIVIADER | 34-50 for the proteins of SEQ No. 373, 484 | 2d |
| SEQ ID No. 679 | FFSDLR | 34-39 for the proteins of SEQ No. 369, 372 | OXA |
| SEQ ID No. 680 | FFSEFQAK | 34-41 for the proteins of SEQ No. 350, 356, 367, 370, 415, 443, 481, 488, 491; 23-30 for the protein of sequence SEQ ID No. 362 | OXA |
| SEQ ID No. 681 | FGLEGQLR | 153-160 for the protein of SEQ No. 359 | 2de |
| SEQ ID No. 682 | FILPIFSISILVSLSACSSIK | 4-24 for the proteins of SEQ No. 364, 365, 371, 414, 449, 506 | 2df |
| SEQ ID No. 683 | FLALLFSAVVVSLGHAQDK | 5-24 for the protein of SEQ No. 363 | 2d |
| SEQ ID No. 684 | FLALLFSAVVLVSLGHAQEK | 5-24 for the protein of SEQ No. 355 | 2d |
| SEQ ID No. 685 | FLESLYLNNLPASK | 169-182 for the proteins of SEQ No. 489, 505 | OXA |
| SEQ ID No. 686 | FLLEGQLR | 153-160 for the protein of SEQ No. 442 | 2de |
| SEQ ID No. 687 | FQQYVDR | 118-124 for the protein of SEQ No. 347 | 2d |
| SEQ ID No. 688 | FSDYVQR | 131-137 for the protein of SEQ No. 351 | 2de |
| SEQ ID No. 689 | FSTASTFK | 63-70 for the protein of SEQ No. 470 | 2df |

-continued

| Peptide SEQ ID No. | Amino acid sequence | Position of the peptide in the OXA protein(s) | Clinical interest |
|---|---|---|---|
| SEQ ID No. 690 | FSWDGK | 117-122 for the protein of SEQ No. 381 | 2df |
| SEQ ID No. 691 | FSYGNQNISGGIDK | 139-152 for the proteins of SEQ No. 352, 357, 358, 359, 368, 383, 435, 442, 501, 504; 130-143 for the proteins of sequence SEQ ID No. 348, 353, 354; 140-153 for the protein of sequence SEQ ID No. 490 | OXA |
| SEQ ID No. 692 | FSYGNQNISGGTDK | 139-152 for the protein of SEQ No. 471 | 2de |
| SEQ ID No. 693 | FSYGSQNISGGIDK | 139-152 for the protein of SEQ No. 492 | 2de |
| SEQ ID No. 694 | FTEYVK | 126-131 for the protein of SEQ No. 349 | 2d |
| SEQ ID No. 695 | FVAHK | 173-177 for the protein of SEQ No. 349 | 2d |
| SEQ ID No. 696 | FVPASTYK | 62-69 for the protein of SEQ No. 380 | 2d |
| SEQ ID No. 697 | FVYDLAQGQLPFK | 184-196 for the proteins of SEQ No. 410, 413, 458 | 2df |
| SEQ ID No. 698 | FVYDLAQGQLPFKPEVQQQVK | 184-204 for the proteins of SEQ No. 410, 413, 458 | 2df |
| SEQ ID No. 699 | FWLEDQLR | 153-160 for the proteins of SEQ No. 358, 435, 471, 492; 144-151 for the proteins of sequence SEQ ID No. 348, 353 | 2de |
| SEQ ID No. 700 | FWLEGPLK | 144-151 for the protein of SEQ No. 377 | 2d |
| SEQ ID No. 701 | FWLEGQLR | 153-160 for the proteins of SEQ No. 352, 357, 368, 383, 489, 501, 504, 505; 144-151 for the protein of sequence SEQ ID No. 354; 154-161 for the protein of sequence SEQ ID No. 490 | OXA |
| SEQ ID No. 702 | FYPASSFK | 53-60 for the protein of SEQ No. 377 | 2d |
| SEQ ID No. 703 | FYPASTFK | 66-73 for the proteins of SEQ No. 386, 429, 430, 477 | 2d |
| SEQ ID No. 704 | GACDK | 44-48 for the protein of SEQ No. 498 | 2d |
| SEQ ID No. 705 | GAEVYFFAFNMDIDNENK | 229-246 for the proteins of SEQ No. 383, 490 | 2d |
| SEQ ID No. 706 | GAIQVSAVPVFQQIAR | 110-125 for the proteins of SEQ No. 352, 357, 358, 359, 368, 383, 435, 442, 471, 489, 492, 501, 504, 505; 101-116 for the proteins of sequence SEQ ID No. 348, 354; 111-126 for the protein of sequence SEQ ID No. 490 | OXA |
| SEQ ID No. 707 | GAIQVSAVPVFQQITR | 101-116 for the protein of SEQ No. 353 | 2de |
| SEQ ID No. 708 | GDYWIDGNLEISAREQISFER | 156-176 for the proteins of SEQ No. 369, 372 | OXA |
| SEQ ID No. 709 | GDYWIDGNLK | 156-165 for the protein of SEQ No. 373 | 2d |
| SEQ ID No. 710 | GELPVSEDALEMTK | 181-194 for the protein of SEQ No. 351 | 2de |
| SEQ ID No. 711 | GEQPAGPAAR | 241-250 for the protein of SEQ No. 498; 252-261 for the protein of sequence SEQ ID No. 351 | OXA |

| Peptide SEQ ID No. | Amino acid sequence | Position of the peptide in the OXA protein(s) | Clinical interest |
|---|---|---|---|
| SEQ ID No. 712 | GFAGHNQDQDLR | 103-114 for the proteins of SEQ No. 350, 367, 370, 415, 443, 481, 488; 92-103 for the protein of sequence SEQ ID No. 362 | OXA |
| SEQ ID No. 713 | GIPSSVR | 254-260 for the proteins of SEQ No. 389, 390, 391, 392, 393, 394, 395, 397, 398, 399, 400, 401, 402, 403, 404, 405, 406, 407, 408, 409, 411, 412, 416, 417, 418, 419, 420, 421, 422, 423, 424, 425, 426, 427, 428, 434, 436, 437, 438, 439, 444, 445, 446, 448, 451, 452, 453, 454, 455, 456, 457, 467, 468, 472, 473, 474, 475, 478, 479, 480, 482, 483, 487, 495, 502, 503, 507, 508; 248-254 for the proteins of sequence SEQ ID No. 431, 432 | 2df |
| SEQ ID No. 714 | GISSSVR | 254-260 for the protein of SEQ No. 388 | 2df |
| SEQ ID No. 715 | GLNGTFVVYDLK | 26-37 for the protein of SEQ No. 377 | 2d |
| SEQ ID No. 716 | GMEIWNSNHTPK | 101-112 for the proteins of SEQ No. 360, 376; 86-97 for the protein of sequence SEQ ID No. 361 | 2d |
| SEQ ID No. 717 | GNQTLVFAR | 230-238 for the protein of SEQ No. 496 | 2d |
| SEQ ID No. 718 | GNYWIDGNLEISAHEQISFLR | 156-176 for the protein of SEQ No. 484 | OXA |
| SEQ ID No. 719 | GPLEISAFEEAR | 164-175 for the protein of SEQ No. 379 | 2df |
| SEQ ID No. 720 | GPLTITPIQEVK | 172-183 for the proteins of SEQ No. 410, 413, 458 | 2df |
| SEQ ID No. 721 | GSGWFVGWIVR | 219-229 for the proteins of SEQ No. 496, 497, 499, 500 | 2d |
| SEQ ID No. 722 | GSLLEWDQK | 66-74 for the protein of SEQ No. 381 | 2df |
| SEQ ID No. 723 | GTEVYFFAFNMDIDNENK | 229-246 for the proteins of SEQ No. 357, 358, 359, 368, 442, 471, 504 | OXA |
| SEQ ID No. 724 | GTEVYFFAFNMDIDNESK | 229-246 for the proteins of SEQ No. 489, 505 | OXA |
| SEQ ID No. 725 | GTFVEYDVQR | 38-47 for the protein of SEQ No. 380 | 2d |
| SEQ ID No. 726 | GTIVVADER | 42-50 for the proteins of SEQ No. 350, 356, 367, 370, 375, 415, 443, 481, 488, 491; 31-39 for the protein of sequence SEQ ID No. 362 | OXA |
| SEQ ID No. 727 | GTIVVLDAR | 63-71 for the protein of SEQ No. 382 | 2df |
| SEQ ID No. 728 | GTIVVVDER | 42-50 for the proteins of SEQ No. 355, 363 | 2d |
| SEQ ID No. 729 | GTLPFSAR | 200-207 for the protein of SEQ No. 382 | 2df |
| SEQ ID No. 730 | GTPSSVR | 254-260 for the protein of SEQ No. 396 | 2df |
| SEQ ID No. 731 | HALSSAFVLLGCIAASAHAK | 5-24 for the proteins of SEQ No. 496, 497, 499, 500 | 2d |
| SEQ ID No. 732 | HIADSK | 234-239 for the protein of SEQ No. 494 | 2de |
| SEQ ID No. 733 | HNGLTHAWLASSLK | 152-165 for the protein of SEQ No. 351 | 2de |

-continued

| Peptide SEQ ID No. | Amino acid sequence | Position of the peptide in the OXA protein(s) | Clinical interest |
|---|---|---|---|
| SEQ ID No. 734 | HNGLTQSWLMSSLTISPK | 147-164 for the protein of SEQ No. 349 | 2d |
| SEQ ID No. 735 | HNGTDGAWIISSLR | 148-161 for the protein of SEQ No. 433 | 2d |
| SEQ ID No. 736 | HTLSVFDQER | 54-63 for the protein of SEQ No. 373 | 2d |
| SEQ ID No. 737 | HVTFASFR | 241-248 for the protein of SEQ No. 494 | 2de |
| SEQ ID No. 738 | IAISLMGYDAGFLR | 57-70 for the proteins of SEQ No. 496, 497, 499, 500 | 2d |
| SEQ ID No. 739 | IALSLMAFDAEIIDQK | 75-90 for the proteins of SEQ No. 360, 376; 60-75 for the protein of sequence SEQ ID No. 361 | 2d |
| SEQ ID No. 740 | IALSLMGFDSGILK | 53-66 for the protein of SEQ No. 494 | 2de |
| SEQ ID No. 741 | IANALIGLENHK | 87-98 for the proteins of SEQ No. 410, 413, 458 | 2df |
| SEQ ID No. 742 | IAWIVGEVYLK | 205-215 for the protein of SEQ No. 385 | 2d |
| SEQ ID No. 743 | IDTFWLDNSLK | 141-151 for the protein of SEQ No. 385 | 2d |
| SEQ ID No. 744 | IDYYNLDR | 41-48 for the protein of SEQ No. 377 | 2d |
| SEQ ID No. 745 | IFNALIALDSGVIK | 62-75 for the protein of SEQ No. 385 | 2d |
| SEQ ID No. 746 | IFNSLLALDSGALDNER | 95-111 for the protein of SEQ No. 382 | 2df |
| SEQ ID No. 747 | IFNTLIGLENGIVK | 61-74 for the protein of SEQ No. 377 | 2d |
| SEQ ID No. 748 | IGLDLMQK | 138-145 for the proteins of SEQ No. 366, 374, 387, 440, 441, 459, 460, 461, 462, 463, 464, 465, 486, 493 | 2df |
| SEQ ID No. 749 | IGLEK | 131-135 for the protein of SEQ No. 477 | OXA |
| SEQ ID No. 750 | IGLELMQQEVQR | 133-144 for the protein of SEQ No. 469 | 2df |
| SEQ ID No. 751 | IGLELMSK | 139-146 for the proteins of SEQ No. 389, 390, 391, 393, 395, 398, 399, 400, 401, 402, 403, 404, 408, 409, 411, 412, 417, 419, 420, 421, 422, 423, 424, 425, 426, 427, 428, 436, 437, 438, 439, 451, 452, 453, 454, 455, 456, 457, 467, 468, 472, 473, 474, 478, 479, 480, 482, 483, 487, 495, 502, 508 | 2df |
| SEQ ID No. 752 | IGLELMSNEVK | 139-149 for the proteins of SEQ No. 388, 392, 394, 396, 397, 405, 406, 407, 416, 418, 434, 444, 445, 446, 448, 475, 503, 507; 133-143 for the proteins of sequence SEQ ID No. 431, 432 | 2df |
| SEQ ID No. 753 | IGLER | 126-130 for the protein of SEQ No. 380 | 2d |
| SEQ ID No. 754 | IGLNK | 130-134 for the proteins of SEQ No. 360, 376; 115-119 for the protein of sequence SEQ ID No. 361 | 2d |
| SEQ ID No. 755 | IGLNLMQK | 140-147 for the protein of SEQ No. 466 | 2df |

| Peptide SEQ ID No. | Amino acid sequence | Position of the peptide in the OXA protein(s) | Clinical interest |
|---|---|---|---|
| SEQ ID No. 756 | IGPSLMQSELQR | 142-153 for the proteins of SEQ No. 410, 413, 458 | 2df |
| SEQ ID No. 757 | IGYGNMQIGTEVDQFWLK | 154-171 for the proteins of SEQ No. 413, 458 | 2df |
| SEQ ID No. 758 | IGYGNMQMGTEVDQFWLK | 154-171 for the protein of SEQ No. 410 | 2df |
| SEQ ID No. 759 | IINHNLPVK | 167-175 for the protein of SEQ No. 361; 182-190 for the protein of sequence SEQ ID No. 360 | 2d |
| SEQ ID No. 760 | IINHNLPVR | 182-190 for the protein of SEQ No. 376 | 2d |
| SEQ ID No. 761 | ILFQQGTQQACAER | 41-54 for the protein of SEQ No. 433 | 2d |
| SEQ ID No. 762 | ILNNWFK | 20-26 for the protein of SEQ No. 385 | 2d |
| SEQ ID No. 763 | ILNTLISLEEK | 71-81 for the protein of SEQ No. 470 | 2df |
| SEQ ID No. 764 | ILSLVCLSISIGACAEHSMSR | 6-26 for the proteins of SEQ No. 410, 413, 458 | 2df |
| SEQ ID No. 765 | INESR | 219-223 for the protein of SEQ No. 349 | 2d |
| SEQ ID No. 766 | INIVK | 255-259 for the proteins of SEQ No. 429, 430, 477; 254-258 for the protein of sequence SEQ ID No. 386 | 2d |
| SEQ ID No. 767 | INLYGNALSR | 61-70 for the proteins of SEQ No. 366, 374, 387, 440, 441, 459, 460, 461, 462, 463, 464, 465, 486, 493 | 2df |
| SEQ ID No. 768 | IPFSLNLEMK | 244-253 for the proteins of SEQ No. 364, 365, 371, 414, 449, 506 | 2df |
| SEQ ID No. 769 | IPHTLFALDADAVR | 76-89 for the protein of SEQ No. 373 | 2d |
| SEQ ID No. 770 | IPHTLFALDAGAAR | 76-89 for the proteins of SEQ No. 356, 491 | 2d |
| SEQ ID No. 771 | IPHTLFALDAGAVR | 76-89 for the proteins of SEQ No. 350, 355, 363, 367, 370, 375, 415, 443, 481, 488; 65-78 for the protein of sequence SEQ ID No. 362 | OXA |
| SEQ ID No. 772 | IPLGK | 255-259 for the protein of SEQ No. 379 | 2df |
| SEQ ID No. 773 | IPNAIIGLETGVIK | 71-84 for the proteins of SEQ No. 352, 358, 359, 368, 383, 442, 471, 492, 504; 62-75 for the proteins of sequence SEQ ID No. 348, 353; 72-85 for the protein of sequence SEQ ID No. 490 | OXA |
| SEQ ID No. 774 | IPNALIGLETGAIK | 71-84 for the proteins of SEQ No. 489, 505 | OXA |
| SEQ ID No. 775 | IPNSLIAFDTGAVR | 78-91 for the protein of SEQ No. 379 | 2df |
| SEQ ID No. 776 | IPSAIIGLETGVIK | 71-84 for the proteins of SEQ No. 357, 435, 501; 62-75 for the protein of sequence SEQ ID No. 354 | 2de |
| SEQ ID No. 777 | ISAFNQVK | 161-168 for the protein of SEQ No. 489 | 2d |
| SEQ ID No. 778 | ISAHEQILFLR | 166-176 for the protein of SEQ No. 373 | 2d |

-continued

| Peptide SEQ ID No. | Amino acid sequence | Position of the peptide in the OXA protein(s) | Clinical interest |
|---|---|---|---|
| SEQ ID No. 779 | ISAMEQTR | 160-167 for the protein of SEQ No. 380 | 2d |
| SEQ ID No. 780 | ISAMEQVK | 165-172 for the proteins of SEQ No. 429, 477; 152-159 for the protein of sequence SEQ ID No. 377; 164-171 for the protein of sequence SEQ ID No. 386 | 2d |
| SEQ ID No. 781 | ISATEQVAFLR | 164-174 for the protein of SEQ No. 384 | 2df |
| SEQ ID No. 782 | ISATQQIAFLR | 164-174 for the protein of SEQ No. 485 | 2df |
| SEQ ID No. 783 | ISAVNQVEFLESLFLNK | 161-177 for the proteins of SEQ No. 357, 358, 359, 368, 383, 442, 471, 504; 162-178 for the protein of sequence SEQ ID No. 490 | OXA |
| SEQ ID No. 784 | ISAVNQVEFLESLYLNK | 161-177 for the proteins of SEQ No. 352, 435, 492, 501; 152-168 for the proteins of sequence SEQ ID No. 348, 353, 354 | OXA |
| SEQ ID No. 785 | ISAVNQVK | 161-168 for the protein of SEQ No. 505 | 2de |
| SEQ ID No. 786 | ISPEEQIQFLR | 170-180 for the proteins of SEQ No. 360, 376; 155-165 for the protein of sequence SEQ ID No. 361 | 2d |
| SEQ ID No. 787 | ISPEEQVR | 166-173 for the protein of SEQ No. 351 | 2de |
| SEQ ID No. 788 | ISPEGQVR | 155-162 for the protein of SEQ No. 498 | 2d |
| SEQ ID No. 789 | ISPLEQLAFLR | 162-172 for the protein of SEQ No. 433 | 2d |
| SEQ ID No. 790 | ITAFQQVDFLR | 188-198 for the protein of SEQ No. 381 | 2df |
| SEQ ID No. 791 | ITLFLLFLNLVFGQDK | 4-19 for the protein of SEQ No. 385 | 2d |
| SEQ ID No. 792 | ITPIQEVNFADDFANNR | 174-190 for the protein of SEQ No. 447 | 2df |
| SEQ ID No. 793 | ITPIQEVNFADDLANNR | 174-190 for the protein of SEQ No. 466 | 2df |
| SEQ ID No. 794 | ITPQQEAQFAYK | 173-184 for the proteins of SEQ No. 388, 389, 390, 391, 392, 393, 394, 395, 396, 397, 398, 399, 400, 401, 402, 403, 404, 406, 407, 408, 409, 411, 412, 416, 417, 418, 419, 420, 421, 422, 423, 424, 425, 426, 427, 428, 434, 436, 437, 438, 439, 444, 445, 446, 448, 451, 452, 453, 454, 455, 456, 457, 467, 468, 472, 473, 474, 475, 478, 479, 480, 482, 483, 487, 495, 502, 503, 507, 508; 167-178 for the proteins of sequence SEQ ID No. 431, 432 | 2df |
| SEQ ID No. 795 | ITPQQEAQFTYK | 173-184 for the protein of SEQ No. 405 | 2df |
| SEQ ID No. 796 | ITPVQEVNFADDLAHNR | 174-190 for the proteins of SEQ No. 364, 365, 371, 414, 449, 506 | 2df |
| SEQ ID No. 797 | IVAFALK | 241-247 for the proteins of SEQ No. 366, 387 | 2df |
| SEQ ID No. 798 | IVAFALNMEMR | 241-251 for the proteins of SEQ No. 440, 459, 460, 461, 462, 463, 464, 465, 486, 493; 242-252 for the proteins of sequence SEQ ID No. 374, 441 | 2df |

| Peptide SEQ ID No. | Amino acid sequence | Position of the peptide in the OXA protein(s) | Clinical interest |
|---|---|---|---|
| SEQ ID No. 799 | IVESTTLADGTVVHGK | 186-201 for the proteins of SEQ No. 496, 497, 499, 500 | 2d |
| SEQ ID No. 800 | IYNSLIGLNEK | 74-84 for the proteins of SEQ No. 386, 429, 430, 477 | 2d |
| SEQ ID No. 801 | KPDIGWWVGWIER | 237-249 for the protein of SEQ No. 382 | 2df |
| SEQ ID No. 802 | LACATNNLAR | 50-59 for the protein of SEQ No. 490 | 2d |
| SEQ ID No. 803 | LAQGELPFPAPVQSTVR | 172-188 for the protein of SEQ No. 380 | 2d |
| SEQ ID No. 804 | LAQNELPYPIEIQK | 177-190 for the proteins of SEQ No. 429, 430, 477 | 2d |
| SEQ ID No. 805 | LAQNELQYPIEIQK | 176-189 for the protein of SEQ No. 386 | 2d |
| SEQ ID No. 806 | LDFGNK | 143-148 for the proteins of SEQ No. 429, 430, 477; 142-147 for the protein of sequence SEQ ID No. 386 | 2d |
| SEQ ID No. 807 | LDGSLNR | 206-212 for the protein of SEQ No. 347 | 2d |
| SEQ ID No. 808 | LEIGK | 244-248 for the protein of SEQ No. 349 | 2d |
| SEQ ID No. 809 | LEILQQALAELGLYPK | 255-270 for the protein of SEQ No. 469 | 2df |
| SEQ ID No. 810 | LENQEQVK | 173-180 for the protein of SEQ No. 377 | 2d |
| SEQ ID No. 811 | LETQEEVEK | 195-203 for the protein of SEQ No. 364 | 2df |
| SEQ ID No. 812 | LETQEEVK | 195-202 for the proteins of SEQ No. 365, 371, 414, 447, 449, 466, 506 | 2df |
| SEQ ID No. 813 | LFAAEGVK | 55-62 for the protein of SEQ No. 382 | 2df |
| SEQ ID No. 814 | LFESAGVK | 58-65 for the protein of SEQ No. 381 | 2df |
| SEQ ID No. 815 | LFGAAGVK | 30-37 for the protein of SEQ No. 380 | 2d |
| SEQ ID No. 816 | LFPEWEK | 110-116 for the proteins of SEQ No. 388, 389, 390, 391, 392, 393, 394, 395, 396, 397, 398, 399, 400, 401, 402, 403, 404, 405, 406, 407, 408, 409, 411, 412, 416, 417, 418, 419, 420, 421, 422, 423, 424, 425, 426, 427, 428, 434, 436, 437, 438, 439, 444, 445, 446, 448, 451, 452, 453, 454, 455, 456, 457, 467, 468, 472, 473, 474, 475, 478, 479, 480, 482, 483, 487, 495, 502, 503, 507, 508; 104-110 for the proteins of sequence SEQ ID No. 431, 432 | 2df |
| SEQ ID No. 817 | LGESR | 126-130 for the protein of SEQ No. 351 | 2de |
| SEQ ID No. 818 | LGVDR | 121-125 for the protein of SEQ No. 349 | 2d |
| SEQ ID No. 819 | LHVSER | 181-186 for the proteins of SEQ No. 378, 384, 450, 476, 485 | 2df |
| SEQ ID No. 820 | LHYGNAK | 131-137 for the protein of SEQ No. 385 | 2d |

-continued

| Peptide SEQ ID No. | Amino acid sequence | Position of the peptide in the OXA protein(s) | Clinical interest |
|---|---|---|---|
| SEQ ID No. 821 | LLNLLSQSK | 160-168 for the protein of SEQ No. 377 | 2d |
| SEQ ID No. 822 | LLQDER | 243-248 for the protein of SEQ No. 433 | 2d |
| SEQ ID No. 823 | LLVQDGDCGR | 38-47 for the proteins of SEQ No. 496, 497, 499, 500 | 2d |
| SEQ ID No. 824 | LNEVGYGNR | 160-168 for the protein of SEQ No. 382 | 2df |
| SEQ ID No. 825 | LNYGNADPSTK | 144-154 for the proteins of SEQ No. 355, 363 | 2d |
| SEQ ID No. 826 | LNYGNK | 130-135 for the protein of SEQ No. 377 | 2d |
| SEQ ID No. 827 | LPASK | 178-182 for the proteins of SEQ No. 489, 505; 172-176 for the protein of sequence SEQ ID No. 498 | 2d |
| SEQ ID No. 828 | LPHTLFALDADAVR | 76-89 for the proteins of SEQ No. 369, 372 | OXA |
| SEQ ID No. 829 | LPHTLFALDAGAVR | 76-89 for the protein of SEQ No. 484 | OXA |
| SEQ ID No. 830 | LPLAIMGFDSGILQSPK | 62-78 for the protein of SEQ No. 349 | 2d |
| SEQ ID No. 831 | LPLAIMGYDADILLDATTPR | 69-88 for the protein of SEQ No. 351 | 2de |
| SEQ ID No. 832 | LPSSLIALETGAVR | 98-111 for the protein of SEQ No. 381 | 2df |
| SEQ ID No. 833 | LPVSAQTLQYTANILK | 170-185 for the protein of SEQ No. 347 | 2d |
| SEQ ID No. 834 | LPVSER | 205-210 for the protein of SEQ No. 381 | 2df |
| SEQ ID No. 835 | LPVSPTAVDMTER | 173-185 for the proteins of SEQ No. 496, 497, 499, 500 | 2d |
| SEQ ID No. 836 | LSASK | 178-182 for the proteins of SEQ No. 352, 357, 358, 359, 368, 383, 435, 442, 471, 492, 501, 504; 169-173 for the proteins of sequence SEQ ID No. 348, 353, 354; 179-183 for the protein of sequence SEQ ID No. 490 | OXA |
| SEQ ID No. 837 | LSAVPIYQEVAR | 121-132 for the protein of SEQ No. 379 | 2df |
| SEQ ID No. 838 | LSAVPVYQELAR | 127-138 for the proteins of SEQ No. 364, 365, 371, 414, 447, 449, 506; 125-136 for the proteins of sequence SEQ ID No. 366, 374, 387, 440, 441, 459, 460, 461, 462, 463, 464, 465, 486, 493 | 2df |
| SEQ ID No. 839 | LSCTLVIDEASGDLLHR | 37-53 for the protein of SEQ No. 351 | 2de |
| SEQ ID No. 840 | LSLQHGWFIGWIEK | 211-224 for the protein of SEQ No. 494 | 2de |
| SEQ ID No. 841 | LSQNSLPFSQEAMNSVK | 164-180 for the protein of SEQ No. 385 | 2d |
| SEQ ID No. 842 | LSVNPK | 168-173 for the protein of SEQ No. 494 | 2de |
| SEQ ID No. 843 | LTQDER | 239-244 for the proteins of SEQ No. 496, 497, 499, 500 | 2d |

-continued

| Peptide SEQ ID No. | Amino acid sequence | Position of the peptide in the OXA protein(s) | Clinical interest |
|---|---|---|---|
| SEQ ID No. 844 | LTVGAR | 245-250 for the protein of SEQ No. 351 | 2de |
| SEQ ID No. 845 | LYGFALNIDMPGGEADIGK | 228-246 for the protein of SEQ No. 380 | 2d |
| SEQ ID No. 846 | LYHNELPFR | 178-186 for the proteins of SEQ No. 356, 491 | 2d |
| SEQ ID No. 847 | LYHNK | 176-180 for the proteins of SEQ No. 378, 384, 450, 476, 485 | 2df |
| SEQ ID No. 848 | LYQNDLPFR | 178-186 for the protein of SEQ No. 375 | 2d |
| SEQ ID No. 849 | MDDLFK | 243-248 for the proteins of SEQ No. 350, 356, 367, 370, 375, 415, 443, 481, 488, 491; 232-237 for the protein of sequence SEQ ID No. 362 | OXA |
| SEQ ID No. 850 | MEDLHK | 243-248 for the proteins of SEQ No. 355, 363 | 2d |
| SEQ ID No. 851 | MLIALIGLENHK | 85-96 for the protein of SEQ No. 506 | 2df |
| SEQ ID No. 852 | MLLIEQQGDAALYAK | 198-212 for the protein of SEQ No. 379 | 2df |
| SEQ ID No. 853 | MLLIK | 204-208 for the proteins of SEQ No. 364, 365, 371, 414, 447, 449, 466, 506 | 2df |
| SEQ ID No. 854 | MLNTALIGLEHHK | 84-95 for the proteins of SEQ No. 388, 389, 390, 391, 392, 393, 394, 395, 396, 397, 398, 399, 400, 401, 402, 403, 404, 405, 406, 408, 409, 411, 412, 416, 417, 418, 419, 420, 421, 422, 423, 424, 425, 426, 427, 428, 434, 436, 437, 438, 439, 444, 445, 446, 448, 451, 452, 453, 454, 455, 456, 457, 467, 468, 472, 473, 474, 475, 478, 479, 480, 482, 487, 495, 502, 503, 507, 508; 78-89 for the proteins of sequence SEQ ID No. 431, 432 | 2df |
| SEQ ID No. 855 | MLNALIGLENHK | 85-96 for the proteins of SEQ No. 364, 365, 371, 414, 447, 449, 466 | 2df |
| SEQ ID No. 856 | MLNALIGLENQK | 83-94 for the proteins of SEQ No. 366, 374, 387, 440, 441, 459, 460, 461, 462, 463, 464, 465, 486, 493 | 2df |
| SEQ ID No. 857 | MLNALIGLEYHK | 84-95 for the protein of SEQ No. 483 | 2df |
| SEQ ID No. 858 | MLNALIGLQHGK | 78-89 for the protein of SEQ No. 469 | 2df |
| SEQ ID No. 859 | MLNALISLEHHK | 84-95 for the protein of SEQ No. 407 | 2df |
| SEQ ID No. 860 | MQAYVDAFDYGNR | 139-151 for the protein of SEQ No. 379 | 2df |
| SEQ ID No. 861 | MQEGLNK | 123-129 for the protein of SEQ No. 377 | 2d |
| SEQ ID No. 862 | MSPASTYK | 87-94 for the protein of SEQ No. 382 | 2df |
| SEQ ID No. 863 | MTAGGK | 234-239 for the protein of SEQ No. 498 | 2d |
| SEQ ID No. 864 | MVSGK | 165-169 for the protein of SEQ No. 347 | 2d |
| SEQ ID No. 865 | NEHDPVLPYR | 71-80 for the proteins of SEQ No. 496, 497, 499, 500 | 2d |

-continued

| Peptide SEQ ID No. | Amino acid sequence | Position of the peptide in the OXA protein(s) | Clinical interest |
|---|---|---|---|
| SEQ ID No. 866 | NEHQIFK | 86-92 for the protein of SEQ No. 490; 85-91 for the protein of sequence SEQ ID No. 383 | 2d |
| SEQ ID No. 867 | NEHQVFK | 85-91 for the proteins of SEQ No. 352, 357, 358, 359, 368, 435, 442, 471, 492, 501, 504; 76-82 for the proteins of sequence SEQ ID No. 348, 353, 354 | OXA |
| SEQ ID No. 868 | NEITYK | 262-267 for the proteins of SEQ No. 364, 365, 371, 414, 447, 449, 466, 506 | 2df |
| SEQ ID No. 869 | NELLMK | 260-265 for the proteins of SEQ No. 366, 387, 440, 459, 460, 462, 463, 464, 465, 486, 493; 261-266 for the proteins of sequence SEQ ID No. 374, 441 | 2df |
| SEQ ID No. 870 | NELMMK | 260-265 for the protein of SEQ No. 461 | 2df |
| SEQ ID No. 871 | NELPFR | 181-186 for the proteins of SEQ No. 350, 355, 356, 363, 367, 370, 415, 443, 481, 488, 491; 170-175 for the protein of sequence SEQ ID No. 362 | OXA |
| SEQ ID No. 872 | NFILIFIFVILISCK | 5-19 for the proteins of SEQ No. 386, 429, 477 | 2d |
| SEQ ID No. 873 | NFILIFIFVILTSCK | 5-19 for the protein of SEQ No. 430 | 2d |
| SEQ ID No. 874 | NISSYGNNLVR | 62-72 for the protein of SEQ No. 466 | 2df |
| SEQ ID No. 875 | NISTYGNNLTR | 62-72 for the protein of SEQ No. 447 | 2df |
| SEQ ID No. 876 | NLFNEVHTTGVLVIR | 43-57 for the protein of SEQ No. 412 | 2df |
| SEQ ID No. 877 | NLSTYGNALAR | 62-72 for the proteins of SEQ No. 364, 365, 371, 414, 449, 506 | 2df |
| SEQ ID No. 878 | NMENLELFGK | 187-196 for the protein of SEQ No. 385 | 2d |
| SEQ ID No. 879 | NMLLLEENNGYK | 201-212 for the protein of SEQ No. 440 | 2df |
| SEQ ID No. 880 | NMLLLEESNGYK | 201-212 for the proteins of SEQ No. 366, 374, 387, 441, 459, 460, 461, 462, 463, 465, 486, 493 | 2df |
| SEQ ID No. 881 | NMLLLEK | 201-207 for the protein of SEQ No. 464 | 2df |
| SEQ ID No. 882 | NMTLGDAMK | 117-125 for the proteins of SEQ No. 388, 392, 393, 396, 397, 402, 405, 406, 416, 419, 422, 424, 434, 445, 446, 448, 475, 503; 111-119 for the proteins of sequence SEQ ID No. 431, 432 | 2df |
| SEQ ID No. 883 | NNGLTEAWLESSLK | 156-169 for the proteins of SEQ No. 360, 376; 141-154 for the protein of sequence SEQ ID No. 361 | 2d |
| SEQ ID No. 884 | NQLPFK | 181-186 for the protein of SEQ No. 373 | 2d |
| SEQ ID No. 885 | NQLPFQVEHQR | 181-191 for the proteins of SEQ No. 369, 372, 484 | OXA |
| SEQ ID No. 886 | NSAIENTIDNMYLQDLENSTK | 191-211 for the protein of SEQ No. 376 | 2d |
| SEQ ID No. 887 | NSAIENTIENMYLQDLDNSTK | 191-211 for the protein of SEQ No. 360 | 2d |

| Peptide SEQ ID No. | Amino acid sequence | Position of the peptide in the OXA protein(s) | Clinical interest |
|---|---|---|---|
| SEQ ID No. 888 | NSAIENTIENMYLQDLENSTK | 176-196 for the protein of SEQ No. 361 | 2d |
| SEQ ID No. 889 | NSAVWVYELFAK | 119-130 for the proteins of SEQ No. 369, 372, 484 | OXA |
| SEQ ID No. 890 | NSQVPAYK | 118-125 for the proteins of SEQ No. 429, 430, 477; 117-124 for the protein of sequence SEQ ID No. 386 | 2d |
| SEQ ID No. 891 | NSTVWIYELFAK | 119-130 for the proteins of SEQ No. 356, 491 | 2d |
| SEQ ID No. 892 | NSTVWVYELFAK | 119-130 for the proteins of SEQ No. 350, 367, 370, 373, 375, 415, 443, 481, 488; 108-119 for the protein of sequence SEQ ID No. 362 | OXA |
| SEQ ID No. 893 | NSTVWVYQLFAK | 119-130 for the proteins of SEQ No. 355, 363 | 2d |
| SEQ ID No. 894 | NTSGALVIQTDK | 48-59 for the protein of SEQ No. 460 | 2df |
| SEQ ID No. 895 | NTSGVLVIQTDK | 48-59 for the proteins of SEQ No. 366, 374, 387, 440, 441, 459, 461, 462, 463, 464, 465, 486, 493 | 2df |
| SEQ ID No. 896 | NVDEMFYYYDGSK | 75-87 for the protein of SEQ No. 377 | 2d |
| SEQ ID No. 897 | NWILR | 204-208 for the proteins of SEQ No. 350, 356, 367, 369, 370, 372, 375, 415, 443, 481, 484, 488, 491; 193-197 for the protein of sequence SEQ ID No. 362 | OXA |
| SEQ ID No. 898 | NWNAAMDLR | 125-133 for the protein of SEQ No. 382 | 2df |
| SEQ ID No. 899 | NYVDAFHYGNQDISGDK | 118-134 for the protein of SEQ No. 494 | 2de |
| SEQ ID No. 900 | QADHAILVFDQAR | 51-63 for the protein of SEQ No. 375 | 2d |
| SEQ ID No. 901 | QAEHALLVFGQER | 51-63 for the proteins of SEQ No. 369, 372, 484 | OXA |
| SEQ ID No. 902 | QAITK | 251-255 for the proteins of SEQ No. 378, 384, 450, 485; 247-251 for the protein of sequence SEQ ID No. 476 | 2df |
| SEQ ID No. 903 | QAMLTEANSDYIIR | 193-206 for the protein of SEQ No. 384 | 2df |
| SEQ ID No. 904 | QEVQFVSALAR | 171-181 for the protein of SEQ No. 469 | 2df |
| SEQ ID No. 905 | QFASIK | 243-248 for the protein of SEQ No. 347 | 2d |
| SEQ ID No. 906 | QGMPGSIR | 254-261 for the protein of SEQ No. 447 | 2df |
| SEQ ID No. 907 | QGMSGSIR | 254-261 for the protein of SEQ No. 466 | 2df |
| SEQ ID No. 908 | QGQTQQSYGNDLAR | 58-71 for the proteins of SEQ No. 388, 389, 390, 391, 392, 393, 394, 395, 396, 397, 398, 399, 400, 401, 402, 403, 404, 405, 406, 407, 408, 409, 411, 412, 416, 417, 418, 419, 420, 421, 422, 423, 424, 425, 426, 427, 428, 436, 437, 438, 439, 444, 445, 446, 448, 451, 452, 453, 454, 455, 456, 457, 467, 468, 472, 473, 474, 475, 478, 479, 480, 482, 483, 487, 495, | 2df |

-continued

| Peptide SEQ ID No. | Amino acid sequence | Position of the peptide in the OXA protein(s) | Clinical interest |
|---|---|---|---|
| | | 502, 503, 507, 508; 52-65 for the proteins of sequence SEQ ID No. 431, 432 | |
| SEQ ID No. 909 | QIDYGNADPSTIK | 143-155 for the proteins of SEQ No. 369, 372, 484 | OXA |
| SEQ ID No. 910 | QIDYGNVDPSTIK | 143-155 for the protein of SEQ No. 373 | 2d |
| SEQ ID No. 911 | QIGEAR | 129-134 for the proteins of SEQ No. 378, 450, 476, 485 | 2df |
| SEQ ID No. 912 | QIGQAR | 129-134 for the protein of SEQ No. 384 | 2df |
| SEQ ID No. 913 | QIMLIEQTPAFTLR | 190-203 for the protein of SEQ No. 470 | 2df |
| SEQ ID No. 914 | QLGSAIDQFWLR | 152-163 for the protein of SEQ No. 379 | 2df |
| SEQ ID No. 915 | QLHDNK | 199-204 for the protein of SEQ No. 381 | 2df |
| SEQ ID No. 916 | QLIFVHTVVQK | 229-239 for the protein of SEQ No. 347 | 2d |
| SEQ ID No. 917 | QLIFVHTVVQKPGK | 229-242 for the protein of SEQ No. 347 | 2d |
| SEQ ID No. 918 | QLPVK | 178-182 for the protein of SEQ No. 433; 184-188 for the protein of sequence SEQ ID No. 379 | OXA |
| SEQ ID No. 919 | QLPVKPR | 184-190 for the protein of SEQ No. 379 | 2df |
| SEQ ID No. 920 | QLSLDVLDK | 265-273 for the proteins of SEQ No. 410, 413, 458 | 2df |
| SEQ ID No. 921 | QLVYAR | 237-242 for the protein of SEQ No. 433 | 2d |
| SEQ ID No. 922 | QMMLTEASTDYIIR | 217-230 for the protein of SEQ No. 381 | 2df |
| SEQ ID No. 923 | QMSIVEATPDYVLHGK | 214-229 for the protein of SEQ No. 382 | 2df |
| SEQ ID No. 924 | QPTDPAR | 99-105 for the protein of SEQ No. 433 | 2d |
| SEQ ID No. 925 | QPTDPTR | 93-99 for the proteins of SEQ No. 496, 497, 499, 500 | 2d |
| SEQ ID No. 926 | QPVSAGIR | 246-253 for the proteins of SEQ No. 496, 497, 499, 500 | 2d |
| SEQ ID No. 927 | QQLVK | 275-279 for the protein of SEQ No. 381 | 2df |
| SEQ ID No. 928 | QTLVFAR | 232-238 for the proteins of SEQ No. 496, 497, 499, 500 | 2d |
| SEQ ID No. 929 | QVGAEK | 126-131 for the protein of SEQ No. 470 | 2df |
| SEQ ID No. 930 | QVVFAR | 238-243 for the protein of SEQ No. 349 | 2d |
| SEQ ID No. 931 | SADEVLPYGGK | 84-94 for the protein of SEQ No. 380 | 2d |
| SEQ ID No. 932 | SADEVLPYGGKPQR | 84-97 for the protein of SEQ No. 380 | 2d |

| Peptide SEQ ID No. | Amino acid sequence | Position of the peptide in the OXA protein(s) | Clinical interest |
|---|---|---|---|
| SEQ ID No. 933 | SCATNDLAR | 50-58 for the proteins of SEQ No. 352, 435, 492, 501; 41-49 for the proteins of sequence SEQ ID No. 348, 353, 354 | OXA |
| SEQ ID No. 934 | SCATNNLAR | 50-58 for the proteins of SEQ No. 357, 358, 359, 368, 383, 442, 471, 504 | OXA |
| SEQ ID No. 935 | SDIPGGSK | 251-258 for the protein of SEQ No. 349 | 2d |
| SEQ ID No. 936 | SDWGK | 29-33 for the protein of SEQ No. 375 | 2d |
| SEQ ID No. 937 | SEDNFHISSQQHEK | 27-40 for the proteins of SEQ No. 364, 365, 371, 414, 449, 506 | 2df |
| SEQ ID No. 938 | SEMPASIR | 252-259 for the proteins of SEQ No. 366, 387, 440, 459, 460, 461, 462, 463, 464, 486, 493; 253-260 for the proteins of sequence SEQ ID No. 374, 441 | 2df |
| SEQ ID No. 939 | SEMPASTR | 252-259 for the protein of SEQ No. 465 | 2df |
| SEQ ID No. 940 | SFAAHNQDQDLR | 103-114 for the proteins of SEQ No. 356, 491 | 2d |
| SEQ ID No. 941 | SFAGHNK | 103-109 for the protein of SEQ No. 375 | 2d |
| SEQ ID No. 942 | SFAGHNQDQDLR | 103-114 for the proteins of SEQ No. 369, 372, 373, 484 | 2d |
| SEQ ID No. 943 | SFAGHNQDQNLR | 103-114 for the proteins of SEQ No. 355, 363 | 2d |
| SEQ ID No. 944 | SFLESWAK | 100-107 for the protein of SEQ No. 386 | 2d |
| SEQ ID No. 945 | SFTAWEK | 109-115 for the proteins of SEQ No. 366, 374, 387, 441, 459, 460, 461, 462, 463, 464, 465, 486, 493; 104-110 for the protein of sequence SEQ ID No. 469 | 2df |
| SEQ ID No. 946 | SFTTWEK | 109-115 for the protein of SEQ No. 440 | 2df |
| SEQ ID No. 947 | SGSGWLR | 207-213 for the protein of SEQ No. 349 | 2d |
| SEQ ID No. 948 | SGWGMAVDPQVGWYVGFVEK | 221-240 for the proteins of SEQ No. 410, 413, 458 | 2df |
| SEQ ID No. 949 | SGWGMDVSPQVGWLTGWVEK | 219-238 for the protein of SEQ No. 466 | 2df |
| SEQ ID No. 950 | SGWGMDVTPQVGWLTGWVEK | 219-238 for the protein of SEQ No. 447 | 2df |
| SEQ ID No. 951 | SIHPASTFK | 69-77 for the protein of SEQ No. 379 | 2df |
| SEQ ID No. 952 | SIPTK | 252-256 for the proteins of SEQ No. 352, 357, 358, 359, 368, 383, 435, 442, 471, 490, 492, 501, 504, 505; 243-247 for the proteins of sequence SEQ ID No. 348, 353, 354 | OXA |
| SEQ ID No. 953 | SISTK | 252-256 for the protein of SEQ No. 489 | 2d |
| SEQ ID No. 959 | SLGLSNNLSR | 76-85 for the protein of SEQ No. 381 | 2df |
| SEQ ID No. 955 | SLSMSGK | 4-10 for the protein of SEQ No. 351 | 2de |

-continued

| Peptide SEQ ID No. | Amino acid sequence | Position of the peptide in the OXA protein(s) | Clinical interest |
|---|---|---|---|
| SEQ ID No. 956 | SMLFIEEK | 202-209 for the proteins of SEQ No. 388, 389, 390, 391, 392, 393, 394, 395, 396, 397, 398, 399, 400, 401, 402, 403, 404, 405, 406, 407, 408, 409, 411, 416, 417, 418, 419, 420, 421, 422, 424, 425, 426, 427, 428, 434, 436, 437, 438, 439, 444, 445, 446, 451, 452, 453, 454, 455, 456, 457, 467, 468, 472, 473, 474, 475, 478, 479, 480, 482, 483, 487, 495, 502, 503, 507, 508; 196-203 for the proteins of sequence SEQ ID No. 431, 432 | 2df |
| SEQ ID No. 957 | SNGEK | 239-243 for the proteins of SEQ No. 447, 466 | 2df |
| SEQ ID No. 958 | SNGLTHSWLGSSLK | 141-154 for the protein of SEQ No. 498 | 2d |
| SEQ ID No. 959 | SNGYK | 208-212 for the proteins of SEQ No. 366, 374, 387, 441, 459, 460, 461, 462, 463, 464, 465, 486, 493 | 2df |
| SEQ ID No. 960 | SPTWELK | 79-85 for the protein of SEQ No. 349 | 2d |
| SEQ ID No. 961 | SPTWELKPEYNPSPR | 79-93 for the protein of SEQ No. 349 | 2d |
| SEQ ID No. 962 | SQDIVR | 208-213 for the protein of SEQ No. 382 | 2df |
| SEQ ID No. 963 | SQQKPTDPTIWLK | 100-112 for the protein of SEQ No. 351 | 2de |
| SEQ ID No. 969 | SQVGWLTGWVEQPDGK | 225-240 for the protein of SEQ No. 486 | 2df |
| SEQ ID No. 965 | SSSNSCTTNNAAR | 46-58 for the protein of SEQ No. 489 | 2d |
| SEQ ID No. 966 | SSSNSCTTNNATR | 46-58 for the protein of SEQ No. 505 | 2de |
| SEQ ID No. 967 | SVYGELR | 139-145 for the protein of SEQ No. 470 | 2df |
| SEQ ID No. 968 | SWILR | 204-208 for the protein of SEQ No. 373 | 2d |
| SEQ ID No. 969 | SYFDEAQTQGVIIIK | 44-58 for the proteins of SEQ No. 364, 365, 371, 414, 447, 449, 466, 506 | 2df |
| SEQ ID No. 970 | SYLEK | 139-143 for the proteins of SEQ No. 355, 363 | 2d |
| SEQ ID No. 971 | SYPMWEK | 111-117 for the proteins of SEQ No. 447, 466 | 2df |
| SEQ ID No. 972 | TAYIPASTFK | 61-70 for the proteins of SEQ No. 489, 505; 77-86 for the proteins of sequence SEQ ID No. 410, 413, 458 | 2df |
| SEQ ID No. 973 | TDDLFK | 243-248 for the proteins of SEQ No. 369, 372, 373, 484 | 2d |
| SEQ ID No. 974 | TDINEIFK | 95-102 for the proteins of SEQ No. 374, 387, 440, 441, 459, 460, 461, 462, 463, 464, 465, 486, 493 | 2df |
| SEQ ID No. 975 | TFIHNDPR | 51-58 for the protein of SEQ No. 470 | 2df |
| SEQ ID No. 976 | TGAGFTANR | 216-224 for the proteins of SEQ No. 360, 376; 201-209 for the protein of sequence SEQ ID No. 361 | 2d |

| Peptide SEQ ID No. | Amino acid sequence | Position of the peptide in the OXA protein(s) | Clinical interest |
|---|---|---|---|
| SEQ ID No. 977 | TGFNDGQK | 197-204 for the protein of SEQ No. 385 | 2d |
| SEQ ID No. 978 | TGLADSK | 210-216 for the proteins of SEQ No. 429, 430; 209-215 for the protein of sequence SEQ ID No. 386 | 2d |
| SEQ ID No. 979 | TGLDLMQK | 140-147 for the protein of SEQ No. 447 | 2df |
| SEQ ID No. 980 | TGLELMQK | 140-147 for the proteins of SEQ No. 364, 365, 371, 414, 449, 506 | 2df |
| SEQ ID No. 981 | TGMGYPK | 198-204 for the protein of SEQ No. 347 | 2d |
| SEQ ID No. 982 | TGNGR | 197-201 for the protein of SEQ No. 494 | 2de |
| SEQ ID No. 983 | TGTGSFIDAR | 200-209 for the protein of SEQ No. 498 | 2d |
| SEQ ID No. 984 | TGTGSLSDAK | 211-220 for the protein of SEQ No. 351 | 2de |
| SEQ ID No. 985 | TGVATEYQPEIGWWAGWVER | 213-232 for the protein of SEQ No. 379 | 2df |
| SEQ ID No. 986 | TGVSYPLLADGTR | 202-214 for the proteins of SEQ No. 496, 497, 499, 500 | 2d |
| SEQ ID No. 987 | TGWAAMDIK | 217-225 for the proteins of SEQ No. 374, 441 | 2df |
| SEQ ID No. 988 | TGWAMDIK | 217-224 for the proteins of SEQ No. 366, 387, 440, 460, 461, 462, 463, 464, 465, 486, 493 | 2df |
| SEQ ID No. 989 | TGWAMDVK | 217-224 for the protein of SEQ No. 459 | 2df |
| SEQ ID No. 990 | TGWATR | 206-211 for the protein of SEQ No. 470 | 2df |
| SEQ ID No. 991 | TGWCFDCTPELGWWVGWVK | 205-223 for the protein of SEQ No. 380 | 2d |
| SEQ ID No. 992 | TGWEGR | 211-216 for the proteins of SEQ No. 350, 356, 367, 369, 370, 372, 373, 415, 443, 481, 484, 488, 491; 200-205 for the protein of sequence SEQ ID No. 362 | OXA |
| SEQ ID No. 993 | TGWFVDK | 230-236 for the protein of SEQ No. 382 | 2df |
| SEQ ID No. 994 | TGYDTK | 209-214 for the protein of SEQ No. 476 | 2df |
| SEQ ID No. 995 | TGYGVR | 233-238 for the protein of SEQ No. 381 | 2df |
| SEQ ID No. 996 | TGYSAR | 209-214 for the protein of SEQ No. 450 | 2df |
| SEQ ID No. 997 | TGYSTR | 209-214 for the proteins of SEQ No. 378, 384, 485 | 2df |
| SEQ ID No. 998 | THESSNWGK | 25-33 for the proteins of SEQ No. 355, 363 | 2d |
| SEQ ID No. 999 | TICTAIADAGTGK | 25-37 for the proteins of SEQ No. 496, 497, 499, 500 | 2d |
| SEQ ID No. 1000 | TIGGAPDAYWVDDSLQISAR | 169-188 for the protein of SEQ No. 382 | 2df |

-continued

| Peptide SEQ ID No. | Amino acid sequence | Position of the peptide in the OXA protein(s) | Clinical interest |
|---|---|---|---|
| SEQ ID No. 1001 | TLPFSASSYETLR | 177-189 for the protein of SEQ No. 470 | 2df |
| SEQ ID No. 1002 | TLPFSLK | 189-195 for the proteins of SEQ No. 399, 403, 411 | 2df |
| SEQ ID No. 1003 | TLPFSPK | 189-195 for the proteins of SEQ No. 389, 395, 412, 423, 428, 439, 445, 467, 482, 483, 495 | 2df |
| SEQ ID No. 1004 | TLPFSQEVQDEVQSILFIEEK | 189-209 for the protein of SEQ No. 448 | 2df |
| SEQ ID No. 1005 | TLPFSQEVQDEVQSMLFIEEK | 189-209 for the proteins of SEQ No. 392, 434 | 2df |
| SEQ ID No. 1006 | TLPFSQK | 189-195 for the proteins of SEQ No. 388, 390, 391, 393, 394, 396, 397, 398, 400, 401, 402, 404, 405, 406, 407, 408, 409, 416, 417, 418, 419, 420, 421, 422, 424, 425, 426, 427, 436, 437, 438, 444, 446, 451, 452, 453, 454, 455, 456, 457, 468, 472, 473, 474, 475, 478, 480, 487, 502, 503, 507, 508; 183-189 for the proteins of sequence SEQ ID No. 431, 432 | 2df |
| SEQ ID No. 1007 | TLPSSQK | 189-195 for the protein of SEQ No. 479 | 2df |
| SEQ ID No. 1008 | TLQNGWFEGFIISK | 225-238 for the proteins of SEQ No. 360, 376; 210-223 for the protein of sequence SEQ ID No. 361 | 2d |
| SEQ ID No. 1009 | TMQEYLNK | 123-130 for the protein of SEQ No. 385 | 2d |
| SEQ ID No. 1010 | TNGNSTSVYNESR | 51-63 for the proteins of SEQ No. 355, 363 | 2d |
| SEQ ID No. 1011 | TQTYQAYDAAR | 72-82 for the protein of SEQ No. 382 | 2df |
| SEQ ID No. 1012 | TTDPTIWEK | 93-101 for the protein of SEQ No. 498 | 2d |
| SEQ ID No. 1013 | TTTTEVFK | 96-103 for the proteins of SEQ No. 395, 428 | 2df |
| SEQ ID No. 1014 | TWASNDFSR | 41-49 for the protein of SEQ No. 385 | 2d |
| SEQ ID No. 1015 | TWDMVQR | 191-197 for the protein of SEQ No. 379 | 2df |
| SEQ ID No. 1016 | TWMQFSVVWVSQEITQK | 113-129 for the proteins of SEQ No. 360, 376; 98-114 for the protein of sequence SEQ ID No. 361 | 2d |
| SEQ ID No. 1017 | TYPMWEK | 111-117 for the proteins of SEQ No. 364, 365, 371, 414, 449, 506 | 2df |
| SEQ ID No. 1018 | TYVVDPAR | 58-65 for the protein of SEQ No. 379 | 2df |
| SEQ ID No. 1019 | VAFSLNIEMK | 244-253 for the protein of SEQ No. 447 | 2df |
| SEQ ID No. 1020 | VANSLIGLSTGAVR | 70-83 for the protein of SEQ No. 380 | 2d |
| SEQ ID No. 1021 | VEHQR | 187-191 for the proteins of SEQ No. 350, 355, 356, 363, 367, 369, 370, 372, 373, 375, 415, 443, 481, 484, 488, 491; 176-180 for the protein of sequence SEQ ID No. 362 | OXA |
| SEQ ID No. 1022 | VELGK | 248-252 for the protein of SEQ No. 380 | 2d |

-continued

| Peptide SEQ ID No. | Amino acid sequence | Position of the peptide in the OXA protein(s) | Clinical interest |
|---|---|---|---|
| SEQ ID No. 1023 | VEDDAGVSGTFVLMDITADR | 38-57 for the protein of SEQ No. 379 | 2df |
| SEQ ID No. 1024 | VFLDSWAK | 88-95 for the protein of SEQ No. 377 | 2d |
| SEQ ID No. 1025 | VFLESWAK | 101-108 for the proteins of SEQ No. 429, 430, 477 | 2d |
| SEQ ID No. 1026 | VFLSSWAQDMNLSSAIK | 89-105 for the protein of SEQ No. 385 | 2d |
| SEQ ID No. 1027 | VGFER | 134-138 for the protein of SEQ No. 379 | 2df |
| SEQ ID No. 1028 | VILVFDQVR | 55-63 for the proteins of SEQ No. 356, 491 | 2d |
| SEQ ID No. 1029 | VITFTK | 228-233 for the protein of SEQ No. 494 | 2de |
| SEQ ID No. 1030 | VMAAMVR | 158-164 for the protein of SEQ No. 381 | 2df |
| SEQ ID No. 1031 | VPLAVMGYDAGILVDAHNPR | 58-77 for the protein of SEQ No. 498 | 2d |
| SEQ ID No. 1032 | VQANVK | 195-200 for the proteins of SEQ No. 366, 374, 387, 440, 441, 459, 460, 461, 462, 463, 464, 465, 486, 493 | 2df |
| SEQ ID No. 1033 | VQDEVK | 196-201 for the protein of SEQ No. 444 | 2df |
| SEQ ID No. 1034 | VQDEVQSMLFIEEK | 196-209 for the proteins of SEQ No. 388, 389, 390, 391, 392, 393, 395, 396, 397, 398, 399, 400, 401, 402, 404, 405, 406, 407, 408, 409, 411, 416, 417, 418, 419, 420, 421, 422, 424, 425, 426, 427, 428, 434, 436, 437, 438, 439, 445, 446, 451, 452, 453, 454, 455, 457, 467, 468, 472, 473, 474, 475, 478, 479, 480, 482, 483, 487, 495, 502, 503, 507, 508; 190-203 for the proteins of sequence SEQ ID No. 431, 432 | 2df |
| SEQ ID No. 1035 | VQDEVQSMLFIEEMNGNK | 196-213 for the proteins of SEQ No. 412, 423 | 2df |
| SEQ ID No. 1036 | VQDGVQSMLFIEEK | 196-209 for the protein of SEQ No. 456 | 2df |
| SEQ ID No. 1037 | VQHEVQSMLFIEEK | 196-209 for the protein of SEQ No. 394 | 2df |
| SEQ ID No. 1038 | VSCLPCYQVVSHK | 138-150 for the protein of SEQ No. 382 | 2df |
| SEQ ID No. 1039 | VSCVWCYQALAR | 114-125 for the protein of SEQ No. 470 | 2df |
| SEQ ID No. 1040 | VSDVCSEVTAEGWQEVR | 37-53 for the protein of SEQ No. 381 | 2df |
| SEQ ID No. 1041 | VSEVEGWQIHGK | 186-197 for the protein of SEQ No. 347 | 2d |
| SEQ ID No. 1042 | VSFSLNIEMK | 244-253 for the protein of SEQ No. 466 | 2df |
| SEQ ID No. 1043 | VSPCSSFK | 54-61 for the protein of SEQ No. 349 | 2d |
| SEQ ID No. 1044 | VSQVPAYK | 105-112 for the protein of SEQ No. 377 | 2d |

-continued

| Peptide SEQ ID No. | Amino acid sequence | Position of the peptide in the OXA protein(s) | Clinical interest |
|---|---|---|---|
| SEQ ID No. 1045 | VVFAR | 229-233 for the protein of SEQ No. 498; 239-243 for the proteins of sequence SEQ ID No. 349.351 | OXA |
| SEQ ID No. 1046 | WDGAK | 97-101 for the proteins of SEQ No. 355, 363 | 2d |
| SEQ ID No. 1047 | WDGEK | 104-108 for the proteins of SEQ No. 393, 402, 419, 422, 424 | 2df |
| SEQ ID No. 1048 | WDGHIYDFPDWNR | 92-104 for the protein of SEQ No. 470 | 2df |
| SEQ ID No. 1049 | WDGIK | 97-101 for the proteins of SEQ No. 356, 491 | 2d |
| SEQ ID No. 1050 | WDGKPR | 92-97 for the proteins of SEQ No. 352, 357, 358, 359, 368, 383, 435, 442, 471, 489, 492, 501, 504, 505; 83-88 for the proteins of sequence SEQ ID No. 348, 353, 354; 107-112 for the proteins of sequence SEQ ID No. 410, 413, 458; 93-98 for the protein of sequence SEQ ID No. 490; 116-121 for the protein of sequence SEQ ID No. 382; | OXA |
| SEQ ID No. 1051 | WDGQK | 104-108 for the proteins of SEQ No. 388, 389, 392, 395, 396, 397, 399, 403, 405, 406, 407, 411, 412, 423, 428, 434, 439, 445, 446, 448, 467, 468, 482, 483, 495, 503, 508; 98-102 for the proteins of sequence SEQ ID No. 431, 432 | 2df |
| SEQ ID No. 1052 | WDGQTR | 95-100 for the proteins of SEQ No. 378, 384, 450, 476, 485 | 2df |
| SEQ ID No. 1053 | WDGVK | 97-101 for the proteins of SEQ No. 369, 372, 375, 484 | 2d |
| SEQ ID No. 1054 | WDGVNR | 97-102 for the proteins of SEQ No. 350, 367, 370, 373, 415, 443, 481, 488; 86-91 for the protein of sequence SEQ ID No. 362 | OXA |
| SEQ ID No. 1055 | WDYKPEFNGYK | 78-88 for the protein of SEQ No. 498; 89-99 for the protein of sequence SEQ ID No. 351 | OXA |
| SEQ ID No. 1056 | WETYSVVWFSQQITEWLGMER | 97-117 for the protein of SEQ No. 347 | 2d |
| SEQ ID No. 1057 | WNGQK | 104-108 for the proteins of SEQ No. 394, 418, 444, 507 | 2df |
| SEQ ID No. 1058 | YAQAK | 155-159 for the protein of SEQ No. 382 | 2df |
| SEQ ID No. 1059 | YFSDFNAK | 34-41 for the proteins of SEQ No. 355, 363 | 2d |
| SEQ ID No. 1060 | YGTHLDR | 68-74 for the proteins of SEQ No. 410, 413, 458 | 2df |
| SEQ ID No. 1061 | YIIHNK | 54-59 for the proteins of SEQ No. 386, 429, 430, 477 | 2d |
| SEQ ID No. 1062 | YLDELVK | 245-251 for the protein of SEQ No. 385 | 2d |
| SEQ ID No. 1063 | YLMITEAGR | 195-203 for the protein of SEQ No. 484 | OXA |
| SEQ ID No. 1064 | YLNLFSYGNANIGGGIDK | 135-152 for the proteins of SEQ No. 489, 505 | OXA |
| SEQ ID No. 1065 | YNGEK | 96-100 for the proteins of SEQ No. 429, 430, 477 | 2d |

| Peptide SEQ ID No. | Amino acid sequence | Position of the peptide in the OXA protein(s) | Clinical interest |
|---|---|---|---|
| SEQ ID No. 1066 | YPHNPR | 88-93 for the protein of SEQ No. 494 | 2de |
| SEQ ID No. 1067 | YPVVWYSQQVAHHLGAQR | 103-120 for the protein of SEQ No. 497 | 2d |
| SEQ ID No. 1068 | YSNVLAFK | 106-113 for the protein of SEQ No. 385 | 2d |
| SEQ ID No. 1069 | YSPASTFK | 68-75 for the proteins of SEQ No. 350, 355, 356, 363, 367, 369, 370, 372, 373, 375, 415, 443, 481, 484, 488, 491; 57-64 for the protein of sequence SEQ ID No. 362 | OXA |
| SEQ ID No. 1070 | YSVVPVYQQLAR | 141-152 for the protein of SEQ No. 381 | 2df |
| SEQ ID No. 1071 | YSVVWYSQLTAK | 109-120 for the protein of SEQ No. 433 | 2d |
| SEQ ID No. 1072 | YSVVWYSQQVAHHLGAQR | 103-120 for the proteins of SEQ No. 496, 499, 500 | 2d |
| SEQ ID No. 1073 | YTPASTFK | 55-62 for the protein of SEQ No. 433 | 2d |
| SEQ ID No. 1074 | YTSAFGYGNADVSGEPGK | 130-147 for the protein of SEQ No. 433 | 2d |
| SEQ ID No. 1075 | YVFVSALTGNLGSNLTSSIK | 228-247 for the protein of SEQ No. 361; 243-262 for the protein of sequence SEQ ID No. 360 | 2d |
| SEQ ID No. 1076 | YVFVSALTGSLGSNLTSSIK | 243-262 for the protein of SEQ No. 376 | 2d |
| SEQ ID No. 1077 | YVGHDR | 50-55 for the protein of SEQ No. 380 | 2d |
| SEQ ID No. 1098 | ANQAFLPASTFK | 62-73 for the proteins of SEQ No. 378, 384, 450, 476, 485 | 2df |
| SEQ ID No. 1099 | DEHQVFK | 88-94 for the proteins of SEQ No. 378, 384, 450, 476, 485 | 2df |
| SEQ ID No. 1100 | DHNLITAMK | 108-116 for the proteins of SEQ No. 378, 450, 476 | 2df |
| SEQ ID No. 1101 | DIATWNR | 101-107 for the proteins of SEQ No. 378, 450, 476 | 2df |
| SEQ ID No. 1102 | IPNSLIALDLGVVK | 74-87 for the proteins of SEQ No. 378, 384, 450, 476, 485 | 2df |
| SEQ ID No. 1103 | ISATEQISFLR | 164-174 for the proteins of SEQ No. 378, 450, 476 | 2df |
| SEQ ID No. 1104 | QAMLTEANGDYIIR | 193-206 for the proteins of SEQ No. 378, 450, 476, 485 | 2df |
| SEQ ID No. 1105 | QQGFTNNLK | 52-60 for the proteins of SEQ No. 378, 384, 450, 476, 485 | 2df |
| SEQ ID No. 1106 | SQGVVVLWNENK | 40-51 for the proteins of SEQ No. 378, 450, 476, 485 | 2df |
| SEQ ID No. 1107 | SWNAHFTEHK | 30-39 for the proteins of SEQ No. 378, 450, 476, 485 | 2df |
| SEQ ID No. 1108 | VLALSAVFLVASIIGMPAVAK | 3-23 for the proteins of SEQ No. 378, 450, 476, 485 | 2df |
| SEQ ID No. 1109 | YSVVPVYQEFAR | 117-128 for the proteins of SEQ No. 378, 384, 450, 476, 485 | 2df |

In the clinical interest column, the entries 2d, 2de, 2df correspond to the functional subgroups of OXA beta-lactamases which the corresponding peptide makes it possible to detect. Therefore, the detection of a 2df peptide will indicate the presence of a carbapenemase beta-lactamase capable of hydrolysing carbapenems.

The entry 2de will indicate the presence of a beta-lactamase with an extended spectrum (ESBL) capable of hydrolysing penicillins, first-generation cephalosporins such as cephaloridine and cefalotin, and at least one antibiotic from the oxyimino-beta-lactam class such as cefotaxime, ceftazidime or monobactams such as aztreonam.

The entry OXA indicates a common peptide between at least two of the subgroups 2d, 2de and 2df. The corresponding peptide indicates the presence of an OXA beta-lactamase and the presence of a mechanism of resistance at least to penicillins and to first-generation cephalosporins.

The detection of a mechanism of resistance to carbapenems induced by an OXA protein is characterised by the detection of at least one resistance-marking carba peptide chosen from the sequences SEQ ID No. 510, 511, 512, 513, 514, 520, 521, 522, 523, 525, 527, 530, 532, 537, 541, 542, 543, 544, 545, 546, 547, 548, 549, 550, 551, 552, 556, 557, 558, 559, 560, 561, 562, 574, 579, 581, 582, 583, 584, 592, 596, 597, 598, 599, 600, 601, 602, 607, 608, 609, 628, 631, 632, 633, 635, 636, 644, 646, 647, 649, 650, 655, 656, 661, 662, 667, 674, 675, 682, 689, 690, 698, 713, 714, 719, 720, 722, 727, 729, 730, 741, 746, 748, 750, 751, 752, 755, 756, 757, 758, 763, 764, 767, 768, 772, 775, 781, 782, 790, 792, 793, 794, 795, 796, 797, 798, 801, 809, 811, 812, 813, 814, 816, 819, 824, 832, 834, 837, 838, 847, 851, 852, 853, 854, 855, 856, 857, 858, 859, 860, 862, 868, 869, 870, 874, 875, 876, 877, 879, 880, 881, 882, 894, 895, 898, 902, 903, 904, 906, 907, 908, 911, 912, 913, 914, 915, 919, 920, 922, 923, 927, 929, 937, 938, 939, 945, 946, 948, 949, 950, 951, 954, 956, 957, 959, 962, 964, 967, 969, 971, 972, 974, 975, 979, 980, 985, 988, 990, 993, 994, 995, 996, 997, 1000, 1001, 1002, 1003, 1004, 1005, 1006, 1007, 1011, 1013, 1015, 1017, 1018, 1019, 1023, 1027, 1030, 1032, 1033, 1034, 1035, 1036, 1037, 1038, 1039, 1040, 1042, 1047, 1048, 1051, 1052, 1057, 1058, 1060, 1070, 1098, 1099, 1100, 1101, 1102, 1103, 1104, 1105, 1106, 1107, 1108, 1109

Certain peptide sequences can be common to several resistance mechanisms. Therefore, the following sequences are identical:
SEQ ID No. 24 and SEQ ID No. 287

In all cases, the sequences above indicate the expression of a mechanism of resistance to penicillins, to cephalosporins, including those of the third generation such as cefotaxime/ceftazidime, to monobactams and to carbapenems.

The method of the invention and its advantages will become apparent from the rest of the present description which presents several non-limiting examples of implementation of said method.

EXAMPLE 1: IDENTIFICATION OF MICROORGANISMS FROM A SAMPLE BY BIOCHEMICAL PROFILE

1. Culturing of the Sample on a Culture Medium

The optimum culture media and the optimum culture conditions are different according to the species of microorganism. By default, the sample is seeded on different media:

sheep blood Columbia agar (bioMérieux ref. 43041) for 18 to 24 h at 35° C., in an aerobic or anaerobic atmosphere;
TSA agar (bioMérieux ref. 43011) for 18 to 24 h at 37° C.

2. Identification of the Microorganisms

The identification is performed as follows:
1. Selection of isolated colonies
2. While maintaining the aseptic conditions, transfer of 3.0 mL of aqueous sterile saline solution (0.45-0.50% NaCl, pH 4.5 to 7.0) into a transparent plastic (polystyrene) test tube
3. With the aid of a stirrer or a sterile swab, transfer of a sufficient number of identical colonies into the saline solution tube prepared in step 2, and adjustment of the bacterial suspension between 0.50 and 0.63 McFarland with a calibrated DENSICHEK from VITEK®
4. Positioning of the bacterial suspension tube and of a VITEK® identification card on a VITEK® cartridge
5. Loading of the cartridge into the VITEK® instrument
6. The filling, sealing, incubation and reading operations are automatic
7. Acquisition of a biochemical profile
8. Identification with the VITEK® system performed by comparing to the biochemical profiles of known strains

EXAMPLE 2: PREPARATION OF A PRIMARY URINE SAMPLE BY MICROORGANISM ENRICHMENT

The following protocol is performed in 16 steps (steps 5 to 12 are optional and could be omitted if the enriched sample is subsequently treated according to examples 4 and onwards):
1. Centrifuging of 5 mL of contaminated urine, at 2000 g for 30 seconds
2. Recovery of the supernatant
3. Centrifuging at 15000 g for 5 minutes
4. Elimination of the supernatant
5. Washing of the pellet with 3 mL of distilled water by resuspension
6. Centrifuging at 15000 g for 5 minutes
7. Elimination of the supernatant
8. Place the pellet in the presence of solvent (8 acetone volumes for 1 methanol volume) for 1/10 dilution
9. Leave for 1 hour at −20° C.
10. Centrifuging at 15000 g for 5 minutes
11. Elimination of the supernatant
12. Place the pellet in the presence of solvent (8 acetone volumes for 1 methanol volume) for 1/10 dilution
13. Leave for 1 hour at −20° C.
14. Centrifuging at 15000 g for 5 minutes
15. Elimination of the supernatant
16. The pellet constitutes the microorganism-enriched sample

EXAMPLE 3: IDENTIFICATION OF MICROORGANISMS FROM A SAMPLE BY MALDI-TOF

The identification is performed as follows:
1. Transfer, with the aid of a 1 µl oese, of a portion of microorganism colony obtained according to Example 1, or of an enriched sample according to Example 2, and uniform deposition on a plate for MALDI-TOF mass spectrometry
2. Covering the deposit with 1 µl of matrix. The matrix used is a saturated solution of HCCA (alpha-cyano-4- hydroxycinnamic acid) in organic solvent (50% acetonitrile and 2.5% trifluoroacetic acid)
3. Drying at ambient temperature
4. Introducing the plate into the mass spectrometer
5. Acquiring a mass spectrum
6. Comparing the obtained spectrum with the spectra contained in a knowledge base
7. Identification of the microorganism by comparing the obtained peaks with those in the knowledge base

EXAMPLE 4: IDENTIFICATION OF MICROORGANISMS FROM A SAMPLE BY ESI-TOF

The identification is performed as follows:
1. Sampling of a microorganism colony, obtained according to Example 1, or of an enriched sample according to Example 2, and suspension in 100 µl of demineralised water.
2. Centrifuging at 3000 g for 5 minutes.
3. Elimination of the supernatant.
4. Resuspension in 100 µl of demineralised water.
5. Centrifuging at 3000 g for 5 minutes.
6. Elimination of the supernatant.
7. Resuspension in 100 µl of an acetonitrile, demineralised water and formic acid mixture (50/50/0.1%).
8. Filtration with a filter with a porosity of 0.45 µm.
9. Injection into a mass spectrometer in single MS mode.
10. Acquisition of a mass spectrum.
11. Comparing the obtained spectrum with the spectra contained in a knowledge base.
12. Identification of the microorganism by referring to reference spectra.

EXAMPLE 5: OBTAINING DIGESTED PROTEINS FROM MICROORGANISMS

The following protocol is conventionally performed in 17 steps:
1. Sampling of a microorganism colony, obtained according to Example 1, or of an enriched sample according to Example 2, and suspension in 10 to 100 µl of a 6M guanidine hydrochloride solution, 50 mM Tris-HCl, pH=8.0.
2. Addition of dithiothreitol (DTT) to achieve an end concentration of 5 mM.
3. Reduction for 20 minutes at 95° C. in a water bath.
4. Cooling the tubes to ambient temperature.
5. Addition of iodoacetamide to obtain an end concentration of 12.5 mM.
6. Alkylation for 40 minutes at ambient temperature and in the dark.
7. Dilution by a factor of 6 with a 50 mM $NH_4HCO_3$ solution, pH=8.0 to obtain an end guanidine hydrochloride concentration of 1M.
8. Addition of 1 µg of trypsin.
9. Digestion at 37° C. for between 6 hours and one night.
10. Addition of formic acid down to a pH below 4 to stop the reaction.
11. The sample volume is made up to 1 mL with water/0.5% (v/v) formic acid
12. Balancing of the Waters Oasis HLB columns with 1 ml of methanol and then 1 ml of $H_2O$/0.1% (v/v) formic acid
13. Deposition of the sample which runs off by gravity
14. Washing with 1 ml of $H_2O$/0.1% (v/v) formic acid
15. Elution with 1 ml of a mixture of 80% methanol and 20% water/0.1% (v/v) formic acid
16. The eluate is evaporated with a SpeedVac® SPD2010 evaporator (Thermo Electron Corporation, Waltham, Mass., United States of America) over 2 hours, in order to obtain a volume of around 100 µl.
17. The eluate is then taken up in a water/0.5% (v/v) formic acid solution in a quantity sufficient for (QSF) 250 µl

EXAMPLE 6: IDENTIFICATION OF A RESISTANCE TO NDM-1 BETA-LACTAMS

Samples Sam1 to Sam9 are identified according to one of the methods described in examples 1, 3 or 4. The identification of the species is set out in TABLE 1.

TABLE 1

| Names | Species |
|---|---|
| Sam1 | K. pneumoniae |
| Sam2 | C. freundii |
| Sam3 | A. baumannii |
| Sam4 | A. caviae |
| Sam5 | C. braakii |
| Sam6 | E. cloacae |
| Sam7 | P. rettgeri |
| Sam8 | E. coli |
| Sam9 | K. pneumoniae |

Samples Sam1 to Sam9 correspond to a species able to comprise an NDM-1 resistance mechanism (Enterobacteriaceae, *Pseudomonas* species, *Acinetobacter* species . . . ). The following method is then performed to search for such a mechanism.

Each sample is treated according to Example 5, then a volume of 50 µl of digested proteins is injected and analysed according to the following conditions:
Dionex Ultimate 3000 chromatographic channel from the Dionex Corporation (Sunnyvale, United States of America).
Waters BEH130 C18 Column, 2.1 mm inner diameter, 100 mm length, 3.5 µm particle size (Waters, Saint-Quentin En Yvelines, France).
Solvent A: $H_2O$+0.1% formic acid.
Solvent B: ACN+0.1% formic acid.
HPLC gradient defined in Table 2 hereafter:

TABLE 2

| Time (min) | Flow (µl) | Solvent A (%) | Solvent B (%) |
|---|---|---|---|
| 0 | 300 | 98 | 2 |
| 3 | 300 | 98 | 2 |
| 34 | 300 | 54.6 | 45.4 |
| 35 | 300 | 0 | 100 |
| 55 | 300 | 0 | 100 |
| 55.1 | 300 | 98 | 2 |
| 74 | 300 | 98 | 2 |

The eluate coming from the chromatographic column is directly injected into the ionising source of the QTRAP® 5500 mass spectrometer from Applied Biosystems (Foster City, United States of America).
The peptides coming from the digestion of the microorganism proteins are analysed by the mass spectrometer in MRM mode. Only the peptides indicated in TABLE 3 are detected. To this end, the fragment(s) indicated in TABLE 3 is/are detected.

TABLE 3

| Transition number | Peptide | Charge state of the precursor | Fragment ion | Retention time (minutes) | (m/z) filtered in Q1 | (m/z) filtered in Q3 | Collision energy (eV) |
|---|---|---|---|---|---|---|---|
| 1 | AAITHTAR | 2 | y4 monocharged | 5.61 | 420.74 | 484.26 | 24 |
| 2 | AAITHTAR | 2 | y5 monocharged | 5.61 | 420.74 | 585.31 | 24 |
| 3 | AAITHTAR | 2 | y6 monocharged | 5.61 | 420.74 | 698.39 | 24 |
| 4 | AFGAAFPK | 2 | y6 monocharged | 16.03 | 404.72 | 590.33 | 23 |
| 5 | AFGAAFPK | 2 | y7 monocharged | 16.03 | 404.72 | 737.4 | 23 |
| 6 | AFGAAFPK | 2 | y7 dicharged | 16.03 | 404.72 | 369.2 | 23 |
| 7 | ASMIVMSHSAPDSR | 2 | y7 monocharged | 13.65 | 744.85 | 769.36 | 38 |
| 8 | ASMIVMSHSAPDSR | 2 | y8 monocharged | 13.65 | 744.85 | 856.39 | 38 |
| 9 | ASMIVMSHSAPDSR | 2 | y9 monocharged | 13.65 | 744.85 | 987.43 | 38 |
| 10 | FGDLVFR | 2 | y4 monocharged | 19.14 | 427.23 | 534.34 | 24 |
| 11 | FGDLVFR | 2 | y5 monocharged | 19.14 | 427.23 | 649.37 | 24 |
| 12 | FGDLVFR | 2 | y6 monocharged | 19.14 | 427.23 | 706.39 | 24 |
| 13 | MELPNIMHPVAK | 2 | y10 dicharged | 19.09 | 690.36 | 560.32 | 35 |
| 14 | MELPNIMHPVAK | 2 | y9 monocharged | 19.09 | 690.36 | 1006.55 | 35 |
| 15 | MELPNIMHPVAK | 2 | y9 dicharged | 19.09 | 690.36 | 503.78 | 35 |
| 16 | QEINLPVALAVVTHAHQDK | 3 | y14 dicharged | 21.34 | 695.05 | 743.41 | 39 |
| 17 | QEINLPVALAVVTHAHQDK | 3 | y7 monocharged | 21.34 | 695.05 | 836.4 | 39 |
| 18 | QEINLPVALAVVTHAHQDK | 3 | y8 monocharged | 21.34 | 695.05 | 935.47 | 39 |
| 19 | SLGNLGDADTEHYAASAR | 2 | y14 dicharged | 14.64 | 924.43 | 738.84 | 46 |
| 20 | SLGNLGDADTEHYAASAR | 2 | y16 dicharged | 14.64 | 924.43 | 824.37 | 46 |
| 21 | SLGNLGDADTEHYAASAR | 2 | y7 monocharged | 14.64 | 924.43 | 775.38 | 46 |
| 22 | VLVVDTAWTDDQTAQILNWIK | 3 | y5 monocharged | 27.16 | 810.43 | 673.4 | 45 |
| 23 | VLVVDTAWTDDQTAQILNWIK | 3 | y6 monocharged | 27.16 | 810.43 | 786.49 | 45 |
| 24 | VLVVDTAWTDDQTAQILNWIK | 3 | y7 monocharged | 27.16 | 810.43 | 914.55 | 45 |

The precursor peptide charge state, its retention time, the fragment ion type and the transitions, i.e. the $(m/z)_1$ ratio in Q1 and $(m/z)_2$ ratio in Q3 are indicated in TABLE 3. The collision energy used to fragment the precursor ion is also indicated in TABLE 3.

The other machine parameters used are as follows:
Scan type: MRM
MRM planned: yes
Polarity: Positive
Ionising source: Turbo V™ (Applied BioSystems)
Q1 setting: Filtering with unit resolution Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 40.00 psi
Collision gas which induces dissociation: 9.00 psi
Dynamic filling: activated
Declustering potential (DP): 80.00 V
Entry potential before Q0 (EP): 10.00 V
Collision cell exit potential (CXP): 35 V
Total cycle time: 1.2 sec
Detection window: 90 sec The areas obtained for each of the transitions and for each of the microorganisms studied were measured. All the transitions having an area greater than or equal to 2500 (arbitrary unit) are considered to be positive and have been labelled "1" in TABLE 4. All the transitions having an area less than 2500 are considered to be negative and have been labelled 0 in TABLE 4. When no signal peak was observed, the transition has been labelled as negative.

TABLE 4

| Transition number | Sam1 | Sam2 | Sam3 | Sam4 | Sam5 | Sam6 | Sam7 | Sam8 | Sam9 |
|---|---|---|---|---|---|---|---|---|---|
| 1 | 1 | 1 | 1 | 1 | 1 | 1 | 0 | 1 | 1 |
| 2 | 1 | 1 | 1 | 1 | 1 | 1 | 1 | 1 | 1 |
| 3 | 1 | 1 | 0 | 1 | 1 | 1 | 0 | 1 | 1 |
| 4 | 1 | 1 | 1 | 1 | 1 | 1 | 1 | 1 | 1 |
| 5 | 1 | 1 | 1 | 1 | 1 | 1 | 1 | 1 | 1 |
| 6 | 1 | 1 | 0 | 1 | 1 | 1 | 1 | 1 | 1 |
| 7 | 0 | 0 | 0 | 0 | 0 | 0 | 0 | 0 | 0 |
| 8 | 0 | 0 | 0 | 0 | 0 | 0 | 0 | 0 | 0 |
| 9 | 0 | 0 | 0 | 0 | 0 | 0 | 0 | 0 | 0 |
| 10 | 1 | 1 | 1 | 1 | 1 | 1 | 1 | 1 | 1 |
| 11 | 1 | 1 | 1 | 1 | 1 | 1 | 1 | 1 | 1 |
| 12 | 1 | 1 | 1 | 1 | 1 | 1 | 1 | 1 | 1 |
| 13 | 0 | 0 | 0 | 0 | 0 | 0 | 0 | 0 | 0 |
| 14 | 0 | 0 | 0 | 0 | 0 | 0 | 0 | 0 | 0 |
| 15 | 0 | 0 | 0 | 0 | 0 | 0 | 0 | 0 | 0 |
| 16 | 1 | 1 | 0 | 1 | 1 | 0 | 0 | 0 | 1 |
| 17 | 1 | 1 | 0 | 1 | 1 | 1 | 1 | 0 | 1 |
| 18 | 1 | 1 | 0 | 1 | 1 | 0 | 1 | 0 | 1 |
| 19 | 0 | 0 | 0 | 0 | 0 | 0 | 0 | 0 | 0 |
| 20 | 0 | 0 | 0 | 0 | 0 | 0 | 0 | 0 | 0 |
| 21 | 0 | 0 | 0 | 0 | 0 | 0 | 0 | 0 | 0 |
| 22 | 0 | 0 | 0 | 0 | 0 | 0 | 0 | 0 | 0 |
| 23 | 0 | 0 | 0 | 0 | 0 | 0 | 0 | 0 | 0 |
| 24 | 0 | 0 | 0 | 0 | 0 | 0 | 0 | 0 | 0 |

The number of positive transitions is then added up and set out in TABLE 5:

TABLE 5

| Names | Species | Number of positive transitions |
|---|---|---|
| Sam1 | K. pneumoniae | 12 |
| Sam2 | C. freundii | 12 |
| Sam3 | A. baumannii | 7 |
| Sam4 | A. caviae | 12 |
| Sam5 | C. braakii | 12 |
| Sam6 | E. cloacae | 10 |
| Sam7 | P. rettgeri | 9 |
| Sam8 | E. coli | 9 |
| Sam9 | K. pneumoniae | 12 |

Samples Sam1 to Sam9 comprise more than 6 positive transitions, they therefore contain bacteria which express the NDM-1 protein. The bacteria of Sam1 to Sam9 are therefore resistant to penicillins, to cephalosporins and to carbapenems.

EXAMPLE 7: IDENTIFICATION OF A RESISTANCE TO KPC BETA-LACTAMS

Samples Sam62 to Sam73 are identified according to one of the methods described in examples 1, 3 or 4. The identification of the species is set out in TABLE 6.

TABLE 6

| Names | Species |
|---|---|
| Sam62 | K. pneumoniae |
| Sam63 | K. pneumoniae |
| Sam64 | K. pneumoniae |
| Sam65 | K. pneumoniae |
| Sam66 | K. pneumoniae |
| Sam67 | K. pneumoniae |
| Sam68 | K. pneumoniae |
| Sam69 | K. pneumoniae |
| Sam70 | K. pneumoniae |
| Sam71 | K. pneumoniae |
| Sam72 | K. pneumoniae |
| Sam73 | K. pneumoniae |

Samples Sam62 to Sam73 correspond to a species able to comprise a KPC resistance mechanism. The following method is then performed to detect such a mechanism.

Each sample is treated according to Example 5, then analysed according to Example 6 by detecting the peptides from TABLE 7 instead of the peptides from TABLE 3.

TABLE 7

| Transition number | Peptide | Methionine oxidation | Charge state of the precursor | Fragment ion | Clinical interest |
|---|---|---|---|---|---|
| 1 | AAVPADWAVGDK | no | 2 | y9 dicharged | 2f |
| 2 | AAVPADWAVGDK | no | 2 | y10 dicharged | 2f |
| 3 | AAVPADWAVGDK | no | 2 | y9 monocharged | 2f |
| 4 | APIVLAVYTR | no | 2 | y7 monocharged | 2f |
| 5 | APIVLAVYTR | no | 2 | y5 monocharged | 2f |
| 6 | APIVLAVYTR | no | 2 | y6 monocharged | 2f |
| 7 | AVTESLQK | no | 2 | y5 monocharged | 2f |

TABLE 7-continued

| Transition number | Peptide | Methionine oxidation | Charge state of the precursor | Fragment ion | Clinical interest |
|---|---|---|---|---|---|
| 8 | AVTESLQK | no | 2 | y6 monocharged | 2f |
| 9 | AVTESLQK | no | 2 | y4 monocharged | 2f |
| 10 | ELGGPAGLTAFMR | yes | 2 | y7 monocharged | 2f |
| 11 | ELGGPAGLTAFMR | yes | 2 | y5 monocharged | 2f |
| 12 | ELGGPAGLTAFMR | yes | 2 | y9 dicharged | 2f |
| 13 | ELGGPAGLTAFMR | no | 2 | y7 monocharged | 2f |
| 14 | ELGGPAGLTAFMR | no | 2 | y5 monocharged | 2f |
| 15 | ELGGPAGLTAFMR | no | 2 | y9 dicharged | 2f |
| 16 | FPLCSSFK | no | 2 | y6 monocharged | 2f |
| 17 | FPLCSSFK | no | 2 | y7 monocharged | 2f |
| 18 | FPLCSSFK | no | 2 | y5 monocharged | 2f |
| 19 | GFLAAAVLAR | no | 2 | y6 monocharged | 2f |
| 20 | GFLAAAVLAR | no | 2 | y7 monocharged | 2f |
| 21 | GFLAAAVLAR | no | 2 | y5 monocharged | 2f |
| 22 | GNTTGNHR | no | 2 | y5 monocharged | 2f |
| 23 | GNTTGNHR | no | 2 | y6 monocharged | 2f |
| 24 | GNTTGNHR | no | 2 | y4 monocharged | 2f |
| 25 | LALEGLGVNGQ | no | 3 | y8 monocharged | 2f |
| 26 | LALEGLGVNGQ | no | 3 | y7 monocharged | 2f |
| 27 | LALEGLGVNGQ | no | 3 | y6 monocharged | 2f |
| 28 | LTLGSALAAPQR | no | 3 | y9 monocharged | 2f |
| 29 | LTLGSALAAPQR | no | 3 | y5 monocharged | 2f |
| 30 | LTLGSALAAPQR | no | 3 | y6 monocharged | 2f |
| 31 | NALVPWSPISEK | no | 2 | y8 monocharged | 2f |
| 32 | NALVPWSPISEK | no | 2 | y8 dicharged | 2f |
| 33 | NALVPWSPISEK | no | 2 | y5 monocharged | 2f |
| 34 | QQFVDWLK | no | 2 | y5 monocharged | 2f |
| 35 | QQFVDWLK | no | 2 | y6 monocharged | 2f |
| 36 | QQFVDWLK | no | 2 | y4 monocharged | 2f |
| 37 | SIGDTTFR | no | 2 | y5 monocharged | 2f |
| 38 | SIGDTTFR | no | 2 | y6 monocharged | 2f |
| 39 | SIGDTTFR | no | 2 | y4 monocharged | 2f |
| 40 | SQQQAGLLDTPIR | no | 2 | y8 monocharged | 2f |
| 41 | SQQQAGLLDTPIR | no | 2 | y9 monocharged | 2f |
| 42 | SQQQAGLLDTPIR | no | 2 | y10 monocharged | 2f |
| 43 | WELELNSAIPGDAR | no | 2 | y5 monocharged | 2f |
| 44 | WELELNSAIPGDAR | no | 2 | y8 monocharged | 2f |
| 45 | WELELNSAIPGDAR | no | 2 | y9 monocharged | 2f |

The transitions mentioned in TABLE 7 are detected by using the parameters set out in TABLE 8.

| Transition number | Retention time (minutes) | (m/z) filtered in Q1 | (m/z) filtered in Q3 | Collision energy (eV) | Positivity threshold |
|---|---|---|---|---|---|
| 1 | 16.29 | 600.31 | 479.73 | 31 | 2000 |
| 2 | 16.29 | 600.31 | 529.27 | 31 | 2000 |
| 3 | 16.29 | 600.31 | 958.46 | 31 | 2000 |
| 4 | 19.07 | 551.83 | 821.49 | 29 | 13000 |
| 5 | 19.07 | 551.83 | 609.33 | 29 | 13000 |
| 6 | 19.07 | 551.83 | 722.42 | 29 | 13000 |
| 7 | 10.38 | 438.25 | 604.33 | 24 | 2000 |
| 8 | 10.38 | 438.25 | 705.38 | 24 | 2000 |
| 9 | 10.38 | 438.25 | 475.29 | 24 | 2000 |
| 10 | 18.55 | 668.34 | 811.41 | 34 | 2000 |
| 11 | 18.55 | 668.34 | 641.31 | 34 | 2000 |
| 12 | 18.55 | 668.34 | 490.26 | 34 | 2000 |
| 13 | 21.72 | 660.34 | 795.42 | 34 | 2000 |
| 14 | 21.72 | 660.34 | 625.31 | 34 | 2000 |
| 15 | 21.72 | 660.34 | 482.26 | 34 | 2000 |
| 16 | 17.56 | 493.24 | 741.36 | 27 | 2000 |
| 17 | 17.56 | 493.24 | 838.41 | 27 | 2000 |
| 18 | 17.56 | 493.24 | 628.28 | 27 | 2000 |
| 19 | 20.67 | 494.8 | 600.38 | 27 | 14000 |
| 20 | 20.67 | 494.8 | 671.42 | 27 | 14000 |
| 21 | 20.67 | 494.8 | 529.35 | 27 | 14000 |
| 22 | 1.19 | 428.7 | 584.29 | 24 | 2000 |
| 23 | 1.19 | 428.7 | 685.34 | 24 | 2000 |
| 24 | 1.19 | 428.7 | 483.24 | 24 | 2000 |
| 25 | 18.89 | 535.8 | 773.38 | 42 | 2000 |
| 26 | 18.89 | 535.8 | 644.34 | 42 | 2000 |
| 27 | 18.89 | 535.8 | 587.31 | 42 | 2000 |
| 28 | 17.37 | 599.35 | 870.48 | 42 | 2000 |
| 29 | 17.37 | 599.35 | 542.3 | 42 | 2000 |
| 30 | 17.37 | 599.35 | 655.39 | 42 | 2000 |
| 31 | 20 | 670.86 | 943.49 | 35 | 2000 |
| 32 | 20 | 670.86 | 472.25 | 35 | 2000 |
| 33 | 20 | 670.86 | 573.32 | 35 | 2000 |
| 34 | 20.48 | 532.28 | 660.37 | 28 | 2000 |
| 35 | 20.48 | 532.28 | 807.44 | 28 | 2000 |
| 36 | 20.48 | 532.28 | 561.3 | 28 | 2000 |
| 37 | 13.42 | 448.73 | 639.31 | 25 | 2000 |
| 38 | 13.42 | 448.73 | 696.33 | 25 | 2000 |
| 39 | 13.42 | 448.73 | 524.28 | 25 | 2000 |
| 40 | 17.6 | 713.89 | 884.52 | 36 | 2000 |
| 41 | 17.6 | 713.89 | 955.56 | 36 | 2000 |
| 42 | 17.6 | 713.89 | 1083.62 | 36 | 2000 |
| 43 | 21.1 | 785.9 | 515.26 | 40 | 2000 |
| 44 | 21.1 | 785.9 | 786.41 | 40 | 2000 |
| 45 | 21.1 | 785.9 | 900.45 | 40 | 2000 |

The areas obtained for each of the transitions and for each of the microorganisms studied were measured. When the areas of the 3 transitions of the same peptide are greater than or equal to the positivity threshold described in TABLE 8, the detection of the peptide is considered to be positive and is labelled "1" in TABLE 9. When at least one transition comprises an area less than the positivity threshold described in TABLE 8, the corresponding peptide is considered non-detected and is labelled "0" in TABLE 9.

TABLE 9

| Transition number | Sam62 | Sam63 | Sam64 | Sam65 | Sam66 | Sam67 | Sam68 | Sam69 | Sam70 | Sam71 | Sam72 | Sam73 |
|---|---|---|---|---|---|---|---|---|---|---|---|---|
| 1 | 0 | 0 | 0 | 0 | 0 | 0 | 1 | 1 | 1 | 1 | 1 | 1 |
| 2 | 0 | 0 | 0 | 0 | 0 | 0 | 1 | 1 | 1 | 1 | 1 | 1 |
| 3 | 0 | 0 | 0 | 0 | 0 | 0 | 1 | 1 | 1 | 1 | 1 | 1 |
| 4 | 0 | 0 | 0 | 0 | 0 | 0 | 1 | 1 | 1 | 1 | 1 | 1 |
| 5 | 0 | 0 | 0 | 0 | 0 | 0 | 1 | 1 | 1 | 1 | 1 | 1 |
| 6 | 0 | 0 | 0 | 0 | 0 | 0 | 1 | 1 | 1 | 1 | 1 | 1 |
| 7 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 |
| 9 | 0 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 | 0 |
| 11 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 |
| 13 | 0 | 0 | 0 | 0 | 0 | 0 | 1 | 1 | 1 | 1 | 1 | 1 |
| 14 | 0 | 0 | 0 | 0 | 0 | 0 | 1 | 1 | 1 | 1 | 1 | 1 |
| 15 | 0 | 0 | 0 | 0 | 0 | 0 | 1 | 1 | 1 | 1 | 1 | 1 |
| 16 | 0 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | 0 | 0 |
| 18 | 0 | 0 | 0 | 0 | 0 | 0 | 0 | 0 | 0 | 0 | 0 | 0 |
| 19 | 0 | 0 | 0 | 0 | 0 | 0 | 1 | 1 | 1 | 1 | 1 | 1 |
| 20 | 0 | 0 | 0 | 0 | 0 | 0 | 1 | 1 | 1 | 1 | 1 | 1 |
| 21 | 0 | 0 | 0 | 0 | 0 | 0 | 1 | 1 | 1 | 1 | 1 | 1 |
| 22 | 0 | 0 | 0 | 0 | 0 | 0 | 0 | 0 | 0 | 0 | 0 | 0 |
| 23 | 0 | 0 | 0 | 0 | 0 | 0 | 0 | 0 | 0 | 0 | 0 | 0 |
| 24 | 0 | 0 | 0 | 0 | 0 | 0 | 0 | 0 | 0 | 0 | 0 | 0 |
| 25 | 0 | 0 | 0 | 0 | 0 | 0 | 0 | 0 | 0 | 0 | 0 | 0 |
| 26 | 0 | 0 | 0 | 0 | 0 | 0 | 0 | 0 | 0 | 0 | 0 | 0 |
| 27 | 0 | 0 | 0 | 0 | 0 | 0 | 0 | 0 | 0 | 0 | 0 | 0 |
| 28 | 0 | 0 | 0 | 0 | 0 | 0 | 1 | 1 | 1 | 1 | 1 | 1 |
| 29 | 0 | 0 | 0 | 0 | 0 | 0 | 1 | 1 | 1 | 1 | 1 | 1 |
| 30 | 0 | 0 | 0 | 0 | 0 | 0 | 1 | 1 | 1 | 1 | 1 | 1 |
| 31 | 0 | 0 | 0 | 0 | 0 | 0 | 1 | 1 | 1 | 1 | 1 | 1 |
| 32 | 0 | 0 | 0 | 0 | 0 | 0 | 1 | 1 | 1 | 1 | 1 | 1 |
| 33 | 0 | 0 | 0 | 0 | 0 | 0 | 1 | 1 | 1 | 1 | 1 | 1 |
| 34 | 0 | 0 | 0 | 0 | 0 | 0 | 0 | 0 | 0 | 0 | 0 | 0 |
| 35 | 0 | 0 | 0 | 0 | 0 | 0 | 0 | 0 | 0 | 0 | 0 | 0 |
| 36 | 0 | 0 | 0 | 0 | 0 | 0 | 0 | 0 | 0 | 0 | 0 | 0 |
| 37 | 0 | 0 | 0 | 0 | 0 | 0 | 1 | 1 | 1 | 1 | 1 | 1 |
| 38 | 0 | 0 | 0 | 0 | 0 | 0 | 1 | 1 | 1 | 1 | 1 | 1 |
| 39 | 0 | 0 | 0 | 0 | 0 | 0 | 0 | 0 | 0 | 0 | 0 | 0 |

TABLE 9-continued

| Transition number | Sam62 | Sam63 | Sam64 | Sam65 | Sam66 | Sam67 | Sam68 | Sam69 | Sam70 | Sam71 | Sam72 | Sam73 |
|---|---|---|---|---|---|---|---|---|---|---|---|---|
| 40 | 0 | 0 | 0 | 0 | 0 | 0 | 1 | 1 | 1 | 1 | 1 | 1 |
| 41 | 0 | 0 | 0 | 0 | 0 | 0 | 1 | 1 | 1 | 1 | 1 | 1 |
| 42 | 0 | 0 | 0 | 0 | 0 | 0 | 1 | 1 | 1 | 1 | 1 | 1 |
| 43 | 0 | 0 | 0 | 0 | 0 | 0 | 0 | 0 | 0 | 0 | 0 | 0 |
| 44 | 0 | 0 | 0 | 0 | 0 | 0 | 0 | 0 | 0 | 0 | 0 | 0 |
| 45 | 0 | 0 | 0 | 0 | 0 | 0 | 0 | 0 | 0 | 0 | 0 | 0 |
| Sum of the transitions | 0 | 0 | 0 | 0 | 0 | 0 | 23 | 23 | 23 | 23 | 23 | 23 |

Samples Sam68 to Sam73 comprise at least one transition which is characteristic of KPCs. The bacteria present in samples Sam68 to Sam73 therefore express a beta-lactamase which confers on them a resistance to penicillins, to cephalosporins, including third-generation cephalosporins such as cefotaxime/ceftazidime, to monobactams and to carbapenems.

Samples Sam62 to Sam67 comprise no transition which is characteristic of KPCs. The bacteria present in samples Sam62 to Sam67 therefore do not express KPC beta-lactamase and may be sensitive to carbapenem antibiotics.

EXAMPLE 8: IDENTIFICATION OF A RESISTANCE TO NDM-1 OR KPC BETA-LACTAMS

The samples corresponding to a species able to comprise an NDM-1 or KPC resistance mechanism can be detected by employing the following method.

Each sample is treated according to Example 5, then analysed according to Example 6 by detecting the peptides from TABLE 10 instead of the peptides from TABLE 3.

TABLE 10

| Proteins | Transition number | Peptide | First-generation fragment ion | Charge state of the precursor | Clinical interest |
|---|---|---|---|---|---|
| NDM-1 | 1 | AAITHTAR | y4 monocharged | 2 | 3a |
| NDM-1 | 2 | AAITHTAR | y5 monocharged | 2 | 3a |
| NDM-1 | 3 | AAITHTAR | y6 monocharged | 2 | 3a |
| NDM-1 | 4 | AFGAAFPK | y6 monocharged | 2 | 3a |
| NDM-1 | 5 | AFGAAFPK | y7 monocharged | 2 | 3a |
| NDM-1 | 6 | AFGAAFPK | y7 dicharged | 2 | 3a |
| NDM-1 | 7 | FGDLVFR | y4 monocharged | 2 | 3a |
| NDM-1 | 8 | FGDLVFR | y5 monocharged | 2 | 3a |
| NDM-1 | 9 | FGDLVFR | y6 monocharged | 2 | 3a |
| NDM-1 | 10 | QEINLPVALAVVTHAHQDK | y14 dicharged | 3 | 3a |
| NDM-1 | 11 | QEINLPVALAVVTHAHQDK | y7 monocharged | 3 | 3a |
| NDM-1 | 12 | QEINLPVALAVVTHAHQDK | y8 monocharged | 3 | 3a |
| KPC | 13 | AAVPADWAVGDK | y9 dicharged | 2 | 2f |
| KPC | 14 | AAVPADWAVGDK | y10 dicharged | 2 | 2f |
| KPC | 15 | AAVPADWAVGDK | y9 monocharged | 2 | 2f |
| KPC | 16 | APIVLAVYTR | y7 monocharged | 2 | 2f |
| KPC | 17 | APIVLAVYTR | y5 monocharged | 2 | 2f |
| KPC | 18 | APIVLAVYTR | y6 monocharged | 2 | 2f |
| KPC | 19 | ELGGPAGLTAFMR | y7 monocharged | 2 | 2f |
| KPC | 20 | ELGGPAGLTAFMR | y5 monocharged | 2 | 2f |
| KPC | 21 | ELGGPAGLTAFMR | y9 dicharged | 2 | 2f |
| KPC | 22 | GFLAAAVLAR | y6 monocharged | 2 | 2f |
| KPC | 23 | GFLAAAVLAR | y7 monocharged | 2 | 2f |

TABLE 10-continued

| Proteins | Transition number | Peptide | First-generation fragment ion | Charge state of the precursor | Clinical interest |
|---|---|---|---|---|---|
| KPC | 24 | GFLAAAVLAR | y5 monocharged | 2 | 2f |
| KPC | 25 | LTLGSALAAPQR | y9 monocharged | 3 | 2f |
| KPC | 26 | LTLGSALAAPQR | y5 monocharged | 3 | 2f |
| KPC | 27 | LTLGSALAAPQR | y6 monocharged | 3 | 2f |
| KPC | 28 | NALVPWSPISEK | y8 monocharged | 2 | 2f |
| KPC | 29 | NALVPWSPISEK | y8 dicharged | 2 | 2f |
| KPC | 30 | NALVPWSPISEK | y5 monocharged | 2 | 2f |
| KPC | 31 | SQQQAGLLDTPIR | y8 monocharged | 2 | 2f |
| KPC | 32 | SQQQAGLLDTPIR | y9 monocharged | 2 | 2f |
| KPC | 33 | SQQQAGLLDTPIR | y10 monocharged | 2 | 2f |

The entry 2f indicates the presence of a carbapenemase beta-lactamase from subgroup 2f according to the Bush and Jacoby classification [Antimicrob Agents Chemother. 2010 March; 54(3):969-76. Epub 2009 Dec. 7. Updated functional classification of beta-lactamases], capable of hydrolysing carbapenems.

The entry 3a indicates the presence of a metallo-beta-lactamase from subgroup 3a according to the Bush and Jacoby classification [9], supra, capable of hydrolysing penicillins, cephalosporins and carbapenems.

The transitions mentioned in TABLE 10 are detected by using the parameters set out in TABLE 11.

TABLE 11

| Transition number | Retention time (minutes) | (m/z) filtered in Q1 | (m/z) filtered in Q3 | Collision energy (eV) | Positivity threshold |
|---|---|---|---|---|---|
| 1 | 5.61 | 420.74 | 484.26 | 24 | 2500 |
| 2 | 5.61 | 420.74 | 585.31 | 24 | 2500 |
| 3 | 5.61 | 420.74 | 698.39 | 24 | 2500 |
| 4 | 16.03 | 404.72 | 590.33 | 23 | 2500 |
| 5 | 16.03 | 404.72 | 737.4 | 23 | 2500 |
| 6 | 16.03 | 404.72 | 369.2 | 23 | 2500 |
| 7 | 19.14 | 427.23 | 534.34 | 24 | 2500 |
| 8 | 19.14 | 427.23 | 649.37 | 24 | 2500 |
| 9 | 19.14 | 427.23 | 706.39 | 24 | 2500 |
| 10 | 21.34 | 695.05 | 743.41 | 39 | 2500 |
| 11 | 21.34 | 695.05 | 836.4 | 39 | 2500 |
| 12 | 21.34 | 695.05 | 935.47 | 39 | 2500 |
| 13 | 16.29 | 600.31 | 479.73 | 31 | 2000 |
| 14 | 16.29 | 600.31 | 529.27 | 31 | 2000 |
| 15 | 16.29 | 600.31 | 958.46 | 31 | 2000 |
| 16 | 19.07 | 551.83 | 821.49 | 29 | 13000 |
| 17 | 19.07 | 551.83 | 609.33 | 29 | 13000 |
| 18 | 19.07 | 551.83 | 722.42 | 29 | 13000 |
| 19 | 21.72 | 660.34 | 795.42 | 34 | 2000 |
| 20 | 21.72 | 660.34 | 625.31 | 34 | 2000 |
| 21 | 21.72 | 660.34 | 482.26 | 34 | 2000 |
| 22 | 20.67 | 494.8 | 600.38 | 27 | 14000 |
| 23 | 20.67 | 494.8 | 671.42 | 27 | 14000 |
| 24 | 20.67 | 494.8 | 529.35 | 27 | 14000 |
| 25 | 17.37 | 599.35 | 870.48 | 42 | 2000 |
| 26 | 17.37 | 599.35 | 542.3 | 42 | 2000 |
| 27 | 17.37 | 599.35 | 655.39 | 42 | 2000 |
| 28 | 20 | 670.86 | 943.49 | 35 | 2000 |
| 29 | 20 | 670.86 | 472.25 | 35 | 2000 |
| 30 | 20 | 670.86 | 573.32 | 35 | 2000 |
| 31 | 17.6 | 713.89 | 884.52 | 36 | 2000 |
| 32 | 17.6 | 713.89 | 955.56 | 36 | 2000 |
| 33 | 17.6 | 713.89 | 1083.62 | 36 | 2000 |

When the areas of at least two transitions of the same peptide are greater than or equal to the positivity threshold described in TABLE 11, the detection of the peptide is considered to be positive. When more than two transitions of the same peptide comprise an area less than the positivity threshold described in TABLE 11, the corresponding peptide is considered non-detected.

A sample contains bacteria which express the NDM-1 protein, when at least one peptide corresponding to the NDM-1 resistance mechanism is detected. These bacteria are resistant to penicillins, to cephalosporins and to carbapenems.

A sample contains bacteria which express the KPC protein, when at least one peptide corresponding to the KPC resistance mechanism is detected. These bacteria are resistant to penicillins, to cephalosporins, including third-generation cephalosporins such as cefotaxime/ceftazidime, to monobactams and to carbapenems.

EXAMPLE 9: IDENTIFICATION OF A RESISTANCE TO IND BETA-LACTAMS

Samples Sam84 to Sam88 are identified according to one of the methods described in examples 1, 3 or 4. The identification of the species is set out in TABLE 12.

TABLE 12

| Names | Species |
|---|---|
| Sam84 | C. indologenes |
| Sam85 | C. indologenes |
| Sam86 | C. indologenes |
| Sam87 | C. indologenes |
| Sam88 | C. indologenes |

Samples Sam84 to Sam88 correspond to a species able to comprise an IND resistance mechanism. The following method is then performed to detect such a mechanism.

Each sample is treated according to Example 5, then analysed according to Example 6 unless otherwise stated in the rest of the example, by detecting the peptides from TABLE 13 instead of the peptides from TABLE 3.

TABLE 13

| Transition number | Peptide | Retention time (minutes) | (m/z) filtered in Q1 | (m/z) filtered in Q3 | Declustering potential (eV) | Collision energy (eV) | Collision cell exit potential (eV) | Positivity threshold |
|---|---|---|---|---|---|---|---|---|
| 1 | AATDLGYIK | 14.66 | 476.26 | 593.37 | 65.8 | 26 | 15 | 2000 |
| 2 | AATDLGYIK | 14.66 | 476.26 | 708.39 | 65.8 | 26 | 15 | 2000 |
| 3 | AATDLGYIK | 14.66 | 476.26 | 809.44 | 65.8 | 26 | 15 | 2000 |
| 4 | AGDLSFFNNK | 18.08 | 556.77 | 522.27 | 71.7 | 29.5 | 15 | 2000 |
| 5 | AGDLSFFNNK | 18.08 | 556.77 | 669.34 | 71.7 | 29.5 | 15 | 2000 |
| 6 | AGDLSFFNNK | 18.08 | 556.77 | 756.37 | 71.7 | 29.5 | 15 | 2000 |
| 7 | AGDLSFYNK | 14.82 | 507.75 | 424.22 | 68.1 | 27.3 | 15 | 2000 |
| 8 | AGDLSFYNK | 14.84 | 507.75 | 571.29 | 68.1 | 27.3 | 15 | 2000 |
| 9 | AGDLSFYNK | 14.84 | 507.75 | 658.32 | 68.1 | 27.3 | 15 | 2000 |
| 10 | AGDLSFYNQK | 14.91 | 571.78 | 552.28 | 72.8 | 30.2 | 15 | 2000 |
| 11 | AGDLSFYNQK | 14.93 | 571.78 | 699.35 | 72.8 | 30.2 | 15 | 2000 |
| 12 | AGDLSFYNQK | 14.93 | 571.78 | 786.38 | 72.8 | 30.2 | 15 | 2000 |
| 13 | AQYQSLMDTIK | 18.01 | 649.33 | 1098.55 | 78.5 | 33.6 | 15 | 2000 |
| 14 | AQYQSLMDTIK | 18.01 | 649.33 | 607.31 | 78.5 | 33.6 | 15 | 2000 |
| 15 | AQYQSLMDTIK | 18.01 | 649.33 | 807.43 | 78.5 | 33.6 | 15 | 2000 |
| 16 | ASLVIPGHDEWK | 16.84 | 676.35 | 434.70 | 80.4 | 34.8 | 15 | 2000 |
| 17 | ASLVIPGHDEWK | 16.8 | 676.35 | 868.40 | 80.4 | 34.8 | 15 | 2000 |
| 18 | ASLVIPGHDEWK | 16.82 | 676.35 | 981.48 | 80.4 | 34.8 | 15 | 2000 |
| 19 | ATLIIPGHDDWK | 17.47 | 683.36 | 427.69 | 80.9 | 35.1 | 15 | 2000 |
| 20 | ATLIIPGHDDWK | 17.47 | 683.36 | 854.38 | 80.9 | 35.1 | 15 | 2000 |
| 21 | ATLIIPGHDDWK | 17.47 | 683.36 | 967.46 | 80.9 | 35.1 | 15 | 2000 |
| 22 | ATLIIPGHDEWK | 17.54 | 690.37 | 1094.56 | 81.4 | 35.4 | 10 | 2000 |
| 23 | ATLIIPGHDEWK | 17.54 | 690.37 | 868.40 | 81.4 | 35.4 | 10 | 2000 |
| 24 | ATLIIPGHDEWK | 17.54 | 690.37 | 981.48 | 81.4 | 35.4 | 10 | 2000 |
| 25 | ATSTELIKPGK | 11.63 | 572.83 | 301.19 | 72.9 | 30.2 | 15 | 2000 |
| 26 | ATSTELIKPGK | 11.67 | 572.83 | 486.79 | 72.9 | 30.2 | 15 | 2000 |
| 27 | ATSTELIKPGK | 11.67 | 572.83 | 655.45 | 72.9 | 30.2 | 15 | 2000 |
| 28 | DFVIEPPIK | 19.93 | 529.30 | 454.30 | 69.7 | 28.3 | 15 | 2000 |
| 29 | DFVIEPPIK | 19.93 | 529.30 | 696.43 | 69.7 | 28.3 | 15 | 2000 |
| 30 | DFVIEPPIK | 19.93 | 529.30 | 795.50 | 69.7 | 28.3 | 15 | 2000 |
| 31 | DFVIEPPVKPNLYLYK | 22.03 | 645.69 | 730.91 | 78.2 | 36.3 | 15 | 2000 |
| 32 | DFVIEPPVKPNLYLYK | 22.03 | 645.69 | 787.45 | 78.2 | 36.3 | 15 | 2000 |
| 33 | DFVIEPPVKPNLYLYK | 22.08 | 645.69 | 836.99 | 78.2 | 36.3 | 15 | 2000 |
| 34 | DFVIEQPFGK | 19.77 | 590.31 | 448.26 | 74.2 | 31 | 15 | 2000 |
| 35 | DFVIEQPFGK | 19.75 | 590.31 | 705.36 | 74.2 | 31 | 15 | 2000 |
| 36 | DFVIEQPFGK | 19.75 | 590.31 | 818.44 | 74.2 | 31 | 15 | 2000 |
| 37 | EANLEQWPK | 15.53 | 557.78 | 430.25 | 71.8 | 29.5 | 15 | 2000 |
| 38 | EANLEQWPK | 15.55 | 557.78 | 558.30 | 71.8 | 29.5 | 15 | 2000 |

TABLE 13-continued

| Transition number | Peptide | Retention time (minutes) | (m/z) filtered in Q1 | (m/z) filtered in Q3 | Declustering potential (eV) | Collision energy (eV) | Collision cell exit potential (eV) | Positivity threshold |
|---|---|---|---|---|---|---|---|---|
| 39 | EANLEQWPK | 15.55 | 557.78 | 687.35 | 71.8 | 29.5 | 15 | 2000 |
| 40 | EANVEQWPITIDK | 19.5 | 514.93 | 343.71 | 68.7 | 29.7 | 10 | 2000 |
| 41 | EANVEQWPITIDK | 19.5 | 514.93 | 686.41 | 68.7 | 29.7 | 10 | 2000 |
| 42 | EANVEQWPITIDK | 19.48 | 514.93 | 872.49 | 68.7 | 29.7 | 10 | 2000 |
| 43 | EANVEQWPK | 13.84 | 550.77 | 430.25 | 71.3 | 29.2 | 15 | 2000 |
| 44 | EANVEQWPK | 13.86 | 550.77 | 558.30 | 71.3 | 29.2 | 15 | 2000 |
| 45 | EANVEQWPK | 13.86 | 550.77 | 687.35 | 71.3 | 29.2 | 15 | 2000 |
| 46 | EQYQTLMDTIQK | 17.9 | 749.37 | 735.37 | 85.7 | 38 | 10 | 2000 |
| 47 | EQYQTLMDTIQK | 17.9 | 749.37 | 848.46 | 85.7 | 38 | 10 | 2000 |
| 48 | EQYQTLMDTIQK | 17.9 | 749.37 | 949.50 | 85.7 | 38 | 10 | 2000 |
| 49 | EYSANAVYLTTK | 15.26 | 680.34 | 1067.57 | 80.7 | 34.9 | 10 | 2000 |
| 50 | EYSANAVYLTTK | 15.28 | 680.34 | 625.36 | 80.7 | 34.9 | 10 | 2000 |
| 51 | EYSANAVYLTTK | 15.26 | 680.34 | 795.46 | 80.7 | 34.9 | 10 | 2000 |
| 52 | EYSANSMYLVTK | 16.5 | 703.34 | 1113.56 | 82.4 | 35.9 | 10 | 2000 |
| 53 | EYSANSMYLVTK | 16.5 | 703.34 | 841.45 | 82.4 | 35.9 | 10 | 2000 |
| 54 | EYSANSMYLVTK | 16.5 | 703.34 | 955.49 | 82.4 | 35.9 | 10 | 2000 |
| 55 | EYSANSVYLVTK | 16.19 | 687.35 | 1081.59 | 81.2 | 35.2 | 10 | 2000 |
| 56 | EYSANSVYLVTK | 16.14 | 687.35 | 623.38 | 81.2 | 35.2 | 10 | 2000 |
| 57 | EYSANSVYLVTK | 16.12 | 687.35 | 923.52 | 81.2 | 35.2 | 10 | 2000 |
| 58 | EYSANSVYLVTQK | 16.19 | 501.26 | 376.22 | 67.7 | 29.1 | 10 | 2000 |
| 59 | EYSANSVYLVTQK | 16.19 | 501.26 | 475.29 | 67.7 | 29.1 | 10 | 2000 |
| 60 | EYSANSVYLVTQK | 16.21 | 501.26 | 751.44 | 67.7 | 29.1 | 10 | 2000 |
| 61 | EYSTNALYLVTK | 18.83 | 701.37 | 1109.62 | 82.2 | 35.9 | 10 | 2000 |
| 62 | EYSTNALYLVTK | 18.83 | 701.37 | 460.31 | 82.2 | 35.9 | 10 | 2000 |
| 63 | EYSTNALYLVTK | 18.81 | 701.37 | 623.38 | 82.2 | 35.9 | 10 | 2000 |
| 64 | GGGHVEHTLELLDK | 15.6 | 502.26 | 730.44 | 67.7 | 29.1 | 10 | 2000 |
| 65 | GGGHVEHTLELLDK | 15.6 | 502.26 | 831.48 | 67.7 | 29.1 | 10 | 2000 |
| 66 | GGGHVEHTLELLDK | 15.6 | 502.26 | 968.54 | 67.7 | 29.1 | 10 | 2000 |
| 67 | GGGHVEHTLELLNK | 15 | 501.94 | 616.37 | 67.7 | 29.1 | 10 | 2000 |
| 68 | GGGHVEHTLELLNK | 15 | 501.94 | 729.45 | 67.7 | 29.1 | 10 | 2000 |
| 69 | GGGHVEHTLELLNK | 15 | 501.94 | 830.50 | 67.7 | 29.1 | 10 | 2000 |
| 70 | GGGHVQHTLDLLDK | 15.35 | 745.39 | 1082.58 | 85.5 | 37.8 | 10 | 2000 |
| 71 | GGGHVQHTLDLLDK | 15.35 | 745.39 | 1181.65 | 85.5 | 37.8 | 10 | 2000 |
| 72 | GGGHVQHTLDLLDK | 15.35 | 745.39 | 488.31 | 85.5 | 37.8 | 10 | 2000 |
| 73 | GIPTYATAK | 12.63 | 461.26 | 376.20 | 64.7 | 25.3 | 15 | 2000 |
| 74 | GIPTYATAK | 12.63 | 461.26 | 654.35 | 64.7 | 25.3 | 15 | 2000 |
| 75 | GIPTYATAK | 12.63 | 461.26 | 751.40 | 64.7 | 25.3 | 15 | 2000 |

TABLE 13-continued

| Transition number | Peptide | Retention time (minutes) | (m/z) filtered in Q1 | (m/z) filtered in Q3 | Declustering potential (eV) | Collision energy (eV) | Collision cell exit potential (eV) | Positivity threshold |
|---|---|---|---|---|---|---|---|---|
| 76 | GNDHVK | 1.3 | 335.17 | 383.24 | 55.6 | 19.7 | 15 | 2000 |
| 77 | GNDHVK | 1.3 | 335.17 | 498.27 | 55.6 | 19.7 | 15 | 2000 |
| 78 | GNDHVK | 1.3 | 335.17 | 612.31 | 55.6 | 19.7 | 15 | 2000 |
| 79 | GVVLFDVPWEK | 23.79 | 644.86 | 559.29 | 78.1 | 33.4 | 15 | 2000 |
| 80 | GVVLFDVPWEK | 23.82 | 644.86 | 658.36 | 78.1 | 33.4 | 15 | 2000 |
| 81 | GVVLFDVPWEK | 23.82 | 644.86 | 920.45 | 78.1 | 33.4 | 15 | 2000 |
| 82 | GVVLFDVPWQK | 23.32 | 644.36 | 558.30 | 78.1 | 33.4 | 15 | 2000 |
| 83 | GVVLFDVPWQK | 23.32 | 644.36 | 772.40 | 78.1 | 33.4 | 15 | 2000 |
| 84 | GVVLFDVPWQK | 23.32 | 644.36 | 919.47 | 78.1 | 33.4 | 15 | 2000 |
| 85 | HNLPVIAVFATHSHSDR | 17.94 | 634.33 | 768.90 | 77.4 | 35.7 | 15 | 2000 |
| 86 | HNLPVIAVFATHSHSDR | 17.95 | 634.33 | 825.44 | 77.4 | 35.7 | 15 | 2000 |
| 87 | HNLPVIAVFATHSHSDR | 17.93 | 634.33 | 882.46 | 77.4 | 35.7 | 15 | 2000 |
| 88 | HNLPVVAVFATHSHDDR | 17.17 | 638.99 | 775.89 | 77.7 | 35.9 | 15 | 2000 |
| 89 | HNLPVVAVFATHSHDDR | 17.17 | 638.99 | 832.43 | 77.7 | 35.9 | 15 | 2000 |
| 90 | HNLPVVAVFATHSHDDR | 17.17 | 638.99 | 889.45 | 77.7 | 35.9 | 15 | 2000 |
| 91 | HTLELLDQQK | 15.02 | 612.83 | 403.23 | 75.8 | 32 | 15 | 2000 |
| 92 | HTLELLDQQK | 15.02 | 612.83 | 518.26 | 75.8 | 32 | 15 | 2000 |
| 93 | HTLELLDQQK | 15.02 | 612.83 | 986.55 | 75.8 | 32 | 15 | 2000 |
| 94 | HTLELLNK | 14.44 | 484.28 | 616.37 | 66.4 | 26.3 | 15 | 2000 |
| 95 | HTLELLNK | 14.44 | 484.28 | 729.45 | 66.4 | 26.3 | 15 | 2000 |
| 96 | HTLELLNK | 14.44 | 484.28 | 830.50 | 66.4 | 26.3 | 15 | 2000 |
| 97 | IQYQSLMDTIK | 19.41 | 670.34 | 1098.55 | 80 | 34.5 | 15 | 2000 |
| 98 | IQYQSLMDTIK | 19.38 | 670.34 | 607.31 | 80 | 34.5 | 15 | 2000 |
| 99 | IQYQSLMDTIK | 19.41 | 670.34 | 807.43 | 80 | 34.5 | 15 | 2000 |
| 100 | NLHIYK | 11.54 | 394.23 | 337.21 | 59.9 | 22.3 | 15 | 2000 |
| 101 | NLHIYK | 11.54 | 394.23 | 423.26 | 59.9 | 22.3 | 15 | 2000 |
| 102 | NLHIYK | 11.54 | 394.23 | 560.32 | 59.9 | 22.3 | 15 | 2000 |
| 103 | NLYIYK | 14.93 | 407.23 | 423.26 | 60.8 | 22.9 | 15 | 2000 |
| 104 | NLYIYK | 14.91 | 407.23 | 586.32 | 60.8 | 22.9 | 15 | 2000 |
| 105 | NLYIYK | 14.93 | 407.23 | 699.41 | 60.8 | 22.9 | 15 | 2000 |
| 106 | NNLHIYK | 11.29 | 451.25 | 423.26 | 64 | 24.9 | 15 | 2000 |
| 107 | NNLHIYK | 11.29 | 451.25 | 560.32 | 64 | 24.9 | 15 | 2000 |
| 108 | NNLHIYK | 11.27 | 451.25 | 673.40 | 64 | 24.9 | 15 | 2000 |
| 109 | QLYLYK | 15.22 | 414.24 | 423.26 | 61.3 | 23.2 | 15 | 2000 |
| 110 | QLYLYK | 15.2 | 414.24 | 586.32 | 61.3 | 23.2 | 15 | 2000 |
| 111 | QLYLYK | 15.22 | 414.24 | 699.41 | 61.3 | 23.2 | 15 | 2000 |
| 112 | QWPETMR | 14.84 | 474.22 | 317.16 | 65.7 | 25.9 | 15 | 2000 |
| 113 | QWPETMR | 14.75 | 474.22 | 407.21 | 65.7 | 25.9 | 15 | 2000 |

TABLE 13-continued

| Transition number | Peptide | Retention time (minutes) | (m/z) filtered in Q1 | (m/z) filtered in Q3 | Declustering potential (eV) | Collision energy (eV) | Collision cell exit potential (eV) | Positivity threshold |
|---|---|---|---|---|---|---|---|---|
| 114 | QWPETMR | 14.73 | 474.22 | 633.30 | 65.7 | 25.9 | 15 | 2000 |
| 115 | SFGVFGGK | 16.69 | 399.71 | 356.20 | 60.3 | 22.6 | 15 | 2000 |
| 116 | SFGVFGGK | 16.69 | 399.71 | 408.22 | 60.3 | 22.6 | 15 | 2000 |
| 117 | SFGVFGGK | 16.69 | 399.71 | 564.31 | 60.3 | 22.6 | 15 | 2000 |
| 118 | SIQLLMMSMFLSPLINAQVK | 32.4 | 755.41 | 441.77 | 86.2 | 41.8 | 15 | 2000 |
| 119 | SIQLLMMSMFLSPLINAQVK | 32.4 | 755.41 | 882.54 | 86.2 | 41.8 | 15 | 2000 |
| 120 | SIQLLMMSMFLSPLINAQVK | 32.4 | 755.41 | 969.57 | 86.2 | 41.8 | 15 | 2000 |
| 121 | SNSATDLGYIK | 14.71 | 584.80 | 593.37 | 73.7 | 30.7 | 15 | 2000 |
| 122 | SNSATDLGYIK | 14.71 | 584.80 | 809.44 | 73.7 | 30.7 | 15 | 2000 |
| 123 | SNSATDLGYIK | 14.71 | 584.80 | 967.51 | 73.7 | 30.7 | 15 | 2000 |
| 124 | TATDLGYTGEANVK | 13.61 | 720.35 | 718.37 | 83.6 | 36.7 | 10 | 2000 |
| 125 | TATDLGYTGEANVK | 13.61 | 720.35 | 881.44 | 83.6 | 36.7 | 10 | 2000 |
| 126 | TATDLGYTGEANVK | 13.61 | 720.35 | 938.46 | 83.6 | 36.7 | 10 | 2000 |
| 127 | TFGVFDGK | 16.56 | 435.72 | 466.23 | 62.9 | 24.2 | 15 | 2000 |
| 128 | TFGVFDGK | 16.58 | 435.72 | 622.32 | 62.9 | 24.2 | 15 | 2000 |
| 129 | TFGVFDGK | 16.58 | 435.72 | 769.39 | 62.9 | 24.2 | 15 | 2000 |
| 130 | TFGVFGGK | 16.78 | 406.72 | 408.22 | 60.8 | 22.9 | 15 | 2000 |
| 131 | TFGVFGGK | 16.76 | 406.72 | 564.31 | 60.8 | 22.9 | 15 | 2000 |
| 132 | TFGVFGGK | 16.78 | 406.72 | 711.38 | 60.8 | 22.9 | 15 | 2000 |
| 133 | TGKPYK | 1.41 | 347.20 | 407.23 | 56.4 | 20.3 | 15 | 2000 |
| 134 | TGKPYK | 1.41 | 347.20 | 535.32 | 56.4 | 20.3 | 15 | 2000 |
| 135 | TGKPYK | 1.41 | 347.20 | 592.35 | 56.4 | 20.3 | 15 | 2000 |
| 136 | TGKPYR | 1.41 | 361.20 | 435.24 | 57.4 | 20.9 | 15 | 2000 |
| 137 | TGKPYR | 1.41 | 361.20 | 563.33 | 57.4 | 20.9 | 15 | 2000 |
| 138 | TGKPYR | 1.41 | 361.20 | 620.35 | 57.4 | 20.9 | 15 | 2000 |
| 139 | TGVVLFDVPWEK | 24.03 | 695.37 | 1033.54 | 81.8 | 35.6 | 10 | 2000 |
| 140 | TGVVLFDVPWEK | 23.97 | 695.37 | 559.29 | 81.8 | 35.6 | 10 | 2000 |
| 141 | TGVVLFDVPWEK | 23.97 | 695.37 | 920.45 | 81.8 | 35.6 | 10 | 2000 |
| 142 | TNEFLK | 12.85 | 376.20 | 407.27 | 58.5 | 21.6 | 15 | 2000 |
| 143 | TNEFLK | 12.88 | 376.20 | 536.31 | 58.5 | 21.6 | 15 | 2000 |
| 144 | TNEFLK | 12.85 | 376.20 | 650.35 | 58.5 | 21.6 | 15 | 2000 |
| 145 | TNELLK | 11.69 | 359.21 | 373.28 | 57.3 | 20.8 | 15 | 2000 |
| 146 | TNELLK | 11.72 | 359.21 | 502.32 | 57.3 | 20.8 | 15 | 2000 |
| 147 | TNELLK | 11.69 | 359.21 | 616.37 | 57.3 | 20.8 | 15 | 2000 |
| 148 | TNQFLK | 12.3 | 375.71 | 407.27 | 58.5 | 21.5 | 15 | 2000 |
| 149 | TNQFLK | 12.27 | 375.71 | 535.32 | 58.5 | 21.5 | 15 | 2000 |
| 150 | TNQFLK | 12.27 | 375.71 | 649.37 | 58.5 | 21.5 | 15 | 2000 |

TABLE 13-continued

| Transition number | Peptide | Retention time (minutes) | (m/z) filtered in Q1 | (m/z) filtered in Q3 | Declustering potential (eV) | Collision energy (eV) | Collision cell exit potential (eV) | Positivity threshold |
|---|---|---|---|---|---|---|---|---|
| 151 | TQYQSLMDTIK | 18.12 | 664.33 | 1098.55 | 79.5 | 34.2 | 15 | 2000 |
| 152 | TQYQSLMDTIK | 18.1 | 664.33 | 607.31 | 79.5 | 34.2 | 15 | 2000 |
| 153 | TQYQSLMDTIK | 18.12 | 664.33 | 807.43 | 79.5 | 34.2 | 15 | 2000 |
| 154 | TYATAK | 1.9 | 327.68 | 319.20 | 55 | 19.4 | 15 | 2000 |
| 155 | TYATAK | 1.85 | 327.68 | 390.24 | 55 | 19.4 | 15 | 2000 |
| 156 | TYATAK | 1.9 | 327.68 | 553.30 | 55 | 19.4 | 15 | 2000 |
| 157 | TYATPK | 7.79 | 340.68 | 345.21 | 56 | 20 | 15 | 2000 |
| 158 | TYATPK | 7.77 | 340.68 | 416.25 | 56 | 20 | 15 | 2000 |
| 159 | TYATPK | 7.79 | 340.68 | 579.31 | 56 | 20 | 15 | 2000 |
| 160 | TYATSK | 1.45 | 335.67 | 335.19 | 55.6 | 19.8 | 15 | 2000 |
| 161 | TYATSK | 1.45 | 335.67 | 406.23 | 55.6 | 19.8 | 15 | 2000 |
| 162 | TYATSK | 1.47 | 335.67 | 569.29 | 55.6 | 19.8 | 15 | 2000 |
| 163 | VIPGHDEWK | 12.43 | 540.78 | 434.70 | 70.5 | 28.8 | 15 | 2000 |
| 164 | VIPGHDEWK | 12.45 | 540.78 | 771.34 | 70.5 | 28.8 | 15 | 2000 |
| 165 | VIPGHDEWK | 12.43 | 540.78 | 868.40 | 70.5 | 28.8 | 15 | 2000 |
| 166 | VLDGGCLVK | 14.44 | 480.76 | 633.34 | 66.2 | 26.2 | 15 | 2000 |
| 167 | VLDGGCLVK | 14.44 | 480.76 | 748.37 | 66.2 | 26.2 | 15 | 2000 |
| 168 | VLDGGCLVK | 14.46 | 480.76 | 861.45 | 66.2 | 26.2 | 15 | 2000 |
| 169 | VQYQSLMDTIQK | 18.24 | 727.37 | 1063.55 | 84.1 | 37 | 10 | 2000 |
| 170 | VQYQSLMDTIQK | 18.24 | 727.37 | 1226.61 | 84.1 | 37 | 10 | 2000 |
| 171 | VQYQSLMDTIQK | 18.24 | 727.37 | 935.49 | 84.1 | 37 | 10 | 2000 |
| 172 | YAQATLVIPGHDEWK | 18.03 | 576.63 | 577.26 | 73.2 | 32.8 | 10 | 2000 |
| 173 | YAQATLVIPGHDEWK | 18.03 | 576.63 | 747.39 | 73.2 | 32.8 | 10 | 2000 |
| 174 | YAQATLVIPGHDEWK | 18.05 | 576.63 | 868.40 | 73.2 | 32.8 | 10 | 2000 |
| 175 | YAQATLVIPGHEEWK | 17.99 | 581.30 | 690.37 | 73.5 | 33.1 | 10 | 2000 |
| 176 | YAQATLVIPGHEEWK | 17.95 | 581.30 | 754.40 | 73.5 | 33.1 | 10 | 2000 |
| 177 | YAQATLVIPGHEEWK | 17.97 | 581.30 | 882.41 | 73.5 | 33.1 | 10 | 2000 |
| 178 | YNVLDGGCLVK | 17.86 | 619.32 | 633.34 | 76.3 | 32.2 | 15 | 2000 |
| 179 | YNVLDGGCLVK | 17.86 | 619.32 | 748.37 | 76.3 | 32.2 | 15 | 2000 |
| 180 | YNVLDGGCLVK | 17.86 | 619.32 | 861.45 | 76.3 | 32.2 | 15 | 2000 |
| 181 | YPSTAK | 4.3 | 333.68 | 319.20 | 55.4 | 19.7 | 15 | 2000 |
| 182 | YPSTAK | 4.44 | 333.68 | 406.23 | 55.4 | 19.7 | 15 | 2000 |
| 183 | YPSTAK | 4.28 | 333.68 | 503.28 | 55.4 | 19.7 | 15 | 2000 |
| 184 | YSEAVLIIPGHDEWK | 19.76 | 586.30 | 753.90 | 73.9 | 33.3 | 15 | 2000 |
| 185 | YSEAVLIIPGHDEWK | 19.72 | 586.30 | 797.42 | 73.9 | 33.3 | 15 | 2000 |
| 186 | YSEAVLIIPGHDEWK | 19.72 | 586.30 | 868.40 | 73.9 | 33.3 | 15 | 2000 |

The other machine parameters used are as follows:
Scan type: MRM
MRM planned: no
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 40.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Entry potential before Q0 (EP): 10.00 V The areas obtained for each of the transitions and for each of the microorganisms studied were measured. When the areas of the transitions are greater than or equal to the positivity threshold described in TABLE 13, the detection of the transition is considered to be positive and is labelled "1" in TABLE 14. When a transition has an area less than the positivity threshold described in TABLE 13, the transition is considered non-detected and is labelled "0" in TABLE 14.

For a given peptide, when at least 3 transitions are labelled "1", the peptide is considered as being detected.

TABLE 14

| Transition number | Sam84 | Sam85 | Sam86 | Sam87 | Sam88 |
|---|---|---|---|---|---|
| 1 | 0 | 1 | 1 | 1 | 1 |
| 2 | 0 | 0 | 1 | 1 | 0 |
| 3 | 0 | 0 | 0 | 1 | 0 |
| 4 | 0 | 0 | 0 | 0 | 0 |
| 5 | 0 | 0 | 0 | 0 | 0 |
| 6 | 0 | 0 | 0 | 0 | 0 |
| 7 | 0 | 0 | 0 | 0 | 0 |
| 8 | 0 | 0 | 0 | 1 | 0 |
| 9 | 0 | 0 | 0 | 0 | 0 |
| 10 | 0 | 1 | 1 | 0 | 1 |
| 11 | 0 | 0 | 0 | 0 | 0 |
| 12 | 0 | 0 | 1 | 0 | 0 |
| 13 | 0 | 0 | 0 | 0 | 0 |
| 14 | 0 | 0 | 0 | 0 | 0 |
| 15 | 0 | 0 | 0 | 0 | 0 |
| 16 | 0 | 0 | 0 | 1 | 0 |
| 17 | 0 | 0 | 0 | 1 | 0 |
| 18 | 0 | 1 | 0 | 1 | 1 |
| 19 | 0 | 0 | 0 | 0 | 0 |
| 20 | 0 | 0 | 0 | 0 | 0 |
| 21 | 1 | 1 | 1 | 1 | 0 |
| 22 | 0 | 0 | 0 | 0 | 0 |
| 23 | 0 | 0 | 0 | 0 | 0 |
| 24 | 0 | 0 | 0 | 0 | 0 |
| 25 | 1 | 1 | 1 | 1 | 1 |
| 26 | 1 | 1 | 0 | 1 | 1 |
| 27 | 1 | 1 | 0 | 1 | 1 |
| 28 | 0 | 1 | 0 | 1 | 1 |
| 29 | 0 | 1 | 0 | 1 | 1 |
| 30 | 0 | 1 | 0 | 1 | 1 |
| 31 | 0 | 0 | 0 | 0 | 0 |
| 32 | 0 | 0 | 0 | 0 | 0 |
| 33 | 0 | 0 | 0 | 0 | 0 |
| 34 | 0 | 0 | 0 | 0 | 0 |
| 35 | 0 | 0 | 0 | 0 | 0 |
| 36 | 0 | 0 | 0 | 0 | 0 |
| 37 | 0 | 0 | 0 | 0 | 0 |
| 38 | 0 | 0 | 0 | 0 | 0 |
| 39 | 0 | 0 | 0 | 0 | 0 |
| 40 | 0 | 0 | 0 | 0 | 0 |
| 41 | 0 | 0 | 0 | 0 | 0 |
| 42 | 0 | 0 | 0 | 0 | 0 |
| 43 | 0 | 0 | 0 | 0 | 0 |
| 44 | 0 | 0 | 0 | 0 | 0 |
| 45 | 0 | 0 | 0 | 0 | 0 |
| 46 | 0 | 0 | 0 | 0 | 0 |
| 47 | 0 | 0 | 0 | 0 | 0 |
| 48 | 0 | 0 | 0 | 0 | 0 |
| 49 | 0 | 0 | 0 | 0 | 0 |
| 50 | 0 | 0 | 0 | 0 | 0 |
| 51 | 0 | 0 | 0 | 0 | 0 |
| 52 | 0 | 0 | 0 | 1 | 0 |
| 53 | 0 | 0 | 0 | 1 | 0 |
| 54 | 0 | 0 | 0 | 1 | 0 |
| 55 | 0 | 0 | 0 | 0 | 0 |
| 56 | 0 | 0 | 0 | 0 | 0 |
| 57 | 0 | 0 | 0 | 0 | 0 |
| 58 | 0 | 0 | 0 | 0 | 0 |
| 59 | 0 | 0 | 0 | 0 | 0 |
| 60 | 0 | 0 | 0 | 0 | 0 |
| 61 | 0 | 0 | 0 | 0 | 0 |
| 62 | 0 | 0 | 0 | 0 | 0 |
| 63 | 0 | 0 | 0 | 0 | 0 |
| 64 | 0 | 0 | 0 | 0 | 0 |
| 65 | 0 | 0 | 0 | 0 | 0 |
| 66 | 0 | 0 | 0 | 0 | 0 |
| 67 | 0 | 0 | 0 | 0 | 0 |
| 68 | 0 | 0 | 0 | 0 | 0 |
| 69 | 0 | 0 | 0 | 0 | 0 |
| 70 | 0 | 0 | 0 | 0 | 0 |
| 71 | 0 | 0 | 0 | 0 | 0 |
| 72 | 0 | 0 | 0 | 0 | 0 |
| 73 | 0 | 0 | 0 | 0 | 0 |
| 74 | 1 | 0 | 0 | 0 | 0 |
| 75 | 0 | 0 | 0 | 0 | 0 |
| 76 | 0 | 0 | 0 | 0 | 0 |
| 77 | 0 | 0 | 0 | 0 | 0 |
| 78 | 1 | 0 | 0 | 0 | 0 |
| 79 | 0 | 0 | 0 | 0 | 0 |
| 80 | 0 | 0 | 0 | 0 | 0 |
| 81 | 0 | 0 | 0 | 0 | 0 |
| 82 | 1 | 0 | 0 | 1 | 0 |
| 83 | 0 | 0 | 0 | 0 | 0 |
| 84 | 0 | 0 | 0 | 0 | 0 |
| 85 | 0 | 0 | 0 | 0 | 0 |
| 86 | 0 | 0 | 0 | 0 | 0 |
| 87 | 0 | 0 | 0 | 0 | 0 |
| 88 | 0 | 0 | 0 | 0 | 0 |
| 89 | 0 | 0 | 0 | 0 | 0 |
| 90 | 0 | 0 | 0 | 0 | 0 |
| 91 | 0 | 0 | 0 | 0 | 0 |
| 92 | 0 | 0 | 0 | 0 | 0 |
| 93 | 0 | 0 | 0 | 0 | 0 |
| 94 | 0 | 0 | 0 | 0 | 0 |
| 95 | 0 | 0 | 0 | 0 | 0 |
| 96 | 0 | 0 | 0 | 0 | 0 |
| 97 | 0 | 0 | 0 | 0 | 0 |
| 98 | 0 | 0 | 0 | 0 | 0 |
| 99 | 0 | 0 | 0 | 0 | 0 |
| 100 | 0 | 0 | 0 | 0 | 0 |
| 101 | 0 | 0 | 0 | 0 | 0 |
| 102 | 0 | 0 | 0 | 0 | 0 |
| 103 | 0 | 0 | 0 | 0 | 0 |
| 104 | 0 | 0 | 0 | 0 | 0 |
| 105 | 0 | 0 | 0 | 0 | 0 |
| 106 | 0 | 0 | 0 | 0 | 0 |
| 107 | 0 | 0 | 0 | 0 | 0 |
| 108 | 0 | 0 | 0 | 0 | 0 |
| 109 | 0 | 0 | 0 | 0 | 0 |
| 110 | 0 | 0 | 0 | 0 | 0 |
| 111 | 0 | 0 | 0 | 0 | 0 |
| 112 | 0 | 0 | 0 | 0 | 0 |
| 113 | 0 | 0 | 0 | 0 | 0 |
| 114 | 0 | 0 | 0 | 0 | 0 |
| 115 | 0 | 0 | 0 | 0 | 0 |
| 116 | 0 | 0 | 0 | 0 | 0 |
| 117 | 0 | 0 | 0 | 0 | 0 |
| 118 | 0 | 0 | 0 | 0 | 0 |
| 119 | 0 | 0 | 0 | 0 | 0 |
| 120 | 0 | 0 | 0 | 0 | 0 |
| 121 | 0 | 0 | 0 | 0 | 0 |

TABLE 14-continued

| Transition number | Sam84 | Sam85 | Sam86 | Sam87 | Sam88 |
|---|---|---|---|---|---|
| 122 | 0 | 0 | 0 | 0 | 0 |
| 123 | 0 | 0 | 0 | 0 | 0 |
| 124 | 0 | 0 | 0 | 0 | 0 |
| 125 | 0 | 0 | 0 | 0 | 0 |
| 126 | 0 | 0 | 0 | 0 | 0 |
| 127 | 0 | 0 | 0 | 0 | 0 |
| 128 | 0 | 0 | 0 | 0 | 0 |
| 129 | 0 | 0 | 0 | 0 | 0 |
| 130 | 0 | 0 | 0 | 0 | 0 |
| 131 | 0 | 0 | 0 | 0 | 0 |
| 132 | 0 | 0 | 0 | 0 | 0 |
| 133 | 0 | 1 | 0 | 0 | 1 |
| 134 | 0 | 1 | 0 | 0 | 1 |
| 135 | 0 | 1 | 0 | 0 | 1 |
| 136 | 1 | 0 | 0 | 0 | 0 |
| 137 | 1 | 0 | 0 | 1 | 0 |
| 138 | 1 | 0 | 0 | 0 | 1 |
| 139 | 0 | 0 | 0 | 0 | 0 |
| 140 | 0 | 0 | 0 | 0 | 0 |
| 141 | 0 | 0 | 0 | 0 | 0 |
| 142 | 0 | 0 | 0 | 0 | 0 |
| 143 | 0 | 0 | 0 | 0 | 0 |
| 144 | 0 | 0 | 0 | 0 | 0 |
| 145 | 1 | 0 | 0 | 0 | 0 |
| 146 | 1 | 0 | 0 | 1 | 0 |
| 147 | 1 | 0 | 0 | 0 | 0 |
| 148 | 0 | 0 | 0 | 0 | 0 |
| 149 | 0 | 0 | 0 | 0 | 0 |
| 150 | 0 | 0 | 0 | 0 | 0 |
| 151 | 0 | 0 | 0 | 0 | 0 |
| 152 | 0 | 0 | 0 | 0 | 0 |
| 153 | 0 | 0 | 0 | 0 | 0 |
| 154 | 0 | 0 | 0 | 0 | 0 |
| 155 | 0 | 0 | 0 | 0 | 0 |
| 156 | 0 | 0 | 0 | 0 | 0 |
| 157 | 0 | 0 | 0 | 0 | 0 |
| 158 | 0 | 0 | 0 | 0 | 0 |
| 159 | 0 | 0 | 0 | 0 | 0 |
| 160 | 0 | 0 | 0 | 0 | 0 |
| 161 | 0 | 0 | 0 | 0 | 0 |
| 162 | 0 | 0 | 0 | 0 | 0 |
| 163 | 0 | 0 | 0 | 0 | 0 |
| 164 | 0 | 0 | 0 | 0 | 0 |
| 165 | 0 | 0 | 0 | 0 | 0 |
| 166 | 0 | 0 | 0 | 0 | 0 |
| 167 | 0 | 0 | 0 | 0 | 0 |
| 168 | 0 | 0 | 0 | 0 | 0 |
| 169 | 0 | 0 | 0 | 0 | 0 |
| 170 | 0 | 0 | 0 | 0 | 0 |
| 171 | 0 | 0 | 0 | 0 | 0 |
| 172 | 0 | 0 | 0 | 0 | 0 |
| 173 | 0 | 0 | 0 | 0 | 0 |
| 174 | 0 | 0 | 0 | 0 | 0 |
| 175 | 0 | 1 | 0 | 1 | 1 |
| 176 | 0 | 1 | 0 | 1 | 1 |
| 177 | 1 | 1 | 0 | 1 | 1 |
| 178 | 0 | 0 | 0 | 0 | 0 |
| 179 | 0 | 0 | 0 | 0 | 0 |
| 180 | 0 | 0 | 0 | 0 | 0 |
| 181 | 0 | 0 | 0 | 0 | 0 |
| 182 | 0 | 0 | 0 | 0 | 0 |
| 183 | 0 | 0 | 0 | 0 | 0 |
| 184 | 0 | 0 | 0 | 0 | 0 |
| 185 | 0 | 0 | 0 | 0 | 0 |
| 186 | 0 | 0 | 0 | 0 | 0 |
| 187 | 0 | 0 | 0 | 1 | 0 |
| 188 | 0 | 0 | 0 | 1 | 0 |
| 189 | 0 | 1 | 0 | 1 | 0 |
| 190 | 0 | 0 | 0 | 0 | 0 |
| 191 | 0 | 0 | 0 | 0 | 0 |
| 192 | 0 | 0 | 0 | 0 | 0 |
| 193 | 0 | 0 | 0 | 0 | 0 |
| 194 | 0 | 0 | 0 | 0 | 0 |
| 195 | 0 | 0 | 0 | 0 | 0 |

Samples Sam84 to Sam88 comprise at least one peptide which is characteristic of INDs. The bacteria present in samples Sam84 to Sam88 therefore express a beta-lactamase which confers on them a resistance to penicillins, to cephalosporins and to carbapenems.

EXAMPLE 10: IDENTIFICATION OF A RESISTANCE TO GES BETA-LACTAMS

Samples Sam89 and Sam90 are identified according to one of the methods described in examples 1, 3 or 4. The identification of the species is set out in TABLE 15.

TABLE 15

| Names | Species |
|---|---|
| Sam89 | *E. coli* |
| Sam90 | *P. aeruginosa* |

Samples Sam89 and Sam90 correspond to a species able to comprise a GES resistance mechanism. The following method is then performed to detect such a mechanism.

Each sample is treated according to Example 5, then analysed according to Example 6 unless otherwise stated in the rest of the example, by detecting the peptides from TABLE 16 instead of the peptides from TABLE 3.

TABLE 16

| Transition number | Peptide | Retention time (minutes) | (m/z) filtered in Q1 | (m/z) filtered in Q3 | Declustering potential (eV) | Collision energy (eV) |
|---|---|---|---|---|---|---|
| 1 | AAEIGVAIVDPQGEIVAGHR | 19.11 | 668.03 | 695.88 | 79.8 | 37.4 |
| 2 | AAEIGVAIVDPQGEIVAGHR | 19.13 | 668.03 | 731.39 | 79.8 | 37.4 |
| 3 | AAEIGVAIVDPQGEIVAGHR | 19.11 | 668.03 | 809.44 | 79.8 | 37.4 |
| 4 | AAQIGVAIVDPQGEIVAGHR | 18.76 | 667.70 | 695.88 | 79.8 | 37.4 |
| 5 | AAQIGVAIVDPQGEIVAGHR | 18.76 | 667.70 | 731.39 | 79.8 | 37.4 |
| 6 | AAQIGVAIVDPQGEIVAGHR | 18.76 | 667.70 | 809.44 | 79.8 | 37.4 |
| 7 | DTTTPIAMAR | 14.23 | 538.77 | 658.37 | 70.4 | 28.7 |
| 8 | DTTTPIAMAR | 14.23 | 538.77 | 759.42 | 70.4 | 28.7 |

TABLE 16-continued

| Transition number | Peptide | Retention time (minutes) | (m/z) filtered in Q1 | (m/z) filtered in Q3 | Declustering potential (eV) | Collision energy (eV) |
|---|---|---|---|---|---|---|
| 9 | DTTTPIAMAR | 14.23 | 538.77 | 860.47 | 70.4 | 28.7 |
| 10 | DWVVGEK | 14.41 | 416.71 | 432.25 | 61.5 | 23.3 |
| 11 | DWVVGEK | 14.43 | 416.71 | 531.31 | 61.5 | 23.3 |
| 12 | DWVVGEK | 14.45 | 416.71 | 717.39 | 61.5 | 23.3 |
| 13 | DYAVAVYTTAPK | 15.83 | 649.84 | 680.36 | 78.5 | 33.6 |
| 14 | DYAVAVYTTAPK | 15.83 | 649.84 | 779.43 | 78.5 | 33.6 |
| 15 | DYAVAVYTTAPK | 15.85 | 649.84 | 850.47 | 78.5 | 33.6 |
| 16 | EIGGPAAMTQYFR | 20.03 | 720.85 | 1198.57 | 83.7 | 36.7 |
| 17 | EIGGPAAMTQYFR | 20.03 | 720.85 | 845.40 | 83.7 | 36.7 |
| 18 | EIGGPAAMTQYFR | 20.03 | 720.85 | 916.44 | 83.7 | 36.7 |
| 19 | EPEMGDNTPGDLR | 13.53 | 715.81 | 557.30 | 83.3 | 36.5 |
| 20 | EPEMGDNTPGDLR | 13.53 | 715.81 | 772.40 | 83.3 | 36.5 |
| 21 | EPEMGDNTPGDLR | 13.53 | 715.81 | 944.44 | 83.3 | 36.5 |
| 22 | ESEMSDNTPGDLR | 12.72 | 725.81 | 557.30 | 84 | 36.9 |
| 23 | ESEMSDNTPGDLR | 12.7 | 725.81 | 887.42 | 84 | 36.9 |
| 24 | ESEMSDNTPGDLR | 12.71 | 725.81 | 974.45 | 84 | 36.9 |
| 25 | FAMCSTFK | 16.14 | 496.22 | 642.29 | 67.3 | 26.8 |
| 26 | FAMCSTFK | 16.12 | 496.22 | 773.33 | 67.3 | 26.8 |
| 27 | FAMCSTFK | 16.12 | 496.22 | 844.37 | 67.3 | 26.8 |
| 28 | FIHALLLAGIAHSAYASEK | 20.93 | 671.37 | 1204.60 | 80.1 | 37.6 |
| 29 | FIHALLLAGIAHSAYASEK | 20.92 | 671.37 | 807.95 | 80.1 | 37.6 |
| 30 | FIHALLLAGIAHSAYASEK | 20.93 | 671.37 | 876.48 | 80.1 | 37.6 |
| 31 | FIHALLLAGTAHSAYASEK | 18.21 | 667.36 | 766.41 | 79.8 | 37.4 |
| 32 | FIHALLLAGTAHSAYASEK | 18.21 | 667.36 | 801.93 | 79.8 | 37.4 |
| 33 | FIHALLLAGTAHSAYASEK | 18.21 | 667.36 | 870.46 | 79.8 | 37.4 |
| 34 | FPLAALVFER | 24.46 | 581.84 | 734.42 | 73.5 | 30.6 |
| 35 | FPLAALVFER | 24.46 | 581.84 | 805.46 | 73.5 | 30.6 |
| 36 | FPLAALVFER | 24.44 | 581.84 | 918.54 | 73.5 | 30.6 |
| 37 | IDSGTER | 1.66 | 389.19 | 462.23 | 59.5 | 22.1 |
| 38 | IDSGTER | 1.84 | 389.19 | 549.26 | 59.5 | 22.1 |
| 39 | IDSGTER | 1.75 | 389.19 | 664.29 | 59.5 | 22.1 |
| 40 | IGDSVSR | 8.48 | 367.20 | 448.25 | 57.9 | 21.2 |
| 41 | IGDSVSR | 8.46 | 367.20 | 563.28 | 57.9 | 21.2 |
| 42 | IGDSVSR | 8.44 | 367.20 | 620.30 | 57.9 | 21.2 |
| 43 | LSAVER | 9.1 | 337.70 | 403.23 | 55.7 | 19.9 |
| 44 | LSAVER | 9.08 | 337.70 | 474.27 | 55.7 | 19.9 |
| 45 | LSAVER | 9.1 | 337.70 | 561.30 | 55.7 | 19.9 |

TABLE 16-continued

| Transition number | Peptide | Retention time (minutes) | (m/z) filtered in Q1 | (m/z) filtered in Q3 | Declustering potential (eV) | Collision energy (eV) |
|---|---|---|---|---|---|---|
| 46 | LSYGPDMIVEWSPATER | 22.31 | 650.98 | 573.30 | 78.6 | 36.5 |
| 47 | LSYGPDMIVEWSPATER | 22.29 | 650.98 | 660.33 | 78.6 | 36.5 |
| 48 | LSYGPDMIVEWSPATER | 22.26 | 650.98 | 846.41 | 78.6 | 36.5 |
| 49 | LSYGPDMIVK | 17.71 | 561.80 | 1009.50 | 72.1 | 29.7 |
| 50 | LSYGPDMIVK | 17.69 | 561.80 | 759.41 | 72.1 | 29.7 |
| 51 | LSYGPDMIVK | 17.69 | 561.80 | 922.47 | 72.1 | 29.7 |
| 52 | NDIGFFK | 17.71 | 420.72 | 498.27 | 61.8 | 23.5 |
| 53 | NDIGFFK | 17.69 | 420.72 | 611.36 | 61.8 | 23.5 |
| 54 | NDIGFFK | 17.74 | 420.72 | 726.38 | 61.8 | 23.5 |
| 55 | TDLEK | 3.66 | 303.16 | 389.24 | 53.2 | 18.3 |
| 56 | TDLEK | 3.73 | 303.16 | 459.21 | 53.2 | 18.3 |
| 57 | TDLEK | 3.6 | 303.16 | 504.27 | 53.2 | 18.3 |
| 58 | TGACANGAR | 1.48 | 439.20 | 648.29 | 63.1 | 24.3 |
| 59 | TGACANGAR | 1.48 | 439.20 | 719.33 | 63.1 | 24.3 |
| 60 | TGACANGAR | 1.48 | 439.20 | 776.35 | 63.1 | 24.3 |
| 61 | TGTCANGAR | 1.48 | 454.21 | 648.29 | 64.2 | 25 |
| 62 | TGTCANGAR | 1.48 | 454.21 | 749.34 | 64.2 | 25 |
| 63 | TGTCANGAR | 1.48 | 454.21 | 806.36 | 64.2 | 25 |
| 64 | TGTCANGGR | 1.48 | 447.20 | 474.24 | 63.7 | 24.7 |
| 65 | TGTCANGGR | 1.48 | 447.20 | 634.27 | 63.7 | 24.7 |
| 66 | TGTCANGGR | 1.48 | 447.20 | 735.32 | 63.7 | 24.7 |
| 67 | VLYGGALTSTSTHTIER | 15.87 | 602.65 | 1245.64 | 75.1 | 34.1 |
| 68 | VLYGGALTSTSTHTIER | 15.85 | 602.65 | 715.87 | 75.1 | 34.1 |
| 69 | VLYGGALTSTSTHTIER | 15.87 | 602.65 | 797.40 | 75.1 | 34.1 |
| 70 | WLIGNQTGDATLR | 18.93 | 722.88 | 1032.51 | 83.8 | 36.8 |
| 71 | WLIGNQTGDATLR | 19.02 | 722.88 | 1145.59 | 83.8 | 36.8 |
| 72 | WLIGNQTGDATLR | 18.96 | 722.88 | 733.38 | 83.8 | 36.8 |
| 73 | WSPATER | 11.37 | 423.71 | 476.25 | 62 | 23.6 |
| 74 | WSPATER | 11.37 | 423.71 | 573.30 | 62 | 23.6 |
| 75 | WSPATER | 11.34 | 423.71 | 660.33 | 62 | 23.6 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 40.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Entry potential before Q0 (EP): 10.00 V
Collision cell exit potential (CXP): 15.00 V The areas obtained for each of the transitions and for each of the microorganisms studied were measured. When the areas of the transitions are greater than or equal to the positivity threshold described in TABLE 16, the detection of the transition is considered to be positive and is labelled "1" in TABLE 17. When a transition has an area less than the positivity threshold described in TABLE 16, the transition is considered non-detected and is labelled "0" in TABLE 17.

For a given peptide, when at least 3 transitions are labelled "1", the peptide is considered as being detected.

TABLE 17

| Transition number | Sam89 | Sam90 |
|---|---|---|
| 1 | 0 | 0 |
| 2 | 0 | 0 |
| 3 | 0 | 0 |
| 4 | 0 | 0 |
| 5 | 1 | 1 |
| 6 | 0 | 0 |
| 7 | 1 | 1 |
| 8 | 1 | 1 |
| 9 | 1 | 1 |
| 10 | 1 | 1 |
| 11 | 1 | 1 |
| 12 | 1 | 1 |
| 13 | 0 | 0 |
| 14 | 0 | 0 |
| 15 | 0 | 0 |
| 16 | 0 | 0 |
| 17 | 0 | 0 |
| 18 | 0 | 0 |
| 19 | 0 | 0 |
| 20 | 0 | 0 |
| 21 | 0 | 0 |
| 22 | 0 | 0 |
| 23 | 0 | 0 |
| 24 | 0 | 0 |
| 25 | 0 | 0 |
| 26 | 0 | 0 |
| 27 | 0 | 0 |
| 28 | 0 | 0 |
| 29 | 0 | 0 |
| 30 | 0 | 0 |
| 31 | 0 | 0 |
| 32 | 0 | 0 |
| 33 | 0 | 0 |
| 34 | 0 | 0 |
| 35 | 0 | 0 |
| 36 | 0 | 0 |
| 37 | 1 | 1 |
| 38 | 1 | 1 |
| 39 | 1 | 1 |
| 40 | 1 | 1 |
| 41 | 1 | 1 |
| 42 | 1 | 1 |
| 43 | 1 | 1 |
| 44 | 1 | 1 |
| 45 | 1 | 1 |
| 46 | 1 | 1 |
| 47 | 1 | 1 |
| 48 | 1 | 1 |
| 49 | 0 | 0 |
| 50 | 0 | 0 |
| 51 | 0 | 0 |
| 52 | 1 | 1 |

TABLE 17-continued

| Transition number | Sam89 | Sam90 |
|---|---|---|
| 53 | 1 | 1 |
| 54 | 1 | 1 |
| 55 | 0 | 0 |
| 56 | 0 | 0 |
| 57 | 0 | 0 |
| 58 | 0 | 0 |
| 59 | 0 | 0 |
| 60 | 0 | 0 |
| 61 | 0 | 0 |
| 62 | 0 | 0 |
| 63 | 0 | 0 |
| 64 | 1 | 0 |
| 65 | 0 | 1 |
| 66 | 1 | 1 |
| 67 | 1 | 1 |
| 68 | 1 | 1 |
| 69 | 1 | 1 |
| 70 | 1 | 1 |
| 71 | 1 | 1 |
| 72 | 1 | 1 |
| 73 | 0 | 0 |
| 74 | 0 | 0 |
| 75 | 0 | 0 |

Samples Sam89 and Sam90 comprise at least one peptide which is characteristic of the carbapenemase phenotype. The bacteria present in samples Sam89 to Sam90 therefore express a beta-lactamase which confers on them a resistance to penicillins, to cephalosporins and to carbapenems.

EXAMPLE 11: IDENTIFICATION OF A RESISTANCE TO SME BETA-LACTAMS

Samples Sam91 to Sam95 are identified according to one of the methods described in examples 1, 3 or 4. The identification of the species is set out in TABLE 18.

TABLE 18

| Names | Species |
|---|---|
| Sam91 | *S. marcescens* |
| Sam92 | *S. marcescens* |
| Sam93 | *S. marcescens* |
| Sam94 | *S. marcescens* |
| Sam95 | *S. marcescens* |

Samples Sam91 to Sam95 correspond to a species able to comprise an SME resistance mechanism. The following method is then performed to detect such a mechanism.

Each sample is treated according to Example 5, then analysed according to Example 6 unless otherwise stated in the rest of the example, by detecting the peptides from TABLE 19 instead of the peptides from TABLE 3.

TABLE 19

| Transition number | Peptide | Retention time (minutes) | (m/z) filtered in Q1 | (m/z) filtered in Q3 | Collision energy (eV) | positivity threshold |
|---|---|---|---|---|---|---|
| 1 | AIYQNWLK | 18.69 | 518.29 | 426.22 | 25.3 | 2500 |
| 2 | AIYQNWLK | 18.69 | 518.29 | 688.38 | 25.3 | 2500 |
| 3 | AIYQNWLK | 18.69 | 518.29 | 851.44 | 25.3 | 2500 |
| 4 | APLIVSIYTTR | 20.21 | 617.36 | 740.39 | 30.9 | 2500 |
| 5 | APLIVSIYTTR | 20.21 | 617.36 | 839.46 | 30.9 | 2500 |

TABLE 19-continued

| Transition number | Peptide | Retention time (minutes) | (m/z) filtered in Q1 | (m/z) filtered in Q3 | Collision energy (eV) | positivity threshold |
|---|---|---|---|---|---|---|
| 6 | APLIVSIYTTR | 20.21 | 617.36 | 952.55 | 30.9 | 2500 |
| 7 | ASVPADWVVGDK | 17.56 | 622.32 | 493.75 | 31.2 | 2500 |
| 8 | ASVPADWVVGDK | 17.56 | 622.32 | 543.29 | 31.2 | 2500 |
| 9 | ASVPADWVVGDK | 17.56 | 622.32 | 986.49 | 31.2 | 2500 |
| 10 | AVANSLNK | 8.75 | 408.73 | 461.27 | 19 | 2500 |
| 11 | AVANSLNK | 8.75 | 408.73 | 575.32 | 19 | 2500 |
| 12 | AVANSLNK | 8.75 | 408.73 | 646.35 | 19 | 2500 |
| 13 | DLEYHSPITTK | 14.48 | 435.22 | 473.75 | 20.6 | 2500 |
| 14 | DLEYHSPITTK | 14.48 | 435.22 | 538.28 | 20.6 | 2500 |
| 15 | DLEYHSPITTK | 14.48 | 435.22 | 646.38 | 20.6 | 2500 |
| 16 | DLEYYSPITTK | 17.4 | 665.33 | 559.35 | 33.7 | 2500 |
| 17 | DLEYYSPITTK | 17.4 | 665.33 | 646.38 | 33.7 | 2500 |
| 18 | DLEYYSPITTK | 17.4 | 665.33 | 809.44 | 33.7 | 2500 |
| 19 | DTSTPK | 1.45 | 324.66 | 345.21 | 14.2 | 2500 |
| 20 | DTSTPK | 1.45 | 324.66 | 432.25 | 14.2 | 2500 |
| 21 | DTSTPK | 1.45 | 324.66 | 533.29 | 14.2 | 2500 |
| 22 | FLGGPEGMTK | 14.94 | 518.76 | 662.32 | 25.3 | 2500 |
| 23 | FLGGPEGMTK | 14.94 | 518.76 | 719.34 | 25.3 | 2500 |
| 24 | FLGGPEGMTK | 14.94 | 518.76 | 776.36 | 25.3 | 2500 |
| 25 | GFLAAAVLER | 20.49 | 523.80 | 587.35 | 25.6 | 2500 |
| 26 | GFLAAAVLER | 20.49 | 523.80 | 658.39 | 25.6 | 2500 |
| 27 | GFLAAAVLER | 20.49 | 523.80 | 729.43 | 25.6 | 2500 |
| 28 | GNTTGDAR | 6.45 | 396.19 | 418.20 | 18.3 | 2500 |
| 29 | GNTTGDAR | 6.45 | 396.19 | 519.25 | 18.3 | 2500 |
| 30 | GNTTGDAR | 6.45 | 396.19 | 620.30 | 18.3 | 2500 |
| 31 | IGVFAIDTGSGNTFGYR | 21.45 | 592.30 | 542.27 | 25.4 | 2500 |
| 32 | IGVFAIDTGSGNTFGYR | 21.45 | 887.94 | 1174.51 | 46.3 | 2500 |
| 33 | IGVFAIDTGSGNTFGYR | 21.45 | 887.94 | 958.44 | 46.3 | 2500 |
| 34 | LALGNVLNAK | 18.56 | 506.81 | 414.75 | 24.6 | 2500 |
| 35 | LALGNVLNAK | 18.56 | 506.81 | 715.41 | 24.6 | 2500 |
| 36 | LALGNVLNAK | 18.56 | 506.81 | 828.49 | 24.6 | 2500 |
| 37 | LDINQK | 10.3 | 365.71 | 389.21 | 16.6 | 2500 |
| 38 | LDINQK | 10.3 | 365.71 | 502.30 | 16.6 | 2500 |
| 39 | LDINQK | 10.3 | 365.71 | 617.33 | 16.6 | 2500 |
| 40 | LEEDFDGR | 12.51 | 490.72 | 609.26 | 23.7 | 2500 |
| 41 | LEEDFDGR | 12.51 | 490.72 | 738.31 | 23.7 | 2500 |
| 42 | LEEDFDGR | 12.51 | 490.72 | 867.35 | 23.7 | 2500 |
| 43 | SDAAAK | 7.06 | 281.65 | 289.19 | 11.8 | 2500 |

TABLE 19-continued

| Transition number | Peptide | Retention time (minutes) | (m/z) filtered in Q1 | (m/z) filtered in Q3 | Collision energy (eV) | positivity threshold |
|---|---|---|---|---|---|---|
| 44 | SDAAAK | 7.06 | 281.65 | 360.22 | 11.8 | 2500 |
| 45 | SDAAAK | 7.06 | 281.65 | 475.25 | 11.8 | 2500 |
| 46 | SIGDNEFR | 12.81 | 469.22 | 565.27 | 22.5 | 2500 |
| 47 | SIGDNEFR | 12.81 | 469.22 | 680.30 | 22.5 | 2500 |
| 48 | SIGDNEFR | 12.81 | 469.22 | 737.32 | 22.5 | 2500 |
| 49 | TGSCGAIGTANDYAVIWPK | 20.29 | 660.99 | 430.25 | 27.6 | 2500 |
| 50 | TGSCGAIGTANDYAVIWPK | 20.29 | 660.99 | 713.43 | 27.6 | 2500 |
| 51 | TGSCGAIGTANDYAVIWPK | 20.29 | 990.98 | 430.25 | 52.2 | 2500 |
| 52 | TGSCGAYGTANDYAVIWPK | 19.78 | 1015.97 | 430.25 | 53.6 | 2500 |
| 53 | TGSCGAYGTANDYAVIWPK | 19.78 | 677.65 | 642.40 | 28.1 | 2500 |
| 54 | TGSCGAYGTANDYAVIWPK | 19.78 | 677.65 | 713.43 | 28.1 | 2500 |
| 55 | TIAEASR | 6.98 | 374.20 | 333.19 | 17.1 | 2500 |
| 56 | TIAEASR | 6.98 | 374.20 | 462.23 | 17.1 | 2500 |
| 57 | TIAEASR | 6.98 | 374.20 | 646.35 | 17.1 | 2500 |
| 58 | WELELNTAIPGDK | 21.06 | 495.92 | 416.21 | 22.5 | 2500 |
| 59 | WELELNTAIPGDK | 21.06 | 743.38 | 1170.64 | 38.1 | 2500 |
| 60 | WELELNTAIPGDK | 21.06 | 743.38 | 416.21 | 38.1 | 2500 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 40.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 10.00 V
Collision cell exit potential (CXP): 15.00 V The areas obtained for each of the transitions and for each of the microorganisms studied were measured. When the areas of the transitions are greater than or equal to the positivity threshold described in TABLE 19, the detection of the transition is considered to be positive and is labelled "1" in TABLE 20. When a transition has an area less than the positivity threshold described in TABLE 19, the transition is considered non-detected and is labelled "0" in TABLE 20.

For a given peptide, when at least 3 transitions are labelled "1", the peptide is considered as being detected.

TABLE 20

| Transition number | Sam91 | Sam92 | Sam93 | Sam94 | Sam95 |
|---|---|---|---|---|---|
| 1 | 0 | 1 | 0 | 0 | 0 |
| 2 | 1 | 1 | 0 | 0 | 1 |
| 3 | 0 | 1 | 0 | 0 | 0 |
| 4 | 0 | 0 | 0 | 0 | 0 |
| 5 | 0 | 0 | 0 | 0 | 0 |
| 6 | 0 | 0 | 0 | 0 | 0 |
| 7 | 1 | 1 | 1 | 1 | 1 |
| 8 | 1 | 1 | 1 | 1 | 1 |
| 9 | 1 | 1 | 1 | 1 | 1 |
| 10 | 1 | 1 | 1 | 1 | 1 |
| 11 | 1 | 1 | 1 | 1 | 1 |
| 12 | 1 | 1 | 1 | 1 | 1 |
| 13 | 1 | 1 | 1 | 1 | 1 |
| 14 | 1 | 1 | 1 | 1 | 1 |
| 15 | 1 | 1 | 1 | 1 | 1 |
| 16 | 0 | 0 | 0 | 0 | 0 |
| 17 | 0 | 0 | 0 | 0 | 0 |
| 18 | 0 | 0 | 0 | 0 | 0 |
| 19 | 0 | 0 | 0 | 0 | 0 |
| 20 | 0 | 0 | 0 | 0 | 0 |
| 21 | 0 | 0 | 0 | 0 | 0 |
| 22 | 1 | 1 | 1 | 0 | 1 |
| 23 | 1 | 1 | 1 | 0 | 1 |
| 24 | 1 | 1 | 1 | 0 | 1 |
| 25 | 1 | 1 | 1 | 1 | 1 |
| 26 | 1 | 1 | 1 | 1 | 1 |
| 27 | 1 | 1 | 1 | 1 | 1 |
| 28 | 0 | 0 | 0 | 0 | 0 |
| 29 | 0 | 0 | 0 | 0 | 0 |
| 30 | 0 | 0 | 0 | 0 | 0 |
| 31 | 0 | 0 | 0 | 0 | 0 |
| 32 | 0 | 0 | 0 | 0 | 0 |
| 33 | 0 | 0 | 0 | 0 | 0 |
| 34 | 1 | 1 | 1 | 1 | 1 |

TABLE 20-continued

| Transition number | Sam91 | Sam92 | Sam93 | Sam94 | Sam95 |
|---|---|---|---|---|---|
| 35 | 1 | 1 | 1 | 1 | 1 |
| 36 | 1 | 1 | 1 | 1 | 1 |
| 37 | 0 | 0 | 0 | 0 | 0 |
| 38 | 0 | 0 | 0 | 0 | 0 |
| 39 | 0 | 0 | 0 | 0 | 0 |
| 40 | 1 | 1 | 1 | 0 | 1 |
| 41 | 1 | 1 | 1 | 0 | 1 |
| 42 | 1 | 1 | 1 | 0 | 1 |
| 43 | 0 | 0 | 0 | 0 | 0 |
| 44 | 0 | 0 | 0 | 0 | 0 |
| 45 | 0 | 0 | 0 | 0 | 0 |
| 46 | 0 | 0 | 1 | 0 | 0 |
| 47 | 0 | 0 | 1 | 0 | 0 |
| 48 | 0 | 0 | 1 | 0 | 0 |
| 49 | 0 | 0 | 0 | 0 | 0 |
| 50 | 0 | 0 | 0 | 0 | 0 |
| 51 | 0 | 0 | 0 | 0 | 0 |
| 52 | 0 | 0 | 0 | 0 | 0 |
| 53 | 0 | 0 | 0 | 0 | 0 |
| 54 | 0 | 0 | 0 | 0 | 0 |
| 55 | 0 | 0 | 0 | 0 | 0 |
| 56 | 0 | 0 | 0 | 0 | 0 |
| 57 | 0 | 0 | 0 | 0 | 0 |
| 58 | 0 | 0 | 0 | 0 | 0 |
| 59 | 0 | 0 | 0 | 0 | 0 |
| 60 | 0 | 0 | 0 | 0 | 0 |

Samples Sam91 to Sam95 comprise at least one peptide which is characteristic of SMEs. The bacteria present in samples Sam91 to Sam95 therefore express a beta-lactamase which confers on them a resistance to penicillins, to cephalosporins and to carbapenems.

EXAMPLE 12: IDENTIFICATION OF A RESISTANCE TO IMP BETA-LACTAMS

The samples corresponding to a species able to comprise an IMP resistance mechanism can be detected by employing the following method.

Each sample is treated according to Example 5, then analysed according to Example 6 by detecting the peptides from TABLE 21 instead of the peptides from TABLE 3.

TABLE 21

| Transition number | Peptide | Retention time (minutes) | (m/z) filtered in Q1 | (m/z) filtered in Q3 | Collision energy (eV) |
|---|---|---|---|---|---|
| 1 | EVNGWGVVPK | 16.02 | 542.79 | 742.35 | 29 |
| 2 | EVNGWGVVPK | 16.02 | 542.79 | 856.47 | 29 |
| 3 | EVNGWGVVPK | 16.02 | 542.79 | 955.54 | 29 |
| 4 | GSISSHFHSDSTGGIGWLNSR | 16.97 | 551.26 | 675.36 | 31 |
| 5 | GSISSHFHSDSTGGIGWLNSR | 16.97 | 551.26 | 732.38 | 31 |
| 6 | GSISSHFHSDSTGGIGWLNSR | 16.97 | 734.68 | 959.51 | 41 |
| 7 | HGLVILVNTDAYLIDTPFTAK | 24.53 | 767.75 | 892.48 | 42 |
| 8 | HGLVILVNTDAYLIDTPFTAK | 24.53 | 767.75 | 1005.56 | 42 |
| 9 | HGLVILVNTDAYLIDTPFTAK | 24.53 | 767.75 | 1133.63 | 42 |
| 10 | HGLVVLVNNDAYLIDTPFTNK | 22.75 | 781.75 | 822.4 | 43 |
| 11 | HGLVVLVNNDAYLIDTPFTNK | 22.75 | 781.75 | 935.48 | 43 |
| 12 | HGLVVLVNNDAYLIDTPFTNK | 22.75 | 781.75 | 1132.61 | 43 |
| 13 | HGLVVLVNTDAYLIDTPFTAK | 23.91 | 763.08 | 779.39 | 42 |
| 14 | HGLVVLVNTDAYLIDTPFTAK | 23.91 | 763.08 | 892.48 | 42 |
| 15 | HGLVVLVNTDAYLIDTPFTAK | 23.91 | 763.08 | 1119.62 | 42 |
| 16 | HGLVVLVNTEAYLIDTPFTAK | 24.53 | 767.75 | 779.39 | 42 |
| 17 | HGLVVLVNTEAYLIDTPFTAK | 24.53 | 767.75 | 892.48 | 42 |
| 18 | HGLVVLVNTEAYLIDTPFTAK | 24.53 | 767.75 | 1133.63 | 42 |
| 19 | IEVFYPGPGHTQDNVVVWLPK | 22.25 | 599.57 | 642.4 | 33 |
| 20 | IEVFYPGPGHTQDNVVVWLPK | 22.25 | 599.57 | 741.47 | 33 |
| 21 | IEVFYPGPGHTQDNVVVWLPK | 22.25 | 799.09 | 872.46 | 44 |
| 22 | ILMEK | 11.28 | 317.19 | 407.2 | 19 |
| 23 | ILMEK | 11.28 | 317.19 | 487.26 | 19 |

TABLE 21-continued

| Transition number | Peptide | Retention time (minutes) | (m/z) filtered in Q1 | (m/z) filtered in Q3 | Collision energy (eV) |
|---|---|---|---|---|---|
| 24 | ILMEK | 11.28 | 317.19 | 520.28 | 19 |
| 25 | ILMSK | 10.48 | 296.18 | 365.19 | 18 |
| 26 | ILMSK | 10.48 | 296.18 | 445.25 | 18 |
| 27 | ILMSK | 10.48 | 296.18 | 478.27 | 18 |
| 28 | LDEGVYVHTSFK | 15.03 | 465.57 | 482.26 | 27 |
| 29 | LDEGVYVHTSFK | 15.03 | 465.57 | 619.32 | 27 |
| 30 | LDEGVYVHTSFK | 15.03 | 465.57 | 881.45 | 27 |
| 31 | LEEGVYVHTSYEEVK | 14.55 | 594.62 | 855.41 | 34 |
| 32 | LEEGVYVHTSYEEVK | 14.55 | 594.62 | 992.47 | 34 |
| 33 | LEEGVYVHTSYEEVK | 14.55 | 891.43 | 992.47 | 44 |
| 34 | LLISK | 12.19 | 287.2 | 347.23 | 18 |
| 35 | LLISK | 12.19 | 287.2 | 427.29 | 18 |
| 36 | LLISK | 12.19 | 287.2 | 460.31 | 18 |
| 37 | LLMSK | 11.18 | 296.18 | 365.19 | 18 |
| 38 | LLMSK | 11.18 | 296.18 | 445.25 | 18 |
| 39 | LLMSK | 11.18 | 296.18 | 478.27 | 18 |
| 40 | LLVSK | 10.48 | 280.19 | 333.21 | 17 |
| 41 | LLVSK | 10.48 | 280.19 | 413.28 | 17 |
| 42 | LLVSK | 10.48 | 280.19 | 446.3 | 17 |
| 43 | LPDLK | 12.56 | 293.18 | 375.22 | 18 |
| 44 | LPDLK | 12.56 | 293.18 | 439.26 | 18 |
| 45 | LPDLK | 12.56 | 293.18 | 472.28 | 18 |
| 46 | LVVSGHSETGDATHLK | 11.41 | 413.47 | 569.34 | 24 |
| 47 | LVVSGHSETGDATHLK | 11.41 | 550.95 | 719.85 | 32 |
| 48 | LVVSGHSETGDATHLK | 11.41 | 550.95 | 1058.51 | 32 |
| 49 | NSFDGVSYVVLAK | 20.75 | 693.84 | 767.41 | 36 |
| 50 | NSFDGVSYWLAK | 20.75 | 693.84 | 1038.53 | 36 |
| 51 | NSFDGVSYWLAK | 20.75 | 693.84 | 1185.59 | 36 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 13: IDENTIFICATION OF A RESISTANCE TO KPC BETA-LACTAMS

The samples corresponding to a species able to comprise a KPC resistance mechanism can be detected by employing the following method.

Each sample is treated according to Example 5, then analysed according to Example 6 by detecting the peptides from TABLE 22 instead of the peptides from TABLE 3.

TABLE 22

| Transition number | Peptide | Retention time (minutes) | (m/z) filtered in Q1 | (m/z) filtered in Q3 | Collision energy (eV) |
|---|---|---|---|---|---|
| 1 | NALVR | 8.14 | 286.68 | 387.27 | 18 |
| 2 | NALVR | 8.14 | 286.68 | 398.24 | 18 |
| 3 | NALVR | 8.14 | 286.68 | 458.31 | 18 |
| 4 | TGTC[CAM]GAYGTANDYAVVWPTGR | 18.76 | 739.67 | 1169.45 | 41 |
| 5 | TGTC[CAM]GAYGTANDYAVVWPTGR | 18.76 | 1109.01 | 1163.58 | 54 |
| 6 | TGTC[CAM]GAYGTANDYAVVWPTGR | 18.76 | 1109.01 | 1169.45 | 54 |
| 7 | WELELNSAIPSDAR | 20.43 | 534.27 | 545.27 | 31 |
| 8 | WELELNSAIPSDAR | 20.43 | 800.9 | 930.46 | 40 |
| 9 | WELELNSAIPSDAR | 20.43 | 800.9 | 1043.55 | 40 |
| 10 | WELEMNSAIPGDAR | 19.35 | 794.87 | 900.45 | 40 |
| 11 | WELEMNSAIPGDAR | 19.35 | 794.87 | 1031.49 | 40 |
| 12 | WELEMNSAIPGDAR | 19.35 | 794.87 | 1074.49 | 40 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 14: IDENTIFICATION OF A RESISTANCE TO NDM BETA-LACTAMS

The samples corresponding to a species able to comprise an NDM resistance mechanism can be detected by employing the following method.

Each sample is treated according to Example 5, then analysed according to Example 6 by detecting the peptides from TABLE 23 instead of the peptides from TABLE 3.

EXAMPLE 15: IDENTIFICATION OF A RESISTANCE TO VIM BETA-LACTAMS

The samples corresponding to a species able to comprise a VIM resistance mechanism can be detected by employing the following method.

Each sample is treated according to Example 5, then analysed according to Example 6 by detecting the peptides from TABLE 24 instead of the peptides from TABLE 3.

TABLE 23

| Transition number | Peptide | Retention time (minutes) | (m/z) filtered in Q1 | (m/z) filtered in Q3 | Collision energy (eV) |
|---|---|---|---|---|---|
| 1 | VLLVDTAWTDDQTAQILNWIK | 27.87 | 815.1 | 914.55 | 45 |
| 2 | VLLVDTAWTDDQTAQILNWIK | 27.86 | 815.1 | 985.58 | 45 |
| 3 | VLLVDTAWTDDQTAQILNWIK | 27.85 | 815.1 | 1086.63 | 45 |

TABLE 24

| Transition number | Peptide | Retention time (minutes) | (m/z) filtered in Q1 | (m/z) filtered in Q3 | Collision energy (eV) |
|---|---|---|---|---|---|
| 1 | LANEIPTHSLEGLSSSGDAVR | 16.72 | 718.37 | 778.37 | 40 |
| 2 | LANEIPTHSLEGLSSSGDAVR | 16.72 | 718.37 | 948.47 | 40 |
| 3 | LANEIPTHSLEGLSSSGDAVR | 16.72 | 718.37 | 1077.52 | 40 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 16: IDENTIFICATION OF A RESISTANCE TO OXA BETA-LACTAMS

The samples corresponding to a species able to comprise an OXA resistance mechanism can be detected by employing the following method.

Each sample is treated according to Example 5, then analysed according to Example 6 by detecting the peptides from TABLE 25 instead of the peptides from TABLE 3.

TABLE 25

| Transition number | Peptide | Retention time (minutes) | (m/z) filtered in Q1 | (m/z) filtered in Q3 | Collision energy (eV) |
|---|---|---|---|---|---|
| 1 | AAAYELAENLFEAGQADGWR | 24.48 | 728.01 | 1249.6 | 40 |
| 2 | AAAYELAENLFEAGQADGWR | 24.48 | 1091.51 | 1193.58 | 53 |
| 3 | AAAYELAENLFEAGQADGWR | 24.48 | 1091.51 | 1249.6 | 53 |
| 4 | AAEGFIPASTFK | 17.74 | 619.82 | 763.43 | 32 |
| 5 | AAEGFIPASTFK | 17.74 | 619.82 | 910.5 | 32 |
| 6 | AAEGFIPASTFK | 17.74 | 619.82 | 967.52 | 32 |
| 7 | ADGQVVAFALNMQMK | 21.27 | 811.91 | 982.48 | 41 |
| 8 | ADGQVVAFALNMQMK | 21.29 | 811.91 | 1053.52 | 41 |
| 9 | ADGQVVAFALNMQMK | 21.27 | 811.91 | 1152.59 | 41 |
| 10 | ADINEIFK | 17.3 | 475.25 | 650.35 | 26 |
| 11 | ADINEIFK | 17.3 | 475.25 | 763.43 | 26 |
| 12 | ADINEIFK | 17.3 | 475.25 | 878.46 | 26 |
| 13 | ADWGK | 6.9 | 288.64 | 390.21 | 18 |
| 14 | ADWGK | 6.91 | 288.64 | 430.17 | 18 |
| 15 | ADWGK | 6.89 | 288.64 | 505.24 | 18 |
| 16 | AEGAIVISDER | 13.52 | 387.2 | 419.19 | 23 |
| 17 | AEGAIVISDER | 13.53 | 387.2 | 506.22 | 23 |
| 18 | AEGAIVISDER | 13.52 | 387.2 | 619.3 | 23 |
| 19 | AFALNLDIDK | 20.16 | 560.31 | 717.38 | 30 |
| 20 | AFALNLDIDK | 20.16 | 560.31 | 830.46 | 30 |
| 21 | AFALNLDIDK | 20.16 | 560.31 | 901.5 | 30 |
| 22 | AFAPMSTFK | 16.96 | 500.25 | 710.35 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 23 | AFAPMSTFK | 16.96 | 500.25 | 781.39 | 27 |
| 24 | AFAPMSTFK | 16.96 | 500.25 | 928.46 | 27 |
| 25 | AFGYGNADVSGDPGQNNGLDR | 15.12 | 708.65 | 873.42 | 39 |
| 26 | AFGYGNADVSGDPGQNNGLDR | 15.12 | 708.65 | 970.47 | 39 |
| 27 | AFGYGNADVSGDPGQNNGLDR | 15.12 | 708.65 | 1154.47 | 39 |
| 28 | AFTMTK | 11.32 | 349.68 | 480.25 | 20 |
| 29 | AFTMTK | 11.33 | 349.68 | 552.25 | 20 |
| 30 | AFTMTK | 11.33 | 349.68 | 627.32 | 20 |
| 31 | AGDDIALR | 12.23 | 415.72 | 587.35 | 23 |
| 32 | AGDDIALR | 12.23 | 415.72 | 702.38 | 23 |
| 33 | AGDDIALR | 12.23 | 415.72 | 759.4 | 23 |
| 34 | AGHVYAFALNIDMPR | 20.63 | 558.95 | 631.32 | 32 |
| 35 | AGHVYAFALNIDMPR | 20.63 | 558.95 | 745.37 | 32 |
| 36 | AGHVYAFALNIDMPR | 20.63 | 558.95 | 817.4 | 32 |
| 37 | AGLWR | 13.44 | 301.67 | 361.2 | 18 |
| 38 | AGLWR | 13.44 | 301.67 | 474.28 | 18 |
| 39 | AGLWR | 13.44 | 301.67 | 531.3 | 18 |
| 40 | AHTEYVPASTFK | 13.18 | 450.89 | 553.3 | 27 |
| 41 | AHTEYVPASTFK | 13.18 | 450.89 | 602.26 | 27 |
| 42 | AHTEYVPASTFK | 13.18 | 450.89 | 650.35 | 27 |
| 43 | AIIPWDGKPR | 15.84 | 384.89 | 428.23 | 23 |
| 44 | AIIPWDGKPR | 15.84 | 384.89 | 457.29 | 23 |
| 45 | AIIPWDGKPR | 15.84 | 384.89 | 572.32 | 23 |
| 46 | AISDITITR | 14.8 | 495.28 | 603.38 | 27 |
| 47 | AISDITITR | 14.8 | 495.28 | 718.41 | 27 |
| 48 | AISDITITR | 14.8 | 495.28 | 805.44 | 27 |
| 49 | ALGQDR | 11.25 | 330.18 | 475.23 | 20 |
| 50 | ALGQDR | 11.25 | 330.18 | 485.24 | 20 |
| 51 | ALGQDR | 11.25 | 330.18 | 588.31 | 20 |
| 52 | ALQAK | 1.86 | 265.67 | 346.21 | 17 |
| 53 | ALQAK | 1.87 | 265.67 | 384.22 | 17 |
| 54 | ALQAK | 1.87 | 265.67 | 459.29 | 17 |
| 55 | AMETFSPASTFK | 17.06 | 658.81 | 737.38 | 34 |
| 56 | AMETFSPASTFK | 17.05 | 658.81 | 985.5 | 34 |
| 57 | AMETFSPASTFK | 17.06 | 658.81 | 1114.54 | 34 |
| 58 | AMLFLQER | 18.48 | 504.27 | 545.3 | 27 |
| 59 | AMLFLQER | 18.48 | 504.27 | 692.37 | 27 |
| 60 | AMLFLQER | 18.48 | 504.27 | 805.46 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 61 | AMLVFDPVR | 19.87 | 524.29 | 732.4 | 28 |
| 62 | AMLVFDPVR | 19.87 | 524.29 | 845.49 | 28 |
| 63 | AMLVFDPVR | 19.87 | 524.29 | 976.53 | 28 |
| 64 | AMTLLESGPGWELHGK | 19.32 | 575.96 | 923.47 | 33 |
| 65 | AMTLLESGPGWELHGK | 19.32 | 575.96 | 980.49 | 33 |
| 66 | AMTLLESGPGWELHGK | 19.32 | 575.96 | 1067.53 | 33 |
| 67 | ANLHITLHGK | 12.18 | 368.55 | 403.24 | 22 |
| 68 | ANLHITLHGK | 12.18 | 368.55 | 555.32 | 22 |
| 69 | ANLHITLHGK | 12.18 | 368.55 | 668.41 | 22 |
| 70 | ANQLIVK | 11.87 | 393.25 | 600.41 | 22 |
| 71 | ANQLIVK | 11.86 | 393.25 | 639.38 | 22 |
| 72 | ANQLIVK | 11.86 | 393.25 | 714.45 | 22 |
| 73 | ANTEYVPASTFK | 14.54 | 664.33 | 912.48 | 34 |
| 74 | ANTEYVPASTFK | 14.54 | 664.33 | 1041.53 | 34 |
| 75 | ANTEYVPASTFK | 14.54 | 664.33 | 1142.57 | 34 |
| 76 | ANVSR | 9.57 | 273.65 | 361.22 | 17 |
| 77 | ANVSR | 9.57 | 273.65 | 372.19 | 17 |
| 78 | ANVSR | 9.57 | 273.65 | 475.26 | 17 |
| 79 | APIGWFIGWATR | 25.58 | 687.87 | 850.46 | 35 |
| 80 | APIGWFIGWATR | 25.58 | 687.87 | 1093.56 | 35 |
| 81 | APIGWFIGWATR | 25.58 | 687.87 | 1206.64 | 35 |
| 82 | APLGWFIGWATHEER | 24.69 | 590.63 | 742.35 | 34 |
| 83 | APLGWFIGWATHEER | 24.69 | 590.63 | 985.45 | 34 |
| 84 | APLGWFIGWATHEER | 24.69 | 590.63 | 1098.53 | 34 |
| 85 | AQDEVQSMLFIEEK | 20.15 | 833.9 | 996.51 | 42 |
| 86 | AQDEVQSMLFIEEK | 20.14 | 833.9 | 1124.57 | 42 |
| 87 | AQDEVQSMLFIEEK | 20.15 | 833.9 | 1223.63 | 42 |
| 88 | AQGVIVLWNENK | 18.95 | 685.87 | 902.47 | 35 |
| 89 | AQGVIVLWNENK | 18.95 | 685.87 | 1015.56 | 35 |
| 90 | AQGVIVLWNENK | 18.95 | 685.87 | 1171.65 | 35 |
| 91 | ASAIAVYQDLAR | 18.05 | 639.35 | 765.39 | 33 |
| 92 | ASAIAVYQDLAR | 18.05 | 639.35 | 864.46 | 33 |
| 93 | ASAIAVYQDLAR | 18.05 | 639.35 | 935.49 | 33 |
| 94 | ASAILVYQDLAR | 19.08 | 660.37 | 765.39 | 34 |
| 95 | ASAILVYQDLAR | 19.08 | 660.37 | 864.46 | 34 |
| 96 | ASAILVYQDLAR | 19.08 | 660.37 | 977.54 | 34 |
| 97 | ASAIPVYQDLAR | 17.45 | 652.35 | 765.39 | 34 |
| 98 | ASAIPVYQDLAR | 17.45 | 652.35 | 864.46 | 34 |

TABLE 25-continued

| Transition number | Peptide | Retention time (minutes) | (m/z) filtered in Q1 | (m/z) filtered in Q3 | Collision energy (eV) |
|---|---|---|---|---|---|
| 99 | ASAIPVYQDLAR | 17.45 | 652.35 | 961.51 | 34 |
| 100 | ASAIPVYQDLPR | 17.59 | 665.36 | 791.4 | 34 |
| 101 | ASAIPVYQDLPR | 17.59 | 665.36 | 890.47 | 34 |
| 102 | ASAIPVYQDLPR | 17.6 | 665.36 | 987.53 | 34 |
| 103 | ASAIQVYQDLAR | 18.37 | 667.86 | 765.39 | 34 |
| 104 | ASAIQVYQDLAR | 18.37 | 667.86 | 864.46 | 34 |
| 105 | ASAIQVYQDLAR | 18.37 | 667.86 | 992.52 | 34 |
| 106 | ASAISVYQDLAR | 17.93 | 647.34 | 765.39 | 33 |
| 107 | ASAISVYQDLAR | 17.93 | 647.34 | 864.46 | 33 |
| 108 | ASAISVYQDLAR | 17.93 | 647.34 | 951.49 | 33 |
| 109 | ASALPVYQDLAR | 17.77 | 652.35 | 864.46 | 34 |
| 110 | ASALPVYQDLAR | 17.77 | 652.35 | 961.51 | 34 |
| 111 | ASALPVYQDLAR | 17.77 | 652.35 | 1074.59 | 34 |
| 112 | ASAMPVYQDLAR | 16.64 | 661.33 | 765.39 | 34 |
| 113 | ASAMPVYQDLAR | 16.64 | 661.33 | 864.46 | 34 |
| 114 | ASAMPVYQDLAR | 16.64 | 661.33 | 961.51 | 34 |
| 115 | ASAVPVYQDLAR | 16.29 | 645.35 | 765.39 | 33 |
| 116 | ASAVPVYQDLAR | 16.29 | 645.35 | 864.46 | 33 |
| 117 | ASAVPVYQDLAR | 16.29 | 645.35 | 961.51 | 33 |
| 118 | ASIEYVPASTFK | 16.7 | 656.84 | 749.42 | 34 |
| 119 | ASIEYVPASTFK | 16.7 | 656.84 | 912.48 | 34 |
| 120 | ASIEYVPASTFK | 16.7 | 656.84 | 1041.53 | 34 |
| 121 | ASNVPVYQELAR | 18.48 | 673.86 | 779.4 | 35 |
| 122 | ASNVPVYQELAR | 18.48 | 673.86 | 878.47 | 35 |
| 123 | ASNVPVYQELAR | 18.48 | 673.86 | 975.53 | 35 |
| 124 | ASPASTFK | 10.29 | 404.71 | 553.3 | 23 |
| 125 | ASPASTFK | 10.29 | 404.71 | 650.35 | 23 |
| 126 | ASPASTFK | 10.28 | 404.71 | 737.38 | 23 |
| 127 | ASTAYIPASTFK | 15.69 | 628.83 | 763.43 | 33 |
| 128 | ASTAYIPASTFK | 15.69 | 628.83 | 926.5 | 33 |
| 129 | ASTAYIPASTFK | 15.69 | 628.83 | 997.54 | 33 |
| 130 | ASTEYVPASTFK | 14.59 | 650.82 | 749.42 | 34 |
| 131 | ASTEYVPASTFK | 14.59 | 650.82 | 912.48 | 34 |
| 132 | ASTEYVPASTFK | 14.6 | 650.82 | 1041.53 | 34 |
| 133 | ASTTEVFK | 11.78 | 441.73 | 623.34 | 24 |
| 134 | ASTTEVFK | 11.78 | 441.73 | 724.39 | 24 |
| 135 | ASTTEVFK | 11.78 | 441.73 | 811.42 | 24 |
| 136 | ATSTEIFK | 13.15 | 448.74 | 637.36 | 25 |

TABLE 25-continued

| Transition number | Peptide | Retention time (minutes) | (m/z) filtered in Q1 | (m/z) filtered in Q3 | Collision energy (eV) |
|---|---|---|---|---|---|
| 137 | ATSTEIFK | 13.15 | 448.74 | 724.39 | 25 |
| 138 | ATSTEIFK | 13.15 | 448.74 | 825.44 | 25 |
| 139 | ATTNEIFK | 13.21 | 462.25 | 650.35 | 25 |
| 140 | ATTNEIFK | 13.21 | 462.25 | 751.4 | 25 |
| 141 | ATTNEIFK | 13.21 | 462.25 | 852.45 | 25 |
| 142 | ATTTAVFK | 11.9 | 419.74 | 464.29 | 23 |
| 143 | ATTTAVFK | 11.9 | 419.74 | 565.33 | 23 |
| 144 | ATTTAVFK | 11.9 | 419.74 | 666.38 | 23 |
| 145 | ATTTEIFK | 13.64 | 455.75 | 637.36 | 25 |
| 146 | ATTTEIFK | 13.65 | 455.75 | 738.4 | 25 |
| 147 | ATTTEIFK | 13.65 | 455.75 | 839.45 | 25 |
| 148 | ATTTEVFK | 11.98 | 448.74 | 623.34 | 25 |
| 149 | ATTTEVFK | 11.98 | 448.74 | 724.39 | 25 |
| 150 | ATTTEVFK | 11.98 | 448.74 | 825.44 | 25 |
| 151 | AVSDITILEQTDNYTLHGK | 19.19 | 706.7 | 974.49 | 39 |
| 152 | AVSDITILEQTDNYTLHGK | 19.19 | 706.7 | 1048.51 | 39 |
| 153 | AVSDITILEQTDNYTLHGK | 19.18 | 706.7 | 1176.56 | 39 |
| 154 | AVSDITILEQTYNYTLHGK | 22.29 | 722.71 | 995.49 | 40 |
| 155 | AVSDITILEQTYNYTLHGK | 22.29 | 722.71 | 998.5 | 40 |
| 156 | AVSDITILEQTYNYTLHGK | 22.28 | 722.71 | 1224.6 | 40 |
| 157 | AVVPHFEAGDWDVQGK | 17.81 | 585.62 | 743.34 | 33 |
| 158 | AVVPHFEAGDWDVQGK | 17.81 | 585.62 | 792.88 | 33 |
| 159 | AVVPHFEAGDWDVQGK | 17.81 | 585.62 | 904.42 | 33 |
| 160 | AWEHDMSLR | 13.99 | 572.76 | 758.36 | 30 |
| 161 | AWEHDMSLR | 13.99 | 572.76 | 887.4 | 30 |
| 162 | AWEHDMSLR | 13.99 | 572.76 | 1073.48 | 30 |
| 163 | AWIGSSLQISPLEQLEFLGK | 26.98 | 739.4 | 963.51 | 41 |
| 164 | AWIGSSLQISPLEQLEFLGK | 26.99 | 739.4 | 1173.65 | 41 |
| 165 | AWIGSSLQISPLEQLEFLGK | 26.98 | 1108.6 | 1173.65 | 54 |
| 166 | DAFLK | 12.42 | 297.17 | 407.27 | 18 |
| 167 | DAFLK | 12.43 | 297.17 | 447.22 | 18 |
| 168 | DAFLK | 12.42 | 297.17 | 478.3 | 18 |
| 169 | DDFILHGK | 13.99 | 472.75 | 714.43 | 26 |
| 170 | DDFILHGK | 13.99 | 472.75 | 798.38 | 26 |
| 171 | DDFILHGK | 13.99 | 472.75 | 829.46 | 26 |
| 172 | DDVLK | 8.62 | 295.16 | 359.27 | 18 |
| 173 | DDVLK | 8.63 | 295.16 | 443.21 | 18 |
| 174 | DDVLK | 8.62 | 295.16 | 474.29 | 18 |

TABLE 25-continued

| Transition number | Peptide | Retention time (minutes) | (m/z) filtered in Q1 | (m/z) filtered in Q3 | Collision energy (eV) |
|---|---|---|---|---|---|
| 175 | DEFHVFR | 15.39 | 475.23 | 705.38 | 26 |
| 176 | DEFHVFR | 15.39 | 475.23 | 775.34 | 26 |
| 177 | DEFHVFR | 15.39 | 475.23 | 834.43 | 26 |
| 178 | DEFQIFR | 19.02 | 477.74 | 520.2 | 26 |
| 179 | DEFQIFR | 19.02 | 477.74 | 563.33 | 26 |
| 180 | DEFQIFR | 19.02 | 477.74 | 710.4 | 26 |
| 181 | DEFQVFR | 17.29 | 470.73 | 549.31 | 26 |
| 182 | DEFQVFR | 17.28 | 470.73 | 619.27 | 26 |
| 183 | DEFQVFR | 17.29 | 470.73 | 696.38 | 26 |
| 184 | DELVR | 9.33 | 316.17 | 387.27 | 19 |
| 185 | DELVR | 9.35 | 316.17 | 457.23 | 19 |
| 186 | DELVR | 9.33 | 316.17 | 516.31 | 19 |
| 187 | DFDYGNQDFSGDK | 14.72 | 754.3 | 967.41 | 38 |
| 188 | DFDYGNQDFSGDK | 14.72 | 754.3 | 1130.47 | 38 |
| 189 | DFDYGNQDFSGDK | 14.72 | 754.3 | 1245.5 | 38 |
| 190 | DFTLGEAMQASTVPVYQELAR | 24.19 | 776.05 | 975.53 | 43 |
| 191 | DFTLGEAMQASTVPVYQELAR | 24.19 | 776.05 | 1074.59 | 43 |
| 192 | DFTLGEAMQASTVPVYQELAR | 24.19 | 1163.57 | 1175.64 | 56 |
| 193 | DHDLITAMK | 14.23 | 522.26 | 563.32 | 28 |
| 194 | DHDLITAMK | 14.23 | 522.26 | 695.34 | 28 |
| 195 | DHDLITAMK | 14.23 | 522.26 | 791.43 | 28 |
| 196 | DIAAWNR | 13.63 | 423.22 | 546.28 | 24 |
| 197 | DIAAWNR | 13.63 | 423.22 | 617.32 | 24 |
| 198 | DIAAWNR | 13.62 | 423.22 | 730.4 | 24 |
| 199 | DILYIQELAGGWK | 24.49 | 753.4 | 888.46 | 38 |
| 200 | DILYIQELAGGWK | 24.48 | 753.4 | 1001.54 | 38 |
| 201 | DILYIQELAGGWK | 24.49 | 753.4 | 1164.6 | 38 |
| 202 | DITILEK | 15.9 | 416.24 | 603.37 | 23 |
| 203 | DITILEK | 15.91 | 416.24 | 685.38 | 23 |
| 204 | DITILEK | 15.91 | 416.24 | 716.46 | 23 |
| 205 | DLLSAK | 12.45 | 323.69 | 429.23 | 19 |
| 206 | DLLSAK | 12.44 | 323.69 | 500.27 | 19 |
| 207 | DLLSAK | 12.45 | 323.69 | 531.35 | 19 |
| 208 | DLMITEAGR | 15.07 | 503.26 | 533.27 | 27 |
| 209 | DLMITEAGR | 15.07 | 503.26 | 646.35 | 27 |
| 210 | DLMITEAGR | 15.07 | 503.26 | 777.39 | 27 |
| 211 | DLMIVEAGR | 16.68 | 502.27 | 531.29 | 27 |
| 212 | DLMIVEAGR | 16.68 | 502.27 | 644.37 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 213 | DLMIVEAGR | 16.68 | 502.27 | 775.41 | 27 |
| 214 | DLMIVEAK | 16.23 | 459.75 | 473.24 | 25 |
| 215 | DLMIVEAK | 16.23 | 459.75 | 559.34 | 25 |
| 216 | DLMIVEAK | 16.23 | 459.75 | 690.39 | 25 |
| 217 | DLSGNPGK | 6.69 | 394.2 | 472.25 | 22 |
| 218 | DLSGNPGK | 6.69 | 394.2 | 559.28 | 22 |
| 219 | DLSGNPGK | 6.7 | 394.2 | 672.37 | 22 |
| 220 | DLSLR | 12.37 | 302.18 | 375.24 | 18 |
| 221 | DLSLR | 12.35 | 302.18 | 429.23 | 18 |
| 222 | DLSLR | 12.36 | 302.18 | 488.32 | 18 |
| 223 | DLTLR | 12.48 | 309.18 | 389.25 | 19 |
| 224 | DLTLR | 12.47 | 309.18 | 443.25 | 19 |
| 225 | DLTLR | 12.47 | 309.18 | 502.33 | 19 |
| 226 | DMTLGDAIK | 15.97 | 482.24 | 503.28 | 26 |
| 227 | DMTLGDAIK | 15.97 | 482.24 | 616.37 | 26 |
| 228 | DMTLGDAIK | 15.97 | 482.24 | 717.41 | 26 |
| 229 | DMTLGDAMALSAVPVYQELAR | 25.76 | 751.04 | 975.53 | 42 |
| 230 | DMTLGDAMALSAVPVYQELAR | 25.76 | 1126.06 | 1145.63 | 55 |
| 231 | DMTLGDAMALSAVPVYQELAR | 25.75 | 1126.06 | 1232.66 | 55 |
| 232 | DMTLGDAMK | 14.46 | 491.22 | 634.32 | 27 |
| 233 | DMTLGDAMK | 14.46 | 491.22 | 735.37 | 27 |
| 234 | DMTLGDAMK | 14.46 | 491.22 | 866.41 | 27 |
| 235 | DMTLGEAMALSAVPVYQDLAR | 25.92 | 751.04 | 961.51 | 42 |
| 236 | DMTLGEAMALSAVPVYQDLAR | 25.92 | 1126.06 | 1131.62 | 55 |
| 237 | DMTLGEAMALSAVPVYQDLAR | 25.92 | 1126.06 | 1218.65 | 55 |
| 238 | DMTLGEAMALSAVPVYQELAR | 26.48 | 755.71 | 779.4 | 42 |
| 239 | DMTLGEAMALSAVPVYQELAR | 26.48 | 755.71 | 975.53 | 42 |
| 240 | DMTLGEAMALSAVPVYQELAR | 26.47 | 1133.07 | 1232.66 | 55 |
| 241 | DMTLGEAMK | 15.09 | 498.23 | 535.25 | 27 |
| 242 | DMTLGEAMK | 15.09 | 498.23 | 648.34 | 27 |
| 243 | DMTLGEAMK | 15.09 | 498.23 | 749.39 | 27 |
| 244 | DMTLGQAMQASAVPVYQELAR | 23.29 | 760.38 | 779.4 | 42 |
| 245 | DMTLGQAMQASAVPVYQELAR | 23.29 | 760.38 | 975.53 | 42 |
| 246 | DMTLGQAMQASAVPVYQELAR | 23.29 | 760.38 | 976.42 | 42 |
| 247 | DQDLR | 2.54 | 323.66 | 403.23 | 19 |
| 248 | DQDLR | 2.55 | 323.66 | 472.2 | 19 |
| 249 | DQDLR | 2.55 | 323.66 | 531.29 | 19 |
| 250 | DQQIGWFVGWASKPGK | 21.64 | 601.98 | 830.45 | 34 |

TABLE 25-continued

| Transition number | Peptide | Retention time (minutes) | (m/z) filtered in Q1 | (m/z) filtered in Q3 | Collision energy (eV) |
|---|---|---|---|---|---|
| 251 | DQQIGWFVGWASKPGK | 21.64 | 902.46 | 929.52 | 45 |
| 252 | DQQIGWFVGWASKPGK | 21.64 | 902.46 | 1076.59 | 45 |
| 253 | DQQVQVYGNDLNR | 13.59 | 774.87 | 851.4 | 39 |
| 254 | DQQVQVYGNDLNR | 13.58 | 774.87 | 950.47 | 39 |
| 255 | DQQVQVYGNDLNR | 13.59 | 774.87 | 1078.53 | 39 |
| 256 | DQTLESAFK | 15.21 | 519.76 | 581.29 | 28 |
| 257 | DQTLESAFK | 15.21 | 519.76 | 694.38 | 28 |
| 258 | DQTLESAFK | 15.21 | 519.76 | 795.42 | 28 |
| 259 | DSIVWYSQELTR | 19.61 | 748.87 | 896.45 | 38 |
| 260 | DSIVWYSQELTR | 19.61 | 748.87 | 1082.53 | 38 |
| 261 | DSIVWYSQELTR | 19.61 | 748.87 | 1181.59 | 38 |
| 262 | DSIVWYSQQLTR | 19.1 | 748.38 | 895.46 | 38 |
| 263 | DSIVWYSQQLTR | 19.11 | 748.38 | 1081.54 | 38 |
| 264 | DSIVWYSQQLTR | 19.1 | 748.38 | 1180.61 | 38 |
| 265 | DSNLR | 1.77 | 302.66 | 402.25 | 18 |
| 266 | DSNLR | 1.77 | 302.66 | 430.19 | 18 |
| 267 | DSNLR | 1.77 | 302.66 | 489.28 | 18 |
| 268 | DSYIAWGGEAWK | 19.67 | 691.82 | 833.39 | 35 |
| 269 | DSYIAWGGEAWK | 19.67 | 691.82 | 904.43 | 35 |
| 270 | DSYIAWGGEAWK | 19.66 | 691.82 | 1017.52 | 35 |
| 271 | DTLNPEWPYK | 17.3 | 631.81 | 819.4 | 33 |
| 272 | DTLNPEWPYK | 17.3 | 631.81 | 933.45 | 33 |
| 273 | DTLNPEWPYK | 17.3 | 631.81 | 1046.53 | 33 |
| 274 | DVDEVFYK | 15.62 | 507.74 | 685.36 | 27 |
| 275 | DVDEVFYK | 15.62 | 507.74 | 800.38 | 27 |
| 276 | DVDEVFYK | 15.62 | 507.74 | 899.45 | 27 |
| 277 | DWILR | 17.44 | 351.7 | 415.2 | 20 |
| 278 | DWILR | 17.44 | 351.7 | 528.28 | 20 |
| 279 | DWILR | 17.44 | 351.7 | 587.37 | 20 |
| 280 | EAFLR | 12.51 | 318.18 | 435.27 | 19 |
| 281 | EAFLR | 12.51 | 318.18 | 461.24 | 19 |
| 282 | EAFLR | 12.51 | 318.18 | 506.31 | 19 |
| 283 | EAIVR | 7.84 | 294.18 | 387.27 | 18 |
| 284 | EAIVR | 7.84 | 294.18 | 413.24 | 18 |
| 285 | EAIVR | 7.84 | 294.18 | 458.31 | 18 |
| 286 | EAIVTEATPEYIVHSK | 16.43 | 596.31 | 746.42 | 34 |
| 287 | EAIVTEATPEYIVHSK | 16.43 | 596.31 | 972.51 | 34 |
| 288 | EAIVTEATPEYIVHSK | 16.42 | 596.31 | 1073.56 | 34 |

TABLE 25-continued

| Transition number | Peptide | Retention time (minutes) | (m/z) filtered in Q1 | (m/z) filtered in Q3 | Collision energy (eV) |
|---|---|---|---|---|---|
| 289 | EALVTEAAPEYLVHSK | 17.3 | 586.31 | 875.46 | 33 |
| 290 | EALVTEAAPEYLVHSK | 17.3 | 586.31 | 972.51 | 33 |
| 291 | EALVTEAAPEYLVHSK | 17.3 | 586.31 | 1114.59 | 33 |
| 292 | EALVTEAPEYLVHSK | 17.58 | 562.63 | 637.32 | 32 |
| 293 | EALVTEAPEYLVHSK | 17.58 | 562.63 | 972.51 | 32 |
| 294 | EALVTEAPEYLVHSK | 17.58 | 562.63 | 1043.55 | 32 |
| 295 | EEIVR | 8.41 | 323.18 | 387.27 | 19 |
| 296 | EEIVR | 8.4 | 323.18 | 471.24 | 19 |
| 297 | EEIVR | 8.4 | 323.18 | 516.31 | 19 |
| 298 | EEVLAALPAQLK | 19.48 | 641.37 | 740.47 | 33 |
| 299 | EEVLAALPAQLK | 19.47 | 641.37 | 811.5 | 33 |
| 300 | EEVLAALPAQLK | 19.47 | 641.37 | 924.59 | 33 |
| 301 | EFSAEAVNGVFVLC[CAM]K | 21.1 | 835.42 | 936.5 | 42 |
| 302 | EFSAEAVNGVFVLC[CAM]K | 21.1 | 835.42 | 1106.6 | 42 |
| 303 | EFSAEAVNGVFVLC[CAM]K | 21.1 | 835.42 | 1235.65 | 42 |
| 304 | EFSSESVHGVFVLC[CAM]K | 18.26 | 575.62 | 666.36 | 33 |
| 305 | EFSSESVHGVFVLC[CAM]K | 18.26 | 575.62 | 822.45 | 33 |
| 306 | EFSSESVHGVFVLC[CAM]K | 18.26 | 575.62 | 959.51 | 33 |
| 307 | EGMSGSIR | 9.88 | 418.7 | 432.26 | 23 |
| 308 | EGMSGSIR | 9.88 | 418.7 | 519.29 | 23 |
| 309 | EGMSGSIR | 9.88 | 418.7 | 707.35 | 23 |
| 310 | EGMTGSIR | 10.63 | 425.71 | 432.26 | 24 |
| 311 | EGMTGSIR | 10.63 | 425.71 | 533.3 | 24 |
| 312 | EGMTGSIR | 10.63 | 425.71 | 664.34 | 24 |
| 313 | EIAVWNR | 14.78 | 444.24 | 475.24 | 25 |
| 314 | EIAVWNR | 14.77 | 444.24 | 574.31 | 25 |
| 315 | EIAVWNR | 14.77 | 444.24 | 645.35 | 25 |
| 316 | EIAYK | 8.46 | 312.17 | 381.21 | 19 |
| 317 | EIAYK | 8.46 | 312.17 | 477.23 | 19 |
| 318 | EIAYK | 8.46 | 312.17 | 494.3 | 19 |
| 319 | EIFER | 11.7 | 347.18 | 451.23 | 20 |
| 320 | EIFER | 11.7 | 347.18 | 519.24 | 20 |
| 321 | EIFER | 11.7 | 347.18 | 564.31 | 20 |
| 322 | EIFYHYR | 13.31 | 514.25 | 785.37 | 28 |
| 323 | EIFYHYR | 13.31 | 514.25 | 853.39 | 28 |
| 324 | EIFYHYR | 13.32 | 514.25 | 898.46 | 28 |
| 325 | EIGDDK | 1.99 | 338.66 | 434.19 | 20 |
| 326 | EIGDDK | 1.99 | 338.66 | 530.21 | 20 |

TABLE 25-continued

| Transition number | Peptide | Retention time (minutes) | (m/z) filtered in Q1 | (m/z) filtered in Q3 | Collision energy (eV) |
|---|---|---|---|---|---|
| 327 | EIGDDK | 1.99 | 338.66 | 547.27 | 20 |
| 328 | EIGDGK | 1.76 | 309.66 | 376.18 | 19 |
| 329 | EIGDGK | 1.75 | 309.66 | 472.2 | 19 |
| 330 | EIGDGK | 1.75 | 309.66 | 489.27 | 19 |
| 331 | EIGEDK | 2.32 | 345.67 | 448.2 | 20 |
| 332 | EIGEDK | 2.33 | 345.67 | 544.22 | 20 |
| 333 | EIGEDK | 2.33 | 345.67 | 561.29 | 20 |
| 334 | EIGEDNAR | 10.05 | 452.21 | 604.27 | 25 |
| 335 | EIGEDNAR | 10.05 | 452.21 | 661.29 | 25 |
| 336 | EIGEDNAR | 10.06 | 452.21 | 774.37 | 25 |
| 337 | EIGENK | 1.86 | 345.18 | 447.22 | 20 |
| 338 | EIGENK | 1.86 | 345.18 | 543.24 | 20 |
| 339 | EIGENK | 1.86 | 345.18 | 560.3 | 20 |
| 340 | EIGSEIDK | 11.04 | 445.73 | 591.3 | 25 |
| 341 | EIGSEIDK | 11.04 | 445.73 | 648.32 | 25 |
| 342 | EIGSEIDK | 11.04 | 445.73 | 761.4 | 25 |
| 343 | EMIYLK | 15.11 | 398.72 | 536.34 | 23 |
| 344 | EMIYLK | 15.11 | 398.72 | 650.32 | 23 |
| 345 | EMIYLK | 15.11 | 398.72 | 667.38 | 23 |
| 346 | EMLYVER | 14.12 | 470.23 | 566.29 | 26 |
| 347 | EMLYVER | 14.12 | 470.23 | 679.38 | 26 |
| 348 | EMLYVER | 14.12 | 470.23 | 810.42 | 26 |
| 349 | ENIEK | 11.07 | 316.67 | 389.24 | 19 |
| 350 | ENIEK | 11.07 | 316.67 | 486.22 | 19 |
| 351 | ENIEK | 11.07 | 316.67 | 503.28 | 19 |
| 352 | ENQLIVK | 12.15 | 422.25 | 472.35 | 24 |
| 353 | ENQLIVK | 12.15 | 422.25 | 600.41 | 24 |
| 354 | ENQLIVK | 12.15 | 422.25 | 714.45 | 24 |
| 355 | EQAILLFR | 19.88 | 495.29 | 548.36 | 27 |
| 356 | EQAILLFR | 19.88 | 495.29 | 661.44 | 27 |
| 357 | EQAILLFR | 19.88 | 495.29 | 732.48 | 27 |
| 358 | EQIQFLLR | 19.45 | 523.8 | 548.36 | 28 |
| 359 | EQIQFLLR | 19.45 | 523.8 | 676.41 | 28 |
| 360 | EQIQFLLR | 19.45 | 523.8 | 789.5 | 28 |
| 361 | EQLAFDPQVQQQVK | 16.43 | 829.43 | 954.54 | 41 |
| 362 | EQLAFDPQVQQQVK | 16.42 | 829.43 | 1069.56 | 41 |
| 363 | EQLAFDPQVQQQVK | 16.42 | 829.43 | 1216.63 | 41 |
| 364 | EQVDFVQR | 13.09 | 510.76 | 549.31 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 365 | EQVDFVQR | 13.09 | 510.76 | 664.34 | 27 |
| 366 | EQVDFVQR | 13.09 | 510.76 | 763.41 | 27 |
| 367 | EVGEIR | 9.35 | 351.69 | 474.27 | 20 |
| 368 | EVGEIR | 9.35 | 351.69 | 528.27 | 20 |
| 369 | EVGEIR | 9.35 | 351.69 | 573.34 | 20 |
| 370 | EVGEVR | 6.91 | 344.68 | 460.25 | 20 |
| 371 | EVGEVR | 6.91 | 344.68 | 514.25 | 20 |
| 372 | EVGEVR | 6.91 | 344.68 | 559.32 | 20 |
| 373 | EYLPASTFK | 15.41 | 528.27 | 553.3 | 28 |
| 374 | EYLPASTFK | 15.41 | 528.27 | 650.35 | 28 |
| 375 | EYLPASTFK | 15.41 | 528.27 | 763.43 | 28 |
| 376 | EYLPVSTFK | 17.16 | 542.29 | 581.33 | 29 |
| 377 | EYLPVSTFK | 17.16 | 542.29 | 678.38 | 29 |
| 378 | EYLPVSTFK | 17.16 | 542.29 | 791.47 | 29 |
| 379 | EYNTSGTFVFYDGK | 18.2 | 814.37 | 1033.5 | 41 |
| 380 | EYNTSGTFVFYDGK | 18.2 | 814.37 | 1120.53 | 41 |
| 381 | EYNTSGTFVFYDGK | 18.2 | 814.37 | 1221.58 | 41 |
| 382 | EYVPASTFK | 13.89 | 521.27 | 553.3 | 28 |
| 383 | EYVPASTFK | 13.89 | 521.27 | 650.35 | 28 |
| 384 | EYVPASTFK | 13.89 | 521.27 | 749.42 | 28 |
| 385 | FAPESTFK | 13.67 | 463.73 | 482.26 | 25 |
| 386 | FAPESTFK | 13.67 | 463.73 | 611.3 | 25 |
| 387 | FAPESTFK | 13.67 | 463.73 | 708.36 | 25 |
| 388 | FAQYAK | 9.39 | 364.19 | 509.27 | 21 |
| 389 | FAQYAK | 9.39 | 364.19 | 580.31 | 21 |
| 390 | FAQYAK | 9.39 | 364.19 | 581.27 | 21 |
| 391 | FDYGNR | 10.1 | 386.17 | 509.25 | 22 |
| 392 | FDYGNR | 10.1 | 386.17 | 597.23 | 22 |
| 393 | FDYGNR | 10.09 | 386.17 | 624.27 | 22 |
| 394 | FEDLYK | 13.52 | 407.7 | 423.26 | 23 |
| 395 | FEDLYK | 13.52 | 407.7 | 538.29 | 23 |
| 396 | FEDLYK | 13.52 | 407.7 | 667.33 | 23 |
| 397 | FEDTFHISNQK | 14.33 | 455.89 | 476.25 | 27 |
| 398 | FEDTFHISNQK | 14.33 | 455.89 | 589.33 | 27 |
| 399 | FEDTFHISNQK | 14.33 | 455.89 | 726.39 | 27 |
| 400 | FEDTFHTSNQQHEK | 10.66 | 583.26 | 870.41 | 33 |
| 401 | FEDTFHTSNQQHEK | 10.66 | 583.26 | 971.45 | 33 |
| 402 | FEDTFHTSNQQHEK | 10.66 | 583.26 | 1108.51 | 33 |

TABLE 25-continued

| Transition number | Peptide | Retention time (minutes) | (m/z) filtered in Q1 | (m/z) filtered in Q3 | Collision energy (eV) |
|---|---|---|---|---|---|
| 403 | FEYGNQDVSGDSGK | 11.95 | 751.82 | 764.34 | 38 |
| 404 | FEYGNQDVSGDSGK | 11.95 | 751.82 | 1063.47 | 38 |
| 405 | FEYGNQDVSGDSGK | 11.95 | 751.82 | 1226.53 | 38 |
| 406 | FFSDFQAK | 16 | 495.24 | 608.3 | 27 |
| 407 | FFSDFQAK | 16 | 495.24 | 695.34 | 27 |
| 408 | FFSDFQAK | 16 | 495.24 | 842.4 | 27 |
| 409 | FFSDLQAEGAIVIADER | 20.44 | 627.65 | 1143.6 | 35 |
| 410 | FFSDLQAEGAIVIADER | 20.43 | 940.97 | 1143.6 | 46 |
| 411 | FFSDLQAEGAIVIADER | 20.44 | 940.97 | 1179.57 | 46 |
| 412 | FFSDLR | 15.38 | 392.7 | 490.26 | 22 |
| 413 | FFSDLR | 15.38 | 392.7 | 610.29 | 22 |
| 414 | FFSDLR | 15.38 | 392.7 | 637.33 | 22 |
| 415 | FFSEFQAK | 16.13 | 502.25 | 622.32 | 27 |
| 416 | FFSEFQAK | 16.13 | 502.25 | 709.35 | 27 |
| 417 | FFSEFQAK | 16.13 | 502.25 | 856.42 | 27 |
| 418 | FGLEGQLR | 15.8 | 460.25 | 473.28 | 25 |
| 419 | FGLEGQLR | 15.8 | 460.25 | 602.33 | 25 |
| 420 | FGLEGQLR | 15.8 | 460.25 | 772.43 | 25 |
| 421 | FLESLYLNNLPASK | 20.75 | 804.94 | 856.49 | 40 |
| 422 | FLESLYLNNLPASK | 20.75 | 804.94 | 1019.55 | 40 |
| 423 | FLESLYLNNLPASK | 20.75 | 804.94 | 1219.67 | 40 |
| 424 | FLLEGQLR | 18.06 | 488.28 | 602.33 | 26 |
| 425 | FLLEGQLR | 18.06 | 488.28 | 715.41 | 26 |
| 426 | FLLEGQLR | 18.06 | 488.28 | 828.49 | 26 |
| 427 | FQQYVDR | 11.19 | 478.24 | 552.28 | 26 |
| 428 | FQQYVDR | 11.19 | 478.24 | 680.34 | 26 |
| 429 | FQQYVDR | 11.19 | 478.24 | 808.39 | 26 |
| 430 | FSDYVQR | 11.83 | 457.72 | 565.31 | 25 |
| 431 | FSDYVQR | 11.83 | 457.72 | 680.34 | 25 |
| 432 | FSDYVQR | 11.83 | 457.72 | 767.37 | 25 |
| 433 | FSTASTFK | 12.71 | 444.73 | 553.3 | 25 |
| 434 | FSTASTFK | 12.7 | 444.73 | 654.35 | 25 |
| 435 | FSTASTFK | 12.7 | 444.73 | 741.38 | 25 |
| 436 | FSWDGK | 14.32 | 370.17 | 505.24 | 21 |
| 437 | FSWDGK | 14.32 | 370.17 | 592.27 | 21 |
| 438 | FSWDGK | 14.32 | 370.17 | 593.24 | 21 |
| 439 | FSYGNQNISGGIDK | 14.61 | 750.36 | 803.43 | 38 |
| 440 | FSYGNQNISGGIDK | 14.61 | 750.36 | 1045.53 | 38 |

TABLE 25-continued

| Transition number | Peptide | Retention time (minutes) | (m/z) filtered in Q1 | (m/z) filtered in Q3 | Collision energy (eV) |
|---|---|---|---|---|---|
| 441 | FSYGNQNISGGIDK | 14.61 | 750.36 | 1102.55 | 38 |
| 442 | FSYGNQNISGGTDK | 12.74 | 744.34 | 791.39 | 38 |
| 443 | FSYGNQNISGGTDK | 12.74 | 744.34 | 1033.49 | 38 |
| 444 | FSYGNQNISGGTDK | 12.74 | 744.34 | 1090.51 | 38 |
| 445 | FSYGSQNISGGIDK | 14.74 | 736.85 | 803.43 | 37 |
| 446 | FSYGSQNISGGIDK | 14.74 | 736.85 | 1075.54 | 37 |
| 447 | FSYGSQNISGGIDK | 14.75 | 736.85 | 1238.6 | 37 |
| 448 | FTEYVK | 11.81 | 393.71 | 538.29 | 22 |
| 449 | FTEYVK | 11.81 | 393.71 | 639.33 | 22 |
| 450 | FTEYVK | 11.81 | 393.71 | 640.3 | 22 |
| 451 | FVPASTYK | 11.76 | 456.74 | 498.26 | 25 |
| 452 | FVPASTYK | 11.76 | 456.74 | 569.29 | 25 |
| 453 | FVPASTYK | 11.77 | 456.74 | 666.35 | 25 |
| 454 | FVYDLAQGQLPFKPEVQQQVK | 20.48 | 821.44 | 955.52 | 45 |
| 455 | FVYDLAQGQLPFKPEVQQQVK | 20.48 | 821.44 | 1108.59 | 45 |
| 456 | FVYDLAQGQLPFKPEVQQQVK | 20.49 | 821.44 | 1109.07 | 45 |
| 457 | FWLEDQLR | 20.39 | 553.79 | 660.33 | 29 |
| 458 | FWLEDQLR | 20.39 | 553.79 | 773.42 | 29 |
| 459 | FWLEDQLR | 20.38 | 553.79 | 959.49 | 29 |
| 460 | FWLEGPLK | 20.63 | 495.28 | 543.31 | 27 |
| 461 | FWLEGPLK | 20.63 | 495.28 | 656.4 | 27 |
| 462 | FWLEGPLK | 20.63 | 495.28 | 842.48 | 27 |
| 463 | FWLEGQLR | 19.49 | 524.78 | 602.33 | 28 |
| 464 | FWLEGQLR | 19.49 | 524.78 | 715.41 | 28 |
| 465 | FWLEGQLR | 19.48 | 524.78 | 901.49 | 28 |
| 466 | FYPASSFK | 14.74 | 473.74 | 636.34 | 26 |
| 467 | FYPASSFK | 14.74 | 473.74 | 799.4 | 26 |
| 468 | FYPASSFK | 14.74 | 473.74 | 800.36 | 26 |
| 469 | FYPASTFK | 14.98 | 480.74 | 553.3 | 26 |
| 470 | FYPASTFK | 14.99 | 480.74 | 650.35 | 26 |
| 471 | FYPASTFK | 14.98 | 480.74 | 813.41 | 26 |
| 472 | GAIQVSAVPVFQQIAR | 21.6 | 842.48 | 958.55 | 42 |
| 473 | GAIQVSAVPVFQQIAR | 21.6 | 842.48 | 1057.62 | 42 |
| 474 | GAIQVSAVPVFQQIAR | 21.59 | 842.48 | 1128.65 | 42 |
| 475 | GAIQVSAVPVFQQITR | 21.52 | 857.49 | 988.56 | 43 |
| 476 | GAIQVSAVPVFQQITR | 21.51 | 857.49 | 1087.63 | 43 |
| 477 | GAIQVSAVPVFQQITR | 21.52 | 857.49 | 1158.66 | 43 |
| 478 | GELPVSEDALEMTK | 18.1 | 759.87 | 936.43 | 38 |

TABLE 25-continued

| Transition number | Peptide | Retention time (minutes) | (m/z) filtered in Q1 | (m/z) filtered in Q3 | Collision energy (eV) |
|---|---|---|---|---|---|
| 479 | GELPVSEDALEMTK | 18.11 | 759.87 | 1023.47 | 38 |
| 480 | GELPVSEDALEMTK | 18.11 | 759.87 | 1122.53 | 38 |
| 481 | GISSSVR | 8.65 | 353.2 | 448.25 | 21 |
| 482 | GISSSVR | 8.65 | 353.2 | 535.28 | 21 |
| 483 | GISSSVR | 8.67 | 353.2 | 648.37 | 21 |
| 484 | GNQTLVFAR | 14.83 | 503.28 | 605.38 | 27 |
| 485 | GNQTLVFAR | 14.83 | 503.28 | 706.42 | 27 |
| 486 | GNQTLVFAR | 14.83 | 503.28 | 834.48 | 27 |
| 487 | GPLEISAFEEAR | 18.95 | 659.84 | 809.38 | 34 |
| 488 | GPLEISAFEEAR | 18.94 | 659.84 | 922.46 | 34 |
| 489 | GPLEISAFEEAR | 18.94 | 659.84 | 1051.51 | 34 |
| 490 | GPLTITPIQEVK | 18.14 | 648.38 | 814.47 | 34 |
| 491 | GPLTITPIQEVK | 18.15 | 648.38 | 927.55 | 34 |
| 492 | GPLTITPIQEVK | 18.14 | 648.38 | 1028.6 | 34 |
| 493 | GSLLLWDQK | 19.61 | 530.3 | 576.28 | 28 |
| 494 | GSLLLWDQK | 19.61 | 530.3 | 689.36 | 28 |
| 495 | GSLLLWDQK | 19.61 | 530.3 | 802.45 | 28 |
| 496 | GTFVLYDVQR | 17.93 | 599.32 | 680.34 | 31 |
| 497 | GTFVLYDVQR | 17.93 | 599.32 | 793.42 | 31 |
| 498 | GTFVLYDVQR | 17.93 | 599.32 | 892.49 | 31 |
| 499 | GTIVVADER | 11.82 | 480.26 | 490.23 | 26 |
| 500 | GTIVVADER | 11.82 | 480.26 | 589.29 | 26 |
| 501 | GTIVVADER | 11.82 | 480.26 | 688.36 | 26 |
| 502 | GTIVVLDAR | 15.77 | 472.28 | 573.34 | 26 |
| 503 | GTIVVLDAR | 15.77 | 472.28 | 672.4 | 26 |
| 504 | GTIVVLDAR | 15.77 | 472.28 | 785.49 | 26 |
| 505 | GTIVVVDER | 13.6 | 494.28 | 518.26 | 27 |
| 506 | GTIVVVDER | 13.6 | 494.28 | 617.33 | 27 |
| 507 | GTIVVVDER | 13.6 | 494.28 | 716.39 | 27 |
| 508 | GTLPFSAR | 14.96 | 424.73 | 577.31 | 24 |
| 509 | GTLPFSAR | 14.96 | 424.73 | 690.39 | 24 |
| 510 | GTLPFSAR | 14.97 | 424.73 | 791.44 | 24 |
| 511 | HIADSK | 11.91 | 335.68 | 420.21 | 20 |
| 512 | HIADSK | 11.9 | 335.68 | 524.25 | 20 |
| 513 | HIADSK | 11.91 | 335.68 | 533.29 | 20 |
| 514 | HNGTDGAWIISSLR | 19.36 | 509.6 | 575.35 | 29 |
| 515 | HNGTDGAWIISSLR | 19.35 | 509.6 | 653.26 | 29 |
| 516 | HNGTDGAWIISSLR | 19.36 | 509.6 | 688.44 | 29 |

TABLE 25-continued

| Transition number | Peptide | Retention time (minutes) | (m/z) filtered in Q1 | (m/z) filtered in Q3 | Collision energy (eV) |
|---|---|---|---|---|---|
| 517 | HTLSVFDQER | 14.25 | 411.21 | 432.22 | 25 |
| 518 | HTLSVFDQER | 14.25 | 411.21 | 547.25 | 25 |
| 519 | HTLSVFDQER | 14.25 | 411.21 | 694.32 | 25 |
| 520 | HVTFASFR | 14.36 | 322.17 | 338.18 | 20 |
| 521 | HVTFASFR | 14.36 | 322.17 | 409.22 | 20 |
| 522 | HVTFASFR | 14.36 | 322.17 | 485.25 | 20 |
| 523 | IAISLMGYDAGFLR | 23.93 | 763.91 | 898.44 | 39 |
| 524 | IAISLMGYDAGFLR | 23.93 | 763.91 | 1029.48 | 39 |
| 525 | IAISLMGYDAGFLR | 23.94 | 763.91 | 1229.6 | 39 |
| 526 | IALSLMGFDSGILK | 24.91 | 732.91 | 836.45 | 37 |
| 527 | IALSLMGFDSGILK | 24.91 | 732.91 | 967.49 | 37 |
| 528 | IALSLMGFDSGILK | 24.91 | 732.91 | 1167.61 | 37 |
| 529 | IANALIGLENHK | 15.95 | 431.58 | 697.36 | 26 |
| 530 | IANALIGLENHK | 15.95 | 646.87 | 697.36 | 33 |
| 531 | IANALIGLENHK | 15.95 | 646.87 | 810.45 | 33 |
| 532 | IDTFWLDNSLK | 21.79 | 676.35 | 689.38 | 35 |
| 533 | IDTFWLDNSLK | 21.79 | 676.35 | 875.46 | 35 |
| 534 | IDTFWLDNSLK | 21.79 | 676.35 | 1123.58 | 35 |
| 535 | IDYYNLDR | 14.85 | 536.26 | 680.34 | 29 |
| 536 | IDYYNLDR | 14.85 | 536.26 | 843.4 | 29 |
| 537 | IDYYNLDR | 14.85 | 536.26 | 958.43 | 29 |
| 538 | IFNALIALDSGVIK | 24.74 | 737.44 | 802.47 | 37 |
| 539 | IFNALIALDSGVIK | 24.74 | 737.44 | 915.55 | 37 |
| 540 | IFNALIALDSGVIK | 24.74 | 737.44 | 1028.64 | 37 |
| 541 | IFNSLLALDSGALDNER | 22.76 | 924.48 | 976.43 | 46 |
| 542 | IFNSLLALDSGALDNER | 22.77 | 924.48 | 1089.52 | 46 |
| 543 | IFNSLLALDSGALDNER | 22.76 | 924.48 | 1160.55 | 46 |
| 544 | IFNTLIGLENGIVK | 23.29 | 765.95 | 829.48 | 39 |
| 545 | IFNTLIGLENGIVK | 23.3 | 765.95 | 942.56 | 39 |
| 546 | IFNTLIGLENGIVK | 23.3 | 765.95 | 1055.65 | 39 |
| 547 | IGLDLMQK | 17.7 | 459.26 | 634.32 | 25 |
| 548 | IGLDLMQK | 17.7 | 459.26 | 747.41 | 25 |
| 549 | IGLDLMQK | 17.7 | 459.26 | 804.43 | 25 |
| 550 | IGLEK | 8.54 | 280.18 | 389.24 | 17 |
| 551 | IGLEK | 8.55 | 280.18 | 413.24 | 17 |
| 552 | IGLEK | 8.54 | 280.18 | 446.26 | 17 |
| 553 | IGLELMQQEVQR | 18.73 | 722.38 | 787.41 | 37 |
| 554 | IGLELMQQEVQR | 18.73 | 722.38 | 918.45 | 37 |

TABLE 25-continued

| Transition number | Peptide | Retention time (minutes) | (m/z) filtered in Q1 | (m/z) filtered in Q3 | Collision energy (eV) |
| --- | --- | --- | --- | --- | --- |
| 555 | IGLELMQQEVQR | 18.73 | 722.38 | 1031.53 | 37 |
| 556 | IGLELMSK | 17.52 | 445.75 | 478.27 | 25 |
| 557 | IGLELMSK | 17.52 | 445.75 | 720.4 | 25 |
| 558 | IGLELMSK | 17.52 | 445.75 | 777.42 | 25 |
| 559 | IGLELMSNEVK | 18.73 | 616.83 | 707.34 | 32 |
| 560 | IGLELMSNEVK | 18.73 | 616.83 | 820.42 | 32 |
| 561 | IGLELMSNEVK | 18.73 | 616.83 | 949.47 | 32 |
| 562 | IGLER | 10.96 | 294.18 | 304.16 | 18 |
| 563 | IGLER | 10.96 | 294.18 | 417.25 | 18 |
| 564 | IGLER | 10.96 | 294.18 | 474.27 | 18 |
| 565 | IGLNK | 9.59 | 272.68 | 374.24 | 17 |
| 566 | IGLNK | 9.59 | 272.68 | 398.24 | 17 |
| 567 | IGLNK | 9.59 | 272.68 | 431.26 | 17 |
| 568 | IGLNLMQK | 17.1 | 458.77 | 633.34 | 25 |
| 569 | IGLNLMQK | 17.09 | 458.77 | 746.42 | 25 |
| 570 | IGLNLMQK | 17.11 | 458.77 | 803.44 | 25 |
| 571 | IGPSLMQSELQR | 17.02 | 679.86 | 760.39 | 35 |
| 572 | IGPSLMQSELQR | 17.02 | 679.86 | 891.44 | 35 |
| 573 | IGPSLMQSELQR | 17.02 | 679.86 | 1188.6 | 35 |
| 574 | IGYGNMQIGTEVDQFWLK | 24.31 | 700.35 | 935.5 | 39 |
| 575 | IGYGNMQIGTEVDQFWLK | 24.32 | 1050.02 | 1164.54 | 51 |
| 576 | IGYGNMQIGTEVDQFWLK | 24.3 | 1050.02 | 1222.61 | 51 |
| 577 | IINHNLPVK | 11.88 | 349.88 | 456.32 | 21 |
| 578 | IINHNLPVK | 11.88 | 349.88 | 570.36 | 21 |
| 579 | IINHNLPVK | 11.88 | 349.88 | 592.32 | 21 |
| 580 | IINHNLPVR | 12.04 | 359.22 | 598.37 | 22 |
| 581 | IINHNLPVR | 12.04 | 538.32 | 598.37 | 29 |
| 582 | IINHNLPVR | 12.04 | 538.32 | 849.47 | 29 |
| 583 | ILFQQGTQQAC[CAM]AER | 14.51 | 550.61 | 606.27 | 32 |
| 584 | ILFQQGTQQAC[CAM]AER | 14.51 | 825.41 | 1020.45 | 41 |
| 585 | ILFQQGTQQAC[CAM]AER | 14.51 | 825.41 | 1148.51 | 41 |
| 586 | ILNNWFK | 18.98 | 467.76 | 594.3 | 26 |
| 587 | ILNNWFK | 18.98 | 467.76 | 708.35 | 26 |
| 588 | ILNNWFK | 18.97 | 467.76 | 821.43 | 26 |
| 589 | ILNTLISLEEK | 19.98 | 636.87 | 718.4 | 33 |
| 590 | ILNTLISLEEK | 19.98 | 636.87 | 1046.57 | 33 |
| 591 | ILNTLISLEEK | 19.98 | 636.87 | 1159.66 | 33 |
| 592 | INIVK | 11.43 | 293.7 | 359.27 | 18 |

TABLE 25-continued

| Transition number | Peptide | Retention time (minutes) | (m/z) filtered in Q1 | (m/z) filtered in Q3 | Collision energy (eV) |
|---|---|---|---|---|---|
| 593 | INIVK | 11.43 | 293.7 | 440.29 | 18 |
| 594 | INIVK | 11.43 | 293.7 | 473.31 | 18 |
| 595 | INLYGNALSR | 16.05 | 560.81 | 617.34 | 30 |
| 596 | INLYGNALSR | 16.05 | 560.81 | 780.4 | 30 |
| 597 | INLYGNALSR | 16.05 | 560.81 | 893.48 | 30 |
| 598 | IPFSLNLEMK | 21.68 | 596.33 | 834.44 | 31 |
| 599 | IPFSLNLEMK | 21.67 | 596.33 | 981.51 | 31 |
| 600 | IPFSLNLEMK | 21.67 | 596.33 | 1078.56 | 31 |
| 601 | IPHTLFALDADAVR | 20 | 513.62 | 531.29 | 30 |
| 602 | IPHTLFALDADAVR | 20 | 513.62 | 646.32 | 30 |
| 603 | IPHTLFALDADAVR | 20 | 769.92 | 1191.64 | 39 |
| 604 | IPHTLFALDAGAAR | 18.58 | 726.9 | 744.4 | 37 |
| 605 | IPHTLFALDAGAAR | 18.58 | 726.9 | 891.47 | 37 |
| 606 | IPHTLFALDAGAAR | 18.58 | 726.9 | 1004.55 | 37 |
| 607 | IPHTLFALDAGAVR | 19.72 | 494.28 | 588.31 | 29 |
| 608 | IPHTLFALDAGAVR | 19.71 | 494.28 | 780.44 | 29 |
| 609 | IPHTLFALDAGAVR | 19.72 | 740.92 | 1133.63 | 38 |
| 610 | IPNAIIGLETGVIK | 21.75 | 719.44 | 816.48 | 37 |
| 611 | IPNAIIGLETGVIK | 21.75 | 719.44 | 929.57 | 37 |
| 612 | IPNAIIGLETGVIK | 21.75 | 719.44 | 1227.73 | 37 |
| 613 | IPNALIGLETGAIK | 20.96 | 705.42 | 788.45 | 36 |
| 614 | IPNALIGLETGAIK | 20.96 | 705.42 | 901.54 | 36 |
| 615 | IPNALIGLETGAIK | 20.96 | 705.42 | 1014.62 | 36 |
| 616 | IPNSLIAFDTGAVR | 20.24 | 737.41 | 765.39 | 37 |
| 617 | IPNSLIAFDTGAVR | 20.24 | 737.41 | 836.43 | 37 |
| 618 | IPNSLIAFDTGAVR | 20.24 | 737.41 | 949.51 | 37 |
| 619 | IPSAIIGLETGVIK | 21.66 | 705.93 | 816.48 | 36 |
| 620 | IPSAIIGLETGVIK | 21.67 | 705.93 | 929.57 | 36 |
| 621 | IPSAIIGLETGVIK | 21.66 | 705.93 | 1200.72 | 36 |
| 622 | ISAFNQVK | 13.02 | 453.76 | 488.28 | 25 |
| 623 | ISAFNQVK | 13.02 | 453.76 | 706.39 | 25 |
| 624 | ISAFNQVK | 13.02 | 453.76 | 793.42 | 25 |
| 625 | ISAHEQILFLR | 18.28 | 442.92 | 548.36 | 26 |
| 626 | ISAHEQILFLR | 18.28 | 442.92 | 789.5 | 26 |
| 627 | ISAHEQILFLR | 18.28 | 663.88 | 918.54 | 34 |
| 628 | ISAMEQTR | 9.84 | 468.23 | 664.31 | 26 |
| 629 | ISAMEQTR | 9.84 | 468.23 | 735.35 | 26 |
| 630 | ISAMEQTR | 9.84 | 468.23 | 822.38 | 26 |

TABLE 25-continued

| Transition number | Peptide | Retention time (minutes) | (m/z) filtered in Q1 | (m/z) filtered in Q3 | Collision energy (eV) |
|---|---|---|---|---|---|
| 631 | ISAMEQVK | 11.65 | 453.24 | 634.32 | 25 |
| 632 | ISAMEQVK | 11.65 | 453.24 | 705.36 | 25 |
| 633 | ISAMEQVK | 11.65 | 453.24 | 792.39 | 25 |
| 634 | ISATEQVAFLR | 17.7 | 412.23 | 435.27 | 25 |
| 635 | ISATEQVAFLR | 17.71 | 412.23 | 506.31 | 25 |
| 636 | ISATEQVAFLR | 17.7 | 412.23 | 605.38 | 25 |
| 637 | ISATQQIAFLR | 18.58 | 624.36 | 747.45 | 32 |
| 638 | ISATQQIAFLR | 18.58 | 624.36 | 1047.59 | 32 |
| 639 | ISATQQIAFLR | 18.58 | 624.36 | 1134.63 | 32 |
| 640 | ISAVNQVEFLESLFLNK | 28.77 | 976.03 | 988.51 | 48 |
| 641 | ISAVNQVEFLESLFLNK | 28.77 | 976.03 | 1110.62 | 48 |
| 642 | ISAVNQVEFLESLFLNK | 28.77 | 976.03 | 1239.66 | 48 |
| 643 | ISAVNQVK | 10.32 | 429.76 | 488.28 | 24 |
| 644 | ISAVNQVK | 10.32 | 429.76 | 658.39 | 24 |
| 645 | ISAVNQVK | 10.32 | 429.76 | 745.42 | 24 |
| 646 | ISPEEQIQFLR | 18.87 | 680.37 | 933.52 | 35 |
| 647 | ISPEEQIQFLR | 18.87 | 680.37 | 1062.56 | 35 |
| 648 | ISPEEQIQFLR | 18.87 | 680.37 | 1159.61 | 35 |
| 649 | ISPEEQVR | 10.49 | 479.25 | 531.29 | 26 |
| 650 | ISPEEQVR | 10.49 | 479.25 | 660.33 | 26 |
| 651 | ISPEEQVR | 10.49 | 479.25 | 757.38 | 26 |
| 652 | ISPEGQVR | 9.86 | 443.24 | 459.27 | 25 |
| 653 | ISPEGQVR | 9.86 | 443.24 | 588.31 | 25 |
| 654 | ISPEGQVR | 9.86 | 443.24 | 685.36 | 25 |
| 655 | ISPLEQLAFLR | 24.02 | 643.88 | 876.49 | 33 |
| 656 | ISPLEQLAFLR | 24.01 | 643.88 | 989.58 | 33 |
| 657 | ISPLEQLAFLR | 24.02 | 643.88 | 1086.63 | 33 |
| 658 | ITAFQQVDFLR | 21.11 | 669.36 | 777.43 | 34 |
| 659 | ITAFQQVDFLR | 21.12 | 669.36 | 905.48 | 34 |
| 660 | ITAFQQVDFLR | 21.12 | 669.36 | 1123.59 | 34 |
| 661 | ITPIQEVNFADDFANNR | 21.25 | 655.32 | 736.34 | 37 |
| 662 | ITPIQEVNFADDFANNR | 21.25 | 655.32 | 851.36 | 37 |
| 663 | ITPIQEVNFADDFANNR | 21.25 | 655.32 | 922.4 | 37 |
| 664 | ITPIQEVNFADDLANNR | 20.95 | 643.99 | 817.38 | 36 |
| 665 | ITPIQEVNFADDLANNR | 20.95 | 965.49 | 1149.53 | 47 |
| 666 | ITPIQEVNFADDLANNR | 20.96 | 965.49 | 1248.6 | 47 |
| 667 | ITPQQEAQFAYK | 14.52 | 712.36 | 856.42 | 36 |
| 668 | ITPQQEAQFAYK | 14.52 | 712.36 | 984.48 | 36 |

TABLE 25-continued

| Transition number | Peptide | Retention time (minutes) | (m/z) filtered in Q1 | (m/z) filtered in Q3 | Collision energy (eV) |
|---|---|---|---|---|---|
| 669 | ITPQQEAQFAYK | 14.52 | 712.36 | 1209.59 | 36 |
| 670 | ITPQQEAQFTYK | 14.33 | 485.25 | 558.29 | 28 |
| 671 | ITPQQEAQFTYK | 14.33 | 727.37 | 1014.49 | 37 |
| 672 | ITPQQEAQFTYK | 14.33 | 727.37 | 1239.6 | 37 |
| 673 | ITPVQEVNFADDLAHNR | 18.98 | 646.99 | 840.4 | 36 |
| 674 | ITPVQEVNFADDLAHNR | 18.98 | 646.99 | 862.92 | 36 |
| 675 | ITPVQEVNFADDLAHNR | 18.98 | 646.99 | 911.43 | 36 |
| 676 | IVAFALK | 17.21 | 381.25 | 478.3 | 22 |
| 677 | IVAFALK | 17.22 | 381.25 | 549.34 | 22 |
| 678 | IVAFALK | 17.21 | 381.25 | 648.41 | 22 |
| 679 | IVAFALNMEMR | 17.95 | 647.84 | 864.41 | 34 |
| 680 | IVAFALNMEMR | 17.95 | 647.84 | 1011.48 | 34 |
| 681 | IVAFALNMEMR | 17.97 | 647.84 | 1082.51 | 34 |
| 682 | IVESTTLADGTWHGK | 13.69 | 542.96 | 697.4 | 31 |
| 683 | IVESTTLADGTWHGK | 13.69 | 542.96 | 812.43 | 31 |
| 684 | IVESTTLADGTWHGK | 13.68 | 542.96 | 883.46 | 31 |
| 685 | IYNSLIGLNEK | 17.37 | 632.35 | 673.39 | 33 |
| 686 | IYNSLIGLNEK | 17.37 | 632.35 | 786.47 | 33 |
| 687 | IYNSLIGLNEK | 17.37 | 632.35 | 987.55 | 33 |
| 688 | KPDIGVVWVGWIER | 24.47 | 547.96 | 660.35 | 31 |
| 689 | KPDIGVVWVGWIER | 24.47 | 547.96 | 883.45 | 31 |
| 690 | KPDIGVVWVGWIER | 24.46 | 821.43 | 1188.59 | 41 |
| 691 | LAC[CAM]ATNNLAR | 11.22 | 552.28 | 688.37 | 29 |
| 692 | LAC[CAM]ATNNLAR | 11.22 | 552.28 | 759.41 | 29 |
| 693 | LAC[CAM]ATNNLAR | 11.22 | 552.28 | 919.44 | 29 |
| 694 | LAQGELPFPAPVQSTVR | 19.84 | 905.5 | 954.54 | 45 |
| 695 | LAQGELPFPAPVQSTVR | 19.84 | 905.5 | 1101.61 | 45 |
| 696 | LAQGELPFPAPVQSTVR | 19.84 | 905.5 | 1198.66 | 45 |
| 697 | LAQNELPYPIEIQK | 19.09 | 828.45 | 929.47 | 41 |
| 698 | LAQNELPYPIEIQK | 19.09 | 828.45 | 987.55 | 41 |
| 699 | LAQNELPYPIEIQK | 19.08 | 828.45 | 1100.64 | 41 |
| 700 | LAQNELQYPIEIQK | 17.98 | 843.96 | 890.5 | 42 |
| 701 | LAQNELQYPIEIQK | 17.98 | 843.96 | 1018.56 | 42 |
| 702 | LAQNELQYPIEIQK | 17.98 | 843.96 | 1131.64 | 42 |
| 703 | LDFGNK | 11.75 | 347.18 | 465.25 | 20 |
| 704 | LDFGNK | 11.74 | 347.18 | 547.25 | 20 |
| 705 | LDFGNK | 11.75 | 347.18 | 580.27 | 20 |
| 706 | LDGSLNR | 9.48 | 387.71 | 402.25 | 22 |

TABLE 25-continued

| Transition number | Peptide | Retention time (minutes) | (m/z) filtered in Q1 | (m/z) filtered in Q3 | Collision energy (eV) |
|---|---|---|---|---|---|
| 707 | LDGSLNR | 9.48 | 387.71 | 546.3 | 22 |
| 708 | LDGSLNR | 9.48 | 387.71 | 661.33 | 22 |
| 709 | LEILQQALAELGLYPK | 29.81 | 900.02 | 1003.58 | 45 |
| 710 | LEILQQALAELGLYPK | 29.81 | 900.02 | 1074.62 | 45 |
| 711 | LEILQQALAELGLYPK | 29.81 | 900.02 | 1202.68 | 45 |
| 712 | LENQEQVK | 7.6 | 494.26 | 631.34 | 27 |
| 713 | LENQEQVK | 7.59 | 494.26 | 745.38 | 27 |
| 714 | LENQEQVK | 7.59 | 494.26 | 874.43 | 27 |
| 715 | LETQEEVEK | 9.88 | 552.77 | 633.31 | 29 |
| 716 | LETQEEVEK | 9.88 | 552.77 | 862.42 | 29 |
| 717 | LETQEEVEK | 9.88 | 552.77 | 991.46 | 29 |
| 718 | LETQEEVK | 9.5 | 488.25 | 504.27 | 26 |
| 719 | LETQEEVK | 9.49 | 488.25 | 733.37 | 26 |
| 720 | LETQEEVK | 9.49 | 488.25 | 862.42 | 26 |
| 721 | LFAAEGVK | 13.53 | 417.74 | 503.28 | 23 |
| 722 | LFAAEGVK | 13.53 | 417.74 | 574.32 | 23 |
| 723 | LFAAEGVK | 13.53 | 417.74 | 721.39 | 23 |
| 724 | LFESAGVK | 12.99 | 425.74 | 461.27 | 24 |
| 725 | LFESAGVK | 12.99 | 425.74 | 590.31 | 24 |
| 726 | LFESAGVK | 12.99 | 425.74 | 737.38 | 24 |
| 727 | LFGAAGVK | 13.94 | 381.73 | 445.28 | 22 |
| 728 | LFGAAGVK | 13.94 | 381.73 | 502.3 | 22 |
| 729 | LFGAAGVK | 13.94 | 381.73 | 649.37 | 22 |
| 730 | LGVDR | 8.51 | 280.16 | 290.15 | 17 |
| 731 | LGVDR | 8.51 | 280.16 | 389.21 | 17 |
| 732 | LGVDR | 8.5 | 280.16 | 446.24 | 17 |
| 733 | LLNLLSQSK | 17.97 | 508.31 | 562.32 | 27 |
| 734 | LLNLLSQSK | 17.97 | 508.31 | 789.45 | 27 |
| 735 | LLNLLSQSK | 17.97 | 508.31 | 902.53 | 27 |
| 736 | LLQDER | 9.34 | 387.21 | 547.25 | 22 |
| 737 | LLQDER | 9.31 | 387.21 | 599.3 | 22 |
| 738 | LLQDER | 9.34 | 387.21 | 660.33 | 22 |
| 739 | LLVQDGDC[CAM]GR | 11.92 | 566.77 | 679.25 | 30 |
| 740 | LLVQDGDC[CAM]GR | 11.92 | 566.77 | 807.3 | 30 |
| 741 | LLVQDGDC[CAM]GR | 11.92 | 566.77 | 906.37 | 30 |
| 742 | LNEVGYGNR | 10.74 | 511.26 | 566.27 | 27 |
| 743 | LNEVGYGNR | 10.74 | 511.26 | 665.34 | 27 |
| 744 | LNEVGYGNR | 10.73 | 511.26 | 794.38 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 745 | LNYGNADPSTK | 10.76 | 590.29 | 732.35 | 31 |
| 746 | LNYGNADPSTK | 10.76 | 590.29 | 789.37 | 31 |
| 747 | LNYGNADPSTK | 10.76 | 590.29 | 952.44 | 31 |
| 748 | LNYGNK | 7.21 | 354.69 | 481.24 | 21 |
| 749 | LNYGNK | 7.24 | 354.69 | 562.26 | 21 |
| 750 | LNYGNK | 7.22 | 354.69 | 595.28 | 21 |
| 751 | LPASK | 1.93 | 258.16 | 305.18 | 16 |
| 752 | LPASK | 1.93 | 258.16 | 369.21 | 16 |
| 753 | LPASK | 1.93 | 258.16 | 402.23 | 16 |
| 754 | LPHTLFALDADAVR | 19.98 | 769.92 | 977.51 | 39 |
| 755 | LPHTLFALDADAVR | 19.98 | 769.92 | 1090.59 | 39 |
| 756 | LPHTLFALDADAVR | 19.98 | 769.92 | 1191.64 | 39 |
| 757 | LPHTLFALDAGAVR | 19.7 | 740.92 | 919.5 | 38 |
| 758 | LPHTLFALDAGAVR | 19.67 | 740.92 | 1032.58 | 38 |
| 759 | LPHTLFALDAGAVR | 19.7 | 740.92 | 1133.63 | 38 |
| 760 | LPLAIMGFDSGILQSPK | 25.08 | 893.99 | 944.5 | 44 |
| 761 | LPLAIMGFDSGILQSPK | 25.08 | 893.99 | 1091.57 | 44 |
| 762 | LPLAIMGFDSGILQSPK | 25.08 | 893.99 | 1148.59 | 44 |
| 763 | LPLAIMGYDADILLDATTPR | 27.86 | 720.39 | 773.42 | 40 |
| 764 | LPLAIMGYDADILLDATTPR | 27.87 | 720.39 | 886.5 | 40 |
| 765 | LPLAIMGYDADILLDATTPR | 27.87 | 720.39 | 1160.57 | 40 |
| 766 | LPSSLIALETGAVR | 20.6 | 713.92 | 816.46 | 36 |
| 767 | LPSSLIALETGAVR | 20.6 | 713.92 | 929.54 | 36 |
| 768 | LPSSLIALETGAVR | 20.6 | 713.92 | 1216.69 | 36 |
| 769 | LPVSAQTLQYTANILK | 21.84 | 880.5 | 950.53 | 44 |
| 770 | LPVSAQTLQYTANILK | 21.84 | 880.5 | 1063.61 | 44 |
| 771 | LPVSAQTLQYTANILK | 21.85 | 880.5 | 1164.66 | 44 |
| 772 | LPVSER | 9.57 | 350.7 | 490.26 | 20 |
| 773 | LPVSER | 9.57 | 350.7 | 526.29 | 20 |
| 774 | LPVSER | 9.57 | 350.7 | 587.31 | 20 |
| 775 | LPVSPTAVDMTER | 16.21 | 708.36 | 1019.48 | 36 |
| 776 | LPVSPTAVDMTER | 16.21 | 708.36 | 1106.51 | 36 |
| 777 | LPVSPTAVDMTER | 16.21 | 708.36 | 1205.58 | 36 |
| 778 | LSASK | 10.72 | 253.15 | 305.18 | 16 |
| 779 | LSASK | 10.71 | 253.15 | 359.19 | 16 |
| 780 | LSASK | 10.71 | 253.15 | 392.21 | 16 |
| 781 | LSAVPIYQEVAR | 17.96 | 673.38 | 765.39 | 35 |
| 782 | LSAVPIYQEVAR | 17.96 | 673.38 | 975.53 | 35 |

TABLE 25-continued

| Transition number | Peptide | Retention time (minutes) | (m/z) filtered in Q1 | (m/z) filtered in Q3 | Collision energy (eV) |
|---|---|---|---|---|---|
| 783 | LSAVPIYQEVAR | 17.95 | 673.38 | 1074.59 | 35 |
| 784 | LSAVPVYQELAR | 18.45 | 449.25 | 616.34 | 26 |
| 785 | LSAVPVYQELAR | 18.44 | 673.38 | 779.4 | 35 |
| 786 | LSAVPVYQELAR | 18.44 | 673.38 | 975.53 | 35 |
| 787 | LSC[CAM]TLVIDEASGDLLHR | 20.38 | 633.66 | 797.43 | 36 |
| 788 | LSC[CAM]TLVIDEASGDLLHR | 20.38 | 633.66 | 868.46 | 36 |
| 789 | LSC[CAM]TLVIDEASGDLLHR | 20.38 | 633.66 | 1112.53 | 36 |
| 790 | LSLQHGWFIGWIEK | 23.95 | 571.98 | 632.34 | 33 |
| 791 | LSLQHGWFIGWIEK | 23.95 | 571.98 | 892.49 | 33 |
| 792 | LSLQHGWFIGWIEK | 23.95 | 571.98 | 969.49 | 33 |
| 793 | LSQNSLPFSQEAMNSVK | 18.64 | 627.31 | 1140.54 | 35 |
| 794 | LSQNSLPFSQEAMNSVK | 18.63 | 940.46 | 1140.54 | 46 |
| 795 | LSQNSLPFSQEAMNSVK | 18.64 | 940.46 | 1237.59 | 46 |
| 796 | LSVNPK | 9.8 | 329.2 | 457.28 | 19 |
| 797 | LSVNPK | 9.79 | 329.2 | 511.29 | 19 |
| 798 | LSVNPK | 9.8 | 329.2 | 544.31 | 19 |
| 799 | LTVGAR | 9.51 | 308.69 | 402.25 | 19 |
| 800 | LTVGAR | 9.51 | 308.69 | 442.27 | 19 |
| 801 | LTVGAR | 9.51 | 308.69 | 503.29 | 19 |
| 802 | LYGFALNIDMPGGEADIGK | 23.35 | 661 | 843.42 | 37 |
| 803 | LYGFALNIDMPGGEADIGK | 23.35 | 990.99 | 1089.49 | 49 |
| 804 | LYGFALNIDMPGGEADIGK | 23.35 | 990.99 | 1202.57 | 49 |
| 805 | LYHNELPFR | 15.29 | 396.88 | 414.21 | 24 |
| 806 | LYHNELPFR | 15.29 | 396.88 | 419.24 | 24 |
| 807 | LYHNELPFR | 15.29 | 396.88 | 657.3 | 24 |
| 808 | LYHNK | 8.54 | 337.68 | 414.21 | 20 |
| 809 | LYHNK | 8.53 | 337.68 | 528.26 | 20 |
| 810 | LYHNK | 8.53 | 337.68 | 561.28 | 20 |
| 811 | LYQNDLPFR | 17.2 | 583.3 | 761.39 | 31 |
| 812 | LYQNDLPFR | 17.2 | 583.3 | 889.45 | 31 |
| 813 | LYQNDLPFR | 17.2 | 583.3 | 1052.52 | 31 |
| 814 | MDDLFK | 15.5 | 384.68 | 522.29 | 22 |
| 815 | MDDLFK | 15.5 | 384.68 | 622.25 | 22 |
| 816 | MDDLFK | 15.5 | 384.68 | 637.32 | 22 |
| 817 | MEDLHK | 6.66 | 386.69 | 512.28 | 22 |
| 818 | MEDLHK | 6.65 | 386.69 | 626.26 | 22 |
| 819 | MEDLHK | 6.66 | 386.69 | 641.33 | 22 |
| 820 | MLIALIGLENHK | 21.33 | 451.26 | 527.26 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 821 | MLIALIGLENHK | 21.33 | 451.26 | 697.36 | 27 |
| 822 | MLIALIGLENHK | 21.33 | 451.26 | 810.45 | 27 |
| 823 | MLLIK | 15.81 | 309.21 | 373.28 | 19 |
| 824 | MLLIK | 15.81 | 309.21 | 471.3 | 19 |
| 825 | MLLIK | 15.81 | 309.21 | 486.36 | 19 |
| 826 | MLNALIGLEHHK | 16.89 | 459.26 | 550.27 | 27 |
| 827 | MLNALIGLEHHK | 16.89 | 459.26 | 720.38 | 27 |
| 828 | MLNALIGLEHHK | 16.89 | 459.26 | 833.46 | 27 |
| 829 | MLNALIGLENHK | 18.39 | 451.58 | 697.36 | 27 |
| 830 | MLNALIGLENHK | 18.38 | 676.87 | 697.36 | 35 |
| 831 | MLNALIGLENHK | 18.39 | 676.87 | 810.45 | 35 |
| 832 | MLNALIGLENQK | 19.71 | 672.37 | 688.36 | 35 |
| 833 | MLNALIGLENQK | 19.71 | 672.37 | 801.45 | 35 |
| 834 | MLNALIGLENQK | 19.71 | 672.37 | 914.53 | 35 |
| 835 | MLNALIGLEYHK | 19.6 | 701.38 | 746.38 | 36 |
| 836 | MLNALIGLEYHK | 19.6 | 701.38 | 859.47 | 36 |
| 837 | MLNALIGLEYHK | 19.6 | 701.38 | 1157.63 | 36 |
| 838 | MLNALIGLQHGK | 17.5 | 432.25 | 582.34 | 26 |
| 839 | MLNALIGLQHGK | 17.5 | 432.25 | 639.36 | 26 |
| 840 | MLNALIGLQHGK | 17.5 | 432.25 | 752.44 | 26 |
| 841 | MLNALISLEHHK | 17.2 | 352.2 | 359.17 | 21 |
| 842 | MLNALISLEHHK | 17.21 | 469.26 | 750.39 | 27 |
| 843 | MLNALISLEHHK | 17.2 | 469.26 | 863.47 | 27 |
| 844 | MQAYVDAFDYGNR | 17.56 | 775.34 | 957.41 | 39 |
| 845 | MQAYVDAFDYGNR | 17.56 | 775.34 | 1056.47 | 39 |
| 846 | MQAYVDAFDYGNR | 17.56 | 775.34 | 1219.54 | 39 |
| 847 | MQEGLNK | 8.68 | 410.21 | 560.3 | 23 |
| 848 | MQEGLNK | 8.66 | 410.21 | 673.3 | 23 |
| 849 | MQEGLNK | 8.68 | 410.21 | 688.36 | 23 |
| 850 | MSPASTYK | 9.49 | 442.71 | 569.29 | 24 |
| 851 | MSPASTYK | 9.49 | 442.71 | 666.35 | 24 |
| 852 | MSPASTYK | 9.49 | 442.71 | 753.38 | 24 |
| 853 | NEHDPVLPYR | 13.09 | 413.88 | 435.24 | 25 |
| 854 | NEHDPVLPYR | 13.09 | 620.31 | 744.44 | 32 |
| 855 | NEHDPVLPYR | 13.09 | 620.31 | 859.47 | 32 |
| 856 | NEHQIFK | 9.91 | 458.24 | 509.21 | 25 |
| 857 | NEHQIFK | 9.91 | 458.24 | 622.29 | 25 |
| 858 | NEHQIFK | 9.91 | 458.24 | 672.38 | 25 |

TABLE 25-continued

| Transition number | Peptide | Retention time (minutes) | (m/z) filtered in Q1 | (m/z) filtered in Q3 | Collision energy (eV) |
|---|---|---|---|---|---|
| 859 | NEHQVFK | 7.74 | 451.23 | 658.37 | 25 |
| 860 | NEHQVFK | 7.74 | 451.23 | 755.35 | 25 |
| 861 | NEHQVFK | 7.74 | 451.23 | 787.41 | 25 |
| 862 | NEITYK | 9.35 | 384.2 | 524.31 | 22 |
| 863 | NEITYK | 9.35 | 384.2 | 621.29 | 22 |
| 864 | NEITYK | 9.35 | 384.2 | 653.35 | 22 |
| 865 | NELLMK | 13.08 | 374.21 | 504.32 | 21 |
| 866 | NELLMK | 13.09 | 374.21 | 601.3 | 21 |
| 867 | NELLMK | 13.09 | 374.21 | 633.36 | 21 |
| 868 | NELPFR | 14.39 | 388.21 | 419.24 | 22 |
| 869 | NELPFR | 14.39 | 388.21 | 532.32 | 22 |
| 870 | NELPFR | 14.4 | 388.21 | 661.37 | 22 |
| 871 | NISSYGNNLVR | 14.36 | 618.82 | 835.44 | 32 |
| 872 | NISSYGNNLVR | 14.36 | 618.82 | 922.47 | 32 |
| 873 | NISSYGNNLVR | 14.36 | 618.82 | 1009.51 | 32 |
| 874 | NISTYGNNLTR | 13.1 | 626.82 | 674.36 | 33 |
| 875 | NISTYGNNLTR | 13.09 | 626.82 | 837.42 | 33 |
| 876 | NISTYGNNLTR | 13.1 | 626.82 | 1025.5 | 33 |
| 877 | NLFNEVHTTGVLVIR | 20.69 | 571.32 | 757.49 | 33 |
| 878 | NLFNEVHTTGVLVIR | 20.7 | 571.32 | 858.54 | 33 |
| 879 | NLFNEVHTTGVLVIR | 20.7 | 571.32 | 995.6 | 33 |
| 880 | NLSTYGNALAR | 14.34 | 590.31 | 764.4 | 31 |
| 881 | NLSTYGNALAR | 14.35 | 590.31 | 865.45 | 31 |
| 882 | NLSTYGNALAR | 14.35 | 590.31 | 952.48 | 31 |
| 883 | NMENLELFGK | 19.08 | 597.79 | 820.46 | 31 |
| 884 | NMENLELFGK | 19.08 | 597.79 | 949.5 | 31 |
| 885 | NMENLELFGK | 19.08 | 597.79 | 1080.54 | 31 |
| 886 | NMLLLEENNGYK | 16.71 | 719.36 | 853.37 | 37 |
| 887 | NMLLLEENNGYK | 16.69 | 719.36 | 966.45 | 37 |
| 888 | NMLLLEENNGYK | 16.68 | 719.36 | 1079.54 | 37 |
| 889 | NMLLLEESNGYK | 18.12 | 705.85 | 939.44 | 36 |
| 890 | NMLLLEESNGYK | 18.13 | 705.85 | 1052.53 | 36 |
| 891 | NMLLLEESNGYK | 18.11 | 705.85 | 1165.61 | 36 |
| 892 | NMLLLEK | 16.99 | 430.75 | 502.32 | 24 |
| 893 | NMLLLEK | 16.98 | 430.75 | 615.41 | 24 |
| 894 | NMLLLEK | 16.98 | 430.75 | 746.45 | 24 |
| 895 | NMTLGDAMK | 14.42 | 490.73 | 521.24 | 27 |
| 896 | NMTLGDAMK | 14.42 | 490.73 | 634.32 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 897 | NMTLGDAMK | 14.42 | 490.73 | 735.37 | 27 |
| 898 | NNGLTEAWLESSLK | 20.61 | 781.4 | 862.47 | 39 |
| 899 | NNGLTEAWLESSLK | 20.6 | 781.4 | 933.5 | 39 |
| 900 | NNGLTEAWLESSLK | 20.62 | 781.4 | 1163.59 | 39 |
| 901 | NQLPFK | 13.49 | 373.71 | 391.23 | 21 |
| 902 | NQLPFK | 13.49 | 373.71 | 504.32 | 21 |
| 903 | NQLPFK | 13.49 | 373.71 | 632.38 | 21 |
| 904 | NQLPFQVEHQR | 14.33 | 698.36 | 796.41 | 36 |
| 905 | NQLPFQVEHQR | 14.33 | 698.36 | 1040.53 | 36 |
| 906 | NQLPFQVEHQR | 14.33 | 698.36 | 1153.61 | 36 |
| 907 | NSAIENTIDNMYLQDLENSTK | 22.77 | 805.04 | 934.45 | 44 |
| 908 | NSAIENTIDNMYLQDLENSTK | 22.77 | 805.04 | 1047.53 | 44 |
| 909 | NSAIENTIDNMYLQDLENSTK | 22.77 | 805.04 | 1210.6 | 44 |
| 910 | NSAIENTIENMYLQDLDNSTK | 23.13 | 805.04 | 920.43 | 44 |
| 911 | NSAIENTIENMYLQDLDNSTK | 23.13 | 805.04 | 1033.52 | 44 |
| 912 | NSAIENTIENMYLQDLDNSTK | 23.14 | 805.04 | 1196.58 | 44 |
| 913 | NSAIENTIENMYLQDLENSTK | 23.7 | 809.72 | 934.45 | 44 |
| 914 | NSAIENTIENMYLQDLENSTK | 23.7 | 809.72 | 1047.53 | 44 |
| 915 | NSAIENTIENMYLQDLENSTK | 23.7 | 809.72 | 1217.55 | 44 |
| 916 | NSAVWVYELFAK | 24.66 | 713.87 | 869.48 | 36 |
| 917 | NSAVWVYELFAK | 24.66 | 713.87 | 1055.56 | 36 |
| 918 | NSAVWVYELFAK | 24.65 | 713.87 | 1154.62 | 36 |
| 919 | NSQVPAYK | 9.78 | 453.74 | 478.27 | 25 |
| 920 | NSQVPAYK | 9.78 | 453.74 | 577.33 | 25 |
| 921 | NSQVPAYK | 9.78 | 453.74 | 705.39 | 25 |
| 922 | NSTVWIYELFAK | 25.64 | 735.88 | 883.49 | 37 |
| 923 | NSTVWIYELFAK | 25.64 | 735.88 | 1069.57 | 37 |
| 924 | NSTVWIYELFAK | 25.64 | 735.88 | 1168.64 | 37 |
| 925 | NSTVWVYELFAK | 24.42 | 728.88 | 770.41 | 37 |
| 926 | NSTVWVYELFAK | 24.43 | 728.88 | 869.48 | 37 |
| 927 | NSTVWVYELFAK | 24.42 | 728.88 | 1055.56 | 37 |
| 928 | NSTVWVYQLFAK | 23.9 | 728.39 | 769.42 | 37 |
| 929 | NSTVWVYQLFAK | 23.91 | 728.39 | 1054.57 | 37 |
| 930 | NSTVWVYQLFAK | 23.91 | 728.39 | 1153.64 | 37 |
| 931 | NTSGALVIQTDK | 13.34 | 623.84 | 816.48 | 32 |
| 932 | NTSGALVIQTDK | 13.34 | 623.84 | 944.54 | 32 |
| 933 | NTSGALVIQTDK | 13.34 | 623.84 | 1031.57 | 32 |
| 934 | NTSGVLVIQTDK | 14.9 | 637.85 | 816.48 | 33 |

TABLE 25-continued

| Transition number | Peptide | Retention time (minutes) | (m/z) filtered in Q1 | (m/z) filtered in Q3 | Collision energy (eV) |
|---|---|---|---|---|---|
| 935 | NTSGVLVIQTDK | 14.9 | 637.85 | 972.57 | 33 |
| 936 | NTSGVLVIQTDK | 14.91 | 637.85 | 1059.6 | 33 |
| 937 | NVDEMFYYYDGSK | 18.86 | 815.84 | 895.38 | 41 |
| 938 | NVDEMFYYYDGSK | 18.86 | 815.84 | 1042.45 | 41 |
| 939 | NVDEMFYYYDGSK | 18.85 | 815.84 | 1173.49 | 41 |
| 940 | NWILR | 16.3 | 351.21 | 414.21 | 20 |
| 941 | NWILR | 16.29 | 351.21 | 527.3 | 20 |
| 942 | NWILR | 16.3 | 351.21 | 587.37 | 20 |
| 943 | NWNAAMDLR | 16.54 | 545.76 | 605.31 | 29 |
| 944 | NWNAAMDLR | 16.55 | 545.76 | 676.34 | 29 |
| 945 | NWNAAMDLR | 16.54 | 545.76 | 790.39 | 29 |
| 946 | NYVDAFHYGNQDISGDK | 15.76 | 648.29 | 933.43 | 36 |
| 947 | NYVDAFHYGNQDISGDK | 15.77 | 648.29 | 1096.49 | 36 |
| 948 | NYVDAFHYGNQDISGDK | 15.76 | 971.93 | 1233.55 | 48 |
| 949 | QADHAILVFDQAR | 16.58 | 495.26 | 523.23 | 29 |
| 950 | QADHAILVFDQAR | 16.61 | 495.26 | 636.31 | 29 |
| 951 | QADHAILVFDQAR | 16.58 | 495.26 | 735.38 | 29 |
| 952 | QAEHALLVFGQER | 16.86 | 499.93 | 636.31 | 29 |
| 953 | QAEHALLVFGQER | 16.85 | 499.93 | 735.38 | 29 |
| 954 | QAEHALLVFGQER | 16.87 | 499.93 | 763.41 | 29 |
| 955 | QAITK | 11 | 280.67 | 361.24 | 17 |
| 956 | QAITK | 11 | 280.67 | 414.23 | 17 |
| 957 | QAITK | 11.01 | 280.67 | 432.28 | 17 |
| 958 | QAMLTEANSDYIIR | 18.26 | 812.9 | 951.49 | 41 |
| 959 | QAMLTEANSDYIIR | 18.25 | 812.9 | 1080.53 | 41 |
| 960 | QAMLTEANSDYIIR | 18.26 | 812.9 | 1181.58 | 41 |
| 961 | QEVQFVSALAR | 17.69 | 624.34 | 763.45 | 32 |
| 962 | QEVQFVSALAR | 17.68 | 624.34 | 891.5 | 32 |
| 963 | QEVQFVSALAR | 17.68 | 624.34 | 990.57 | 32 |
| 964 | QFASIK | 11.66 | 347.2 | 434.2 | 20 |
| 965 | QFASIK | 11.66 | 347.2 | 547.29 | 20 |
| 966 | QFASIK | 11.68 | 347.2 | 565.33 | 20 |
| 967 | QGMPGSIR | 11.4 | 423.22 | 529.31 | 24 |
| 968 | QGMPGSIR | 11.43 | 423.22 | 660.35 | 24 |
| 969 | QGMPGSIR | 11.4 | 423.22 | 717.37 | 24 |
| 970 | QGMSGSIR | 9.44 | 418.21 | 519.29 | 23 |
| 971 | QGMSGSIR | 9.45 | 418.21 | 650.33 | 23 |
| 972 | QGMSGSIR | 9.44 | 418.21 | 707.35 | 23 |

TABLE 25-continued

| Transition number | Peptide | Retention time (minutes) | (m/z) filtered in Q1 | (m/z) filtered in Q3 | Collision energy (eV) |
|---|---|---|---|---|---|
| 973 | QGQTQQSYGNDLAR | 11.16 | 783.37 | 895.43 | 39 |
| 974 | QGQTQQSYGNDLAR | 11.17 | 783.37 | 1023.49 | 39 |
| 975 | QGQTQQSYGNDLAR | 11.16 | 783.37 | 1151.54 | 39 |
| 976 | QIDYGNADPSTIK | 13.41 | 711.35 | 845.44 | 36 |
| 977 | QIDYGNADPSTIK | 13.42 | 711.35 | 902.46 | 36 |
| 978 | QIDYGNADPSTIK | 13.42 | 711.35 | 1065.52 | 36 |
| 979 | QIDYGNVDPSTIK | 15.08 | 725.36 | 873.47 | 37 |
| 980 | QIDYGNVDPSTIK | 15.07 | 725.36 | 930.49 | 37 |
| 981 | QIDYGNVDPSTIK | 15.07 | 725.36 | 1093.55 | 37 |
| 982 | QIGQAR | 2.3 | 336.69 | 431.24 | 20 |
| 983 | QIGQAR | 2.33 | 336.69 | 498.27 | 20 |
| 984 | QIGQAR | 2.32 | 336.69 | 544.32 | 20 |
| 985 | QIMLIEQTPAFTLR | 24.42 | 830.96 | 933.52 | 42 |
| 986 | QIMLIEQTPAFTLR | 24.42 | 830.96 | 1062.56 | 42 |
| 987 | QIMLIEQTPAFTLR | 24.42 | 830.96 | 1175.64 | 42 |
| 988 | QLGSAIDQFWLR | 22.67 | 717.38 | 864.44 | 37 |
| 989 | QLGSAIDQFWLR | 22.68 | 717.38 | 977.52 | 37 |
| 990 | QLGSAIDQFWLR | 22.67 | 717.38 | 1192.61 | 37 |
| 991 | QLPVK | 9.57 | 292.69 | 343.23 | 18 |
| 992 | QLPVK | 9.58 | 292.69 | 438.27 | 18 |
| 993 | QLPVK | 9.57 | 292.69 | 456.32 | 18 |
| 994 | QLSLDVLDK | 18.63 | 515.79 | 589.32 | 28 |
| 995 | QLSLDVLDK | 18.62 | 515.79 | 789.44 | 28 |
| 996 | QLSLDVLDK | 18.63 | 515.79 | 902.52 | 28 |
| 997 | QLVYAR | 11.04 | 375.22 | 508.29 | 22 |
| 998 | QLVYAR | 11.04 | 375.22 | 575.32 | 22 |
| 999 | QLVYAR | 11.04 | 375.22 | 621.37 | 22 |
| 1000 | QMMLTEASTDYIIR | 19.82 | 836.41 | 867.46 | 42 |
| 1001 | QMMLTEASTDYIIR | 19.82 | 836.41 | 1067.54 | 42 |
| 1002 | QMMLTEASTDYIIR | 19.82 | 836.41 | 1168.58 | 42 |
| 1003 | QMSIVEATPDYVLHGK | 18.77 | 894.45 | 1029.54 | 44 |
| 1004 | QMSIVEATPDYVLHGK | 18.77 | 894.45 | 1100.57 | 44 |
| 1005 | QMSIVEATPDYVLHGK | 18.77 | 894.45 | 1229.62 | 44 |
| 1006 | QTLVFAR | 14.65 | 417.75 | 492.29 | 23 |
| 1007 | QTLVFAR | 14.65 | 417.75 | 605.38 | 23 |
| 1008 | QTLVFAR | 14.65 | 417.75 | 706.42 | 23 |
| 1009 | QVVFAR | 12.06 | 360.21 | 492.29 | 21 |
| 1010 | QVVFAR | 12.04 | 360.21 | 545.31 | 21 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1011 | QVVFAR | 12.06 | 360.21 | 591.36 | 21 |
| 1012 | SADEVLPYGGKPQR | 12.96 | 506.26 | 642.37 | 29 |
| 1013 | SADEVLPYGGKPQR | 12.96 | 506.26 | 805.43 | 29 |
| 1014 | SADEVLPYGGKPQR | 12.96 | 506.26 | 902.48 | 29 |
| 1015 | SC[CAM]ATNDLAR | 9.37 | 504.23 | 689.36 | 27 |
| 1016 | SC[CAM]ATNDLAR | 9.37 | 504.23 | 760.39 | 27 |
| 1017 | SC[CAM]ATNDLAR | 9.37 | 504.23 | 920.43 | 27 |
| 1018 | SC[CAM]ATNNLAR | 8.66 | 503.74 | 688.37 | 27 |
| 1019 | SC[CAM]ATNNLAR | 8.66 | 503.74 | 759.41 | 27 |
| 1020 | SC[CAM]ATNNLAR | 8.67 | 503.74 | 919.44 | 27 |
| 1021 | SDIPGGSK | 7.63 | 380.7 | 558.32 | 22 |
| 1022 | SDIPGGSK | 7.63 | 380.7 | 614.28 | 22 |
| 1023 | SDIPGGSK | 7.63 | 380.7 | 673.35 | 22 |
| 1024 | SDWGK | 5.75 | 296.64 | 390.21 | 18 |
| 1025 | SDWGK | 5.75 | 296.64 | 446.17 | 18 |
| 1026 | SDWGK | 5.75 | 296.64 | 505.24 | 18 |
| 1027 | SEDNFHISSQQHEK | 10.36 | 422.19 | 541.27 | 24 |
| 1028 | SEDNFHISSQQHEK | 10.36 | 422.19 | 730.28 | 24 |
| 1029 | SEDNFHISSQQHEK | 10.36 | 422.19 | 756.36 | 24 |
| 1030 | SEMPASIR | 12.02 | 445.72 | 674.37 | 25 |
| 1031 | SEMPASIR | 12.02 | 445.72 | 716.33 | 25 |
| 1032 | SEMPASIR | 12.02 | 445.72 | 803.41 | 25 |
| 1033 | SEMPASIR | 8.2 | 439.71 | 662.33 | 24 |
| 1034 | SEMPASTR | 8.19 | 439.71 | 704.29 | 24 |
| 1035 | SEMPASTR | 8.19 | 439.71 | 791.37 | 24 |
| 1036 | SFAAHNQDQDLR | 10.35 | 467.89 | 531.29 | 27 |
| 1037 | SFAAHNQDQDLR | 10.35 | 467.89 | 871.37 | 27 |
| 1038 | SFAAHNQDQDLR | 10.35 | 467.89 | 888.42 | 27 |
| 1039 | SFAGHNK | 9.4 | 380.69 | 455.24 | 22 |
| 1040 | SFAGHNK | 9.4 | 380.69 | 526.27 | 22 |
| 1041 | SFAGHNK | 9.38 | 380.69 | 673.34 | 22 |
| 1042 | SFAGHNQDQDLR | 10.18 | 694.32 | 888.42 | 36 |
| 1043 | SFAGHNQDQDLR | 10.18 | 694.32 | 1025.48 | 36 |
| 1044 | SFAGHNQDQDLR | 10.18 | 694.32 | 1082.5 | 36 |
| 1045 | SFAGHNQDQNLR | 9.8 | 462.89 | 530.3 | 27 |
| 1046 | SFAGHNQDQNLR | 9.8 | 462.89 | 773.39 | 27 |
| 1047 | SFAGHNQDQNLR | 9.8 | 462.89 | 887.43 | 27 |
| 1048 | SFLESWAK | 18.27 | 484.25 | 491.26 | 26 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1049 | SFLESWAK | 18.27 | 484.25 | 620.3 | 26 |
| 1050 | SFLESWAK | 18.27 | 484.25 | 733.39 | 26 |
| 1051 | SFTAWEK | 14.44 | 434.71 | 462.23 | 24 |
| 1052 | SFTAWEK | 14.44 | 434.71 | 533.27 | 24 |
| 1053 | SFTAWEK | 14.44 | 434.71 | 634.32 | 24 |
| 1054 | SFTTWEK | 14.1 | 449.72 | 462.23 | 25 |
| 1055 | SFTTWEK | 14.1 | 449.72 | 563.28 | 25 |
| 1056 | SFTTWEK | 14.1 | 449.72 | 664.33 | 25 |
| 1057 | SGSGWLR | 13.25 | 381.7 | 531.3 | 22 |
| 1058 | SGSGWLR | 13.25 | 381.7 | 618.34 | 22 |
| 1059 | SGSGWLR | 13.25 | 381.7 | 675.36 | 22 |
| 1060 | SGWGMAVDPQVGWYVGFVEK | 24.65 | 738.02 | 841.45 | 41 |
| 1061 | SGWGMAVDPQVGWYVGFVEK | 24.65 | 738.02 | 1029.45 | 41 |
| 1062 | SGWGMAVDPQVGWYVGFVEK | 24.68 | 1106.53 | 1128.51 | 54 |
| 1063 | SGWGMDVSPQVGWLTGWVEK | 26.32 | 1110.03 | 1144.51 | 54 |
| 1064 | SGWGMDVSPQVGWLTGWVEK | 26.32 | 1110.03 | 1174.63 | 54 |
| 1065 | SGWGMDVSPQVGWLTGWVEK | 26.32 | 1110.03 | 1201.53 | 54 |
| 1066 | SGWGMDVTPQVGWLTGWVEK | 26.61 | 745.03 | 832.46 | 41 |
| 1067 | SGWGMDVTPQVGWLTGWVEK | 26.61 | 745.03 | 1018.54 | 41 |
| 1068 | SGWGMDVTPQVGWLTGWVEK | 26.61 | 745.03 | 1075.56 | 41 |
| 1069 | SIHPASTFK | 10.74 | 494.27 | 650.35 | 27 |
| 1070 | SIHPASTFK | 10.73 | 494.27 | 787.41 | 27 |
| 1071 | SIHPASTFK | 10.73 | 494.27 | 900.49 | 27 |
| 1072 | SISTK | 10.41 | 268.16 | 335.19 | 17 |
| 1073 | SISTK | 10.42 | 268.16 | 389.2 | 17 |
| 1074 | SISTK | 10.42 | 268.16 | 448.28 | 17 |
| 1075 | SLGLSNNLSR | 14.23 | 530.79 | 690.35 | 28 |
| 1076 | SLGLSNNLSR | 14.23 | 530.79 | 803.44 | 28 |
| 1077 | SLGLSNNLSR | 14.23 | 530.79 | 860.46 | 28 |
| 1078 | SLSMSGK | 9.31 | 355.18 | 509.24 | 21 |
| 1079 | SLSMSGK | 9.32 | 355.18 | 563.25 | 21 |
| 1080 | SLSMSGK | 9.32 | 355.18 | 622.32 | 21 |
| 1081 | SMLFIEEK | 17.82 | 498.76 | 518.28 | 27 |
| 1082 | SMLFIEEK | 17.82 | 498.76 | 665.35 | 27 |
| 1083 | SMLFIEEK | 17.82 | 498.76 | 778.43 | 27 |
| 1084 | SNGLTHSWLGSSLK | 16.78 | 743.89 | 877.48 | 38 |
| 1085 | SNGLTHSWLGSSLK | 16.78 | 743.89 | 1014.54 | 38 |
| 1086 | SNGLTHSWLGSSLK | 16.78 | 743.89 | 1115.58 | 38 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1087 | SPTWELKPEYNPSPR | 16.02 | 600.97 | 733.36 | 34 |
| 1088 | SPTWELKPEYNPSPR | 16.02 | 600.97 | 808.91 | 34 |
| 1089 | SPTWELKPEYNPSPR | 16.02 | 600.97 | 959.46 | 34 |
| 1090 | SQDIVR | 8.4 | 359.2 | 502.3 | 21 |
| 1091 | SQDIVR | 8.38 | 359.2 | 543.28 | 21 |
| 1092 | SQDIVR | 8.4 | 359.2 | 630.36 | 21 |
| 1093 | SQQKPTDPTIWLK | 16.6 | 514.62 | 660.41 | 30 |
| 1094 | SQQKPTDPTIWLK | 16.6 | 514.62 | 757.46 | 30 |
| 1095 | SQQKPTDPTIWLK | 16.6 | 514.62 | 785.38 | 30 |
| 1096 | SQVGWLTGWVEQPDGK | 22.27 | 893.94 | 1015.5 | 44 |
| 1097 | SQVGWLTGWVEQPDGK | 22.28 | 893.94 | 1116.53 | 44 |
| 1098 | SQVGWLTGWVEQPDGK | 22.28 | 893.94 | 1229.62 | 44 |
| 1099 | SSSNSC[CAM]TTNNAAR | 16.84 | 685.29 | 907.41 | 35 |
| 1100 | SSSNSC[CAM]TTNNAAR | 16.85 | 685.29 | 994.44 | 35 |
| 1101 | SSSNSC[CAM]TTNNAAR | 16.84 | 685.29 | 1108.48 | 35 |
| 1102 | SVYGELR | 12.65 | 412.22 | 417.25 | 23 |
| 1103 | SVYGELR | 12.65 | 412.22 | 474.27 | 23 |
| 1104 | SVYGELR | 12.65 | 412.22 | 637.33 | 23 |
| 1105 | SWILR | 16.33 | 337.7 | 401.29 | 20 |
| 1106 | SWILR | 16.32 | 337.7 | 500.29 | 20 |
| 1107 | SWILR | 16.33 | 337.7 | 587.37 | 20 |
| 1108 | SYLEK | 9.09 | 320.17 | 389.24 | 19 |
| 1109 | SYLEK | 9.09 | 320.17 | 493.23 | 19 |
| 1110 | SYLEK | 9.1 | 320.17 | 552.3 | 19 |
| 1111 | TAYIPASTFK | 15.43 | 549.8 | 650.35 | 29 |
| 1112 | TAYIPASTFK | 15.43 | 549.8 | 763.43 | 29 |
| 1113 | TAYIPASTFK | 15.43 | 549.8 | 926.5 | 29 |
| 1114 | TDDLFK | 13.48 | 369.69 | 407.27 | 21 |
| 1115 | TDDLFK | 13.48 | 369.69 | 522.29 | 21 |
| 1116 | TDDLFK | 13.48 | 369.69 | 637.32 | 21 |
| 1117 | TDINEIFK | 17.44 | 490.26 | 650.35 | 27 |
| 1118 | TDINEIFK | 17.44 | 490.26 | 763.43 | 27 |
| 1119 | TDINEIFK | 17.44 | 490.26 | 878.46 | 27 |
| 1120 | TFIHNDPR | 18.92 | 500.25 | 751.38 | 27 |
| 1121 | TFIHNDPR | 18.92 | 500.25 | 825.39 | 27 |
| 1122 | TFIHNDPR | 18.92 | 500.25 | 898.45 | 27 |
| 1123 | TGAGFTANR | 9.64 | 447.72 | 461.25 | 25 |
| 1124 | TGAGFTANR | 9.64 | 447.72 | 665.34 | 25 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1125 | TGAGFTANR | 9.64 | 447.72 | 793.4 | 25 |
| 1126 | TGFNDGQK | 7.5 | 433.7 | 561.26 | 24 |
| 1127 | TGFNDGQK | 7.5 | 433.7 | 708.33 | 24 |
| 1128 | TGFNDGQK | 7.5 | 433.7 | 765.35 | 24 |
| 1129 | TGLADSK | 9.7 | 346.18 | 533.29 | 20 |
| 1130 | TGLADSK | 9.67 | 346.18 | 545.26 | 20 |
| 1131 | TGLADSK | 9.7 | 346.18 | 590.31 | 20 |
| 1132 | TGLDLMQK | 15.32 | 453.24 | 634.32 | 25 |
| 1133 | TGLDLMQK | 15.32 | 453.24 | 747.41 | 25 |
| 1134 | TGLDLMQK | 15.32 | 453.24 | 804.43 | 25 |
| 1135 | TGLELMQK | 15.03 | 460.25 | 648.34 | 25 |
| 1136 | TGLELMQK | 15.03 | 460.25 | 761.42 | 25 |
| 1137 | TGLELMQK | 15.03 | 460.25 | 818.44 | 25 |
| 1138 | TGMGYPK | 10.28 | 377.18 | 464.25 | 22 |
| 1139 | TGMGYPK | 10.28 | 377.18 | 595.29 | 22 |
| 1140 | TGMGYPK | 10.28 | 377.18 | 652.31 | 22 |
| 1141 | TGNGR | 0.8 | 252.63 | 330.14 | 16 |
| 1142 | TGNGR | 0.8 | 252.63 | 346.18 | 16 |
| 1143 | TGNGR | 0.81 | 252.63 | 403.2 | 16 |
| 1144 | TGTGSFIDAR | 13.35 | 512.76 | 708.37 | 28 |
| 1145 | TGTGSFIDAR | 13.35 | 512.76 | 765.39 | 28 |
| 1146 | TGTGSFIDAR | 13.35 | 512.76 | 866.44 | 28 |
| 1147 | TGTGSLSDAK | 8.32 | 468.74 | 620.32 | 26 |
| 1148 | TGTGSLSDAK | 8.32 | 468.74 | 677.35 | 26 |
| 1149 | TGTGSLSDAK | 8.32 | 468.74 | 778.39 | 26 |
| 1150 | TGVATEYQPEIGWWAGWVER | 25.49 | 779.04 | 903.45 | 43 |
| 1151 | TGVATEYQPEIGWWAGWVER | 25.5 | 779.04 | 1146.55 | 43 |
| 1152 | TGVATEYQPEIGWWAGWVER | 25.52 | 1168.06 | 1189.57 | 56 |
| 1153 | TGVSYPLLADGTR | 17.4 | 675.36 | 842.47 | 35 |
| 1154 | TGVSYPLLADGTR | 17.41 | 675.36 | 1005.54 | 35 |
| 1155 | TGVSYPLLADGTR | 17.4 | 675.36 | 1092.57 | 35 |
| 1156 | TGWAMDIK | 16.71 | 461.23 | 577.3 | 25 |
| 1157 | TGWAMDIK | 16.71 | 461.23 | 763.38 | 25 |
| 1158 | TGWAMDIK | 16.72 | 461.23 | 820.4 | 25 |
| 1159 | TGWATR | 9.71 | 346.18 | 517.24 | 20 |
| 1160 | TGWATR | 9.69 | 346.18 | 533.28 | 20 |
| 1161 | TGWATR | 9.69 | 346.18 | 590.3 | 20 |
| 1162 | TGWC[CAM]FDC[CAM]TPELGWWVGWVK | 28.39 | 795.36 | 960.51 | 44 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1163 | TGWC[CAM]FDC[CAM]TPELGWWVGWVK | 28.39 | 795.36 | 1017.53 | 44 |
| 1164 | TGWC[CAM]FDC[CAM]TPELGWWVGWVK | 28.38 | 795.36 | 1028.36 | 44 |
| 1165 | TGWEGR | 9.1 | 353.17 | 531.22 | 21 |
| 1166 | TGWEGR | 9.09 | 353.17 | 547.26 | 21 |
| 1167 | TGWEGR | 9.09 | 353.17 | 604.28 | 21 |
| 1168 | TGWFVDK | 16.08 | 426.72 | 694.36 | 24 |
| 1169 | TGWFVDK | 16.1 | 426.72 | 706.32 | 24 |
| 1170 | TGWFVDK | 16.08 | 426.72 | 751.38 | 24 |
| 1171 | TGYDTK | 2.09 | 342.66 | 526.25 | 20 |
| 1172 | TGYDTK | 2.09 | 342.66 | 538.21 | 20 |
| 1173 | TGYDTK | 2.08 | 342.66 | 583.27 | 20 |
| 1174 | TGYGVR | 8.09 | 326.67 | 478.23 | 19 |
| 1175 | TGYGVR | 8.1 | 326.67 | 494.27 | 19 |
| 1176 | TGYGVR | 8.1 | 326.67 | 551.29 | 19 |
| 1177 | TGYSAR | 2.24 | 327.66 | 480.21 | 19 |
| 1178 | TGYSAR | 2.24 | 327.66 | 496.25 | 19 |
| 1179 | TGYSAR | 2.24 | 327.66 | 553.27 | 19 |
| 1180 | TGYSTR | 2.08 | 342.67 | 510.22 | 20 |
| 1181 | TGYSTR | 2.08 | 342.67 | 526.26 | 20 |
| 1182 | TGYSTR | 2.08 | 342.67 | 583.28 | 20 |
| 1183 | THESSNWGK | 5.36 | 523.24 | 678.32 | 28 |
| 1184 | THESSNWGK | 5.37 | 523.24 | 807.36 | 28 |
| 1185 | THESSNWGK | 5.37 | 523.24 | 944.42 | 28 |
| 1186 | TIC[CAM]TAIADAGTGK | 14.35 | 639.82 | 732.39 | 33 |
| 1187 | TIC[CAM]TAIADAGTGK | 14.35 | 639.82 | 904.47 | 33 |
| 1188 | TIC[CAM]TAIADAGTGK | 14.35 | 639.82 | 1064.5 | 33 |
| 1189 | TIGGAPDAYWVDDSLQISAR | 21.22 | 712.35 | 1004.5 | 40 |
| 1190 | TIGGAPDAYWVDDSLQISAR | 21.22 | 712.35 | 1103.57 | 40 |
| 1191 | TIGGAPDAYWVDDSLQISAR | 21.21 | 1068.02 | 1103.57 | 52 |
| 1192 | TLPFSASSYETLR | 18.73 | 736.37 | 855.42 | 37 |
| 1193 | TLPFSASSYETLR | 18.73 | 736.37 | 1013.49 | 37 |
| 1194 | TLPFSASSYETLR | 18.73 | 736.37 | 1160.56 | 37 |
| 1195 | TLPFSPK | 15 | 395.23 | 478.27 | 22 |
| 1196 | TLPFSPK | 15 | 395.23 | 575.32 | 22 |
| 1197 | TLPFSPK | 15 | 395.23 | 688.4 | 22 |
| 1198 | TLPFSQEVQDEVQSILFIEEK | 28.55 | 827.09 | 891.52 | 45 |
| 1199 | TLPFSQEVQDEVQSILFIEEK | 28.56 | 827.09 | 978.55 | 45 |
| 1200 | TLPFSQEVQDEVQSILFIEEK | 28.56 | 827.09 | 1106.61 | 45 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1201 | TLPFSQEVQDEVQSMLFIEEK | 27.7 | 833.08 | 996.51 | 46 |
| 1202 | TLPFSQEVQDEVQSMLFIEEK | 27.69 | 833.08 | 1124.57 | 46 |
| 1203 | TLPFSQEVQDEVQSMLFIEEK | 27.7 | 833.08 | 1223.63 | 46 |
| 1204 | TLQNGWFEGFIISK | 24.12 | 820.43 | 940.51 | 41 |
| 1205 | TLQNGWFEGFIISK | 24.11 | 820.43 | 1126.59 | 41 |
| 1206 | TLQNGWFEGFIISK | 24.11 | 820.43 | 1183.61 | 41 |
| 1207 | TMQEYLNK | 12.6 | 513.75 | 666.35 | 28 |
| 1208 | TMQEYLNK | 12.6 | 513.75 | 794.4 | 28 |
| 1209 | TMQEYLNK | 12.6 | 513.75 | 925.44 | 28 |
| 1210 | TQTYQAYDAAR | 11.2 | 644.3 | 666.32 | 33 |
| 1211 | TQTYQAYDAAR | 11.2 | 644.3 | 957.44 | 33 |
| 1212 | TQTYQAYDAAR | 11.2 | 644.3 | 1058.49 | 33 |
| 1213 | TTDPTIWEK | 14.39 | 545.77 | 676.37 | 29 |
| 1214 | TTDPTIWEK | 14.39 | 545.77 | 773.42 | 29 |
| 1215 | TTDPTIWEK | 14.39 | 545.77 | 888.45 | 29 |
| 1216 | TTTTEVFK | 12.06 | 463.75 | 522.29 | 25 |
| 1217 | TTTTEVFK | 12.06 | 463.75 | 623.34 | 25 |
| 1218 | TTTTEVFK | 12.06 | 463.75 | 724.39 | 25 |
| 1219 | TWASNDFSR | 13.73 | 542.25 | 638.29 | 29 |
| 1220 | TWASNDFSR | 13.73 | 542.25 | 725.32 | 29 |
| 1221 | TWASNDFSR | 13.73 | 542.25 | 796.36 | 29 |
| 1222 | TWDMVQR | 14.28 | 468.22 | 648.31 | 26 |
| 1223 | TWDMVQR | 14.28 | 468.22 | 761.33 | 26 |
| 1224 | TWDMVQR | 14.28 | 468.22 | 834.39 | 26 |
| 1225 | TYWDPAR | 12.15 | 460.75 | 557.3 | 25 |
| 1226 | TYWDPAR | 12.14 | 460.75 | 656.37 | 25 |
| 1227 | TYWDPAR | 12.15 | 460.75 | 819.44 | 25 |
| 1228 | VAFSLNIEMK | 20.65 | 576.31 | 747.41 | 30 |
| 1229 | VAFSLNIEMK | 20.65 | 576.31 | 834.44 | 30 |
| 1230 | VAFSLNIEMK | 20.65 | 576.31 | 981.51 | 30 |
| 1231 | VANSLIGLSTGAVR | 17.97 | 679.39 | 760.43 | 35 |
| 1232 | VANSLIGLSTGAVR | 17.97 | 679.39 | 873.52 | 35 |
| 1233 | VANSLIGLSTGAVR | 17.97 | 679.39 | 986.6 | 35 |
| 1234 | VELGK | 7.74 | 273.17 | 342.2 | 17 |
| 1235 | VELGK | 7.75 | 273.17 | 399.22 | 17 |
| 1236 | VELGK | 7.74 | 273.17 | 446.26 | 17 |
| 1237 | VFLDSWAK | 18.2 | 483.26 | 606.29 | 26 |
| 1238 | VFLDSWAK | 18.2 | 483.26 | 719.37 | 26 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1239 | VFLDSWAK | 18.2 | 483.26 | 866.44 | 26 |
| 1240 | VFLESWAK | 18.11 | 490.27 | 620.3 | 27 |
| 1241 | VFLESWAK | 18.11 | 490.27 | 733.39 | 27 |
| 1242 | VFLESWAK | 18.11 | 490.27 | 880.46 | 27 |
| 1243 | VFLSSWAQDMNLSSAIK | 23.66 | 948.98 | 978.49 | 47 |
| 1244 | VFLSSWAQDMNLSSAIK | 23.66 | 948.98 | 1106.55 | 47 |
| 1245 | VFLSSWAQDMNLSSAIK | 23.66 | 948.98 | 1177.59 | 47 |
| 1246 | VGFER | 10.32 | 304.16 | 433.21 | 18 |
| 1247 | VGFER | 10.32 | 304.16 | 451.23 | 18 |
| 1248 | VGFER | 10.32 | 304.16 | 508.25 | 18 |
| 1249 | VILVFDQVR | 19.69 | 544.83 | 664.34 | 29 |
| 1250 | VILVFDQVR | 19.69 | 544.83 | 763.41 | 29 |
| 1251 | VILVFDQVR | 19.69 | 544.83 | 876.49 | 29 |
| 1252 | VMAAMVR | 12.3 | 389.21 | 476.26 | 22 |
| 1253 | VMAAMVR | 12.3 | 389.21 | 547.3 | 22 |
| 1254 | VMAAMVR | 12.3 | 389.21 | 678.34 | 22 |
| 1255 | VPLAVMGYDAGILVDAHNPR | 21.61 | 703.37 | 709.34 | 39 |
| 1256 | VPLAVMGYDAGILVDAHNPR | 21.61 | 703.37 | 808.41 | 39 |
| 1257 | VPLAVMGYDAGILVDAHNPR | 21.61 | 703.37 | 921.49 | 39 |
| 1258 | VQDEVQSMLFIEEK | 20.48 | 847.92 | 996.51 | 42 |
| 1259 | VQDEVQSMLFIEEK | 20.48 | 847.92 | 1124.57 | 42 |
| 1260 | VQDEVQSMLFIEEK | 20.47 | 847.92 | 1223.63 | 42 |
| 1261 | VQDGVQSMLFIEEK | 20.26 | 811.91 | 996.51 | 41 |
| 1262 | VQDGVQSMLFIEEK | 20.27 | 811.91 | 1124.57 | 41 |
| 1263 | VQDGVQSMLFIEEK | 20.25 | 811.91 | 1223.63 | 41 |
| 1264 | VSC[CAM]LPC[CAM]YQVVSHK | 14.32 | 526.26 | 569.34 | 30 |
| 1265 | VSC[CAM]LPC[CAM]YQVVSHK | 14.32 | 526.26 | 860.46 | 30 |
| 1266 | VSC[CAM]LPC[CAM]YQVVSHK | 14.31 | 526.26 | 1020.49 | 30 |
| 1267 | VSC[CAM]VWC[CAM]YQALAR | 18.41 | 756.86 | 881.43 | 38 |
| 1268 | VSC[CAM]VWC[CAM]YQALAR | 18.41 | 756.86 | 1067.51 | 38 |
| 1269 | VSC[CAM]VWC[CAM]YQALAR | 18.41 | 756.86 | 1166.58 | 38 |
| 1270 | VSDVC[CAM]SEVTAEGWQEVR | 17.33 | 650.97 | 774.39 | 37 |
| 1271 | VSDVC[CAM]SEVTAEGWQEVR | 17.34 | 975.95 | 1075.52 | 48 |
| 1272 | VSDVC[CAM]SEVTAEGWQEVR | 17.34 | 975.95 | 1174.59 | 48 |
| 1273 | VSEVEGWQIHGK | 13.92 | 456.9 | 582.34 | 27 |
| 1274 | VSEVEGWQIHGK | 13.92 | 456.9 | 768.42 | 27 |
| 1275 | VSEVEGWQIHGK | 13.92 | 456.9 | 825.44 | 27 |
| 1276 | VSFSLNIEMK | 20.65 | 584.31 | 834.44 | 31 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1277 | VSFSLNIEMK | 20.64 | 584.31 | 981.51 | 31 |
| 1278 | VSFSLNIEMK | 20.65 | 584.31 | 1068.54 | 31 |
| 1279 | VSPC[CAM]SSFK | 11.04 | 456.22 | 468.25 | 25 |
| 1280 | VSPC[CAM]SSFK | 11.04 | 456.22 | 628.28 | 25 |
| 1281 | VSPC[CAM]SSFK | 11.04 | 456.22 | 725.33 | 25 |
| 1282 | VSQVPAYK | 10.68 | 446.25 | 478.27 | 25 |
| 1283 | VSQVPAYK | 10.68 | 446.25 | 577.33 | 25 |
| 1284 | VSQVPAYK | 10.68 | 446.25 | 705.39 | 25 |
| 1285 | WFAR | 11.17 | 296.18 | 393.22 | 18 |
| 1286 | WFAR | 11.17 | 296.18 | 417.25 | 18 |
| 1287 | WFAR | 11.17 | 296.18 | 492.29 | 18 |
| 1288 | WDGAK | 4.9 | 288.64 | 302.11 | 18 |
| 1289 | WDGAK | 4.9 | 288.64 | 390.2 | 18 |
| 1290 | WDGAK | 4.9 | 288.64 | 430.17 | 18 |
| 1291 | WDGHIYDFPDWNR | 20.52 | 574.25 | 590.27 | 33 |
| 1292 | WDGHIYDFPDWNR | 20.52 | 574.25 | 687.32 | 33 |
| 1293 | WDGHIYDFPDWNR | 20.52 | 574.25 | 887.37 | 33 |
| 1294 | WDGIK | 12.03 | 309.67 | 359.13 | 19 |
| 1295 | WDGIK | 12.03 | 309.67 | 432.25 | 19 |
| 1296 | WDGIK | 12.03 | 309.67 | 472.22 | 19 |
| 1297 | WDGKPR | 6.36 | 379.7 | 457.29 | 22 |
| 1298 | WDGKPR | 6.35 | 379.7 | 572.32 | 22 |
| 1299 | WDGKPR | 6.36 | 379.7 | 584.28 | 22 |
| 1300 | WDGQTR | 7.41 | 381.68 | 461.25 | 22 |
| 1301 | WDGQTR | 7.41 | 381.68 | 576.27 | 22 |
| 1302 | WDGQTR | 7.41 | 381.68 | 588.24 | 22 |
| 1303 | WDGVK | 10.1 | 302.66 | 359.13 | 18 |
| 1304 | WDGVK | 10.1 | 302.66 | 418.23 | 18 |
| 1305 | WDGVK | 10.1 | 302.66 | 458.2 | 18 |
| 1306 | WDGVNR | 10.39 | 373.68 | 445.25 | 21 |
| 1307 | WDGVNR | 10.39 | 373.68 | 560.28 | 21 |
| 1308 | WDGVNR | 10.42 | 373.68 | 572.25 | 21 |
| 1309 | YAQAK | 12.58 | 290.66 | 363.17 | 18 |
| 1310 | YAQAK | 12.58 | 290.66 | 417.25 | 18 |
| 1311 | YAQAK | 12.58 | 290.66 | 434.2 | 18 |
| 1312 | YFSDFNAK | 14.21 | 496.23 | 681.32 | 27 |
| 1313 | YFSDFNAK | 14.21 | 496.23 | 828.39 | 27 |
| 1314 | YFSDFNAK | 14.21 | 496.23 | 828.39 | 27 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1315 | YGTHLDR | 8.51 | 431.21 | 641.34 | 24 |
| 1316 | YGTHLDR | 8.52 | 431.21 | 687.31 | 24 |
| 1317 | YGTHLDR | 8.51 | 431.21 | 698.36 | 24 |
| 1318 | YLDELVK | 15.52 | 440.24 | 488.31 | 24 |
| 1319 | YLDELVK | 15.53 | 440.24 | 603.33 | 24 |
| 1320 | YLDELVK | 15.52 | 440.24 | 716.42 | 24 |
| 1321 | YLMITEAGR | 15.86 | 527.27 | 533.27 | 28 |
| 1322 | YLMITEAGR | 15.86 | 527.27 | 646.35 | 28 |
| 1323 | YLMITEAGR | 15.86 | 527.27 | 777.39 | 28 |
| 1324 | YLNLFSYGNANIGGGIDK | 22.16 | 639.32 | 773.42 | 36 |
| 1325 | YLNLFSYGNANIGGGIDK | 22.16 | 958.48 | 1015.52 | 47 |
| 1326 | YLNLFSYGNANIGGGIDK | 22.16 | 958.48 | 1178.58 | 47 |
| 1327 | YPVVWYSQQVAHHLGAQR | 18.11 | 535.53 | 544.32 | 30 |
| 1328 | YPVVWYSQQVAHHLGAQR | 18.11 | 535.53 | 681.38 | 30 |
| 1329 | YPVVWYSQQVAHHLGAQR | 18.11 | 535.53 | 889.48 | 30 |
| 1330 | YSNVLAFK | 16.44 | 471.26 | 478.3 | 26 |
| 1331 | YSNVLAFK | 16.44 | 471.26 | 691.41 | 26 |
| 1332 | YSNVLAFK | 16.44 | 471.26 | 778.45 | 26 |
| 1333 | YSPASTFK | 12.22 | 450.73 | 553.3 | 25 |
| 1334 | YSPASTFK | 12.22 | 450.73 | 650.35 | 25 |
| 1335 | YSPASTFK | 12.22 | 450.73 | 737.38 | 25 |
| 1336 | YSVVPVYQQLAR | 18.42 | 711.89 | 778.42 | 36 |
| 1337 | YSVVPVYQQLAR | 18.42 | 711.89 | 974.54 | 36 |
| 1338 | YSVVPVYQQLAR | 18.43 | 711.89 | 1073.61 | 36 |
| 1339 | YSVVWYSQLTAK | 19.75 | 722.88 | 810.44 | 37 |
| 1340 | YSVVWYSQLTAK | 19.76 | 722.88 | 996.51 | 37 |
| 1341 | YSVVWYSQLTAK | 19.76 | 722.88 | 1095.58 | 37 |
| 1342 | YSVVWYSQQVAHHLGAQR | 18.61 | 533.02 | 544.32 | 30 |
| 1343 | YSVVWYSQQVAHHLGAQR | 18.61 | 533.02 | 681.38 | 30 |
| 1344 | YSVVWYSQQVAHHLGAQR | 18.61 | 533.02 | 889.48 | 30 |
| 1345 | YTPASTFK | 11.95 | 305.49 | 553.3 | 19 |
| 1346 | YTPASTFK | 11.98 | 457.73 | 553.3 | 25 |
| 1347 | YTPASTFK | 11.98 | 457.73 | 650.35 | 25 |
| 1348 | YTSAFGYGNADVSGEPGK | 15.03 | 607.28 | 673.35 | 34 |
| 1349 | YTSAFGYGNADVSGEPGK | 15.02 | 607.28 | 788.38 | 34 |
| 1350 | YTSAFGYGNADVSGEPGK | 15.02 | 910.41 | 1030.48 | 45 |
| 1351 | YVFVSALTGNLGSNLTSSIK | 23.66 | 691.04 | 906.49 | 39 |
| 1352 | YVFVSALTGNLGSNLTSSIK | 23.66 | 1036.06 | 1165.63 | 51 |

TABLE 25-continued

| Transition number | Peptide | Retention time (minutes) | (m/z) filtered in Q1 | (m/z) filtered in Q3 | Collision energy (eV) |
|---|---|---|---|---|---|
| 1353 | YVFVSALTGNLGSNLTSSIK | 23.67 | 1036.06 | 1190.64 | 51 |
| 1354 | YVFVSALTGSLGSNLTSSIK | 24.04 | 682.04 | 906.49 | 38 |
| 1355 | YVFVSALTGSLGSNLTSSIK | 24.04 | 1022.55 | 1106.61 | 50 |
| 1356 | YVFVSALTGSLGSNLTSSIK | 24.04 | 1022.55 | 1163.63 | 50 |

The areas obtained for each of the transitions and for each of the microorganisms studied were measured. When the areas of the three transitions of the same peptide are greater than or equal to 2500, the detection of the peptide is considered to be positive and is labelled "1". When at least one transition comprises an area less than 2500, the corresponding peptide is considered non-detected and is labelled "0".

EXAMPLE 17: IDENTIFICATION OF A RESISTANCE TO IMP BETA-LACTAMS

Samples Sam145 to Sam154 are identified according to one of the methods described in examples 1, 3 or 4. The identification of the species is set out in TABLE 26.

TABLE 26

| Names | Species |
|---|---|
| Sam145 | A. baumannii |
| Sam146 | A. baumannii |
| Sam147 | E. coli |
| Sam148 | K. pneumoniae |
| Sam149 | K. pneumoniae |
| Sam150 | P. aeruginosa |
| Sam151 | P. aeruginosa |
| Sam152 | P. aeruginosa |
| Sam153 | P. aeruginosa |
| Sam154 | P. putida |

Samples Sam145 to Sam154 correspond to a species able to comprise an IMP resistance mechanism. The following method is then performed to detect such a mechanism.

Each sample is treated according to Example 5, then analysed according to Example 6 unless otherwise stated in the rest of the example, by detecting the peptides from TABLE 27 instead of the peptides from TABLE 3.

TABLE 27

| Transition number | Peptide | Retention time (minutes) | (m/z) filtered in Q1 | (m/z) filtered in Q3 | Collision energy (eV) | Positivity threshold |
|---|---|---|---|---|---|---|
| 1 | DTENLVNWFVER | 24.3 | 761.37 | 550.3 | 39.1 | 2000 |
| 2 | DTENLVNWFVER | 24.3 | 761.37 | 850.42 | 39.1 | 2000 |
| 3 | DTENLVNWFVER | 24.3 | 761.37 | 949.49 | 39.1 | 2000 |
| 4 | GDASLMK | 10.6 | 361.18 | 391.24 | 16.3 | 2000 |
| 5 | GDASLMK | 10.6 | 361.18 | 478.27 | 16.3 | 2000 |
| 6 | GDASLMK | 10.6 | 361.18 | 549.31 | 16.3 | 2000 |
| 7 | GFNESK | 2 | 341.16 | 312.65 | 15.2 | 2000 |
| 8 | GFNESK | 2 | 341.16 | 363.19 | 15.2 | 2000 |
| 9 | GFNESK | 2 | 341.16 | 477.23 | 15.2 | 2000 |
| 10 | GLNESK | 1.1 | 324.17 | 363.19 | 14.2 | 2000 |
| 11 | GLNESK | 1.1 | 324.17 | 477.23 | 14.2 | 2000 |
| 12 | GLNESK | 1.1 | 324.17 | 590.31 | 14.2 | 2000 |
| 13 | GLNESR | 2.2 | 338.18 | 309.66 | 15 | 2000 |
| 14 | GLNESR | 2.2 | 338.18 | 391.19 | 15 | 2000 |
| 15 | GLNESR | 2.1 | 338.18 | 505.24 | 15 | 2000 |
| 16 | GVYVHTSFEEVK | 15.1 | 465.57 | 488.74 | 21.5 | 2000 |

TABLE 27-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 17 | GVYVHTSFEEVK | 15.1 | 465.57 | 538.28 | 21.5 | 2000 |
| 18 | GVYVHTSFEEVK | 15.1 | 465.57 | 619.81 | 21.5 | 2000 |
| 19 | GWGVVTK | 14.3 | 373.71 | 345.2 | 17 | 2000 |
| 20 | GWGVVTK | 14.3 | 373.71 | 347.23 | 17 | 2000 |
| 21 | GWGVVTK | 14.3 | 373.71 | 503.32 | 17 | 2000 |
| 22 | GWSVVTK | 14.2 | 388.72 | 347.23 | 17.9 | 2000 |
| 23 | GWSVVTK | 14.2 | 388.72 | 446.3 | 17.9 | 2000 |
| 24 | GWSVVTK | 14.2 | 388.72 | 533.33 | 17.9 | 2000 |
| 25 | HGLVVLVK | 15.4 | 432.79 | 557.4 | 20.4 | 2000 |
| 26 | HGLVVLVK | 15.5 | 432.79 | 670.49 | 20.4 | 2000 |
| 27 | HGLVVLVK | 15.4 | 432.79 | 727.51 | 20.4 | 2000 |
| 28 | HSFNGVSYSLIK | 17 | 451.24 | 460.31 | 21.1 | 2000 |
| 29 | HSFNGVSYSLIK | 17 | 451.24 | 623.38 | 21.1 | 2000 |
| 30 | HSFNGVSYSLIK | 17 | 451.24 | 710.41 | 21.1 | 2000 |
| 31 | LEEGVYVHTSFEEVK | 16.9 | 589.29 | 697.85 | 25.4 | 2000 |
| 32 | LEEGVYVHTSFEEVK | 16.9 | 589.29 | 762.37 | 25.4 | 2000 |
| 33 | LEEGVYVHTSFEEVK | 16.9 | 589.29 | 826.89 | 25.4 | 2000 |
| 34 | LFVLCVCFLCSITAAGAR | 19.5 | 686.68 | 659.38 | 28.4 | 2000 |
| 35 | LFVLCVCFLCSITAAGAR | 19.6 | 686.68 | 906.45 | 28.4 | 2000 |
| 36 | LFVLCVCFLCSITAAGAR | 19.5 | 1029.52 | 374.22 | 54.4 | 2000 |
| 37 | LFVLCVCFLCSITAAGAR | 19.5 | 1029.52 | 659.38 | 54.4 | 2000 |
| 38 | LTLEQAVK | 15.2 | 451.27 | 574.32 | 21.5 | 2000 |
| 39 | LTLEQAVK | 15.2 | 451.27 | 687.4 | 21.5 | 2000 |
| 40 | LTLEQAVK | 15.2 | 451.27 | 788.45 | 21.5 | 2000 |
| 41 | LTWEQAVK | 16.3 | 487.77 | 574.32 | 23.5 | 2000 |
| 42 | LTWEQAVK | 16.3 | 487.77 | 760.4 | 23.5 | 2000 |
| 43 | LTWEQAVK | 16.3 | 487.77 | 861.45 | 23.5 | 2000 |
| 44 | LTWEQTVK | 15.4 | 502.77 | 395.71 | 24.4 | 2000 |
| 45 | LTWEQTVK | 15.4 | 502.77 | 604.33 | 24.4 | 2000 |
| 46 | LTWEQTVK | 15.4 | 502.77 | 790.41 | 24.4 | 2000 |
| 47 | LVAWFVGR | 21.3 | 474.28 | 478.28 | 22.8 | 2000 |
| 48 | LVAWFVGR | 21.3 | 474.28 | 664.36 | 22.8 | 2000 |
| 49 | LVAWFVGR | 21.3 | 474.28 | 735.39 | 22.8 | 2000 |
| 50 | LVNWFIEHGYR | 20.1 | 478.58 | 611.29 | 21.9 | 2000 |
| 51 | LVNWFIEHGYR | 20.1 | 478.58 | 660.83 | 21.9 | 2000 |
| 52 | LVNWFIEHGYR | 20.1 | 478.58 | 661.31 | 21.9 | 2000 |
| 53 | LVNWFVER | 20.9 | 531.79 | 550.3 | 26 | 2000 |
| 54 | LVNWFVER | 20.9 | 531.79 | 736.38 | 26 | 2000 |

TABLE 27-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 55 | LVNWFVER | 20.9 | 531.79 | 850.42 | 26 | 2000 |
| 56 | LVTWFVER | 20.6 | 525.29 | 550.3 | 25.7 | 2000 |
| 57 | LVTWFVER | 20.6 | 525.29 | 736.38 | 25.7 | 2000 |
| 58 | LVTWFVER | 20.6 | 525.29 | 837.43 | 25.7 | 2000 |
| 59 | LVVPGHSEVGDASLLK | 17.6 | 540.97 | 655.34 | 23.9 | 2000 |
| 60 | LVVPGHSEVGDASLLK | 17.6 | 540.97 | 704.88 | 23.9 | 2000 |
| 61 | LVVPGHSEVGDASLLK | 17.6 | 810.95 | 655.34 | 42 | 2000 |
| 62 | LVVPSHSDIGDASLLK | 18 | 550.97 | 670.35 | 24.2 | 2000 |
| 63 | LVVPSHSDIGDASLLK | 18 | 550.97 | 719.88 | 24.2 | 2000 |
| 64 | LVVPSHSDIGDASLLK | 18 | 825.96 | 670.35 | 42.8 | 2000 |
| 65 | LVVPSHSDIGDSSLLK | 17.7 | 556.31 | 678.34 | 24.3 | 2000 |
| 66 | LVVPSHSDIGDSSLLK | 17.7 | 556.31 | 719.39 | 24.3 | 2000 |
| 67 | LVVPSHSDIGDSSLLK | 17.7 | 556.31 | 727.88 | 24.3 | 2000 |
| 68 | LVVPSHSDVGDASLLK | 17.5 | 546.3 | 663.34 | 24 | 2000 |
| 69 | LVVPSHSDVGDASLLK | 17.5 | 546.3 | 712.87 | 24 | 2000 |
| 70 | LVVPSHSDVGDASLLK | 17.5 | 818.95 | 663.34 | 42.4 | 2000 |
| 71 | LVVPSHSEAGDASLLK | 16.1 | 541.63 | 656.33 | 23.9 | 2000 |
| 72 | LVVPSHSEAGDASLLK | 16.1 | 541.63 | 705.87 | 23.9 | 2000 |
| 73 | LVVPSHSEAGDASLLK | 16.1 | 541.63 | 755.4 | 23.9 | 2000 |
| 74 | LVVPSHSEVGDASLLK | 17.5 | 550.97 | 670.35 | 24.2 | 2000 |
| 75 | LVVPSHSEVGDASLLK | 17.5 | 550.97 | 719.88 | 24.2 | 2000 |
| 76 | LVVPSHSEVGDASLLK | 17.5 | 825.96 | 670.35 | 42.8 | 2000 |
| 77 | LVVSGHSEIGNASLLK | 16.8 | 541.97 | 656.85 | 23.9 | 2000 |
| 78 | LVVSGHSEIGNASLLK | 16.8 | 541.97 | 706.38 | 23.9 | 2000 |
| 79 | LVVSGHSEIGNASLLK | 16.8 | 541.97 | 755.92 | 23.9 | 2000 |
| 80 | LVVSSHSDIGDVSLLK | 18.9 | 556.98 | 679.35 | 24.3 | 2000 |
| 81 | LVVSSHSDIGDVSLLK | 18.9 | 556.98 | 728.89 | 24.3 | 2000 |
| 82 | LVVSSHSDIGDVSLLK | 18.9 | 556.98 | 778.42 | 24.3 | 2000 |
| 83 | LVVSSHSEIGDASLLK | 17.6 | 552.31 | 672.34 | 24.2 | 2000 |
| 84 | LVVSSHSEIGDASLLK | 17.6 | 552.31 | 721.88 | 24.2 | 2000 |
| 85 | LVVSSHSEIGDASLLK | 17.6 | 552.31 | 771.41 | 24.2 | 2000 |
| 86 | LVVSSHSEIGNASLLQR | 16.8 | 604 | 416.26 | 25.8 | 2000 |
| 87 | LVVSSHSEIGNASLLQR | 16.8 | 604 | 616.38 | 25.8 | 2000 |
| 88 | LVVSSHSEIGNASLLQR | 16.8 | 604 | 799.42 | 25.8 | 2000 |
| 89 | LVVSSHSEK | 8.1 | 329.18 | 387.19 | 17.3 | 2000 |
| 90 | LVVSSHSEK | 8.1 | 329.18 | 587.28 | 17.3 | 2000 |
| 91 | LVVSSHSEK | 8.1 | 493.27 | 773.38 | 23.9 | 2000 |
| 92 | LVVSSHSETGNASLLK | 14.7 | 547.97 | 665.83 | 24.1 | 2000 |

TABLE 27-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 93 | LVVSSHSETGNASLLK | 14.7 | 547.97 | 715.37 | 24.1 | 2000 |
| 94 | LVVSSHSETGNASLLK | 14.7 | 547.97 | 764.9 | 24.1 | 2000 |
| 95 | NDAYLIDTPITAK | 18.8 | 717.88 | 745.41 | 36.7 | 2000 |
| 96 | NDAYLIDTPITAK | 18.8 | 717.88 | 858.49 | 36.7 | 2000 |
| 97 | NDAYLIDTPITAK | 18.8 | 717.88 | 971.58 | 36.7 | 2000 |
| 98 | NSFGGVNYWLVK | 21.4 | 692.36 | 822.45 | 35.2 | 2000 |
| 99 | NSFGGVNYWLVK | 21.4 | 692.36 | 1035.56 | 35.2 | 2000 |
| 100 | NSFGGVNYWLVK | 21.4 | 692.36 | 1182.63 | 35.2 | 2000 |
| 101 | NSFSGASYWLVK | 20.8 | 679.84 | 795.44 | 34.5 | 2000 |
| 102 | NSFSGASYWLVK | 20.8 | 679.84 | 923.5 | 34.5 | 2000 |
| 103 | NSFSGASYWLVK | 20.8 | 679.84 | 1010.53 | 34.5 | 2000 |
| 104 | NSFSGGSYWLVNNK | 18.8 | 786.88 | 375.2 | 40.6 | 2000 |
| 105 | NSFSGGSYWLVNNK | 18.8 | 786.88 | 474.27 | 40.6 | 2000 |
| 106 | NSFSGGSYWLVNNK | 18.8 | 786.88 | 1224.6 | 40.6 | 2000 |
| 107 | NSFSGVSYWLLK | 23.6 | 700.86 | 809.46 | 35.7 | 2000 |
| 108 | NSFSGVSYWLLK | 23.6 | 700.86 | 1052.58 | 35.7 | 2000 |
| 109 | NSFSGVSYWLLK | 23.6 | 700.86 | 1199.65 | 35.7 | 2000 |
| 110 | NSFSGVSYWLVK | 22.3 | 693.86 | 795.44 | 35.3 | 2000 |
| 111 | NSFSGVSYWLVK | 22.3 | 693.86 | 951.53 | 35.3 | 2000 |
| 112 | NSFSGVSYWLVK | 22.3 | 693.86 | 1038.56 | 35.3 | 2000 |
| 113 | SIPTYASELTNELLK | 23.8 | 560.3 | 717.41 | 24.5 | 2000 |
| 114 | SIPTYASELTNELLK | 23.8 | 560.3 | 739.89 | 24.5 | 2000 |
| 115 | SIPTYASELTNELLK | 23.8 | 839.95 | 739.89 | 43.6 | 2000 |
| 116 | TLEQAVK | 10.5 | 394.73 | 445.28 | 18.2 | 2000 |
| 117 | TLEQAVK | 10.5 | 394.73 | 574.32 | 18.2 | 2000 |
| 118 | TLEQAVK | 10.5 | 394.73 | 687.4 | 18.2 | 2000 |
| 119 | TWEQALK | 15.1 | 438.24 | 459.29 | 20.7 | 2000 |
| 120 | TWEQALK | 15.1 | 438.24 | 588.34 | 20.7 | 2000 |
| 121 | TWEQALK | 15.1 | 438.24 | 774.41 | 20.7 | 2000 |
| 122 | TWEQAVK | 12.8 | 431.23 | 445.28 | 20.3 | 2000 |
| 123 | TWEQAVK | 12.8 | 431.23 | 574.32 | 20.3 | 2000 |
| 124 | TWEQAVK | 12.8 | 431.23 | 760.4 | 20.3 | 2000 |
| 125 | VQATNSFSGVNYWLVK | 22.1 | 604.98 | 708.41 | 25.8 | 2000 |
| 126 | VQATNSFSGVNYWLVK | 22.1 | 604.98 | 822.45 | 25.8 | 2000 |
| 127 | VQATNSFSGVNYWLVK | 22.1 | 906.97 | 1212.64 | 47.4 | 2000 |
| 128 | VQATNSFSGVSYSLIK | 19.9 | 567.63 | 710.41 | 24.7 | 2000 |
| 129 | VQATNSFSGVSYSLIK | 19.9 | 567.63 | 953.53 | 24.7 | 2000 |
| 130 | VQATNSFSGVSYSLIK | 19.9 | 850.95 | 710.41 | 44.2 | 2000 |

TABLE 27-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 131 | VQATNSFSGVSYWLVK | 22.5 | 595.98 | 708.41 | 25.6 | 2000 |
| 132 | VQATNSFSGVSYWLVK | 22.5 | 595.98 | 795.44 | 25.6 | 2000 |
| 133 | VQATNSFSGVSYWLVK | 22.5 | 893.46 | 1038.56 | 46.7 | 2000 |
| 134 | YSFSEVSYWLVK | 23.8 | 754.38 | 795.44 | 38.7 | 2000 |
| 135 | YSFSEVSYWLVK | 23.8 | 754.38 | 894.51 | 38.7 | 2000 |
| 136 | YSFSEVSYWLVK | 23.8 | 754.38 | 1110.58 | 38.7 | 2000 |
| 137 | YSFSGVSYWLVK | 23.4 | 718.37 | 795.44 | 36.7 | 2000 |
| 138 | YSFSGVSYWLVK | 23.4 | 718.37 | 951.53 | 36.7 | 2000 |
| 139 | YSFSGVSYWLVK | 23.4 | 718.37 | 1185.63 | 36.7 | 2000 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 1 sec
Detection window: 120 sec The areas obtained for each of the transitions and for each of the microorganisms studied were measured. When the areas of the transitions are greater than or equal to the positivity threshold described in TABLE 27, the detection of the transition is considered to be positive and is labelled "1" in TABLE 28. When a transition has an area less than the positivity threshold described in TABLE 27, the transition is considered non-detected and is labelled "0" in TABLE 28.

For a given peptide, when at least 3 transitions are labelled "1", the peptide is considered as being detected.

TABLE 28

| Transition number | Sam145 | Sam146 | Sam147 | Sam148 | Sam149 | Sam150 | Sam151 | Sam152 | Sam153 | Sam154 |
|---|---|---|---|---|---|---|---|---|---|---|
| 1 | 0 | 0 | 1 | 0 | 0 | 0 | 0 | 0 | 0 | 0 |
| 2 | 0 | 0 | 1 | 0 | 0 | 0 | 0 | 0 | 0 | 0 |
| 3 | 0 | 0 | 0 | 0 | 0 | 0 | 0 | 0 | 0 | 0 |
| 4 | 0 | 0 | 0 | 0 | 0 | 0 | 0 | 0 | 1 | 0 |
| 5 | 0 | 0 | 0 | 0 | 0 | 0 | 0 | 0 | 1 | 0 |
| 6 | 0 | 0 | 0 | 0 | 0 | 0 | 0 | 0 | 1 | 0 |
| 7 | 0 | 0 | 0 | 0 | 0 | 0 | 0 | 0 | 0 | 0 |
| 8 | 0 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 1 | 1 | 0 | 0 | 0 | 0 | 0 | 0 | 0 | 0 |
| 11 | 1 | 1 | 0 | 0 | 0 | 0 | 0 | 0 | 0 | 0 |
| 12 | 0 | 0 | 0 | 0 | 0 | 0 | 0 | 0 | 0 | 0 |
| 13 | 0 | 0 | 0 | 0 | 0 | 0 | 0 | 0 | 0 | 0 |
| 14 | 0 | 0 | 0 | 0 | 0 | 0 | 0 | 0 | 0 | 0 |
| 15 | 0 | 0 | 0 | 0 | 0 | 0 | 0 | 0 | 0 | 0 |
| 16 | 0 | 0 | 0 | 0 | 0 | 0 | 0 | 0 | 0 | 0 |
| 17 | 0 | 0 | 0 | 0 | 0 | 1 | 1 | 0 | 1 | 0 |
| 18 | 0 | 0 | 0 | 0 | 0 | 0 | 0 | 0 | 0 | 0 |
| 19 | 0 | 1 | 0 | 0 | 0 | 0 | 0 | 0 | 0 | 0 |
| 20 | 0 | 0 | 0 | 0 | 0 | 1 | 0 | 1 | 1 | 0 |
| 21 | 0 | 0 | 0 | 0 | 0 | 0 | 0 | 1 | 0 | 0 |
| 22 | 0 | 0 | 0 | 0 | 1 | 0 | 0 | 0 | 0 | 0 |
| 23 | 0 | 0 | 1 | 1 | 1 | 0 | 0 | 0 | 1 | 0 |
| 24 | 0 | 0 | 0 | 0 | 0 | 0 | 0 | 0 | 0 | 0 |
| 25 | 0 | 0 | 0 | 0 | 0 | 0 | 0 | 0 | 0 | 0 |
| 26 | 0 | 0 | 0 | 0 | 0 | 0 | 0 | 0 | 0 | 0 |
| 27 | 0 | 0 | 0 | 0 | 0 | 0 | 0 | 0 | 0 | 0 |
| 28 | 0 | 0 | 0 | 0 | 0 | 0 | 0 | 0 | 0 | 0 |
| 29 | 0 | 0 | 0 | 0 | 0 | 0 | 0 | 0 | 0 | 0 |
| 30 | 0 | 0 | 0 | 0 | 0 | 0 | 0 | 0 | 0 | 0 |

TABLE 28-continued

| Transition number | Sam145 | Sam146 | Sam147 | Sam148 | Sam149 | Sam150 | Sam151 | Sam152 | Sam153 | Sam154 |
|---|---|---|---|---|---|---|---|---|---|---|
| 31 | 0 | 0 | 0 | 0 | 0 | 0 | 0 | 0 | 0 | 0 |
| 32 | 0 | 0 | 0 | 0 | 0 | 0 | 0 | 0 | 0 | 0 |
| 33 | 1 | 0 | 0 | 0 | 0 | 0 | 0 | 0 | 0 | 0 |
| 34 | 0 | 0 | 0 | 0 | 0 | 0 | 0 | 0 | 0 | 0 |
| 35 | 0 | 0 | 0 | 0 | 0 | 0 | 0 | 0 | 0 | 0 |
| 36 | 0 | 0 | 0 | 0 | 0 | 0 | 0 | 0 | 0 | 0 |
| 37 | 0 | 0 | 0 | 0 | 0 | 0 | 0 | 0 | 0 | 0 |
| 38 | 0 | 1 | 1 | 1 | 0 | 0 | 0 | 1 | 0 | 0 |
| 39 | 0 | 1 | 1 | 1 | 0 | 0 | 0 | 1 | 0 | 0 |
| 40 | 0 | 1 | 1 | 1 | 0 | 0 | 0 | 1 | 0 | 0 |
| 41 | 0 | 0 | 1 | 0 | 0 | 0 | 0 | 0 | 0 | 1 |
| 42 | 0 | 0 | 0 | 0 | 0 | 0 | 0 | 0 | 0 | 1 |
| 43 | 0 | 0 | 0 | 0 | 0 | 0 | 0 | 0 | 0 | 1 |
| 44 | 0 | 0 | 0 | 0 | 0 | 0 | 0 | 0 | 0 | 0 |
| 45 | 0 | 0 | 0 | 0 | 0 | 0 | 0 | 0 | 0 | 0 |
| 46 | 0 | 0 | 0 | 0 | 0 | 0 | 0 | 0 | 0 | 0 |
| 47 | 0 | 0 | 0 | 0 | 0 | 0 | 0 | 0 | 0 | 0 |
| 48 | 0 | 0 | 0 | 0 | 0 | 0 | 0 | 0 | 0 | 1 |
| 49 | 0 | 0 | 0 | 0 | 0 | 0 | 0 | 0 | 0 | 0 |
| 50 | 0 | 0 | 0 | 0 | 0 | 0 | 0 | 0 | 0 | 0 |
| 51 | 0 | 0 | 0 | 0 | 0 | 0 | 0 | 0 | 0 | 0 |
| 52 | 0 | 0 | 0 | 0 | 0 | 1 | 0 | 0 | 0 | 0 |
| 53 | 1 | 0 | 0 | 0 | 1 | 1 | 0 | 0 | 1 | 0 |
| 54 | 1 | 0 | 1 | 0 | 0 | 1 | 0 | 0 | 1 | 0 |
| 55 | 1 | 1 | 1 | 0 | 1 | 1 | 0 | 0 | 1 | 0 |
| 56 | 0 | 1 | 1 | 1 | 1 | 0 | 1 | 1 | 0 | 0 |
| 57 | 0 | 1 | 1 | 1 | 1 | 0 | 1 | 1 | 0 | 0 |
| 58 | 0 | 1 | 1 | 1 | 1 | 0 | 1 | 1 | 0 | 0 |
| 59 | 0 | 0 | 0 | 0 | 0 | 1 | 1 | 0 | 0 | 0 |
| 60 | 0 | 0 | 0 | 0 | 0 | 1 | 1 | 0 | 0 | 0 |
| 61 | 0 | 0 | 0 | 0 | 0 | 1 | 1 | 0 | 0 | 0 |
| 62 | 0 | 0 | 0 | 1 | 0 | 0 | 1 | 1 | 0 | 0 |
| 63 | 0 | 0 | 0 | 1 | 0 | 0 | 1 | 1 | 0 | 0 |
| 64 | 0 | 0 | 0 | 1 | 0 | 0 | 1 | 1 | 0 | 0 |
| 65 | 0 | 0 | 0 | 0 | 0 | 1 | 1 | 1 | 1 | 0 |
| 66 | 0 | 0 | 0 | 0 | 0 | 0 | 0 | 0 | 0 | 0 |
| 67 | 0 | 0 | 0 | 0 | 0 | 0 | 0 | 0 | 0 | 0 |
| 68 | 0 | 0 | 0 | 0 | 0 | 0 | 0 | 0 | 0 | 0 |
| 69 | 0 | 0 | 0 | 0 | 0 | 0 | 0 | 0 | 0 | 0 |
| 70 | 0 | 1 | 0 | 0 | 0 | 0 | 0 | 0 | 0 | 0 |
| 71 | 1 | 1 | 1 | 0 | 0 | 0 | 0 | 0 | 0 | 0 |
| 72 | 0 | 1 | 1 | 0 | 0 | 0 | 0 | 0 | 0 | 0 |
| 73 | 0 | 1 | 1 | 0 | 0 | 0 | 0 | 0 | 0 | 0 |
| 74 | 0 | 0 | 0 | 1 | 0 | 0 | 1 | 1 | 0 | 0 |
| 75 | 0 | 0 | 0 | 1 | 0 | 0 | 1 | 1 | 0 | 0 |
| 76 | 0 | 0 | 0 | 1 | 0 | 0 | 1 | 1 | 0 | 0 |
| 77 | 0 | 0 | 0 | 0 | 0 | 0 | 0 | 0 | 0 | 1 |
| 78 | 0 | 0 | 0 | 0 | 0 | 0 | 0 | 0 | 0 | 1 |
| 79 | 0 | 1 | 1 | 0 | 0 | 0 | 0 | 0 | 0 | 1 |
| 80 | 0 | 0 | 0 | 0 | 0 | 0 | 0 | 0 | 0 | 0 |
| 81 | 0 | 0 | 0 | 0 | 0 | 0 | 0 | 0 | 0 | 0 |
| 82 | 0 | 1 | 0 | 0 | 0 | 0 | 0 | 0 | 0 | 0 |
| 83 | 1 | 0 | 0 | 0 | 1 | 1 | 0 | 0 | 0 | 1 |
| 84 | 1 | 0 | 0 | 0 | 1 | 1 | 0 | 0 | 1 | 0 |
| 85 | 1 | 0 | 1 | 1 | 1 | 1 | 1 | 1 | 1 | 0 |
| 86 | 0 | 0 | 1 | 0 | 0 | 0 | 0 | 0 | 0 | 0 |
| 87 | 0 | 0 | 1 | 0 | 0 | 0 | 0 | 0 | 0 | 0 |
| 88 | 0 | 0 | 0 | 0 | 0 | 0 | 0 | 0 | 0 | 0 |
| 89 | 0 | 0 | 0 | 0 | 0 | 0 | 0 | 0 | 0 | 0 |
| 90 | 0 | 0 | 0 | 0 | 0 | 0 | 0 | 0 | 1 | 0 |
| 91 | 0 | 0 | 0 | 0 | 0 | 0 | 0 | 0 | 1 | 0 |
| 92 | 1 | 0 | 0 | 0 | 0 | 0 | 0 | 0 | 0 | 0 |
| 93 | 0 | 0 | 0 | 0 | 0 | 0 | 0 | 0 | 0 | 0 |
| 94 | 0 | 0 | 0 | 0 | 0 | 0 | 0 | 0 | 0 | 0 |
| 95 | 0 | 1 | 0 | 0 | 0 | 0 | 0 | 0 | 0 | 0 |
| 96 | 0 | 0 | 0 | 0 | 0 | 0 | 0 | 0 | 0 | 0 |
| 97 | 0 | 0 | 0 | 0 | 0 | 0 | 0 | 0 | 0 | 0 |
| 98 | 0 | 1 | 1 | 0 | 0 | 0 | 0 | 0 | 0 | 0 |
| 99 | 0 | 1 | 1 | 0 | 0 | 0 | 0 | 0 | 0 | 0 |
| 100 | 0 | 1 | 1 | 1 | 0 | 0 | 0 | 0 | 0 | 0 |
| 101 | 0 | 0 | 0 | 0 | 0 | 0 | 0 | 0 | 0 | 0 |
| 102 | 0 | 0 | 0 | 0 | 0 | 0 | 0 | 0 | 0 | 0 |
| 103 | 0 | 0 | 0 | 0 | 0 | 0 | 1 | 1 | 0 | 0 |
| 104 | 0 | 0 | 0 | 1 | 0 | 0 | 0 | 0 | 0 | 0 |
| 105 | 0 | 0 | 0 | 1 | 1 | 0 | 0 | 0 | 0 | 0 |
| 106 | 0 | 0 | 0 | 0 | 0 | 0 | 0 | 0 | 0 | 0 |
| 107 | 0 | 0 | 0 | 0 | 0 | 0 | 0 | 0 | 0 | 0 |

TABLE 28-continued

| Transition number | Sam145 | Sam146 | Sam147 | Sam148 | Sam149 | Sam150 | Sam151 | Sam152 | Sam153 | Sam154 |
|---|---|---|---|---|---|---|---|---|---|---|
| 108 | 0 | 0 | 0 | 0 | 0 | 0 | 0 | 0 | 0 | 0 |
| 109 | 0 | 0 | 0 | 0 | 0 | 0 | 0 | 0 | 0 | 0 |
| 110 | 1 | 1 | 0 | 0 | 0 | 0 | 0 | 0 | 0 | 0 |
| 111 | 1 | 1 | 0 | 0 | 0 | 0 | 0 | 0 | 1 | 0 |
| 112 | 1 | 0 | 0 | 0 | 0 | 0 | 0 | 0 | 0 | 0 |
| 113 | 0 | 0 | 0 | 1 | 0 | 0 | 0 | 0 | 0 | 0 |
| 114 | 0 | 0 | 0 | 1 | 0 | 0 | 0 | 1 | 0 | 0 |
| 115 | 0 | 0 | 0 | 1 | 0 | 0 | 0 | 0 | 0 | 0 |
| 116 | 0 | 1 | 0 | 1 | 0 | 0 | 1 | 0 | 0 | 0 |
| 117 | 0 | 1 | 1 | 1 | 0 | 0 | 1 | 0 | 0 | 0 |
| 118 | 0 | 1 | 0 | 1 | 0 | 0 | 1 | 0 | 0 | 0 |
| 119 | 0 | 0 | 0 | 0 | 0 | 0 | 0 | 0 | 1 | 0 |
| 120 | 0 | 0 | 0 | 0 | 0 | 0 | 0 | 0 | 1 | 0 |
| 121 | 0 | 0 | 0 | 0 | 0 | 0 | 0 | 0 | 1 | 0 |
| 122 | 1 | 0 | 0 | 0 | 1 | 1 | 0 | 0 | 0 | 0 |
| 123 | 1 | 0 | 0 | 0 | 1 | 1 | 0 | 0 | 0 | 0 |
| 124 | 1 | 0 | 0 | 0 | 1 | 1 | 0 | 0 | 0 | 0 |
| 125 | 0 | 0 | 0 | 0 | 0 | 0 | 0 | 0 | 0 | 0 |
| 126 | 0 | 0 | 0 | 0 | 0 | 0 | 0 | 1 | 0 | 0 |
| 127 | 0 | 0 | 0 | 1 | 1 | 0 | 0 | 0 | 0 | 0 |
| 128 | 0 | 0 | 0 | 0 | 0 | 0 | 0 | 0 | 0 | 1 |
| 129 | 0 | 0 | 0 | 0 | 0 | 0 | 0 | 0 | 0 | 0 |
| 130 | 0 | 0 | 0 | 0 | 0 | 0 | 0 | 0 | 0 | 0 |
| 131 | 0 | 0 | 0 | 0 | 0 | 0 | 0 | 0 | 0 | 0 |
| 132 | 0 | 0 | 0 | 0 | 0 | 0 | 0 | 0 | 0 | 0 |
| 133 | 0 | 0 | 0 | 0 | 0 | 0 | 0 | 0 | 0 | 0 |
| 134 | 0 | 0 | 0 | 0 | 0 | 0 | 0 | 0 | 0 | 0 |
| 135 | 0 | 0 | 0 | 0 | 0 | 0 | 1 | 0 | 0 | 0 |
| 136 | 0 | 0 | 0 | 0 | 0 | 0 | 0 | 0 | 0 | 0 |
| 137 | 1 | 0 | 0 | 0 | 0 | 0 | 0 | 0 | 0 | 0 |
| 138 | 0 | 0 | 0 | 0 | 0 | 0 | 0 | 0 | 0 | 0 |
| 139 | 0 | 0 | 0 | 0 | 0 | 0 | 0 | 0 | 0 | 0 |

Samples Sam145 to Sam154 comprise at least one peptide which is characteristic of IMPs. The bacteria present in samples Sam145 to Sam154 therefore express a beta-lactamase which confers on them a resistance to penicillins, to cephalosporins and to carbapenems.

EXAMPLE 18: IDENTIFICATION OF A RESISTANCE TO OXA-48 BETA-LACTAMS

Samples Sam155 to Sam164 are identified according to one of the methods described in examples 1, 3 or 4. The identification of the species is set out in TABLE 29.

TABLE 29

| Names | Species |
|---|---|
| Sam155 | K. pneumoniae |
| Sam156 | K. pneumoniae |

TABLE 29-continued

| Names | Species |
|---|---|
| Sam157 | K. pneumoniae |
| Sam158 | E. cloacae |
| Sam159 | E. cloacae |
| Sam160 | K. pneumoniae |
| Sam161 | K. pneumoniae |
| Sam162 | K. pneumoniae |
| Sam163 | K. pneumoniae |
| Sam164 | K. pneumoniae |

Samples Sam155 to Sam164 correspond to a species able to comprise an OXA-48 resistance mechanism. The following method is then performed to detect such a mechanism.

Each sample is treated according to Example 5, then analysed according to Example 6 unless otherwise stated in the rest of the example, by detecting the peptides from TABLE 30 instead of the peptides from TABLE 3.

TABLE 30

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 1 | ANQAFLPASTFK | 2 | y6 monocharged | 18.09 | 647.84 | 650.35 | 32.7 | 2000 |
| 2 | ANQAFLPASTFK | 2 | y7 monocharged | 18.11 | 647.84 | 763.44 | 32.7 | 2000 |
| 3 | ANQAFLPASTFK | 2 | y8 monocharged | 18.09 | 647.84 | 910.5 | 32.7 | 2000 |
| 4 | DEHQVFK | 3 | y5 dicharged | 9.89 | 301.48 | 329.69 | 16.4 | 2000 |
| 5 | DEHQVFK | 2 | y4 monocharged | 9.89 | 451.72 | 521.31 | 21.5 | 2000 |

TABLE 30-continued

| Transition number | Peptide | Charge state of the precursor | Fragment ion | Retention time (minutes) | (m/z) filtered in Q1 | (m/z) filtered in Q3 | Collision energy (eV) | Positivity threshold |
|---|---|---|---|---|---|---|---|---|
| 6 | DEHQVFK | 2 | y5 monocharged | 9.91 | 451.72 | 658.37 | 21.5 | 2000 |
| 7 | DHNLITAMK | 3 | y3 monocharged | 14.57 | 348.18 | 349.19 | 17.9 | 2000 |
| 8 | DHNLITAMK | 3 | y4 monocharged | 14.57 | 348.18 | 450.24 | 17.9 | 2000 |
| 9 | DHNLITAMK | 2 | y7 monocharged | 14.57 | 521.77 | 790.45 | 25.5 | 2000 |
| 10 | DIATWNR | 2 | y3 monocharged | 13.79 | 438.22 | 475.24 | 20.7 | 2000 |
| 11 | DIATWNR | 2 | y4 monocharged | 13.79 | 438.22 | 576.29 | 20.7 | 2000 |
| 12 | DIATWNR | 2 | y5 monocharged | 13.79 | 438.22 | 647.33 | 20.7 | 2000 |
| 13 | IPNSLIALDLGVVK | 3 | y6 monocharged | 23.68 | 484.63 | 630.38 | 22.1 | 2000 |
| 14 | IPNSLIALDLGVVK | 2 | y13 dicharged | 23.68 | 726.45 | 669.9 | 37.1 | 2000 |
| 15 | IPNSLIALDLGVVK | 2 | y8 monocharged | 23.68 | 726.45 | 814.5 | 37.1 | 2000 |
| 16 | ISATEQISFLR | 2 | y4 monocharged | 19.17 | 632.85 | 522.3 | 31.8 | 2000 |
| 17 | ISATEQISFLR | 2 | y5 monocharged | 19.17 | 632.85 | 635.39 | 31.8 | 2000 |
| 18 | ISATEQISFLR | 2 | y6 monocharged | 19.17 | 632.85 | 763.45 | 31.8 | 2000 |
| 19 | QAMLTEANGDYIIR | 3 | y4 monocharged | 18.36 | 532.27 | 564.35 | 23.6 | 2000 |
| 20 | QAMLTEANGDYIIR | 3 | y6 monocharged | 18.36 | 532.27 | 736.4 | 23.6 | 2000 |
| 21 | QAMLTEANGDYIIR | 2 | y10 monocharged | 18.36 | 797.9 | 1151.57 | 41.2 | 2000 |
| 22 | QQGFTNNLK | 2 | y4 monocharged | 12.58 | 525.27 | 488.28 | 25.7 | 2000 |
| 23 | QQGFTNNLK | 2 | y5 monocharged | 12.58 | 525.27 | 589.33 | 25.7 | 2000 |
| 24 | QQGFTNNLK | 2 | y7 monocharged | 12.58 | 525.27 | 793.42 | 25.7 | 2000 |
| 25 | SQGVVVLWNENK | 2 | y5 monocharged | 18.54 | 686.87 | 690.32 | 34.9 | 2000 |
| 26 | SQGVVVLWNENK | 2 | y6 monocharged | 18.54 | 686.87 | 803.41 | 34.9 | 2000 |
| 27 | SQGVVVLWNENK | 2 | y7 monocharged | 18.52 | 686.87 | 902.47 | 34.9 | 2000 |
| 28 | SWNAHFTEHK | 3 | y8 dicharged | 12.23 | 419.53 | 492.24 | 20.1 | 2000 |
| 29 | SWNAHFTEHK | 3 | y9 dicharged | 12.23 | 419.53 | 585.28 | 20.1 | 2000 |
| 30 | SWNAHFTEHK | 3 | y5 monocharged | 12.23 | 419.53 | 661.33 | 20.1 | 2000 |
| 31 | VLALSAVFLVASIIGMPAVAK | 3 | y6 monocharged | 34.92 | 690.75 | 616.35 | 28.5 | 2000 |
| 32 | VLALSAVFLVASIIGMPAVAK | 3 | y7 monocharged | 34.94 | 690.75 | 673.37 | 28.5 | 2000 |
| 33 | VLALSAVFLVASIIGMPAVAK | 3 | y8 monocharged | 34.94 | 690.75 | 786.45 | 28.5 | 2000 |
| 34 | YSVVPVYQEFAR | 3 | y5 monocharged | 20.05 | 486.59 | 650.33 | 22.2 | 2000 |
| 35 | YSVVPVYQEFAR | 2 | y8 dicharged | 20.07 | 729.38 | 505.26 | 37.3 | 2000 |
| 36 | YSVVPVYQEFAR | 2 | y8 monocharged | 20.07 | 729.38 | 1009.51 | 37.3 | 2000 |

The other machine parameters used are as follows:
Scan type: MRM
MRM planned: no
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 40.00 psi
Cone voltage: 5500.00 V
Source temperature: 500.00° C.

Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 1.1 sec The areas obtained for each of the transitions and for each of the microorganisms studied were measured. When the areas of the transitions are greater than or equal to the positivity threshold described in TABLE 30, the detection of the transition is considered to be positive and is labelled "1" in TABLE 31. When a transition has an area less than the positivity threshold described in TABLE 30, the transition is considered non-detected and is labelled "0" in TABLE 31.

For a given peptide, when at least 3 transitions are labelled "1", the peptide is considered as being detected.

EXAMPLE 19: IDENTIFICATION OF A RESISTANCE TO VIM BETA-LACTAMS

Samples Sam165 to Sam170 are identified according to one of the methods described in examples 1, 3 or 4. The identification of the species is set out in TABLE 32.

TABLE 32

| Names | Species |
| --- | --- |
| Sam165 | *P. aeruginosa* |
| Sam166 | *E. coli* |
| Sam167 | *A. baumannii* complex |
| Sam168 | *A. junii* |
| Sam169 | *E. coli* |
| Sam170 | *K. pneumoniae* ssp *pneumoniae* |

TABLE 31

| Transition number | Sam155 | Sam156 | Sam157 | Sam158 | Sam159 | Sam160 | Sam161 | Sam162 | Sam163 | Sam164 |
| --- | --- | --- | --- | --- | --- | --- | --- | --- | --- | --- |
| 1 | 0 | 1 | 1 | 0 | 1 | 1 | 1 | 1 | 1 | 0 |
| 2 | 0 | 1 | 1 | 0 | 1 | 1 | 1 | 0 | 1 | 0 |
| 3 | 0 | 1 | 0 | 0 | 0 | 1 | 1 | 0 | 0 | 0 |
| 4 | 0 | 0 | 0 | 0 | 0 | 0 | 0 | 0 | 0 | 0 |
| 5 | 0 | 0 | 0 | 0 | 0 | 0 | 0 | 0 | 0 | 0 |
| 6 | 0 | 0 | 0 | 0 | 0 | 0 | 0 | 0 | 0 | 0 |
| 7 | 0 | 1 | 0 | 0 | 0 | 1 | 1 | 0 | 0 | 0 |
| 8 | 0 | 1 | 1 | 1 | 0 | 1 | 1 | 0 | 1 | 0 |
| 9 | 1 | 1 | 1 | 1 | 1 | 1 | 1 | 1 | 1 | 0 |
| 10 | 0 | 0 | 0 | 0 | 0 | 0 | 0 | 0 | 0 | 0 |
| 11 | 0 | 0 | 0 | 1 | 1 | 0 | 0 | 0 | 0 | 0 |
| 12 | 0 | 0 | 0 | 0 | 0 | 0 | 0 | 1 | 0 | 0 |
| 13 | 0 | 1 | 1 | 1 | 1 | 1 | 1 | 1 | 1 | 0 |
| 14 | 0 | 1 | 1 | 1 | 1 | 1 | 1 | 1 | 1 | 1 |
| 15 | 0 | 1 | 1 | 1 | 1 | 1 | 1 | 1 | 1 | 0 |
| 16 | 1 | 1 | 1 | 1 | 1 | 1 | 1 | 1 | 1 | 1 |
| 17 | 1 | 1 | 1 | 1 | 1 | 1 | 1 | 1 | 1 | 1 |
| 18 | 1 | 1 | 1 | 1 | 1 | 1 | 1 | 1 | 1 | 1 |
| 19 | 1 | 1 | 1 | 1 | 1 | 1 | 1 | 1 | 1 | 1 |
| 20 | 1 | 1 | 1 | 1 | 1 | 1 | 1 | 1 | 1 | 0 |
| 21 | 1 | 1 | 1 | 1 | 1 | 1 | 1 | 1 | 1 | 1 |
| 22 | 1 | 1 | 1 | 1 | 1 | 1 | 1 | 1 | 1 | 0 |
| 23 | 1 | 1 | 1 | 1 | 1 | 1 | 1 | 1 | 1 | 1 |
| 24 | 1 | 1 | 1 | 1 | 1 | 1 | 1 | 1 | 1 | 0 |
| 25 | 0 | 0 | 0 | 0 | 0 | 0 | 0 | 0 | 0 | 0 |
| 26 | 0 | 0 | 0 | 0 | 0 | 0 | 0 | 0 | 0 | 0 |
| 27 | 0 | 0 | 0 | 0 | 0 | 0 | 0 | 0 | 0 | 0 |
| 28 | 1 | 1 | 1 | 1 | 1 | 1 | 1 | 1 | 1 | 1 |
| 29 | 1 | 1 | 1 | 1 | 1 | 1 | 1 | 1 | 1 | 1 |
| 30 | 1 | 1 | 1 | 1 | 1 | 1 | 1 | 1 | 1 | 0 |
| 31 | 1 | 0 | 0 | 0 | 1 | 0 | 0 | 0 | 0 | 0 |
| 32 | 1 | 1 | 1 | 1 | 1 | 1 | 1 | 1 | 1 | 0 |
| 33 | 1 | 1 | 0 | 1 | 1 | 1 | 1 | 1 | 1 | 0 |
| 34 | 0 | 1 | 1 | 0 | 1 | 1 | 1 | 0 | 1 | 0 |
| 35 | 0 | 1 | 1 | 0 | 1 | 1 | 1 | 0 | 1 | 0 |
| 36 | 0 | 1 | 1 | 0 | 1 | 1 | 1 | 0 | 1 | 0 |

Samples Sam155 to Sam164 comprise at least one peptide which is characteristic of the OXA-48 group. The bacteria present in samples Sam155 to Sam164 therefore express a beta-lactamase which confers on them a resistance to penicillins, to first-generation and second-generation cephalosporins (but not to broad-spectrum cephalosporins), and to carbapenems.

Samples Sam165 to Sam170 correspond to a species able to comprise a VIM resistance mechanism. The following method is then performed to detect such a mechanism.

Each sample is treated according to Example 5, then analysed according to Example 6 unless otherwise stated in the rest of the example, by detecting the peptides from TABLE 33 instead of the peptides from TABLE 3.

TABLE 33

| Transition number | Peptide | Retention time (minutes) | (m/z) filtered in Q1 | (m/z) filtered in Q3 | Collision energy (eV) | Positivity threshold |
|---|---|---|---|---|---|---|
| 1 | AAGVATYASPSAR | 12.3 | 611.32 | 588.31 | 30.6 | 2500 |
| 2 | AAGVATYASPSAR | 12.3 | 611.32 | 852.42 | 30.6 | 2500 |
| 3 | AAGVATYASPSAR | 12.3 | 611.32 | 923.46 | 30.6 | 2500 |
| 4 | AAGVATYASPSIR | 14.5 | 632.34 | 630.36 | 31.8 | 2500 |
| 5 | AAGVATYASPSIR | 14.5 | 632.34 | 894.47 | 31.8 | 2500 |
| 6 | AAGVATYASPSIR | 14.5 | 632.34 | 965.51 | 31.8 | 2500 |
| 7 | AAGVATYASPSTR | 12 | 626.32 | 618.32 | 31.4 | 2500 |
| 8 | AAGVATYASPSTR | 12 | 626.32 | 882.43 | 31.4 | 2500 |
| 9 | AAGVATYASPSTR | 12 | 626.32 | 953.47 | 31.4 | 2500 |
| 10 | AAGVATYTSPLTR | 15.7 | 654.35 | 674.38 | 33 | 2500 |
| 11 | AAGVATYTSPLTR | 15.7 | 654.35 | 938.49 | 33 | 2500 |
| 12 | AAGVATYTSPLTR | 15.7 | 654.35 | 1009.53 | 33 | 2500 |
| 13 | AGVATYASPSTR | 11.8 | 590.8 | 547.28 | 29.4 | 2500 |
| 14 | AGVATYASPSTR | 11.8 | 590.8 | 618.32 | 29.4 | 2500 |
| 15 | AGVATYASPSTR | 11.8 | 590.8 | 781.38 | 29.4 | 2500 |
| 16 | ALSSSGDVVR | 11.3 | 495.76 | 632.34 | 24 | 2500 |
| 17 | ALSSSGDVVR | 11.3 | 495.76 | 719.37 | 24 | 2500 |
| 18 | ALSSSGDVVR | 11.3 | 495.76 | 806.4 | 24 | 2500 |
| 19 | AVSTHFHDDR | 9.2 | 395.52 | 413.68 | 19.3 | 2500 |
| 20 | AVSTHFHDDR | 9.2 | 395.52 | 507.72 | 19.3 | 2500 |
| 21 | AVSTHFHDDR | 9.2 | 395.52 | 689.3 | 19.3 | 2500 |
| 22 | DADELLLIDTAWGAK | 24.3 | 544.28 | 748.36 | 24 | 2500 |
| 23 | DADELLLIDTAWGAK | 24.3 | 815.92 | 544.31 | 42.2 | 2500 |
| 24 | DADELLLIDTAWGAK | 24.3 | 815.92 | 748.36 | 42.2 | 2500 |
| 25 | DADELLLIDTAWGAK | 24.3 | 815.92 | 861.45 | 42.2 | 2500 |
| 26 | DGDELLLIDTAWGAK | 24 | 539.61 | 748.36 | 23.8 | 2500 |
| 27 | DGDELLLIDTAWGAK | 24 | 808.91 | 748.36 | 41.8 | 2500 |
| 28 | DGDELLLIDTAWGAK | 24 | 808.91 | 861.45 | 41.8 | 2500 |
| 29 | DGDELLLIDTAWGTK | 24.1 | 549.61 | 778.37 | 24.1 | 2500 |
| 30 | DGDELLLIDTAWGTK | 24.1 | 823.92 | 778.37 | 42.7 | 2500 |
| 31 | DGDELLLIDTAWGTK | 24.1 | 823.92 | 891.46 | 42.7 | 2500 |
| 32 | ESAGNVADANLAEWPATIK | 20.2 | 652.99 | 529.33 | 27.3 | 2500 |
| 33 | ESAGNVADANLAEWPATIK | 20.2 | 652.99 | 715.41 | 27.3 | 2500 |
| 34 | ESAGNVADANLAEWPATIK | 20.2 | 978.99 | 529.33 | 51.5 | 2500 |
| 35 | GEYPTVSEIPVGEVR | 18.4 | 544.61 | 656.37 | 24 | 2500 |
| 36 | GEYPTVSEIPVGEVR | 18.4 | 816.42 | 641.85 | 42.3 | 2500 |
| 37 | GEYPTVSEIPVGEVR | 18.4 | 816.42 | 656.37 | 42.3 | 2500 |
| 38 | HTTNVVK | 1.3 | 399.73 | 345.25 | 18.5 | 2500 |

TABLE 33-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 39 | HTTNVVK | 1.3 | 399.73 | 560.34 | 18.5 | 2500 |
| 40 | HTTNVVK | 1.3 | 399.73 | 661.39 | 18.5 | 2500 |
| 41 | IGDGVWSHIATQK | 17 | 471.25 | 563.8 | 21.7 | 2500 |
| 42 | IGDGVWSHIATQK | 17 | 471.25 | 621.32 | 21.7 | 2500 |
| 43 | IGDGVWSHIATQK | 17 | 471.25 | 649.83 | 21.7 | 2500 |
| 44 | LGDTVYSSNGLIVR | 17.9 | 747.4 | 387.27 | 38.3 | 2500 |
| 45 | LGDTVYSSNGLIVR | 17.9 | 747.4 | 845.48 | 38.3 | 2500 |
| 46 | LGDTVYSSNGLIVR | 17.9 | 747.4 | 1008.55 | 38.3 | 2500 |
| 47 | LYQIADGVWSHIATK | 20.8 | 567.97 | 592.81 | 24.7 | 2500 |
| 48 | LYQIADGVWSHIATK | 20.8 | 567.97 | 649.35 | 24.7 | 2500 |
| 49 | LYQIADGVWSHIATK | 20.8 | 567.97 | 713.38 | 24.7 | 2500 |
| 50 | LYQIADGVWSHIATR | 21 | 577.31 | 606.81 | 25 | 2500 |
| 51 | LYQIADGVWSHIATR | 21 | 577.31 | 663.35 | 25 | 2500 |
| 52 | LYQIADGVWSHIATR | 21 | 577.31 | 727.38 | 25 | 2500 |
| 53 | NTAALLAEIEK | 19.8 | 586.83 | 589.32 | 29.2 | 2500 |
| 54 | NTAALLAEIEK | 19.8 | 586.83 | 702.4 | 29.2 | 2500 |
| 55 | NTAALLAEIEK | 19.8 | 586.83 | 886.52 | 29.2 | 2500 |
| 56 | NTVALLAEIEK | 21.2 | 600.85 | 589.32 | 30 | 2500 |
| 57 | NTVALLAEIEK | 21.2 | 600.85 | 702.4 | 30 | 2500 |
| 58 | NTVALLAEIEK | 21.2 | 600.85 | 886.52 | 30 | 2500 |
| 59 | QIGLPVTR | 15.6 | 442.27 | 472.29 | 20.9 | 2500 |
| 60 | QIGLPVTR | 15.6 | 442.27 | 642.39 | 20.9 | 2500 |
| 61 | QIGLPVTR | 15.6 | 442.27 | 755.48 | 20.9 | 2500 |
| 62 | QLAEAAGNEVPAHSLK | 13.8 | 545.62 | 597.32 | 24 | 2500 |
| 63 | QLAEAAGNEVPAHSLK | 13.8 | 545.62 | 652.38 | 24 | 2500 |
| 64 | QLAEAAGNEVPAHSLK | 13.8 | 545.62 | 697.36 | 24 | 2500 |
| 65 | SFDGAVYPSNGLIVR | 19.2 | 797.92 | 559.32 | 41.2 | 2500 |
| 66 | SFDGAVYPSNGLIVR | 19.2 | 797.92 | 855.51 | 41.2 | 2500 |
| 67 | SFDGAVYPSNGLIVR | 19.2 | 797.92 | 1018.57 | 41.2 | 2500 |
| 68 | SISTHFHDDR | 10.6 | 405.52 | 413.68 | 19.7 | 2500 |
| 69 | SISTHFHDDR | 10.6 | 405.52 | 507.72 | 19.7 | 2500 |
| 70 | SISTHFHDDR | 10.6 | 405.52 | 689.3 | 19.7 | 2500 |
| 71 | SVSTHFHDDR | 9.2 | 400.85 | 413.68 | 19.5 | 2500 |
| 72 | SVSTHFHDDR | 9.2 | 400.85 | 507.72 | 19.5 | 2500 |
| 73 | SVSTHFHDDR | 9.2 | 400.85 | 689.3 | 19.5 | 2500 |
| 74 | TSAGNVADADLAEWPGSVER | 19.2 | 682.32 | 322.67 | 28.2 | 2500 |
| 75 | TSAGNVADADLAEWPGSVER | 19.2 | 682.32 | 644.34 | 28.2 | 2500 |
| 76 | TSAGNVADADLAEWPGSVER | 19.2 | 682.32 | 830.42 | 28.2 | 2500 |

TABLE 33-continued

| Transition number | Peptide | Retention time (minutes) | (m/z) filtered in Q1 | (m/z) filtered in Q3 | Collision energy (eV) | Positivity threshold |
|---|---|---|---|---|---|---|
| 77 | TSAGNVADADLAEWPGSVER | 19.2 | 1022.98 | 644.34 | 54 | 2500 |
| 78 | TSAGNVADADLAEWPTSIER | 20.7 | 701.67 | 351.69 | 28.8 | 2500 |
| 79 | TSAGNVADADLAEWPTSIER | 20.7 | 701.67 | 702.38 | 28.8 | 2500 |
| 80 | TSAGNVADADLAEWPTSIER | 20.7 | 701.67 | 888.46 | 28.8 | 2500 |
| 81 | TSAGNVADADLAEWPTSIER | 20.7 | 1052 | 702.38 | 55.7 | 2500 |
| 82 | TSAGNVADADLAEWPTSVER | 19.6 | 697 | 344.69 | 28.7 | 2500 |
| 83 | TSAGNVADADLAEWPTSVER | 19.6 | 697 | 688.36 | 28.7 | 2500 |
| 84 | TSAGNVADADLAEWPTSVER | 19.6 | 697 | 874.44 | 28.7 | 2500 |
| 85 | TSAGNVADADLAEWPTSVER | 19.6 | 1045 | 688.36 | 55.3 | 2500 |
| 86 | VGGVDALR | 12.8 | 393.73 | 474.27 | 18.2 | 2500 |
| 87 | VGGVDALR | 12.8 | 393.73 | 630.36 | 18.2 | 2500 |
| 88 | VGGVDALR | 12.8 | 393.73 | 687.38 | 18.2 | 2500 |
| 89 | VGGVDVLR | 14.8 | 407.74 | 502.3 | 19 | 2500 |
| 90 | VGGVDVLR | 14.8 | 407.74 | 658.39 | 19 | 2500 |
| 91 | VGGVDVLR | 14.8 | 407.74 | 715.41 | 19 | 2500 |
| 92 | VLFGGCAVHEASR | 15.1 | 468.24 | 522.24 | 21.6 | 5100 |
| 93 | VLFGGCAVHEASR | 15.1 | 468.24 | 595.77 | 21.6 | 5100 |
| 94 | VLFGGCAVHEASR | 15.1 | 468.24 | 599.29 | 21.6 | 5100 |
| 95 | VLYGGCAVHELSR | 15.3 | 487.58 | 543.26 | 22.2 | 2500 |
| 96 | VLYGGCAVHELSR | 15.3 | 487.58 | 624.79 | 22.2 | 2500 |
| 97 | VLYGGCAVHELSR | 15.3 | 487.58 | 641.34 | 22.2 | 2500 |

The other machine parameters used are as follows:
Scan type: MRM
MRM planned: yes
Polarity: Positive
Ionising source: Turbo V™ (Applied BioSystems)
Q1 setting: Filtering with unit resolution
Q3 setting: Filtering with unit resolution
Inter-scan pause: 5.00 msec
Scanning speed: 10 Da/s
Curtain gas: 50.00 psi
Cone voltage: 5500.00 V
Source temperature: 500.00° C.
Nebulising gas: 50.00 psi
Heating gas: 50.00 psi
Collision gas which induces dissociation: 9.00 psi
Dynamic filling: activated
Declustering potential (DP): 100.00 V
Entry potential before Q0 (EP): 6.00 V
Collision cell exit potential (CXP): 15 V
Total cycle time: 0.04 sec
Detection window: 120 sec The areas obtained for each of the transitions and for each of the microorganisms studied were measured. When the areas of the transitions are greater than or equal to the positivity threshold described in TABLE 33, the detection of the transition is considered to be positive and is labelled "1" in TABLE 34. When a transition has an area less than the positivity threshold described in TABLE 33, the transition is considered non-detected and is labelled "0" in TABLE 34.

For a given peptide, when at least 3 transitions are labelled "1", the peptide is considered as being detected.

TABLE 34

| Transition number | Sam165 | Sam166 | Sam167 | Sam168 | Sam169 | Sam170 |
|---|---|---|---|---|---|---|
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| 6 | 0 | 0 | 0 | 0 | 0 | 0 |
| 7 | 0 | 0 | 0 | 0 | 0 | 1 |
| 8 | 0 | 0 | 0 | 0 | 0 | 1 |
| 9 | 0 | 0 | 0 | 0 | 0 | 1 |
| 10 | 0 | 0 | 0 | 0 | 0 | 0 |
| 11 | 0 | 0 | 0 | 0 | 0 | 0 |
| 12 | 0 | 0 | 0 | 0 | 0 | 0 |
| 13 | 0 | 0 | 0 | 0 | 0 | 1 |
| 14 | 0 | 0 | 0 | 0 | 0 | 1 |
| 15 | 0 | 0 | 0 | 0 | 0 | 1 |
| 16 | 0 | 0 | 0 | 0 | 0 | 0 |
| 17 | 0 | 0 | 0 | 0 | 0 | 0 |
| 18 | 0 | 0 | 0 | 0 | 0 | 0 |
| 19 | 1 | 1 | 1 | 1 | 1 | 1 |

TABLE 34-continued

| Transition number | Sam165 | Sam166 | Sam167 | Sam168 | Sam169 | Sam170 |
|---|---|---|---|---|---|---|
| 20 | 1 | 1 | 1 | 1 | 1 | 1 |
| 21 | 1 | 1 | 1 | 1 | 1 | 1 |
| 22 | 0 | 0 | 0 | 0 | 0 | 0 |
| 23 | 0 | 0 | 0 | 0 | 0 | 0 |
| 24 | 0 | 0 | 0 | 0 | 0 | 0 |
| 25 | 0 | 0 | 0 | 0 | 0 | 0 |
| 26 | 0 | 0 | 0 | 0 | 0 | 0 |
| 27 | 0 | 0 | 0 | 0 | 0 | 0 |
| 28 | 0 | 0 | 0 | 0 | 0 | 0 |
| 29 | 0 | 0 | 0 | 0 | 0 | 0 |
| 30 | 0 | 0 | 0 | 0 | 0 | 0 |
| 31 | 0 | 0 | 0 | 0 | 0 | 0 |
| 32 | 0 | 0 | 0 | 0 | 0 | 0 |
| 33 | 0 | 0 | 0 | 0 | 0 | 0 |
| 34 | 0 | 0 | 0 | 0 | 0 | 0 |
| 35 | 0 | 0 | 0 | 0 | 0 | 0 |
| 36 | 0 | 0 | 0 | 0 | 0 | 0 |
| 37 | 0 | 0 | 0 | 0 | 0 | 0 |
| 38 | 0 | 0 | 0 | 0 | 0 | 0 |
| 39 | 0 | 0 | 0 | 0 | 0 | 0 |
| 40 | 0 | 0 | 0 | 0 | 0 | 0 |
| 41 | 0 | 0 | 0 | 0 | 0 | 0 |
| 42 | 0 | 0 | 0 | 0 | 0 | 0 |
| 43 | 0 | 0 | 0 | 0 | 0 | 0 |
| 44 | 0 | 0 | 0 | 0 | 0 | 0 |
| 45 | 0 | 0 | 0 | 0 | 0 | 0 |
| 46 | 0 | 0 | 0 | 0 | 0 | 0 |
| 47 | 0 | 0 | 0 | 0 | 0 | 0 |
| 48 | 0 | 0 | 0 | 0 | 0 | 0 |
| 49 | 0 | 0 | 0 | 0 | 0 | 0 |
| 50 | 0 | 0 | 0 | 0 | 0 | 0 |
| 51 | 0 | 0 | 0 | 0 | 0 | 0 |
| 52 | 0 | 0 | 0 | 0 | 0 | 0 |
| 53 | 0 | 0 | 0 | 0 | 0 | 0 |
| 54 | 0 | 0 | 0 | 0 | 0 | 0 |
| 55 | 0 | 0 | 0 | 0 | 0 | 0 |
| 56 | 0 | 0 | 0 | 0 | 0 | 0 |
| 57 | 0 | 0 | 0 | 0 | 0 | 0 |
| 58 | 0 | 0 | 0 | 0 | 0 | 0 |
| 59 | 0 | 0 | 0 | 0 | 0 | 0 |
| 60 | 0 | 0 | 0 | 0 | 0 | 0 |
| 61 | 0 | 0 | 0 | 0 | 0 | 0 |
| 62 | 0 | 0 | 0 | 0 | 0 | 0 |
| 63 | 0 | 0 | 0 | 0 | 0 | 0 |
| 64 | 0 | 0 | 0 | 0 | 0 | 0 |
| 65 | 0 | 0 | 0 | 0 | 0 | 0 |
| 66 | 0 | 0 | 0 | 0 | 0 | 0 |
| 67 | 0 | 0 | 0 | 0 | 0 | 0 |
| 68 | 0 | 0 | 0 | 0 | 0 | 0 |
| 69 | 0 | 0 | 0 | 0 | 0 | 0 |
| 70 | 0 | 0 | 0 | 0 | 0 | 0 |
| 71 | 0 | 0 | 0 | 0 | 0 | 0 |
| 72 | 0 | 0 | 0 | 0 | 0 | 0 |
| 73 | 0 | 0 | 0 | 0 | 0 | 0 |
| 74 | 0 | 0 | 0 | 0 | 0 | 0 |
| 75 | 0 | 0 | 0 | 0 | 0 | 0 |
| 76 | 0 | 0 | 0 | 0 | 0 | 0 |
| 77 | 0 | 0 | 0 | 0 | 0 | 0 |
| 78 | 1 | 0 | 1 | 0 | 0 | 0 |
| 79 | 1 | 0 | 1 | 0 | 0 | 0 |
| 80 | 1 | 0 | 1 | 0 | 0 | 0 |
| 81 | 1 | 0 | 1 | 0 | 0 | 0 |
| 82 | 0 | 0 | 0 | 1 | 1 | 0 |
| 83 | 0 | 0 | 0 | 1 | 1 | 0 |
| 84 | 0 | 0 | 0 | 1 | 1 | 0 |
| 85 | 0 | 0 | 0 | 1 | 1 | 0 |
| 86 | 0 | 0 | 0 | 0 | 0 | 0 |
| 87 | 0 | 0 | 0 | 0 | 0 | 0 |
| 88 | 0 | 0 | 0 | 0 | 0 | 0 |
| 89 | 1 | 1 | 1 | 1 | 1 | 1 |
| 90 | 1 | 1 | 1 | 1 | 1 | 1 |
| 91 | 1 | 1 | 1 | 1 | 1 | 1 |
| 92 | 0 | 0 | 0 | 0 | 0 | 0 |
| 93 | 0 | 0 | 0 | 0 | 0 | 0 |
| 94 | 0 | 0 | 0 | 0 | 0 | 0 |
| 95 | 0 | 0 | 0 | 0 | 1 | 1 |
| 96 | 0 | 0 | 0 | 0 | 1 | 1 |
| 97 | 0 | 0 | 0 | 0 | 1 | 1 |

Samples Sam165 to Sam170 comprise at least one peptide which is characteristic of VIMs. The bacteria present in samples Sam165 to Sam170 therefore express a beta-lactamase which confers on them a resistance to penicillins, to cephalosporins and to carbapenems.

The detection methods described in examples 6 to 11 are particularly advantageous because they make it possible to assay a large number of peptides and at the same time to detect the presence of one or more resistance mechanisms induced by one or more carbapenemases.

Furthermore, the detection is performed in a short time, less than one hour. In fact, only the part of the gradient between 3 and 34 minutes is useful to the analysis. Furthermore, the retention times of the assayed peptides are all below 34 minutes.

In addition, the detection methods described in examples 6 to 11 are more advantageous than the molecular biology methods because they detect the product of the expression of the genes, and not the genes themselves. The detection of a resistance may not have any clinical meaning if this gene is not expressed, or it if is expressed too weakly to lead to an effective resistance. The detection of a peptide characterising a protein characteristic of a resistance mechanism does not have this disadvantage.

Surprisingly, the above examples show that it is possible to attain by mass spectrometry the sensitivity necessary for the specific detection of the existence of a mechanism of resistance to at least one antimicrobial of a microorganism contained in a sample, without employing an amplification method as is usually the case when molecular biology methods are used.

BIBLIOGRAPHIC REFERENCES

[1] J. Anhalt & C. Fenselau, 1975, Anal. Chem., 47(2):219-225.
[2] A. Fox et al., ed., 1990, Analytical microbiology methods: chromatography and mass spectrometry, Plenum Press, New York, N.Y.
[3] M. Claydon et al., 1996, Nature Biotech. 14:1584-1586.
[4] T. Krishnamurthy & P. Ross, 1996, Rapid Com. Mass Spec., 10:1992-1996.
[5] P. Seng et al. 2009, Clin. Infect. Dis., 49:543-551.
[6] C. Fenselau et al., 2008, Appl. Environ. Microbial., 904-906.
[7] S. Hofstadler et al., 2005, Int. J. Mass Spectrom., 242:23-41.
[8] D. Ecker, 2008, Nat. Rev. Microbial., 6(7):553-558.
[9] Bush and Jacoby, 2010, Antimicrobial Agents and Chemotherapy; 54 (3): 969-976
[10] W.-J. Chen et al., 2008, Anal. Chem., 80: 9612-9621
[11] D. Lopez-Ferrer et al., 2008, Anal. Chem., 80:8930-8936
[12] D. Lopez-Ferrer et al., 2005, J. Proteome res., 4(5): 1569-1574
[13] T. Fortin et al., 2009, Mol. Cell Proteomics, 8(5): 1006-1015.
[14] H. Keshishian et al., 2007, Mol. Cell Proteomics, 2212-2229.

[15] J. Stal-Zeng et al., 2007, Mol. Cell Proteomics, 1809-1817.
[16] Gaskell, Electrospray: principles and practise, 1997, J. Mass Spectrom., 32, 677-688).
[17] V. Fusaro et al., 2009, Nature Biotech. 27, 190-198.
[18] J. Mead et al., 15 Nov. 2008, Mol. Cell Proteomics, E-pub.
[19] F. Desiere et al., 2006, Nucleic Acids Res., 34 (database issue): D655-8).
[20] L. Anderson & C. Hunter, 2006, Mol. Cell Proteomics, 573-588).
[21] B. Han & R. Higgs, 2008, Brief Funct Genomic Proteomic., 7(5):340-54).
[22] K.-Y. Wang et al., 2008, Anal. Chem, 80(16) 6159-6167).
[23] J. Bundy & C. Fenselau, 1999, Anal. Chem. 71: 1460-1463.
[24] K-C Ho et al., 2004, Anal. Chem. 76: 7162-7268.
[25] Y. S. Lin et al., 2005, Anal. Chem., 77: 1753-1760.
[26] S. Vaidyanathan et al., 2001, Anal. Chem., 73:4134-4144.
[27] R. Everley et al., 2009, J. Microbial. Methods, 77:152-158.
[28] P. Seng et al., 2009, Clin. Infect. Dis., 49:543-551.
[29] Manes N. et al., 2007, Mol. & Cell. Proteomics, 6(4): 717-727.
[30] R. Nandakumar et al., 2009, Oral Microbiology Immunology, 24:347-352).
[31] L. Hernychova et al., 2008, Anal. Chem., 80:7097-7104.
[32] J.-M. Pratt et al., 2006, Nat. Protoc., 1:1029-1043.
[33] V. Brun et al., 2007, Mol. Cell Proteomics, 2139-2149.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09874568B2). An electronic copy of the "Sequence Listing" will also be available from the USPTO upon request and payment of the fee set forth in 37 CFR 1.19(b)(3).

The invention claimed is:

1. A method of detecting a VIM protein in a sample, comprising:
subjecting the sample to MS/MS spectrometry in MRM mode and detecting whether one or more VIM fragments selected from the group consisting of SEQ ID NOs: 314-318 and 320-346 is present, wherein detection of any of the VIM fragments by the MRM mass spectrometry indicates the presence of VIM protein in the sample.

2. The method according to claim 1, further comprising, before performing MS/MS spectrometry in MRM mode, digesting proteins to produce peptides in the sample.

3. The method according to claim 2, wherein the digestion is performed by an enzyme.

4. The method according to claim 3, wherein the enzyme is trypsin.

5. The method according to claim 1, wherein the one or more VIM fragments is selected from the group consisting of SEQ ID NOs: 316, 318, 321, 341, 342, 344, and 346.

6. The method according to claim 1, further comprising performing MS/MS spectometry in MRM mode on the sample to determine whether the sample includes NDM, GES, IMP, IND, SME, and OXA.

7. A method of detecting an OXA protein in a sample, comprising:
subjecting the sample to MS/MS spectrometry in MRM mode and detecting whether one or more OXA fragments selected from the group consisting of SEQ ID NOs: 509-523, 525-572, 574-604, 606-618, 620-696, 698-1077, and 1098-1109 is present, wherein detection of any of the OXA fragments by the MRM mass spectrometry indicates the presence of OXA protein in the sample.

8. The method according to claim 7, further comprising, before performing MS/MS spectrometry in MRM mode, digesting proteins to produce peptides in the sample.

9. The method according to claim 8, wherein the digestion is performed by an enzyme.

10. The method according to claim 9, wherein the enzyme is trypsin.

11. The method according to claim 7, wherein the one or more OXA fragments is selected from the group consisting of SEQ ID NOs: 509, 510, 512, 513, 514, 515, 516, 517, 518, 519, 520, 521, 522, 523, 525, 526, 528, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 571, 572, 574, 575, 576, 577, 578, 580, 581, 583, 584, 586, 587, 588, 589, 590, 591, 593, 594, 595, 596, 597, 598, 599, 600, 601, 602, 604, 606, 607, 609, 611, 612, 613, 614, 615, 616, 618, 620, 622, 623, 624, 625, 626, 627, 632, 633, 635, 636, 637, 638, 639, 640, 641, 642, 643, 645, 648, 649, 651, 652, 653, 654, 655, 656, 659, 660, 664, 665, 666, 667, 669, 670, 672, 673, 674, 675, 676, 677, 678, 679, 680, 681, 685, 686, 687, 688, 689, 690, 691, 692, 693, 694, 696, 698, 699, 700, 701, 702, 703, 706, 707, 710, 714, 717, 719, 720, 722, 725, 726, 727, 728, 729, 732, 735, 736, 737, 738, 740, 741, 743, 744, 745, 746, 747, 748, 749, 750, 751, 752, 753, 754, 755, 756, 757, 759, 760, 762, 763, 766, 767, 768, 769, 770, 771, 773, 774, 775, 776, 777, 778, 779, 780, 781, 782, 783, 785, 786, 787, 788, 789, 790, 792, 793, 794, 795, 796, 797, 798, 799, 800, 801, 803, 804, 805, 806, 807, 809, 810, 811, 812, 813, 814, 815, 818, 821, 822, 824, 825, 826, 827, 828, 829, 830, 831, 832, 833, 834, 835, 836, 837, 838, 840, 841, 842, 844, 845, 846, 847, 848, 849, 850, 851, 853, 854, 855, 856, 857, 858, 859, 860, 861, 862, 865, 866, 867, 868, 869, 871, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 912, 913, 914, 918, 920, 921, 922, 923, 928, 930, 932, 935, 936, 937, 938, 939, 940, 941, 942, 943, 944, 945, 946, 947, 948, 949, 950, 951, 953, 954, 955, 956, 958, 961, 962, 963, 964, 967, 968, 970, 972, 973, 974, 975, 976, 977, 978, 979, 980, 981, 982, 983, 984, 985, 986, 988, 990, 992, 993, 994, 995, 996, 997, 998, 1000, 1001, 1003, 1004, 1005, 1008, 1009, 1011, 1012, 1013, 1014, 1015, 1018, 1019, 1020, 1022, 1024, 1025, 1026, 1027, 1028, 1030, 1031, 1034, 1036, 1041, 1042, 1044, 1045, 1046, 1048, 1049, 1050, 1052, 1053, 1054, 1058, 1059, 1060, 1062, 1063, 1064, 1067, 1068, 1069, 1070, 1071, 1072, 1073, 1074, 1075, 1076, 1098, 1099, 1100, 1101, 1102, 1103, 1104, 1105, 1106, 1107, 1108, and 1109.

12. The method according to claim 7, wherein the one or more OXA fragments is selected from the group consisting of SEQ ID NOs: 510, 512, 513, 514, 520, 521, 522, 523, 525, 530, 532, 537, 541, 542, 543, 544, 545, 546, 547, 548, 549, 550, 551, 552, 556, 557, 558, 559, 560, 561, 562, 574, 581, 582, 583, 584, 596, 597, 598, 599, 600, 601, 602, 607, 609, 632, 633, 635, 636, 649, 655, 656, 667, 674, 675, 689, 690, 698, 714, 719, 720, 722, 727, 729, 741, 746, 748, 750, 751, 752, 755, 756, 757, 763, 767, 768, 772, 775, 781, 782, 790, 792, 793, 794, 795, 796, 797, 798, 801, 809, 811, 812, 813, 814, 824, 832, 834, 837, 838, 847, 851, 853, 854, 855, 856, 857, 858, 859, 860, 862, 868, 869, 870, 874, 875, 876, 877, 879, 880, 881, 882, 894, 895, 898, 902, 903, 904, 906, 907, 908, 912, 913, 914, 920, 922, 923, 937, 938, 939, 945, 946, 948, 949, 950, 951, 954, 956, 962, 964, 967, 969, 971, 972, 974, 975, 979, 980, 985, 988, 990, 993, 994, 995, 996, 997, 1000, 1001, 1003, 1004, 1005, 1011, 1013, 1015, 1018, 1019, 1027, 1030, 1034, 1035, 1036, 1042, 1048, 1052, 1058, 1060, 1070, 1098, 1099, 1100, 1101, 1102, 1103, 1104, 1105, 1106, 1107, 1108, and 1109.

13. The method according to claim 7, wherein the one or more OXA fragments is selected from the group consisting of SEQ ID NOs: 1098, 1100, 1102, 1103, 1104, 1105, 1107, 1108, and 1109.

14. The method according to claim 7, further comprising performing MS/MS spectometry in MRM mode on the sample to determine whether the sample includes NDM, GES, IMP, IND, SME, and VIM.

* * * * *